US011952623B2

(12) United States Patent
Quake et al.

(10) Patent No.: US 11,952,623 B2
(45) Date of Patent: *Apr. 9, 2024

(54) SIMULTANEOUS DETERMINATION OF ANEUPLOIDY AND FETAL FRACTION

(71) Applicant: Verinata Health, Inc., Redwood City, CA (US)

(72) Inventors: Stephen Quake, Stanford, CA (US); Richard P. Rava, Redwood City, CA (US); Manjula Chinnappa, Foster City, CA (US); David A Comstock, Sunnyvale, CA (US); Gabrielle Heilek, Mountain View, CA (US)

(73) Assignee: VERINATA HEALTH, INC., Redwood City, CA (US)

( * ) Notice: Subject to any disclaimer, the term of this patent is extended or adjusted under 35 U.S.C. 154(b) by 160 days.

This patent is subject to a terminal disclaimer.

(21) Appl. No.: 17/465,163

(22) Filed: Sep. 2, 2021

(65) Prior Publication Data

US 2022/0017958 A1   Jan. 20, 2022

Related U.S. Application Data

(63) Continuation of application No. 15/664,008, filed on Jul. 31, 2017, now Pat. No. 11,130,995, which is a continuation of application No. 13/365,240, filed on Feb. 2, 2012, now abandoned, which is a continuation of application No. 12/958,356, filed on Dec. 1, 2010, now abandoned.

(60) Provisional application No. 61/455,849, filed on Oct. 26, 2010, provisional application No. 61/407,017, filed on Oct. 26, 2010, provisional application No. 61/360,837, filed on Jul. 1, 2010, provisional application No. 61/296,358, filed on Jan. 19, 2010.

(51) Int. Cl.
| | |
|---|---|
| *C12Q 1/6869* | (2018.01) |
| *C12Q 1/6806* | (2018.01) |
| *C12Q 1/6809* | (2018.01) |
| *C12Q 1/6883* | (2018.01) |
| *G16B 20/10* | (2019.01) |
| *G16B 30/10* | (2019.01) |
| *G16H 10/40* | (2018.01) |

(52) U.S. Cl.
CPC ......... *C12Q 1/6869* (2013.01); *C12Q 1/6806* (2013.01); *C12Q 1/6809* (2013.01); *G16B 20/10* (2019.02); *G16B 30/10* (2019.02); *G16H 10/40* (2018.01); *C12Q 1/6883* (2013.01); *C12Q 2600/106* (2013.01); *C12Q 2600/112* (2013.01)

(58) Field of Classification Search
None
See application file for complete search history.

(56) References Cited

U.S. PATENT DOCUMENTS

| | | |
|---|---|---|
| 5,994,057 A | 11/1999 | Mansfield |
| 6,258,540 B1 | 7/2001 | Lo et al. |
| 6,440,706 B1 | 8/2002 | Vogelstein et al. |
| 6,555,315 B1 | 4/2003 | Short |
| 7,252,946 B2 | 8/2007 | Szasz |
| 7,332,277 B2 | 2/2008 | Dhallan |
| 7,645,576 B2 | 1/2010 | Lo et al. |
| 7,888,017 B2 | 2/2011 | Quake et al. |
| 8,008,018 B2 | 8/2011 | Quake et al. |
| 8,137,912 B2 | 3/2012 | Kapur et al. |
| 8,195,415 B2 | 6/2012 | Fan et al. |
| 8,318,430 B2 | 11/2012 | Chuu et al. |
| 8,532,936 B2 | 9/2013 | Rava |
| 2002/0142324 A1 | 10/2002 | Wang |
| 2003/0044388 A1 | 3/2003 | Lo et al. |
| 2003/0064368 A1 | 4/2003 | Sakai et al. |
| 2003/0194704 A1 | 10/2003 | Penn |
| 2004/0209299 A1 | 10/2004 | Pinter et al. |
| 2005/0221341 A1 | 10/2005 | Shimkets |
| 2006/0046258 A1 | 3/2006 | Lapidus et al. |
| 2006/0121452 A1 | 6/2006 | Dhallan |
| 2006/0134599 A1 | 6/2006 | Toner et al. |
| 2006/0257895 A1 | 11/2006 | Pinkel et al. |
| 2006/0286558 A1 | 12/2006 | Novoradovskaya et al. |
| 2007/0134658 A1 | 6/2007 | Bohmer et al. |
| 2007/0207466 A1 | 9/2007 | Cantor et al. |
| 2008/0020390 A1 | 1/2008 | Mitchell et al. |
| 2008/0050739 A1 | 2/2008 | Stoughton et al. |
| 2008/0064098 A1 | 3/2008 | Allickson |
| 2008/0070792 A1 | 3/2008 | Stoughton et al. |
| 2008/0138809 A1 | 6/2008 | Kapur et al. |
| 2008/0193927 A1 | 8/2008 | Mann et al. |

(Continued)

FOREIGN PATENT DOCUMENTS

| | | |
|---|---|---|
| EP | 2334812 | 6/2011 |
| GB | 2479471 | 10/2011 |

(Continued)

OTHER PUBLICATIONS

European Office Action issued in EP 12 716 939.9, dated Mar. 10, 2015.
"Extended European Search Report for European Patent Application No. 14192160.1", dated Feb. 13, 2015, 10 pages.
"European Search Report in EP Patent Application No. 10825822.9", dated Feb. 22, 2012, 4 pages.
"European Search Report in EP Patent Application No. 10830939.4", dated Feb. 22, 2012, 4 pages.

(Continued)

*Primary Examiner* — Katherine D Salmon
(74) *Attorney, Agent, or Firm* — Mueting Raasch Group

(57) ABSTRACT

The invention provides compositions and methods for simultaneously determining the presence or absence of fetal aneuploidy and the relative amount of fetal nucleic acids in a sample obtained from a pregnant female. The method encompasses the use of sequencing technologies and exploits the occurrence of polymorphisms to provide a streamlined noninvasive process applicable to the practice of prenatal diagnostics.

19 Claims, 18 Drawing Sheets

Specification includes a Sequence Listing.

(56) References Cited

U.S. PATENT DOCUMENTS

| | | |
|---|---|---|
| 2008/0220422 A1 | 9/2008 | Shoemaker et al. |
| 2008/0299562 A1 | 12/2008 | Oeth et al. |
| 2009/0029377 A1 | 1/2009 | Lo et al. |
| 2009/0087847 A1 | 4/2009 | Lo et al. |
| 2009/0098547 A1 | 4/2009 | Ghosh |
| 2009/0117542 A1 | 5/2009 | Maybruck et al. |
| 2009/0215042 A1 | 8/2009 | Sella-Tavor et al. |
| 2009/0270601 A1 | 10/2009 | Benner et al. |
| 2009/0291443 A1 | 11/2009 | Stoughton et al. |
| 2009/0299645 A1 | 12/2009 | Colby et al. |
| 2009/0307181 A1 | 12/2009 | Colby et al. |
| 2009/0317817 A1 | 12/2009 | Oeth et al. |
| 2009/0317818 A1 | 12/2009 | Ehrich et al. |
| 2010/0068711 A1 | 3/2010 | Umansky et al. |
| 2010/0093835 A1 | 5/2010 | Fan et al. |
| 2010/0112590 A1 | 5/2010 | Lo et al. |
| 2010/0138165 A1 | 6/2010 | Fan et al. |
| 2010/0167954 A1 | 7/2010 | Earnshaw et al. |
| 2010/0184043 A1 | 7/2010 | Mitchell et al. |
| 2010/0184075 A1 | 7/2010 | Cantor et al. |
| 2010/0196426 A1 | 8/2010 | Skog et al. |
| 2010/0216151 A1 | 8/2010 | Lapidus et al. |
| 2010/0216153 A1 | 8/2010 | Lapidus et al. |
| 2011/0105353 A1 | 5/2011 | Lo et al. |
| 2011/0118145 A1 | 5/2011 | Akmaev et al. |
| 2011/0177517 A1 | 7/2011 | Rava et al. |
| 2011/0201507 A1 | 8/2011 | Rava et al. |
| 2011/0224087 A1 | 9/2011 | Quake et al. |
| 2011/0230358 A1 | 9/2011 | Rava |
| 2011/0245085 A1 | 10/2011 | Rava et al. |
| 2011/0312503 A1 | 12/2011 | Chuu et al. |
| 2012/0010085 A1 | 1/2012 | Rava et al. |
| 2012/0034603 A1 | 2/2012 | Oliphant et al. |
| 2012/0034685 A1 | 2/2012 | Sparks et al. |
| 2012/0040859 A1 | 2/2012 | Sparks et al. |
| 2012/0094849 A1 | 4/2012 | Rava et al. |
| 2012/0100548 A1 | 4/2012 | Rava et al. |
| 2012/0149582 A1 | 6/2012 | Rava et al. |
| 2012/0149583 A1 | 6/2012 | Rava et al. |
| 2012/0184449 A1 | 7/2012 | Hixson et al. |
| 2012/0208710 A1 | 8/2012 | Fan et al. |
| 2012/0214678 A1 | 8/2012 | Rava et al. |
| 2012/0214680 A1 | 8/2012 | Oeth et al. |
| 2012/0237928 A1 | 9/2012 | Rava et al. |
| 2012/0238738 A1 | 9/2012 | Hendrickson |
| 2013/0029852 A1 | 1/2013 | Rava et al. |
| 2013/0034546 A1 | 2/2013 | Rava et al. |
| 2013/0096011 A1 | 4/2013 | Rava et al. |
| 2014/0038830 A1 | 2/2014 | Srinivasan et al. |
| 2014/0199691 A1 | 7/2014 | Chuu et al. |

FOREIGN PATENT DOCUMENTS

| | | |
|---|---|---|
| GB | 2479476 | 10/2011 |
| GB | 2479080 | 1/2012 |
| GB | 2484764 | 4/2012 |
| WO | WO 1996/19586 | 6/1996 |
| WO | WO 1998/14275 | 4/1998 |
| WO | WO 1998/44151 | 10/1998 |
| WO | WO 00/18957 | 4/2000 |
| WO | WO 2000/18957 | 4/2000 |
| WO | WO 2003/004677 | 1/2003 |
| WO | WO 03/074740 | 9/2003 |
| WO | WO 2003/074740 | 9/2003 |
| WO | WO 2006/010610 | 2/2006 |
| WO | WO 2006/0281 53 | 3/2006 |
| WO | WO 2006/028152 | 3/2006 |
| WO | WO 2007/092473 | 8/2007 |
| WO | WO 2007/100911 | 9/2007 |
| WO | WO 2007/147079 | 12/2007 |
| WO | WO 2009/013492 | 1/2009 |
| WO | WO 2009/013496 | 1/2009 |
| WO | WO 2010/033578 | 3/2010 |
| WO | WO 2011 /051283 | 5/2011 |
| WO | WO 2012/019187 | 2/2012 |
| WO | WO 2012/019193 | 2/2012 |
| WO | WO 2012/019198 | 2/2012 |
| WO | WO 2012/019200 | 2/2012 |
| WO | WO 2012/071621 | 6/2012 |
| WO | WO 2012/078792 | 6/2012 |
| WO | WO 2012/088348 | 6/2012 |
| WO | WO 2012/103031 | 8/2012 |
| WO | WO 2012/108920 | 8/2012 |
| WO | WO 2012/142334 | 10/2012 |
| WO | WO 2013/015793 | 1/2013 |

OTHER PUBLICATIONS

Ashoor, et al., "Fetal Fraction in maternal plasma cell-free DNA at 11-13 weeks' gestation: effect of maternal and fetal factors." May 2012 *Fetal Diagnosis and Therapy*, 31(4) : 237-243. Published online, a reference cited in the instructions, May 4, 2012, 7 pages.

Bentley et al., "Accurate whole human genome sequencing using reversible terminator chemistry." Nov. 2008 *Nature*, 456 (7218): 53-59.

Beroukhim et al., "The landscape of somatic copy-number alteration across human cancers." Feb. 2010 *Nature*, 463 (7283): 899-905.

Børsting et al., "Multiplex PCR, amplicon size and hybridization efficiency on the NanoChip electronic microarray." Jan. 2004 *International Journal of Legal Medicine*, 118 (2): 75-82.

Botezatu et al., "Genetic analysis of DNA excreted in urine: a new approach for detecting specific genomic DNA sequences from cells dying in an organism." Aug. 2000 *Clinical Chemistry*, 46 (8 Pt 1): 1078-1084.

Buck et al., "Design Strategies and Performance of Custom DNA Sequencing Primers." Aug. 1999 *BioTechniques*, 27 (3): 528-536.

Butler, "Short tandem repeat typing technologies used in human identity testing." Oct. 2007 *BioTechniques*, 43 (4): Sii-Sv.

Butler et al., "The Development of reduced size STR amplicons as tools for analysis of degraded DNA." Sep. 2003 *Journal of Forensic Sciences*, 48 (5): 1054-1064.

Chan et al., "Size Distributions of Maternal and Fetal DNA in Maternal Plasma." Jan. 2004 *Clinical Chemistry*. 50 (1): 88-92.

Chen, et al., "Microsatellite alterations in plasma DNA of small cell lung cancer Patients." Sep. 1996 *Nat Medicine*, 2 (9): 1033-1035.

Chiang et al., "High-resolution mapping of copy-number alterations with massively parallel sequencing." Dec. 2008 *Nature Methods*, 6 (1): 99-103.

Chiu et al., "Maternal Plasma DNA Analysis with Massively Parallel Sequencing by Ligation for Noninvasive Prenatal Diagnosis of Trisomy 21." Mar. 2010 *Clinical Chemistry*, 56 (3): 459-463.

Chiu et al., "Non-invasive prenatal assessment of trisomy 21 by multiplexed maternal plasma DNA sequencing: large scale validity study." Jan. 2011 *British Medical Journal*, 342: c7401.

Chiu et al., "Non-invasive prenatal diagnosis by single molecule counting technologies." Jul. 2009 *Trends in Genetics*, 25 (7): 324-331.

Chiu et al., "Noninvasive prenatal diagnosis of fetal chromosomal aneuploidy by massively parallel genomic sequencing of DNA in maternal plasma." Dec. 2008 *Proceedings of the National Academy of Sciences*. 105 (51): 20458-20463.

Chu et al., "Statistical model for whole genome sequencing and its application to minimally invasive diagnosis of fetal genetic disease." May 2009 *Bioinformatics*, 25 (10): 1244-1250.

Clarke et al., "Effects of radiotherapy and of differences in the extent of surgery for early breast cancer on local recurrence and 15-year survival: an overview of the randomised trials." May 2005 *Lancet*, 366 (9503): 2087-2106.

Clarke, et al., "Effects of radiotherapy and of differences in the extent of surgery for early breast cancer on local recurrence and 15-year survival: an overview of the randomised trials." Dec. 2005 *Lancet*, 366(9503): 2087-2106.

Coble et al., "Characterization of new miniSTR loci to aid analysis of degraded DNA." Jan. 2005 *Journal of Forensic Sciences*, 50 (1): 43-53.

(56) References Cited

OTHER PUBLICATIONS

Deng, et al., "Enumeration and microfluidic chip separation of circulating fetal cells early in pregnancy from maternal blood", Dec. 2008 *American Journal of Obstetrics & Gynecology* 199(6): S134.
Dhallan, et al., "A non-invasive test for prenatal diagnosis based on fetal DNA present in maternal blood: a preliminary study." Feb. 2007 *Lancet*, 369(9560): 474-481.
Ding et al., "MS analysis of single-nucleotide differences in circulating nucleic acids: Application to noninvasive prenatal diagnosis." Jul. 2004 *Proceedings of the National Academy of Sciences of the United States of America*, 101 (29): 10762-10767.
Dixon et al., "Analysis of artificially degraded DNA using STRs and SNPs—results of a collaborative European (EDNAP) exercise." Dec. 2006 *Forensic Science International*, 164 (1): 33-44.
Ehrich et al., "Noninvasive detection of fetal trisomy 21 by sequencing of DNA in maternal blood: a study in a clinical setting." Mar. 2011 *American Journal of Obstetrics and Gynecology*, 204 (3): 205.e201-205.e211.
Fan et al., "Analysis of the Size Distributions of Fetal and Maternal Cell-Free DNA by Paired-End Sequencing." Aug. 2010 *Clinical Chemistry*, 56 (8): 1279-1286.
Fan et al., "Detection of Aneuploidy with Digital Polymerase Chain Reaction." Oct. 2007 *Analytical Chemistry*, 79 (19): 7576-7579.
Fan et al., "In Principle Method for Noninvasive Determination of the Fetal Genome." Dec. 2010 *Nature Precedings*, 10.1038/npre, 5373.1.
Fan et al., "Microfluidic digital PCR enables rapid prenatal diagnosis of fetal aneuploidy." May 2009 *American Journal of Obstetrics and Gynecology*, 200 (5): 543.e541-547.
Fan et al., "Noninvasive diagnosis of fetal aneuploidy by shotgun sequencing DNA from maternal blood." Oct. 2008 *Proceedings of the National Academy of Sciences*, 105 (42): 16266-16271.
Fan et al., "Sensitivity of noninvasive prenatal detection of fetal aneuploidy from maternal plasma using shotgun sequencing is limited only by counting statistics." Mar. 2010 *Peer-Reviewed Open Access Scientific Journal One*, 5 (5): e10439, 1-7.
Fan, et al., "Noninvasive diagnosis of fetal aneuploidy by shotgun sequencing DNA from maternal blood." Oct. 2008, *Proceedings of the National Academy of Sciences*, 105(42): "Supporting Information," p. 1-7.
Fan, et al., "U.S. Appl. No. 13/452,083", filed Apr. 20, 2012.
Fan et al., "Whole-genome molecular haplotyping of single cells." Dec. 2010 *Nature Biotechnology*, 29 (1): 51-57.
Fröhling et al., "Chromosomal Abnormalities in Cancer." Aug. 2008 *New England Journal of Medicine*, 359 (7): 722-734.
Ghanta et al., "Non-Invasive Prenatal Detection of Trisomy 21 Using Tandem Single Nucleotide Polymorphisms." Oct. 2010 *Peer-Reviewed Open Access Scientific Journal One*, 5 (10): e13184, p. 1-10.
Goossens et al., "Simultaneous mutation and copy number variation (CNV) detection by multiplex PCR-based GS-FLX sequencing." Dec. 2009 *Human Mutation*, 30 (3): 472-476.
Grubwieser et al., "A new "miniSTR-multiplex" displaying reduced amplicon lengths for the analysis of degraded DNA." Jul. 2006 *International Journal of Legal Medicine*, 120 (2): 115-120.
Hanson et al., "Whole genome amplification strategy for forensic genetic analysis using single or few cell equivalents of genomic DNA." Nov. 2005 *Analytical Biochemistry*, 346 (2): 246-257.
Harris et al., "Single-molecule DNA sequencing of a viral genome." Month (2008) *Science*, 320 (5872): 106-109 and "Supplemental Material," p. 1-25.
Harrison et al., "Polymer-stimulated ligation: enhanced ligation of oligo- and polynucleotides by T4 RNA ligase in polymer solutions." Nov. 1984 *Nucleic Acids Research*, 12 (21): 8235-8251.
Hayashi et al., "Regulation of inter- and intramolecular ligation with T4 DNA ligase in the presence of polyethylene glycol." Oct. 1986 *Nucleic Acids Research*, 14 (19): 7617-7631.
Hill, et al., "Characterization of 26 new miniSTR Loci", Poster #44—17th International Symposium on Human Identification, Nashville, TN, Oct. 10-12, 2006.
Hoffman, "The genome-enabled electronic medical record." Mar. 2007 *Journal of Biomedical Informatics*, 40 (1): 44-46.
Huang et al., "Isolation of cell-free DNA from maternal plasma using manual and automated systems."(2008) *Methods in Molecular Biology*, 444: 203-208.
Hung et al., "Detection of circulating fetal nucleic acids: a review of methods and applications." Apr. 2009 *Journal of Clinical Pathology*, 62 (4): 308-313.
Illumina, "Preparing Samples for ChIP sequencing of DNA", E-pub at grcf.jhmi.edu/hts/protocols/11257047 Ch IP Sample_Prep.pdf., 2007.
International, "The International HapMap Consortium Project." Dec. 2003 *Nature* 426:789-796.
Jama, et al., "Quantification of cell-free fetal DNA Levels on maternal plasma by STR analysis." (2010) *ACMG Annual Clinical Genetics Meeting*, 2 pages.
Jensen et al., "Detection of Microdeletion 22q11.2 in a Fetus by Next-Generation Sequencing of Maternal Plasma." Jul. 2012 *Clinical Chemistry*, 58 (7): 1148-1151.
Jorgez et al., "Improving Enrichment of Circulating Fetal DNA for Genetic Testing: Size Fractionation Followed by Whole Gene Amplification." Sep. 2009 *Fetal Diagnosis and Therapy*, 25: 314-319.
Ju et al., "Four-color DNA sequencing by synthesis using cleavable fluorescent nucleotide reversible terminators." Oct. 2006 *Proceedings of the National Academy of Sciences*, 103 (52): 19635-19640.
Kidd et al., "Developing a SNP panel for forensic identification of individuals." Dec. 2006 *Forensic Science International*, 164 (1): 20-32.
Kim et al., "rSW-seq: Algorithm for detection of copy No. alterations in deep sequencing data." Aug. 2010 *BMC Bioinformatics*, 11 (1): 432.
Klintschar et al., "Genetic variation at the STR loci D12S391 and CSFIPO in four populations from Austria, Italy, Egypt and Yemen." Oct. 1998 *Forensic Science International*, 97 (1): 37-45.
Koide et al., "Fragmentation of cell-free fetal DNA in plasma and urine of pregnant women." Jul. 2005 *Prenatal Diagnosis*, 25 (7): 604-607.
Kozarewa et al., "Amplification-free Illumina sequencing-library preparation facilitates improved mapping and assembly of (G+C)-biased genomes." Apr. 2009 *Nature Methods*, 6 (4): 291-295.
Lazinski, et al., "Modified Protocol for Illumina Paired-End Library Construction" downloaded from genomics.med.tufts.edu/documents/hfseq_protocol_for_illumina_paired.pdf, Feb. 27, 2009.
Leon et al., "Free DNA in the serum of cancer patients and the effect of therapy." Mar. 1977 *Cancer Research*, 37 (3): 646-650.
Levy et al., "The Diploid Genome Sequence of an Individual Human." Oct. 2007 *Public Library of Science Biology*, 5 (10): e254, 2113-2144.
Li et al., "Size separation of circulatory DNA in maternal plasma permits ready detection of fetal DNA polymorphisms." Jun. 2004 *Clinical Chemistry*, 50 (6): 1002-1011.
Liao et al., "Targeted Massively Parallel Sequencing of Maternal Plasma DNA Permits Efficient and Unbiased Detection of Fetal Alleles." Jan. 2011 *Clinical Chemistry*. 57 (1): 92-101.
Liu et al., "Feasibility study of using fetal DNA in maternal plasma for non-invasive prenatal diagnosis." (2007) *Acta Obstetricia et Gynecologica Scandinavica*, 86 (5): 535-541.
Lo et al., "Digital PCR for the molecular detection of fetal chromosomal aneuploidy." Aug. 2007 *Proceedings of the National Academy of Sciences*, 104 (32): 13116-13121.
Lo et al., "Increased Fetal DNA Concentrations in the Plasma of Pregnant Women Carrying Fetuses with Trisomy 21." Oct. 1999 *Clinical Chemistry*, 45 (10): 1747-1751.
Lo et al., "Maternal plasma DNA sequencing reveals the genome-wide genetic and mutational profile of the fetus." Dec. 2010 *Science Translational Medicine*, 2 (61): 61ra91.
Lo, "Noninvasive prenatal detection of fetal chromosomal aneuploidies by maternal plasma nucleic acid analysis: a review of the current state of the art." Dec. 2008 *BJOG: An International Journal of Obstetrics & Gynaecology*. 116 (2): 152-157.

(56) References Cited

OTHER PUBLICATIONS

Lo, et al., "Noninvasive prenatal diagnosis of fetal chromosomal aneuploidies by maternal plasma nucleic acid analysis." Jan. 2008 *Clinical Chemistry*, 54(3):461-466.
Lo et al., "Prenatal Diagnosis of Fetal RhD Status by Molecular Analysis of Maternal Plasma." Dec. 1998 *New England Journal of Medicine*, 339 (24): 1734-1738.
Lo et al., "Presence of fetal DNA in maternal plasma and serum." Aug. 1997 *Lancet*, 350 (9076): 485-487.
Lo et al., "Quantitative Analysis of Fetal DNA in Maternal Plasma and Serum: Implications for Noninvasive Prenatal Diagnosis." Apr. 1998 *The American Journal of Human Genetics*, 62 (4): 768-775.
Lo, et al., "Rapid Clearance of fetal DNA from Maternal Plasma." Jan. 1999 *American Journal of Human Genetics*, 64(1): 218-24.
Lun et al., "Microfluidics Digital PCR Reveals a Higher than Expected Fraction of Fetal DNA in Maternal Plasma." Oct. 2008 *Clinical Chemistry*, 54 (10): 1664-1672.
Lun et al., "Noninvasive prenatal diagnosis of monogenic diseases by digital size selection and relative mutation dosage on DNA in maternal plasma." Dec. 2008 *Proceedings of the National Academy of Sciences of the United States of America*, 105 (50): 19920-19925.
McKernan et al., "Sequence and structural variation in a human genome uncovered by short-read, massively parallel ligation sequencing using two-base encoding." Sep. 2009 *Genome Research*, 19 (9): 1527-1541.
Metzker, "Sequencing technologies—the next generation." Jan. 2010 *Nature Reviews Genetics*, 11 (1): 31-46.
Meyerson et al., "Advances in understanding cancer genomes through second-generation sequencing." Sep. 2010 *Nature Reviews Genetics*. 11 (10): 685-696.
Mullighan et al., "Genome-wide profiling of genetic alterations in acute lymphoblastic leukemia: recent insights and future directions." Feb. 2009 *Leukemia*, 23 (7): 1209-1218.
Nakamoto et al., "Detection of Microsatellite Alterations in Plasma DNA of Malignant Mucosal Melanoma Using Whole Genome Amplification." May 2008 *The Bulletin of Tokyo Dental College*, 49 (2): 77-87.
Nicklas et al., "A real-time multiplex SNP melting assay to discriminate individuals." Nov. 2008 *Journal of Forensic Sciences*, 53 (6): 1316-1324.
Norton et al., "Non-Invasive Chromosomal Evaluation (NICE) Study: results of a multicenter prospective cohort study for detection of fetal trisomy 21 and trisomy 18." May 2012 *American Journal of Obstetrics and Gynecology*, 207 (2): 137.e131-137.e138.
Oliphant et al., U.S. Appl. No. 61/371,605, filed Aug. 6, 2010.
Pakstis et al., "Candidate SNPs for a universal individual identification panel." May 2007 *Human Genetics*, 121 (3-4): 305-317.
Pakstis et al., "SNPs for a universal individual identification panel." Mar. 2010 *Human Genetics*, 127 (3): 315-324.
Pandey, et al., "Chapter 3 Applied Biosystems SOLID™ Systems: Ligation-Based Sequencing" in *Next Generation Genome Sequencing: Towards Personalized Medicine*, Janitz (Ed.), 2008.
Pathak et al., "Circulating Cell-Free DNA in Plasma/Serum of Lung Cancer Patients as a Potential Screening and Prognostic Tool." Oct. 2006 *Clinical Chemistry*, 52 (10): 1833-1842.
Pertl et al., "Detection of male and female fetal DNA in maternal plasma by multiplex fluorescent polymerase chain reaction amplification of short tandem repeats." Jan. 2000 *Human Genetics*, 106 (1): 45-49.
Peters et al., "Noninvasive Prenatal Diagnosis of a Fetal Microdeletion Syndrome." Nov. 2011 *New England Journal of Medicine*, 365 (19): 1847-1848.
Pheiffer et al., "Polymer-stimulated ligation: enhanced blunt- or cohesive-end ligation of DNA or deoxyribooligonucleotides by T4 DNA ligase in polymer solutions." Nov. 1983 *Nucleic Acids Research*, 11 (22): 7853-7871.
Pui et al., "Acute lymphoblastic leukaemia." Mar. 2008 *Lancet*, 371 (9617): 1030-1043.
Pushkarev et al., "Single-molecule sequencing of an individual human genome." Sep. 2009 *Nature Biotechnology*, 27 (9): 847-850.

Quail et al., "A large genome center's improvements to the Illumina sequencing system." Nov. 2008 *Nature Methods*, 5 (12): 1005-1010.
Schwarzenbach et al., "Cell-free tumor DNA in blood plasma as a marker for circulating tumor cells in prostate cancer." Feb. 2009 *Clinical Cancer Research*, 15 (3): 1032-1038.
Schwarzenbach et al., "Comparative evaluation of cell-free tumor DNA in blood and disseminated tumor cells in bone marrow of patients with primary breast cancer." Sep. 2009 *Breast Cancer Research*, 11 (5): R71.
Sehnert, et al., "Optimal Detection of Fetal Chromosomal Abnormalities by Massively Parallel DNA Sequencing of Cell-Free Fetal DNA from Maternal Blood", Apr. 2011 *Clinical Chemistry*, 57 (7): doi:10.1373/clinchem.2011.165910., Apr. 25, 2011, 1042-1049.
Sehnert et al., "Optimal detection of fetal chromosomal abnormalities by massively parallel DNA sequencing of cell-free fetal DNA from maternal blood." Apr. 2011 *Clinical Chemistry*, 57 (7): 1042-1049.
Shendure et al., "Next-generation DNA sequencing." Oct. 2008 *Nature Biotechnology*, 26 (10): 1135-1145.
Sparks et al., "Noninvasive prenatal detection and selective analysis of cell-free DNA obtained from maternal blood: evaluation for trisomy 21 and trisomy 18." Jan. 2012 *American Journal of Obstetrics and Gynecology*, 206 (4): 319.e311-319.e319.
National Center for Biotechnology Information, National Library of Medicine, National Institutes of Health, Short Genetic Variations, dbSNP cluster report: rs131828, NCBI Assay ID: SS139539. Bethesda, MD, entry date Jun. 8, 2000.
National Center for Biotechnology Information, National Library of Medicine, National Institutes of Health, Short Genetic Variations, dbSNP cluster report: rs560681, NCBI Assay ID: SS3206919. Bethesda, MD, entry date Sep. 5, 2001.
National Center for Biotechnology Information, National Library of Medicine, National Institutes of Health, Short Genetic Variations, dbSNP cluster report: rs807841, NCBI Assay ID: SS3470339. Bethesda, MD, entry date Sep. 24, 2001.
Stoughton et al., U.S. Appl. No. 13/433,232, filed Mar. 28, 2012.
Su et al., "Human Urine Contains Small, 150 to 250 Nucleotide-Sized, Soluble DNA Derived from the Circulation and May be Useful in the Detection of Colorectal Cancer." May 2004 *The Journal of Molecular Diagnostics*, 6 (2): 101-107.
Teixeira et al., "Multiple numerical chromosome aberrations in cancer: what are their causes and what are their consequences?" Feb. 2005 *Seminars in Cancer Biology*, 15 (1): 3-12.
Thorstenson et al., "An Automated Hydrodynamic Process for Controlled, Unbiased DNA Shearing." Aug. 1998 *Genome Research*, 8 (8): 848-855.
Tong et al., "Noninvasive Prenatal Detection of Fetal Trisomy 18 by Epigenetic Allelic Ratio Analysis in Maternal Plasma: Theoretical and Empirical Considerations." Dec. 2006 *Clinical Chemistry*, 52 (12): 2194-2202.
Tong et al., "Noninvasive Prenatal Detection of Trisomy 21 by an Epigenetic-Genetic Chromosome-Dosage Approach." Jan. 2010 *Clinical Chemistry*, 56 (1): 90-98.
Vallone, et al., "Demonstration of rapid multiplex PCR amplification involving 16 genetic loci." Dec. 2008 *Forensic Science International Genetics*, 3(1): 42-5.
Voelkerding et al., "Next-generation sequencing: from basic research to diagnostics." Apr. 2009 *Clinical Chemistry*, 55 (4): 641-658.
Voelkerding et al., "Digital Fetal Aneuploidy Diagnosis by Next-Generation Sequencing." Mar. 2010 *Clinical Chemistry*, 56 (3): 336-338.
Vogelstein et al., "Digital PCR." Aug. 1999 *Proceedings of the National Academy of Sciences*, 96 (16): 9236-9241.
Wheeler et al., "The complete genome of an individual by massively parallel DNA sequencing." Apr. 2008 *Nature*, 452 (7189): 872-876.
Wright et al., "The use of cell-free fetal nucleic acids in maternal blood for non-invasive prenatal diagnosis." Oct. 2008 *Human Reproduction Update*, 15 (1): 139-151.
Yamazawa et al., "Monozygotic female twins discordant for Silver-Russell syndrome and hypomethylation of the H19-DMR." Oct. 2008 *Journal of Human Genetics*, 53 (10): 950-955.
Zimmerman et al., "Macromolecular Crowding Allows Blunt-End Ligation by DNA Ligases from Rat Liver or *Escherichia coli*." Oct.

(56) References Cited

OTHER PUBLICATIONS

1983 *Proceedings of the National Academy of Sciences of the United States of America*, 80 (19): 5852-5856.

SEQUENCE LISTING

```
<160> NUMBER OF SEQ ID NOS: 427

<210> SEQ ID NO 1
<211> LENGTH: 111
<212> TYPE: DNA
<213> ORGANISM: Homo sapiens

<400> SEQUENCE: 1
cacatgcaca gccagcaacc ctgtcagcag gagttcccac cagtttcttt ctgagaacat      60
ctgttcaggt ttctctccat ctctatttac tcaggtcaca ggaccttggg g              111

<210> SEQ ID NO 2
<211> LENGTH: 111
<212> TYPE: DNA
<213> ORGANISM: Homo sapiens

<400> SEQUENCE: 2
cacatgcaca gccagcaacc ctgtcagcag gagttcccac cagtttcttt ctgagaacat      60
ctgttcaggt ttctctccat ctctgtttac tcaggtcaca ggaccttggg g              111

<210> SEQ ID NO 3
<211> LENGTH: 126
<212> TYPE: DNA
<213> ORGANISM: Homo sapiens

<400> SEQUENCE: 3
tgaggaagtg aggctcagag ggtaagaaac tttgtcacag agctggtggt gagggtggag      60
attttacact ccctgcctcc cacaccagtt tctccagagt ggaaagactt tcatctcgca     120
ctggca                                                                126

<210> SEQ ID NO 4
<211> LENGTH: 126
<212> TYPE: DNA
<213> ORGANISM: Homo sapiens

<400> SEQUENCE: 4
tgaggaagtg aggctcagag ggtaagaaac tttgtcacag agctggtggt gagggtggag      60
attttacact ccctgcctcc cacaccagtt tctccggagt ggaaagactt tcatctcgca     120
ctggca                                                                126
```

<210> SEQ ID NO 5
<211> LENGTH: 121
<212> TYPE: DNA
<213> ORGANISM: Homo sapiens

<400> SEQUENCE: 5

```
gtgccttcag aacctttgag atctgattct attttaaag cttcttagaa gagagattgc    60
aaagtgggtt gtttctctag ccagacaggg caggcaaata ggggtggctg gtgggatggg   120
a                                                                   121
```

<210> SEQ ID NO 6
<211> LENGTH: 121
<212> TYPE: DNA
<213> ORGANISM: Homo sapiens

<400> SEQUENCE: 6

```
gtgccttcag aacctttgag atctgattct attttaaag cttcttagaa gagagattgc    60
aaagtgggtt gtttctctag ccagacaggg caggtaaata ggggtggctg gtgggatggg   120
a                                                                   121
```

<210> SEQ ID NO 7
<211> LENGTH: 111
<212> TYPE: DNA
<213> ORGANISM: Homo sapiens

<400> SEQUENCE: 7

```
aggtgtgtct ctcttttgtg aggggagggg tcccttctgg cctagtagag ggcctggcct    60
gcagtgagca ttcaaatcct caaggaacag ggtggggagg tgggacaaag g            111
```

<210> SEQ ID NO 8
<211> LENGTH: 111
<212> TYPE: DNA
<213> ORGANISM: Homo sapiens

<400> SEQUENCE: 8

```
aggtgtgtct ctcttttgtg aggggagggg tcccttctgg cctagtagag ggcctggcct    60
gcagtgagca ttcaaatcct cgaggaacag ggtggggagg tgggacaaag g            111
```

<210> SEQ ID NO 9
<211> LENGTH: 139
<212> TYPE: DNA
<213> ORGANISM: Homo sapiens

<400> SEQUENCE: 9

```
cctcgcctac tgtgctgttt ctaaccatca tgcttttccc tgaatctctt gagtcttttt    60
ctgctgtgga ctgaaacttg atcctgagat tcacctctag tccctctgag cagcctcctg   120
gaatactcag ctgggatgg                                                139
```

<210> SEQ ID NO 10
<211> LENGTH: 139
<212> TYPE: DNA
<213> ORGANISM: Homo sapiens

<400> SEQUENCE: 10

```
cctcgcctac tgtgctgttt ctaaccatca tgcttttccc tgaatctctt gagtcttttt    60
ctgctgtgga ctgaaacttg atcctgagat tcacctctag tccctctggg cagcctcctg   120
```

```
gaatactcag ctgggatgg                                              139
```

<210> SEQ ID NO 11
<211> LENGTH: 117
<212> TYPE: DNA
<213> ORGANISM: Homo sapiens

<400> SEQUENCE: 11

```
aattgcaatg gtgagaggtt gatggtaaaa tcaaacggaa cttgttattt tgtcattctg   60
atggactgga actgaggatt ttcaatttcc tctccaaccc aagacacttc tcactgg     117
```

<210> SEQ ID NO 12
<211> LENGTH: 117
<212> TYPE: DNA
<213> ORGANISM: Homo sapiens

<400> SEQUENCE: 12

```
aattgcaatg gtgagaggtt gatggtaaaa tcaaacggaa cttgttattt tgtcattctg   60
atggactgga actgaggatt ttcaatttcc tttccaaccc aagacacttc tcactgg     117
```

<210> SEQ ID NO 13
<211> LENGTH: 114
<212> TYPE: DNA
<213> ORGANISM: Homo sapiens

<400> SEQUENCE: 13

```
gaaatgcctt ctcaggtaat ggaaggttat ccaaatattt ttcgtaagta tttcaaatag   60
caatggctcg tctatggtta gtctcacagc cacattctca gaactgctca aacc        114
```

<210> SEQ ID NO 14
<211> LENGTH: 114
<212> TYPE: DNA
<213> ORGANISM: Homo sapiens

<400> SEQUENCE: 14

```
gaaatgcctt ctcaggtaat ggaaggttat ccaaatattt ttcgtaagta tttcaaatag   60
caatggctcg tctatggtta gtctcgcagc cacattctca gaactgctca aacc        114
```

<210> SEQ ID NO 15
<211> LENGTH: 128
<212> TYPE: DNA
<213> ORGANISM: Homo sapiens

<400> SEQUENCE: 15

```
acccaaaaca ctggaggggc ctcttctcat tttcggtaga ctgcaagtgt tagccgtcgg   60
gaccagcttc tgtctggaag ttcgtcaaat tgcagttaag tccaagtatg ccacatagca  120
gataaggg                                                          128
```

<210> SEQ ID NO 16
<211> LENGTH: 128
<212> TYPE: DNA
<213> ORGANISM: Homo sapiens

<400> SEQUENCE: 16

```
acccaaaaca ctggaggggc ctcttctcat tttcggtaga ctgcaagtgt tagccgtcgg   60
gaccagcttc tgtctggaag ttcgtcaaat tgcagttagg tccaagtatg ccacatagca  120
gataaggg                                                          128
```

```
<210> SEQ ID NO 17
<211> LENGTH: 110
<212> TYPE: DNA
<213> ORGANISM: Homo sapiens

<400> SEQUENCE: 17
gcaccagaat ttaaacaacg ctgacaataa atatgcagtc gatgatgact tcccagagct    60
ccagaagcaa ctccagcaca cagagaggcg ctgatgtgcc tgtcaggtgc              110

<210> SEQ ID NO 18
<211> LENGTH: 110
<212> TYPE: DNA
<213> ORGANISM: Homo sapiens

<400> SEQUENCE: 18
gcaccagaat ttaaacaacg ctgacaataa atatgcagtc gatgatgact tcccagagct    60
ccagaagcaa ctccagcaca cggagaggcg ctgatgtgcc tgtcaggtgc              110

<210> SEQ ID NO 19
<211> LENGTH: 116
<212> TYPE: DNA
<213> ORGANISM: Homo sapiens

<400> SEQUENCE: 19
tgactgtata ccccaggtgc acccttgggt catctctatc atagaactta tctcacagag    60
tataagagct gatttctgtg tctgcctctc acactagact tccacatcct tagtgc       116

<210> SEQ ID NO 20
<211> LENGTH: 116
<212> TYPE: DNA
<213> ORGANISM: Homo sapiens

<400> SEQUENCE: 20
tgactgtata ccccaggtgc acccttgggt catctctatc atagaactta tctcacagag    60
tataagagct gatttctgtg tctgcctgtc acactagact tccacatcct tagtgc       116

<210> SEQ ID NO 21
<211> LENGTH: 110
<212> TYPE: DNA
<213> ORGANISM: Homo sapiens

<400> SEQUENCE: 21
tgtacgtggt caccagggga cgcctggcgc tgcgagggag gccccgagcc tcgtgccccc    60
gtgaagcttc agctcccctc cccggctgtc cttgaggctc ttctcacact              110

<210> SEQ ID NO 22
<211> LENGTH: 110
<212> TYPE: DNA
<213> ORGANISM: Homo sapiens

<400> SEQUENCE: 22
tgtacgtggt caccagggga cgcctggcgc tgcgagggag gccccgagcc tcgtgccccc    60
gtgaagcttc agctcccctc cctggctgtc cttgaggctc ttctcacact              110

<210> SEQ ID NO 23
<211> LENGTH: 114
<212> TYPE: DNA
<213> ORGANISM: Homo sapiens

<400> SEQUENCE: 23
```

```
cagtggaccc tgctgcacct ttcctccct cccatcaacc tcttttgtgc ctccccctcc      60
gtgtaccacc ttctctgtca ccaaccctgg cctcacaact ctctcctttg ccac          114

<210> SEQ ID NO 24
<211> LENGTH: 114
<212> TYPE: DNA
<213> ORGANISM: Homo sapiens

<400> SEQUENCE: 24
cagtggaccc tgctgcacct ttcctccct cccatcaacc tcttttgtgc ctccccctcc      60
gtgtaccacc ttctctgtca ccaccctgg cctcacaact ctctcctttg ccac           114

<210> SEQ ID NO 25
<211> LENGTH: 110
<212> TYPE: DNA
<213> ORGANISM: Homo sapiens

<400> SEQUENCE: 25
cagtggcata gtagtccagg ggctcctcct cagcacctcc agcacttcc aggaggcagc      60 agcgcaggca gagaacccgc tggaagaatc ggcggaagtt gtcggagagg              110

<210> SEQ ID NO 26
<211> LENGTH: 110
<212> TYPE: DNA
<213> ORGANISM: Homo sapiens

<400> SEQUENCE: 26
cagtggcata gtagtccagg ggctcctcct cagcacctcc agcacttcc aggaggcagc      60 agcgcaggca gagaacccgc tggaaggatc ggcggaagtt gtcggagagg              110

<210> SEQ ID NO 27
<211> LENGTH: 129
<212> TYPE: DNA
<213> ORGANISM: Homo sapiens

<400> SEQUENCE: 27
aggtctgggg gccgctgaat gccaagctgg gaatcttaaa tgttaaggaa caaggtcata     60
caatgaatgg tgtgatgtaa aagcttggga ggtgattttct gagggtaggt gctgggttta   120
atgggagga                                                           129

<210> SEQ ID NO 28
<211> LENGTH: 129
<212> TYPE: DNA
<213> ORGANISM: Homo sapiens

<400> SEQUENCE: 28
aggtctgggg gccgctgaat gccaagctgg gaatcttaaa tgttaaggaa caaggtcata     60
caatgaatgg tgtgatgtaa aagcttggga ggtgatttt gagggtaggt gctgggttta     120
atgggagga                                                           129

<210> SEQ ID NO 29
<211> LENGTH: 107
<212> TYPE: DNA
<213> ORGANISM: Homo sapiens

<400> SEQUENCE: 29
acggttctgt cctgtagggg agaaaagtcc tcgttgttcc tctgggatgc aacatgagag     60
agcagcacac tgaggcttta tggattgccc tgccacaagt gaacagg                 107
```

<210> SEQ ID NO 30
<211> LENGTH: 107
<212> TYPE: DNA
<213> ORGANISM: Homo sapiens

<400> SEQUENCE: 30
acggttctgt cctgtagggg agaaaagtcc tcgttgttcc tctgggatgc aacatgagag    60
agcagcacac tgaggcttta tgggttgccc tgccacaagt gaacagg                107

<210> SEQ ID NO 31
<211> LENGTH: 127
<212> TYPE: DNA
<213> ORGANISM: Homo sapiens

<400> SEQUENCE: 31
gcgcagtcag atgggcgtgc tggcgtctgt cttctctctc tcctgctctc tggcttcatt    60
tttctctcct tctgtctcac cttctttcgt gtgcctgtgc acacacgt ttgggacaag    120 ggctgga                                                             127

<210> SEQ ID NO 32
<211> LENGTH: 127
<212> TYPE: DNA
<213> ORGANISM: Homo sapiens

<400> SEQUENCE: 32
gcgcagtcag atgggcgtgc tggcgtctgt cttctctctc tcctgctctc tggcttcatt    60
tttctctcct tctgtctcac cttctttcgt gtgcctgtgc atacacacgt ttgggacaag   120
ggctgga                                                             127

<210> SEQ ID NO 33
<211> LENGTH: 130
<212> TYPE: DNA
<213> ORGANISM: Homo sapiens

<400> SEQUENCE: 33
gccggacctg cgaaatccca aaatgccaaa cattcccgcc tcacatgatc ccagagagag    60
gggacccagt gttcccagct tgcagctgag gagcccgagg ttgccgtcag atcagagccc   120
cagttgcccg                                                          130

<210> SEQ ID NO 34
<211> LENGTH: 130
<212> TYPE: DNA
<213> ORGANISM: Homo sapiens

<400> SEQUENCE: 34
gccggacctg cgaaatccca aaatgccaaa cattcccgcc tcacatgatc ccagagagag    60
gggacccagt gttcccagct tgcagctgag gagcccgagt ttgccgtcag atcagagccc   120
cagttgcccg                                                          130

<210> SEQ ID NO 35
<211> LENGTH: 121
<212> TYPE: DNA
<213> ORGANISM: Homo sapiens

<400> SEQUENCE: 35
agcagcctcc ctcgactagc tcacactacg ataaggaaaa ttcatgagct ggtgtccaag    60

```
gagggctggg tgactcgtgg ctcagtcagc atcaagattc ctttcgtctt tccctctgc    120 c                                                                   121

<210> SEQ ID NO 36
<211> LENGTH: 121
<212> TYPE: DNA
<213> ORGANISM: Homo sapiens

<400> SEQUENCE: 36
agcagcctcc ctcgactagc tcacactacg ataaggaaaa ttcatgagct ggtgtccaag    60
gagggctggg tgactcgtgg ctcagtcagc gtcaagattc ctttcgtctt tccctctgc    120 c                                                                   121

<210> SEQ ID NO 37
<211> LENGTH: 138
<212> TYPE: DNA
<213> ORGANISM: Homo sapiens

<400> SEQUENCE: 37
tggcattgcc tgtaatatac atagccatgg ttttttatag gcaatttaag atgaatagct    60
tctaaactat agataagttt cattacccca ggaagctgaa ctatagctac tttacccaaa   120
atcattagaa tggtgctt                                                 138

<210> SEQ ID NO 38
<211> LENGTH: 138
<212> TYPE: DNA
<213> ORGANISM: Homo sapiens

<400> SEQUENCE: 38
tggcattgcc tgtaatatac atagccatgg ttttttatag gcaatttaag atgaatagct    60
tctaaactat agataagttt cattacccca ggaagctgaa ctatagctac tttccccaaa   120
atcattagaa tggtgctt                                                 138

<210> SEQ ID NO 39
<211> LENGTH: 136
<212> TYPE: DNA
<213> ORGANISM: Homo sapiens

<400> SEQUENCE: 39
atgaagcctt ccaccaactg cctgtatgac tcatctgggg acttctgctc tatactcaaa    60
gtggcttagt cactgccaat gtatttccat atgagggacg atgattacta aggaaatata   120
gaaacaacaa ctgatc                                                   136

<210> SEQ ID NO 40
<211> LENGTH: 136
<212> TYPE: DNA
<213> ORGANISM: Homo sapiens

<400> SEQUENCE: 40
atgaagcctt ccaccaactg cctgtatgac tcatctgggg acttctgctc tatactcaaa    60
gtggcttagt cactgccaat gtatttccat atgagggacg gtgattacta aggaaatata   120
gaaacaacaa ctgatc                                                   136

<210> SEQ ID NO 41
<211> LENGTH: 118
<212> TYPE: DNA
<213> ORGANISM: Homo sapiens
```

<400> SEQUENCE: 41
acaacagaat caggtgattg gagaaaagat cacaggccta ggcacccaag gcttgaagga    60
tgaaagaatg aaagatggac ggaacaaaat taggacctta attctttgtt cagttcag    118

<210> SEQ ID NO 42
<211> LENGTH: 118
<212> TYPE: DNA
<213> ORGANISM: Homo sapiens

<400> SEQUENCE: 42
acaacagaat caggtgattg gagaaaagat cacaggccta ggcacccaag gcttgaagga    60
tgaaagaatg aaagatggac ggaagaaaat taggacctta attctttgtt cagttcag    118

<210> SEQ ID NO 43
<211> LENGTH: 150
<212> TYPE: DNA
<213> ORGANISM: Homo sapiens

<400> SEQUENCE: 43
ttggggtaaa ttttcattgt catatgtgga atttaaatat accatcatct acaaagaatt    60
ccacagagtt aaatatctta agttaaacac ttaaaataag tgtttgcgtg atattttgat   120
gacagataaa cagagtctaa ttcccacccc                                    150

<210> SEQ ID NO 44
<211> LENGTH: 150
<212> TYPE: DNA
<213> ORGANISM: Homo sapiens

<400> SEQUENCE: 44
ttggggtaaa ttttcattgt catatgtgga atttaaatat accatcatct acaaagaatt    60
ccacagagtt aaatatctta agttaaacac ttaaaataag tgtttgcgtg atattttgat   120
gatagataaa cagagtctaa ttcccacccc                                    150

<210> SEQ ID NO 45
<211> LENGTH: 145
<212> TYPE: DNA
<213> ORGANISM: Homo sapiens

<400> SEQUENCE: 45
tgcaattcaa atcaggaagt atgaccaaaa gacagagatc tttttttggat gatccctagc    60 ctagcaatgc ctggcagcca tgcaggtgca atgtcaacct taaataatgt attgcaaact   120
cagagctgac aaacctcgat gttgc                                         145

<210> SEQ ID NO 46
<211> LENGTH: 145
<212> TYPE: DNA
<213> ORGANISM: Homo sapiens

<400> SEQUENCE: 46
tgcaattcaa atcaggaagt atgaccaaaa gacagagatc tttttttggat gatccctagc    60 ctagcaatgc ctggcagcca tgcaggtgca atgtcaacct taaataatgt attgcaaatt   120
cagagctgac aaacctcgat gttgc                                         145

<210> SEQ ID NO 47
<211> LENGTH: 124
<212> TYPE: DNA

<213> ORGANISM: Homo sapiens

<400> SEQUENCE: 47
ctgtgctctg cgaatagctg cagaagtaac ttggggaccc aaaataaagc agaatgctaa    60
tgtcaagtcc tgagaaccaa gccctgggac tctggtgcca tttcggattc tccatgagca   120
tggt                                                                124

<210> SEQ ID NO 48
<211> LENGTH: 124
<212> TYPE: DNA
<213> ORGANISM: Homo sapiens

<400> SEQUENCE: 48
ctgtgctctg cgaatagctg cagaagtaac ttggggaccc aaaataaagc agaatgctaa    60
tgtcaagtcc tgagaaccaa gccctgggac tctggtgcca ttttggattc tccatgagca   120
tggt                                                                124

<210> SEQ ID NO 49
<211> LENGTH: 118
<212> TYPE: DNA
<213> ORGANISM: Homo sapiens

<400> SEQUENCE: 49
tttttccagc caactcaagg ccaaaaaaaa tttcttaata tagttattat gcgaggggag    60
gggaagcaaa ggagcacagg tagtccacag aataagacac aagaaacctc aagctgtg    118

<210> SEQ ID NO 50
<211> LENGTH: 118
<212> TYPE: DNA
<213> ORGANISM: Homo sapiens

<400> SEQUENCE: 50
tttttccagc caactcaagg ccaaaaaaaa tttcttaata tagttattat gcgaggggag    60
gggaagcaaa ggagcacagg tagtccacag aataggacac aagaaacctc aagctgtg    118

<210> SEQ ID NO 51
<211> LENGTH: 110
<212> TYPE: DNA
<213> ORGANISM: Homo sapiens

<400> SEQUENCE: 51
tcttctcgtc ccctaagcaa acaacatccg cttgcttctg tctgtgtaac cacagtgaat    60
gggtgtgcac gcttgatggg cctctgagcc cctgttgcac aaaccagaaa               110

<210> SEQ ID NO 52
<211> LENGTH: 110
<212> TYPE: DNA
<213> ORGANISM: Homo sapiens

<400> SEQUENCE: 52
tcttctcgtc ccctaagcaa acaacatccg cttgcttctg tctgtgtaac cacagtgaat    60
gggtgtgcac gcttggtggg cctctgagcc cctgttgcac aaaccagaaa               110

<210> SEQ ID NO 53
<211> LENGTH: 110
<212> TYPE: DNA
<213> ORGANISM: Homo sapiens

<400> SEQUENCE: 53

```
cacatggggg cattaagaat cgcccaggga ggaggaggga gaacgcgtgc ttttcacatt    60
tgcatttgaa ttttcgagtt cccaggatgt gttttttgtgc tcatcgatgt             110

<210> SEQ ID NO 54
<211> LENGTH: 110
<212> TYPE: DNA
<213> ORGANISM: Homo sapiens

<400> SEQUENCE: 54
cacatggggg cattaagaat cgcccaggga ggaggaggga gaacgcgtgc ttttcacatt    60
tgcatttgaa ttttttgagtt cccaggatgt gttttttgtgc tcatcgatgt            110

<210> SEQ ID NO 55
<211> LENGTH: 128
<212> TYPE: DNA
<213> ORGANISM: Homo sapiens

<400> SEQUENCE: 55
gggctctgag gtgtgtgaaa taaaaacaaa tgtccatgtc tgtccttttta tggcattttg   60 ggactttaca tttcaaacat ttcagacatg tatcacaaca cgaaggaata acagttccag   120
ggatatct                                                            128

<210> SEQ ID NO 56
<211> LENGTH: 128
<212> TYPE: DNA
<213> ORGANISM: Homo sapiens

<400> SEQUENCE: 56
gggctctgag gtgtgtgaaa taaaaacaaa tgtccatgtc tgtccttttta tggcattttg   60 ggactttaca tttcaaacat ttcagacatg tatcacaaca cgagggaata acagttccag   120
ggatatct                                                            128

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cacatgcaca gccagcaacc c                                              21

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ccccaaggtc ctgtgacctg agt                                            23

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 59
tgaggaagtg aggctcagag ggt                                          23

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tgccagtgcg agatgaaagt cttt                                         24

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gtgccttcag aacctttgag atctgat                                      27

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tcccatccca ccagccaccc                                              20

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
aggtgtgtct ctcttttgtg agggg                                        25

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cctttgtccc acctccccac c                                            21

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 65
cctcgcctac tgtgctgttt ctaacc                                      26

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ccatcccagc tgagtattcc aggag                                       25

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
aattgcaatg gtgagaggtt gatggt                                      26

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ccagtgagaa gtgtcttggg ttgg                                        24

<210> SEQ ID NO 69
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69 gaaatgccett ctcaggtaat ggaaggt                                    27

<210> SEQ ID NO 70
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ggtttgagca gttctgagaa tgtggct                                     27

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
acccaaaaca ctggaggggc ct                                          22

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cccttatctg ctatgtggca tacttgg                                     27

<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gcaccagaat ttaaacaacg ctgacaa                                     27

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gcacctgaca ggcacatcag cg                                          22

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tgactgtata ccccaggtgc accc                                        24

<210> SEQ ID NO 76
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gcactaagga tgtggaagtc tagtgtg                                     27

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tgtacgtggt caccagggga cg                                            22

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
agtgtgagaa gagcctcaag gacagc                                        26

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cagtggaccc tgctgcacct t                                             21

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gtggcaaagg agagagttgt gagg                                          24

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
cagtggcata gtagtccagg ggct                                          24

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cctctccgac aacttccgcc g                                             21

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
aggtctgggg gccgctgaat                                               20

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tcctcccatt aaacccagca cct                                             23

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
acggttctgt cctgtagggg aga                                             23

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cctgttcact tgtggcaggg ca                                              22

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gcgcagtcag atgggcgtgc                                                 20

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
tccagccctt gtcccaaacg tgt                                             23

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gccggacctg cgaaatccca a                                               21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
cgggcaactg gggctctgat c                                              21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
agcagcctcc ctcgactagc t                                              21

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ggcagagggg aaagacgaaa gga                                            23

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
tggcattgcc tgtaatatac atag                                           24

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
aagcaccatt ctaatgattt tgg                                            23

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
atgaagcctt ccaccaactg                                                20

```
<210> SEQ ID NO 96
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gatcagttgt tgtttctata tttcctt                                           27

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
acaacagaat caggtgattg ga                                                22

<210> SEQ ID NO 98
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ctgaactgaa caaagaatta aggtc                                             25

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
ttggggtaaa ttttcattgt ca                                                22

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ggggtgggaa ttagactctg                                                   20

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tgcaattcaa atcaggaagt atg                                               23

<210> SEQ ID NO 102
```

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gcaacatcga ggtttgtcag                                                   20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ctgtgctctg cgaatagctg                                                   20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
accatgctca tggagaatcc                                                   20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
tttttccagc caactcaagg                                                   20

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
cacagcttga ggtttcttgt g                                                 21

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
tcttctcgtc ccctaagcaa                                                   20

<210> SEQ ID NO 108
<211> LENGTH: 20
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
tttctggttt gtgcaacagg                                              20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
cacatggggg cattaagaat                                              20

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
acatcgatga gcacaaaaac ac                                           22

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gggctctgag gtgtgtgaaa                                              20

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
agatatccct ggaactgtta ttcc                                         24

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
acagtaactg ccttcataga tag                                          23

<210> SEQ ID NO 114
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 114
gtgtcagacc ctgttctaag ta                                              22

<210> SEQ ID NO 115
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
aaataaaatt aggcatattt acaagc                                          26

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
gctgagtgat ttgtctgtaa ttg                                             23

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
cctgttcctc ccttatttcc c                                               21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gggaacacag actccatggt g                                               21

<210> SEQ ID NO 119
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
cttagggaac cctcactgaa tg                                              22

<210> SEQ ID NO 120
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 120
gtccttgtca gcgtttattt gc                                                  22

<210> SEQ ID NO 121
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
aataatcagt atgtgacttg gattga                                              26

<210> SEQ ID NO 122
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
ataggatgga tggatagatg ga                                                  22

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
cagagcaaga ccctgtctca t                                                   21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
tcaacagagg cttgcatgta t                                                   21

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gggtgatttt cctctttggt                                                     20

<210> SEQ ID NO 126
<211> LENGTH: 33
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 126
aacatttgta tctttatctg tatccttatt tat                                    33

<210> SEQ ID NO 127
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gaacacttgt catagtttag aacgaac                                           27

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
tcattgacag aattgcacca                                                   20

<210> SEQ ID NO 129
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
tttgtatttc atgtgtacat tcgtatc                                           27

<210> SEQ ID NO 130
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
acctatcctg tagattattt tcactgtg                                          28

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
tctgacccat ctaacgccta                                                   20

<210> SEQ ID NO 132
<211> LENGTH: 27
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 132
cagacagaaa gatagataga tgattga                                          27

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
atacagacag acagacaggt g                                                21

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gcatgtatct atcatccatc tct                                              23

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
tgagtgacaa attgagacct t                                                21

<210> SEQ ID NO 136
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
gtcttacaat aacagttgct actatt                                           26

<210> SEQ ID NO 137
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
attccccaag tgaattgc                                                    18

<210> SEQ ID NO 138
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
ggtagataga ctggatagat agacga                                               26

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
tggaaacaga aatggcttgg                                                      20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gattgcagga gggaaggaag                                                      20

<210> SEQ ID NO 141
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
gagcaagaca ccatctcaag aa                                                   22

<210> SEQ ID NO 142
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
gaaattttac atttatgttt atgattctct                                           30

<210> SEQ ID NO 143
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
ggcgactgag caagactc                                                        18

<210> SEQ ID NO 144
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 144
ggttattaat tgagaaaact ccttaca                                          27

<210> SEQ ID NO 145
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
attttccccg atgatagtag tct                                              23

<210> SEQ ID NO 146
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
gcgaatgtat gattggcaat attttt                                           26

<210> SEQ ID NO 147
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
acatgtatcc cagaacttaa agtaaac                                          27

<210> SEQ ID NO 148
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
gcagaaggga aaattgaagc tg                                               22

<210> SEQ ID NO 149
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
cagagacacc gaaccaataa ga                                               22

<210> SEQ ID NO 150
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
```
gccacatgaa tcaattccta taataaa                                    27

<210> SEQ ID NO 151
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
gcacatgtac cctaaaactt aaaat                                      25

<210> SEQ ID NO 152
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
gtcaaccaaa actcaacaag tagtaa                                     26

<210> SEQ ID NO 153
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
aagatgaaat tgccatgtaa aaata                                      25

<210> SEQ ID NO 154
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
gtgtgtataa caaaattcct atgatgg                                    27

<210> SEQ ID NO 155
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
gcacccaaaa ctgaatgtca ta                                         22

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156

```
ggtgagagtg agaccctgtc                                        20
```

<210> SEQ ID NO 157
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157

```
tgtaataact ctacgactgt ctgtctg                                27
```

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158

```
gaataggagg tggatggatg g                                      21
```

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159

```
gagcgagacc ctgtctcaag                                        20
```

<210> SEQ ID NO 160
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160

```
ggaaaagaca taggatagca attt                                   24
```

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161

```
tctggattga tctgtctgtc c                                      21
```

<210> SEQ ID NO 162
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162

```
gaattaaata ccatctgagc actgaa                                 26
```

<210> SEQ ID NO 163
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
tgttataatg cattgagttt tattctg                                   27

<210> SEQ ID NO 164
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
gcctgtctca aaataaaga gatagaca                                   28

<210> SEQ ID NO 165
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
ttaatgaatt gaacaaatga gtgag                                     25

<210> SEQ ID NO 166
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
gcaactctgg ttgtattgtc ttcat                                     25

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
caaagcgaga ctctgtctca a                                         21

<210> SEQ ID NO 168
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
gaaaatgcta tcctctttgg tataaat                                   27

<210> SEQ ID NO 169
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
gggtatttca agataactgt agatagg                                       27

<210> SEQ ID NO 170
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
gcttctgaaa gcttctagtt tacc                                          24

<210> SEQ ID NO 171
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
tccacatcct caccaacac                                                19

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
gcctaggaag gctactgtca a                                             21

<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
ccacccgtcc atttaggc                                                 18

<210> SEQ ID NO 174
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
gtgaaaaagt agatataatg gttggtg                                       27

-continued

<210> SEQ ID NO 175
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
ggttttccaa gagatagacc aatta                                         25

<210> SEQ ID NO 176
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
gtcctctcat aaatccctac tcatatc                                       27

<210> SEQ ID NO 177
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
ctgttggtac ataataggta ggtaggt                                       27

<210> SEQ ID NO 178
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
gtcgtgggcc ccataaatc                                                19

<210> SEQ ID NO 179
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
aaggtacata acagttcaat agaaagc                                       27

<210> SEQ ID NO 180
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
gtgaaatgac tgaaaaatag taacca                                        26

<210> SEQ ID NO 181

-continued

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
ctaggagatc atgtgggtat gatt                                                24

<210> SEQ ID NO 182
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
gcagtgaata aatgaacgaa tgga                                                24

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
cccaaaatta cttgagccaa t                                                   21

<210> SEQ ID NO 184
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
gagacaaaat gaagaaacag acag                                                24

<210> SEQ ID NO 185
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
tctttgctct catgaataga tcagt                                               25

<210> SEQ ID NO 186
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
gtttgtgata atgaacccac tcag                                                24

<210> SEQ ID NO 187
<211> LENGTH: 27
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
tgaacacaga tgttaagtgt gtatatg                                           27

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
gtctgaggtg gacagttatg aaa                                               23

<210> SEQ ID NO 189
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
ctgtggctca tctatgaaaa ctt                                               23

<210> SEQ ID NO 190
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
gaagtggctg tggtgttatg at                                                22

<210> SEQ ID NO 191
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
ttctgttggt atagagcagt gttt                                              24

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
gtgacaggaa ggacggaatg                                                   20

<210> SEQ ID NO 193
<211> LENGTH: 27
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 193
catgaggttt gcaaatacta tcttaac                                          27

<210> SEQ ID NO 194
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
gttttaattt tctccaaatc tcca                                             24

<210> SEQ ID NO 195
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
tcttagccta gatagatact tgcttcc                                          27

<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
gtcaaccttt gaggctatag gaa                                              23

<210> SEQ ID NO 197
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
tcctggaaac aaaagtatt                                                   19

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
aaccttacaa caaagctaga a                                                21

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
actaagcctt ggggatccag                                           20

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
tgctgtggaa atactaaaag g                                         21

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
ctccagaggt aatcctgtga                                           20

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
tggtgtgaga tggtatctag g                                         21

<210> SEQ ID NO 203
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
gtataatcca tgaatcttgt tt                                        22

<210> SEQ ID NO 204
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
ttcaaattgt atataagaga gt                                        22

<210> SEQ ID NO 205
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 205
gcaggaaagt tatttttaat                                                  20

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
tgcttgagaa agctaacact t                                                21

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
cagtgtttgg aaattgtctg                                                  20

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
ggcactggga gattattgta                                                  20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
tcctgttgtt aagtacacat                                                  20

<210> SEQ ID NO 210
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
gggccgtaat tacttttg                                                    18

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 211
actcagtagg cactttgtgt c                                              21

<210> SEQ ID NO 212
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
tcttccacca caccaatc                                                  18

<210> SEQ ID NO 213
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
tggcttttca aggtaaaa                                                  19

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
gcaacgttaa catctgaatt t                                              21

<210> SEQ ID NO 215

<400> SEQUENCE: 215

000

<210> SEQ ID NO 216
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
attttatatg tcatgatcta ag                                             22

<210> SEQ ID NO 217
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
agagattaca ggtgtgagc                                                 19

```
<210> SEQ ID NO 218
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
atgatcctca actgcctct                                                19

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
tgaaactcaa aagagaaaag                                               20

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
acagatttct acttaaaatt                                               20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
tgaaactcaa aagagaaaag                                               20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
acagatttct acttaaaatt                                               20

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
gcaaaggggt actctatgta                                               20

<210> SEQ ID NO 224
```

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
tatcgggtca tcttgttaaa                                                   20

<210> SEQ ID NO 225
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
tctaacaaag ctctgtccaa aa                                                22

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
ccacactgaa taactggaac a                                                 21

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
gcaagcaagc tctctacctt c                                                 21

<210> SEQ ID NO 228
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
tgttcttcca aaattcacat gc                                                22

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
atttcactat tccttcattt t                                                 21

<210> SEQ ID NO 230
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
taattgttgc acactaaatt ac                                          22

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
aaaaagccac agaaatcagt c                                           21

<210> SEQ ID NO 232
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
ttcttatatc tcactgggca tt                                          22

<210> SEQ ID NO 233
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
ggatggtaga agagaagaaa gg                                          22

<210> SEQ ID NO 234
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
ggatggtaga agagaagaaa gg                                          22

<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
tgcaaagatg cagaaccaac                                             20

<210> SEQ ID NO 236
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 236
ttttgttcct tgtcctggct ga                                              22

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
tgcaaagatg cagaaccaac                                                 20

<210> SEQ ID NO 238
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
gcctccagct ctatccaagt t                                               21

<210> SEQ ID NO 239
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
ccttaatatc ttcccatgtc ca                                              22

<210> SEQ ID NO 240
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
attgttagtg cctcttctgc tt                                              22

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
gagaagtgag gtcagcagct                                                 20

<210> SEQ ID NO 242
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 242
tttctaaatt tccattgaac ag                                              22

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
gaaattggca atctgattct                                                 20

<210> SEQ ID NO 244
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
caacttgtcc tttattgatg t                                               21

<210> SEQ ID NO 245
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
ctatgttgat aaaacattga aa                                              22

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
gcctgtctgg aatatagttt                                                 20

<210> SEQ ID NO 247
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
cagggcatat aatctaagct gt                                              22

<210> SEQ ID NO 248
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 248
caatgactct gagttgagca c                                              21

<210> SEQ ID NO 249
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
actctctccc tcccctct                                                  18

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
tatggcccca aaactattct                                                20

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
acaagtactg ggcagattga                                                20

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
gccaggttta gctttcaagt                                                20

<210> SEQ ID NO 253
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
ttttatatca ggagaaacac tg                                             22

<210> SEQ ID NO 254
<211> LENGTH: 21
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 254
ccagaatttt ggaggtttaa t                                              21

<210> SEQ ID NO 255
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
tgtcattcct cctttatctc ca                                             22

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
ttcttttgcc tctcccaaag                                                20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
accctggcac agtgttgact                                                20

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
tgggcctgag ttgagaagat                                                20

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
aatttgtaag tatgtgcaac g                                              21

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 260
tttttcccat ttccaactct                                              20

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
aaaagatgag acaggcaggt                                              20

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
acccctgtga atctcaaaat                                              20

<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
gcacttgctt ctattgtttg t                                            21

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
cccttcctct cttccattct                                              20

<210> SEQ ID NO 265
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
agcactgcag gta                                                     13

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 266
acagatacca aagaactgca a    21

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
tggacacctt tcaacttaga    20

<210> SEQ ID NO 268
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
gaacagtaat gttgaacttt tt    22

<210> SEQ ID NO 269
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
tcttgcaaaa agcttagcac a    21

<210> SEQ ID NO 270
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
aaaaagatct caaagggtcc a    21

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
gcttttgctg aacatcaagt    20

<210> SEQ ID NO 272
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
ccttccagca gcatagtct                                                19

<210> SEQ ID NO 273
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
aaatccagga tgtgcagt                                                 18

<210> SEQ ID NO 274
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
atgatgaggt cagtggtgt                                                19

<210> SEQ ID NO 275
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
catcacagat catagtaaat gg                                            22

<210> SEQ ID NO 276
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
aattattatt ttgcaggcaa t                                             21

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
catgaggcaa acacctttcc                                               20

<210> SEQ ID NO 278
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278

```
gctggactca ggataaagaa ca                                              22

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
tggaagcctg agctgactaa                                                 20

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
ccttcttttc ccccagaatc                                                 20

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
taggagaaca gaagatcaga g                                               21

<210> SEQ ID NO 282
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
aaagactatt gctaaatgct tg                                              22

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
taagcgtagg gctgtgtgtg                                                 20

<210> SEQ ID NO 284
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
ggacggatag actccagaag g                                               21
```

<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
gaatgacctt ggcactttta tca                                             23

<210> SEQ ID NO 286
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
aaggatagag atatacagat gaatgga                                         27

<210> SEQ ID NO 287
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
catgcaccgc gcaaatac                                                   18

<210> SEQ ID NO 288
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
atgcctcacc cacaaacac                                                  19

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
tccaagccct tctcactcac                                                 20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
ctgggacggt gacattttct                                                 20

```
<210> SEQ ID NO 291
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
cccaggaaga gtggaaagat t                                              21

<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 292
ttagcttgca tgtacctgtg t                                              21

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
agctagatgg ggtgaatttt                                                20

<210> SEQ ID NO 294
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
tgggctgagg ggagattc                                                  18

<210> SEQ ID NO 295
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
atcaagctaa ttaatgttat ct                                             22

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
aatgaataag gtcctcagag                                                20
```

```
<210> SEQ ID NO 297
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
tttaatctga tcattgccct a                                              21

<210> SEQ ID NO 298
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
agctgtgggt gaccttga                                                  18

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
tgtcccacca ttgtgtatta                                                20

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
tcagacttga agtccaggat                                                20

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
gcttcagggg tgttagtttt                                                20

<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
ctttgtgaaa agtcgtccag                                                20

<210> SEQ ID NO 303
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
ccatcatgga aagcatgg                                                  18

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
tcatctccat gactgcacta                                                20

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
gagatgacgg agtagctcat                                                20

<210> SEQ ID NO 306
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
cccagctgca ctgtctac                                                  18

<210> SEQ ID NO 307
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
tcttgttcca atcacaggac                                                20

<210> SEQ ID NO 308
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
atgctgttag ctgaagctct                                                20

<210> SEQ ID NO 309
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
tgaaagctcc taaagcagag                                                 20

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
ttgaagagat gtgctatcat                                                 20

<210> SEQ ID NO 311
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
gccgcctgca gcccgcgccc cccgtgcccc cgccccgccg ccggcccggg cgcc          54

<210> SEQ ID NO 312
<211> LENGTH: 601
<212> TYPE: DNA
<213> ORGANISM: Homo sapiens

<400> SEQUENCE: 312
catagtgaca ggtatatgcc caactaactg tggaaaacag ttctttcttt caaccttact     60
catcaccctc acggtctgtt tatgaggctc tcctccacca gccagaaagg atgacgtgcc    120
atacctgcaa aacttataca gcatcaacag aatgaatctt tccaacaagc cgaaacattg    180
agtattgtgg cacagaatat gccccaccca ttactcaatc tagatatcct tttattccac    240
cgtctcatga ttttcttttt cctggaaaac aaaagtattt cttttcatagc ccagctagca    300 ygataaatca gcgagtcaga attctagctt tgttgtaagg ttttgcgaat atctgatcct    360
cttattttgt acttttctat ttcctaggca aatctgagta tttcacccag ttttccttaa    420
ctaggcattg aaaactcagt ttttttctta caaaccttca tgtcttcctg ctcatttgca    480
cagtcttatc ttgcacctcc tataaaatgg agaaacttga cattaaaacg taattttttat   540 tacattttga gggattccca gagaattttt ccccaatctc cttaggtagg gacttcttta    600
c                                                                   601

<210> SEQ ID NO 313
<211> LENGTH: 601
<212> TYPE: DNA
<213> ORGANISM: Homo sapiens

<400> SEQUENCE: 313
gtgggaacta tagtaaagaa gtccctacct aaggagattg gggaaaaatt ctctgggaat     60
ccctcaaaat gtaataaaaa ttacgtttta atgtcaagtt tctccatttt ataggaggtg    120
caagataaga ctgtgcaaat gagcaggaag acatgaaggt ttgtaagaaa aaaactgagt    180
```

```
tttcaatgcc tagttaagga aaactgggtg aaatactcag atttgcctag gaaatagaaa    240
agtacaaaat aagaggatca gatattcgca aaaccttaca acaaagctag aattctgact    300
ygctgattta tcgtgctagc tgggctatga agaaatact tttgttttcc aggaaaaaga    360
aaatcatgag acgtggaat aaaaggatat ctagattgag taatgggtgg gcatattct      420 gtgccacaat actcaatgtt tcggcttgtt ggaaagattc attctgttga tgctgtataa    480
gttttgcagg tatggcacgt catcctttct ggctggtgga ggagagcctc ataaacagac    540
cgtgagggtg atgagtaagg ttgaaagaaa gaactgtttt ccacagttag ttgggcatat    600
a                                                                    601
```

<210> SEQ ID NO 314
<211> LENGTH: 650
<212> TYPE: DNA
<213> ORGANISM: Homo sapiens

<400> SEQUENCE: 314

```
tttattggtc ctgactggta caaatactga taaaaggat tttaagatca tattcatact     60
tttggggaat gagagccaca attaattaac aatgtctgcc atgagattgg atgcaagagt   120
atggcactca tactattcct acttctgtct aattcacta tttgtttctg tgtgcaaaaa    180
tctttggtag gtggtggatg tgcccaagac acagggaaga aaagaagta aacagggaag    240 tacaacacag actctgaaat ggggcatcat ggaagacgga gctttgtcgt cttggtcttt    300
gctgtatatt cacttcctac aacagtgcta aataccttgt ggatgcttaa atatattaaa    360
tgaatgcata aatgaaaaga gtaaataaag agtgtatatg aaagtatgta gataaaattc    420
ttcactaagc cttggggatc cagctgcttm aggactaaga ccgtatctag ctccttttag    480
tatttccaca gcatgccatg gagatacatg tttctgatta tatatgatac atggaaatta    540
tatgttgttg aatgagtgat tgagtaaatg tgtactaggg cagctaatca taaatatttc    600
tactattgct aaaatgactg gatttatcca ttccttctga gagtttatac                650
```

<210> SEQ ID NO 315
<211> LENGTH: 626
<212> TYPE: DNA
<213> ORGANISM: Homo sapiens

<400> SEQUENCE: 315

```
ctgcttaagg actaagaccr tatctagctc cttttagtat ttccacagca tgccatggag    60
atacatgttt ctgattatat atgatacatg gaaattatat gttgttgaat gagtgattga   120
gtaaatgtgt actagggcag ctaatcataa atatttctac tattgctaaa atgactggat    180
ttatccattc cttctgagag tttatactga ttgcttatat tgtatcaaat accgtaactg    240
agggcaatgt ttactcaaac taatagcacc attcaaattt atgcaaacaa taacactata    300
tctttaaaat gttttcacta aaagctgcat aaagagtgta ttcaacaaca atagaataat    360
tttacaatct ttttctcttgc ttaatggcca tttgtgcctt ctgacatgct gctagccatt    420
caaaggtcac actaccttga agttgaagat caagacaaat gattagactc ataaagaca     480 aatcacgtct ttctgacag gtgattatta ataattaatt agcatttaaa catgtattat    540
ttaagttctt tttaagttat aaagtctttg atttgctaaa cagtttaaat aatgaataaa    600
acataaaata ataatagtta ccattt                                        626
```

<210> SEQ ID NO 316

```
<211> LENGTH: 1113
<212> TYPE: DNA
<213> ORGANISM: Homo sapiens

<400> SEQUENCE: 316
caagagctgc atctcactcc aattttcctt ctccctataa ccttatctag attcccagtt      60
gagggaaccg atgacctaat tcctctcagt ttaaatgcaa cacaggagca aattccaaat     120
atctatgctg gtcttgctgg gattgcagaa ccccagggtg ttatcctcc tccagaggta      180
atcctgtgat cagcactaac rccacatacc agcccttta tcagcttgtt ggagaagcat      240
ctttacttcc caccaagcag tgacctagat accatctcac accagttaga atcaggatca     300
ttaaaaagtc aagaaaaaac agatgctgaa gaggatgtgg agaaatagga atgcttttac     360
actgttagtg ggaatgtaaa ttagttcaac cattgtcaaa acagtgtgg cgatccctca      420
cagatctaga accagaaata ccatttgacc cagcaatccc attactgggt ctataccca      480
aggattataa attactctac tataaagaca catgcacaca tatgtttatt gcagcaccat     540
tcacaatagc aaagaattgc aaccaaccct aatgcccatc aatgacagac tggataaaga     600
aaatctggca catatacacc atggaatact acgcagccat aaaaaaggat gagtttatgt     660
cctttacagg gacatggatg aagctggaaa ccatcattct cagcaaacta acacaggaac     720
agaaaaccaa acacatgttc tcactcacaa gtgggagttg aacaatgaga acacatggac     780
acagggaggg gaacatcaca caccactgct tgtcagggg tggggggcta ggggaaggat       840
agcattagga gaaataccta atgtagatga agggttgatg ggtgcagcaa accaccatgg     900
catgtgtata cctgtgtaac aaacctccat gttctgcacg tgtatcccag aacttaaagt     960
acaatacaaa aaaaaaaaaa agtgtaatcc agtttacatt ttcaaggtca aagtgggtac    1020
aatgctatct atcttgggct aagaagagaa aaggaaaaat tcttgcttta aatcttagaa    1080
gtctggtttt tttccctgtt ttgtacccca tcc                                  1113

<210> SEQ ID NO 317
<211> LENGTH: 1113
<212> TYPE: DNA
<213> ORGANISM: Homo sapiens

<400> SEQUENCE: 317
ttcccagttg agggaaccga tgacctaatt cctctcagtt taaatgcaac acaggagcaa      60
attccaaata tctatgctgg tcttgctggg attgcagaac cccagggtgg ttatcctcct     120
ccagaggtaa tcctgtgatc agcactaacg ccacatacca gccctttcat cagcttgttg     180
gagaagcatc tttacttccc rccaagcagt gacctagata ccatctcaca ccagttagaa     240
tcaggatcat taaaaagtca agaaaaaaca gatgctgaag aggatgtgga gaaataggaa     300
tgcttttaca ctgttagtgg gaatgtaaat tagttcaacc attgtcaaag acagtgtggc     360
gatccctcac agatctagaa ccagaaatac catttgaccc agcaatccca ttactgggtc     420
tatacccaaa ggattataaa ttactctact ataaagacac atgcacacat atgtttattg     480
cagcaccatt cacaatagca aagaattgca accaacccta atgcccatca atgacagact     540
ggataaagaa atctggcaca tatacacca tggaatacta cgcagccata aaaaaggatg      600
agtttatgtc ctttacaggg acatggatga agctggaaac catcattctc agcaaactaa     660
cacaggaaca gaaaaccaaa cacatgttct cactcacaag tgggagttga acaatgaaa      720
cacatggaca cagggagggg aacatcacac accactgctt gtcagggggt gggggctag      780
gggaaggata gcattaggag aaatacctaa tgtagatgaa gggttgatgg gtgcagcaaa     840
```

| | |
|---|---|
| ccaccatggc atgtgtatac ctgtgtaaca aacctccatg ttctgcacgt gtatcccaga | 900 |
| acttaaagta caatacaaaa aaaaaaaaaa gtgtaatcca gtttacatttt tcaaggtcaa | 960 |
| agtgggtaca atgctatcta tcttgggcta agaagagaaa aggaaaaatt cttgctttaa | 1020 |
| atcttagaag tctggttttt ttccctgttt tgtaccccat cctcttggtc tctctagata | 1080 |
| tatttaagac tcacatagga cttgtctttt cta | 1113 |

<210> SEQ ID NO 318
<211> LENGTH: 1001
<212> TYPE: DNA
<213> ORGANISM: Homo sapiens

<400> SEQUENCE: 318

| | |
|---|---|
| tcatcaacta aatagttgat gaggggaaat tgttctgtat atgttcatac ttcagctaat | 60 |
| caattaaaaa tgatgaaata ataagattac cattttgcaa acccctaatg caatgttgga | 120 |
| tccaggcaat gatcatcaat ggccactaaa atcacacaaa aggagataac cagaatatgt | 180 |
| gctttgtgat ggaagcatta aatacaacta atgagatatt gtttataaga aagaaaggaa | 240 |
| gcaagaaagc aatcacacca agctctgtat ctagctacca catttaagga aaaaagaga | 300 |
| cagaagagca tgttaaatgt taccaagaag atacagtcag tcggaaaaaa tacagacaag | 360 |
| aaaatacaga gcaaacaac ccagcttctt cagcaaatca atataaaaaa attttaagaa | 420 |
| agagttaaag tataaactga gagacttcag aaacatatta tccaagtata atccatgaat | 480 |
| cttgtttaaa tatagatcaa rtaaaccact ataccaaaaa catcaaaaga caactgggta | 540 |
| aatttttttaa atgactagct atttgatgtt aaggaagtaa tgttactctc ttatatacaa | 600 |
| tttgaaataa tctagcgagg agcagcaaat gtgcggctat gaggaagaaa cacaattggc | 660 |
| cattcttgaa tcattagctg gatggtggct atatgggggt agattttact actctctaat | 720 |
| tttacatata tttaaaatgt tccataataa attgttgagt tatcaaaaga aatatttcta | 780 |
| tataatagct aaaattattt ataaaagtta gtggtctcat aactttattt atttatttac | 840 |
| ttattttgag accgagtctc cctctgttat gcaggctgga gtgcagtggc tccatctcgg | 900 |
| ctcactgcaa acttcacctc ctggattgaa gcgattctcc tgcctcagcc cccccgagta | 960 |
| gctgggatta caggcttgca ccccacgcc cagctaatttt t | 1001 |

<210> SEQ ID NO 319
<211> LENGTH: 601
<212> TYPE: DNA
<213> ORGANISM: Homo sapiens

<400> SEQUENCE: 319

| | |
|---|---|
| agctaccaca tttaaggaaa aaagagaca gaagagcatg ttaaatgtta ccaagaagat | 60 |
| acagtcagtc ggaaaaaata cagacaagaa atacagagc aaacaaccc agcttcttca | 120 |
| gcaaatcaat ataaaaaaat tttaagaaag agttaaagta taaactgaga gacttcagaa | 180 |
| acatattatc caagtataat ccatgaatct tgtttaaata tagatcaaat aaaccactat | 240 |
| accaaaaaca tcaaaagaca actgggtaaa tttttttaaat gactagctat ttgatgttaa | 300 |
| rgaagtaatg ttactctctt atatacaatt tgaaataatc tagcgaggag cagcaaatgt | 360 |
| gcggctatga ggaagaaaca caattggcca ttcttgaatc attagctgga tggtggctat | 420 |
| atgggggtag attttactac tctctaattt tacatatatt taaaatgttc cataataaat | 480 |
| tgttgagtta tcaaaagaaa tatttctata taatagctaa aattatttat aaaagttagt | 540 |

```
ggtctcataa ctttatttat ttatttactt attttgagac cgagtctccc tctgttatgc    600
a                                                                    601

<210> SEQ ID NO 320
<211> LENGTH: 601
<212> TYPE: DNA
<213> ORGANISM: Homo sapiens

<400> SEQUENCE: 320
ccaactgatc taattagata aacttagtca atatatttga atcccacatt ccagcagcta     60
ttttctccat ttgcttttat tgctgtttgt ggtgagtttg atatataatt ttaaggtgtt    120
aacatcccta acttatgtat gggtacagct cataaatacg aacctgtgtc atgcaactca    180
tatatgactg tgttcaaaat aatgtgtatt agactgtaaa acgattttaa tattttaaat    240
aactttcctg catttgtcgg tttcagcagg aaagttattt ttaataactt ccctgtattt    300
sttggtttca gtattaatta atctcattaa tgctaaactt tgtgatccta ggttaaaaaa    360
catattcaag atagcttcag aatgtttggt atacaaatag gtctggctaa atataagtgt    420
tagctttctc aagcatctaa atgctggcgg gcttttaaaa aaccagggct ttaaggagaa    480
aacacctgct ctgtggtttt gtagcagata tgaagtattc aaatttctta ataaatagaa    540
aaagaaatat ataacagaaa caggttgcac ttgtctttct cattaagcag gtggttagta    600
c                                                                    601

<210> SEQ ID NO 321
<211> LENGTH: 501
<212> TYPE: DNA
<213> ORGANISM: Homo sapiens

<400> SEQUENCE: 321
agctcataaa tacgaacctg tgtcatgcaa ctcatatatg actgtgttca aaataatgtg     60
tattagactg taaaacgatt ttaatatttt aaataacttt cctgcatttg tcggtttcag    120
caggaaagtt attttaata acttccctgt atttgttggt ttcagtatta attaatctca    180
ttaatgctaa actttgtgat cctaggttaa aaaacatatt caagatagct tcagaatgtt    240
tggtatacaa rtaggtctgg ctaaatataa gtgttagctt tctcaagcat ctaaatgctg    300
gcgggctttt aaaaaccag ggctttaagg agaaaacacc tgctctgtgg ttttgtagca    360
gatatgaagt attcaaattt cttaataaat agaaaaagaa atatataaca gaaacaggtt    420
gcacttgtct ttctcattaa gcaggtggtt agtaccatta tttgcattct catagcctta    480
atatacattt tccttctcta g                                              501

<210> SEQ ID NO 322
<211> LENGTH: 601
<212> TYPE: DNA
<213> ORGANISM: Homo sapiens

<400> SEQUENCE: 322
ttttgagttt ctactttagt gtcttagtgc tttctcgata tgggagaatt catgtcctcc     60
attcagaagt atgcactaag taagaggtat catgtctggt tcttgattag gtactaatct    120
tgaaatatta tcctacaata ggttagagca cgtatatctc ctgataatat attgaatatg    180
atagatttaa ataattggtt aactaaatac taaagcaaat tgctgcacgt atcatttatt    240
attcattgtg tagaaagtgc ctgactcagt gtttggaaat tgtctgactt ttcctcatat    300
rtagtgtggt ttcatgttat tgtatataag acctgacatg aactctgttt acaataatct    360
```

```
cccagtgcca taaagaccat aataaataat ataaccaatt ggtttcttta tgctgtcatt    420
tattagggca tatggcatta gtggaggatt accttgtatt acccatagtg cttagagtat    480
gaatcacaca tgcaccttga aggaaaagag gtgcaatgta ataagaaacc agatattgaa    540
aatgcaagtt ttgttatgtt attctgggta tgttaacctt tattcctgcc ctccatatgc    600
a                                                                   601
```

<210> SEQ ID NO 323
<211> LENGTH: 501
<212> TYPE: DNA
<213> ORGANISM: Homo sapiens

<400> SEQUENCE: 323

```
aagaggtatc atgtctggtt cttgattagg tactaatctt gaaatactat cctacagtag     60
gttagagcac gtatatctcc tgataatata ttgaatatga tagatttaaa taattggtta    120
actaaatact aaagcaaatt gctgcacgta tcatttatta ttcattgtgt agaaagtgcc    180
tgactcagtg tttggaaatt gtctgacttt tcctcatata tagtgtggtt tcatgttatt    240
gtatataaga mctgacatga accctgttta caataatctc ccagtgccat aaagaccata    300
ataaataata taaccaattg gtttctttat gctgtcattt attagggcat atggcattag    360
tggaggatta ccttgtatta cccatagtgc ttagagtatg aatcacacat gcaccttgaa    420
ggaaaagagg tgcaatgtaa taagaaacca gatattgaaa atgcaagttt tgttatgtta    480
ttctgggtat gttaaccttt a                                              501
```

<210> SEQ ID NO 324
<211> LENGTH: 854
<212> TYPE: DNA
<213> ORGANISM: Homo sapiens

<400> SEQUENCE: 324

```
tttcagcact gagagccaga gtggaattgt ctccttcatt gccactgcct tcacgttttg     60
tgtgtcgtat ctgttttgtg atcactgaga cccaagaacc cccgacttgc cgacatacta    120
tgtggccccg agagaggact tgagctctct gggtttcatc attaccatca attaaataaa    180
caggacagta gcttcttcct tggattgtta atttaaggct ctggataata catgtaaccg    240
ccttatgata gagcagaatt gtaagtaggc tcatggtaga atcgttcaat gacatttccc    300
tttcctttgg gagaaacaga aattcacagg tctaattctt ttcctattaa tagttcctgr    360
ccattattcc agaactgtcc taaaggaatt ctttctcctt aaggacacca cctcccagga    420
gggtatttaa agatttgcac aggccgggca cggtggctca tgcttgtaat cccagcagtt    480
tgggaggcca aggcgggtgg atcacttgtg tcaggggtt caagaccggc ctggccaaca    540
tggtgaaacc ctatctctac taaaaacaca aaagttagct gggcctggct atgcatgcct    600
gtaattccag ctactcggga ggctgaggct ggagaatagc ttgaaccagg aggtggaga    660 taacagtgag ctgagatgcc actatgacac tccagcctgg gtgacagagc aagactctct    720
ctcaaaaaaa aaaaaagatt tttatagtcc agtattcaac gttcatagta cacctttctt    780
atcctagtaa atcttctttt atcaaggtat atgatcccat atagtagtta actcttactc    840
ttactttatg acaa                                                      854
```

<210> SEQ ID NO 325
<211> LENGTH: 501
<212> TYPE: DNA

<213> ORGANISM: Homo sapiens

<400> SEQUENCE: 325

```
aaatacttac tattaaatat gagaaactgt ggtgtttatc ggtaagatcc acgaaggaag      60
aagtttttaaa gaaaaatact ttaaccgtgg aaaaaaaaaa ctttaatgtc tattatcgaa     120
taggggccgt aattactttt gcaaaataaa aaaacaaaca agactagcta tagtgtaaat     180
gtaatctgta tgcttttttaa tgaaacaatt aagtaggttg cccatttaca attagcctga     240
ttttctcctg ytgtggtatta tgtgtactta acaacaggac ccagtggaaa ttcactcatt     300
taacaaagtc tgcctacatg gtttcaaata tgggcctaac ttgaaaattc agtcataatt     360
aaatctaagg actaaaacaa atctgtataa aaagattctg ctaaataagg gaaaattcaa     420
gtctagggct acattctgaa agatattgaa gtagaacctc tgcagcaaga ctaggcttgg    480
aaagtgcggg gaggagggaa a                                               501
```

<210> SEQ ID NO 326
<211> LENGTH: 601
<212> TYPE: DNA
<213> ORGANISM: Homo sapiens

<400> SEQUENCE: 326

```
ccacatcaga aacatgagga aattctacat ggtaaaaaca gcaacaacca aaaaatactt      60
aaagtcaaca aaccaggaaa agacatctct gaatatagga atgccaaacc tttaacacaa    120
taaaacacag attatatttc agaaggctat attatatgtg tataccaaca tcaatatgtc    180
cagagtagct gcacagagtt ccatattttta gtctttataa gttcccctcc tcaccctact    240
cagtaggcac tttgtgtcta gaaacttctg tgtcaacagt tttccctctc tctggaattc    300
mtcaggacag aagtgattgg tgtggtggaa gagggttgtg ctaagagtga agttatatga    360
aagtaggatg gaggttagca agtagttaaa gtccagaaag gcaataaggt gttaaggaag    420
aacttttcca ttttacaggt ctgagcaagc aggaaatcaa ctctacaaac tttgaaactt    480
ggtaaatatg aaaacattct caataccatt tgtcatttaa taaatacaaa ttatactatt    540
ttactgcttg catctagaag tttgtcaaag atctcgtctt aattattcat tgtgtcggcg    600
a                                                                    601
```

<210> SEQ ID NO 327
<211> LENGTH: 601
<212> TYPE: DNA
<213> ORGANISM: Homo sapiens

<400> SEQUENCE: 327

```
gacgagatct ttgacaaact tctagatgca agcagtaaaa tagtataatt tgtatttatt      60
aaatgacaaa tggtattgag aatgttttca tatttaccaa gtttcaaagt ttgtagagtt    120
gatttcctgc ttgctcagac ctgtaaaatg gaaaagttct tccttaacac cttattgcct    180
ttctggactt taactacttg ctaacctcca tcctactttc atataacttc actcttagca    240
caaccctctt ccaccacacc aatcacttct gtcctgatga attccagaga gagggaaaac    300
ygttgacaca gaagtttcta gacacaaagt gcctactgag tagggtgagg aggggaactt    360
ataaagacta aatatggaa ctctgtgcag ctactctgga catattgatg ttggtataca    420
catataatat agccttctga aatataatct gtgtttatt gtgttaaagg tttggcattc    480
ctatattcag agatgtcttt tcctggtttg ttgacttttaa gtattttttg gttgttgctg    540
tttttaccat gtagaatttc ctcatgtttc tgatgtggaa agtataagaa tatcagccag    600
``` a                                                                                    601

<210> SEQ ID NO 328
<211> LENGTH: 811
<212> TYPE: DNA
<213> ORGANISM: Homo sapiens

<400> SEQUENCE: 328
taaataatct ctaattagta taatgggtgt tcttagtgca gtgggtactt ttaaagtgct      60
ttgtggcttt tgatgaaaat tgtcttagta tttaaaactt tttcttaccc aattttttgt     120
tcccatcgaa ttagcaatgc tgtaaagaaa ggcatcttat tccatttttt gttgctataa     180
aggaatactt gaggctgggt aatttataaa gatgaaaagt ttatttggct cgcaattctg     240
gatggctgga aggttaagta ctgggccaca gcatctggtg ggggcctcga gctgcttcta     300
gtcataatgg aaggtgaagg gtgtaaagat catgtgacaa gggaggaaag aagagaagga     360
aggaggtgct ggttctttct atcaaccaat tcgcaagaga actaatagag aaagaactca     420
cttagccctg tgggaacaca ttaatctatt cataagggat ctggctgtat gatacaaaca     480
cctcccatta ggccccacct ccaaattgta tcccattggg gatcaaattt caaaagaga     540 tttggaagga acaaacaaac catatctaag ccatagtaaa aggaatggct tttcaaaggt     600
aaaatttact ragtgtatta atattttacc aatttccagc caggagagta tgaatgttgc     660
attattacat tgctttgaaa caaagcatta gtcttaattc agaagtttaa attcagatgt     720
taacgttgca tatttaataa tgcacaacca gtactaaaat cctcattgaa atgacaaata     780
attttatttc gaatccctta tagaggttca c                                   811

<210> SEQ ID NO 329
<211> LENGTH: 811
<212> TYPE: DNA
<213> ORGANISM: Homo sapiens

<400> SEQUENCE: 329
tgtcttagta tttaaaactt tttcttaccc aattttttgt tcccatcgaa ttagcaatgc      60
tgtaaagaaa ggcatcttat tccatttttt gttgctataa aggaatactt gaggctgggt     120
aatttataaa gatgaaaagt ttatttggct cgcaattctg gatggctgga aggttaagta     180
ctgggccaca gcatctggtg ggggcctcga gctgcttcta gtcataatgg aaggtgaagg     240
gtgtaaagat catgtgacaa gggaggaaag aagagaagga aggaggtgct ggttctttct     300
atcaaccaat tcgcaagaga actaatagag aaagaactca cttagccctg tgggaacaca     360
ttaatctatt cataagggat ctggctgtat gatacaaaca cctcccatta ggccccacct     420
ccaaattgta tcccattggg gatcaaattt caaaagaga tttggaagga acaaacaaac      480
catatctaag ccatagtaaa aggaatggct tttcaaaggt aaaatttact aagtgtatta     540
atattttacc aatttccagc caggagagta tgaatgttgc attattacat tgctttgaaa     600
caaagcatta ktcttaattc agaagtttaa attcagatgt taacgttgca tatttaataa     660
tgcacaacca gtactaaaat cctcattgaa atgacaaata attttatttc gaatccctta     720
tagaggttca caatgtttta acaatgtagt tttgactaaa tagaagtagt caaaacctgt     780
cagattggaa atagtattta taaaacataa a                                   811

<210> SEQ ID NO 330
<211> LENGTH: 601
<212> TYPE: DNA

<213> ORGANISM: Homo sapiens

<400> SEQUENCE: 330

| | | | | | |
|---|---|---|---|---|---|
| gctcatcaat | tttgacttaa | gaaaattcta | gcaacattta | tagattttgc | caaaattcag | 60 |
| cttcttccca | aatcaatcta | taagaaggct | cttccttaaa | cataattttt | atatctatga | 120 |
| actgcactag | catttactat | atatttttat | cactctcacc | attactggat | aataaataaa | 180 |
| agctcattaa | aagagttaac | aaaacatatt | tattttaggc | atcctgaaaa | aaagattcaa | 240 |
| ttttattatc | atttctacaa | taagtattga | agaaaggaga | atttaaatta | cttcatatac | 300 |
| stgataaagg | aaaacatatg | caaggcaaat | aaacatctta | gatcatgaca | tataaaataa | 360 |
| tagattatta | ctaaagatta | aaatactttc | ttaagaatta | aagcaattct | aaaagcaata | 420 |
| gtaaataaca | ttcttttctag | tgatcagaca | ctggatacta | tgtttgagat | agacagtgaa | 480 |
| ttgggaatgt | tgttttacag | aagctcctac | cttgcaagga | caggcaagtt | taaatgtcag | 540 |
| ctagaaaact | atcttgagtt | ttcagtaatg | taagattttc | ctattcaatt | tcacacttta | 600 |
| a | | | | | | 601 |

<210> SEQ ID NO 331
<211> LENGTH: 601
<212> TYPE: DNA
<213> ORGANISM: Homo sapiens

<400> SEQUENCE: 331

| | | | | | |
|---|---|---|---|---|---|
| agaaaattct | agcaacattt | atagattttg | ccaaaattca | gcttcttccc | aaatcaatct | 60 |
| ataagaaggc | tcttccttaa | acataattttt | tatatctatg | aactgcacta | gcatttacta | 120 |
| tatattttta | tcactctcac | cattactgga | taataaataa | aagctcatta | aaagagttaa | 180 |
| caaaacatat | ttattttagg | catcctgaaa | aaaagattca | attttattat | catttctaca | 240 |
| ataagtattg | aagaaaggag | aatttaaatt | acttcatata | cctgataaag | gaaaacatat | 300 |
| rcaaggcaaa | taaacatctt | agatcatgac | atataaaata | atagattatt | actaaagatt | 360 |
| aaaatacttt | cttaagaatt | aaagcaattc | taaaagcaat | agtaaataac | attcttttcta | 420 |
| gtgatcagac | actggatact | atgtttgaga | tagacagtga | attgggaatg | ttgttttaca | 480 |
| gaagctccta | ccttgcaagg | acaggcaagt | ttaaatgtca | gctagaaaac | tatcttgagt | 540 |
| tttcagtaat | gtaagatttt | cctattcaat | ttcacacttt | aaattttata | tatatataaa | 600 |
| a | | | | | | 601 |

<210> SEQ ID NO 332
<211> LENGTH: 1110
<212> TYPE: DNA
<213> ORGANISM: Homo sapiens

<400> SEQUENCE: 332

| | | | | | |
|---|---|---|---|---|---|
| tgtagaagtt | cttatcactt | cctggccttt | tggctaagat | caagtgtgaa | atgtagaagt | 60 |
| tcctctaagc | tttacttccc | tcaaaaacta | gttttatctt | gtcagcagga | ttcacttaaa | 120 |
| aagacaaatt | cagattatga | attttttttct | tttttacagg | gtctgctctg | ttgcccaggc | 180 |
| tggagtgcag | aggcacaatc | tcggctcact | gcagcctccg | cctcctgggt | tcaagcaatt | 240 |
| ctcttgcctc | agcctcccga | gtaactggga | ttacaggcat | gtgccaccac | ccagctaatt | 300 |
| tttgtatttt | tagtagagat | ggggtttcac | cacattggtc | aggctggtct | cgaactgctg | 360 |
| gcctcaagtg | atccacttgc | ctcggcctcc | caaagtgcag | agattacagg | tgtgagccac | 420 |
| cgtgcccagc | ctcataaccg | tttcaactac | ttttttcactt | gacaagcaga | tgtgaagtta | 480 |

| | |
|---|---|
| acaaagtcac ccatatttga aataaagata gtatattcct ggggyaggca gaggcagttg | 540 |
| aggatcatga ataactatg ttggcatagt tatttaggtg ttgatactgt tattatgcca | 600 |
| ttgaaagtta aacagagaac cctctgggta catgttttat accaatgcac actatcttat | 660 |
| tagtccctct cataatgtgc agtcatcatt actgttacgg gttgaggtgt ccccatcctc | 720 |
| tatgggacac ctctatgttg aagtctcaga ttccctagaa tctcagaatg tgaccttgtt | 780 |
| tggaaacaga tttgctacag acgcaattag ttgagatgcg cttatatggg taggtcctaa | 840 |
| ttcagtgact ggtgtcctta aaaaaatgga aatgtacaca cggtggtaga catgcataga | 900 |
| gggaagagag atggagaaaa tggtcaccta caagccaaag acaggggtct ggagcagatc | 960 |
| cttccctcac agccctcaga aggaaccaat cttgccaata ccttgatttt ggacttccac | 1020 |
| ctccagaact ataacacatt tctgttcttc aagcaatttg tagccatttg ttacagctaa | 1080 |
| tacaatcaca catagaaatg acttgtaaat | 1110 |

<210> SEQ ID NO 333
<211> LENGTH: 691
<212> TYPE: DNA
<213> ORGANISM: Homo sapiens

<400> SEQUENCE: 333

| | |
|---|---|
| taaaacatgt acccagaggg ttctctgttt aactttcaat ggcataataa cagtatcaac | 60 |
| acctaaataa ctatgccaac atagttattt catgatcctc aactgcctct gcctacccca | 120 |
| ggaatatact atctttattt caaatatggg tgacttgtt aacttcacat ctgcttgtca | 180 |
| agtgaaaaag tagttgaaac rgttatgagg ctgggcacgg tggctcacac ctgtaatctc | 240 |
| tgcactttgg gaggccgagg caagtggatc acttgaggcc agcagttcga gaccagcctg | 300 |
| accaatgtgg tgaaacccca tctctactaa aaatacaaaa attagctggg tggtggcaca | 360 |
| tgcctgtaat cccagttact cgggaggctg aggcaagaga attgcttgaa cccaggaggc | 420 |
| ggaggctgca gtgagccgag attgtgcctc tgcactccag cctgggcaac agagcagacc | 480 |
| ctgtaaaaaa gaaaaaaatt cataatctga atttgtctttt ttaagtgaat cctgctgaca | 540 |
| agataaaact agttttgag ggaagtaaag cttagaggaa cttctacatt tcacacttga | 600 |
| tcttagccaa aaggccagga agtgataaga acttctacat tttaagttat tcacaagata | 660 |
| actattaatg aacctgaaat agtttgtaaa g | 691 |

<210> SEQ ID NO 334
<211> LENGTH: 640
<212> TYPE: DNA
<213> ORGANISM: Homo sapiens

<400> SEQUENCE: 334

| | |
|---|---|
| aaaccttttt cctgttttac tattactaaa ggtggcacaa cagcaacctc aacaactttg | 60 |
| caccatgcca acactgatgt ttacacccag cacagcattt ttggtctcta tttttattct | 120 |
| cctctgaatg taatgaggat tcctagatgg ctagccaatt cgaatattta aggcaactga | 180 |
| aagttagaat gtttctgaaa catagtgttg ttgccagaga gtacgaaagt tttcaagaat | 240 |
| atcgggcaat tctgaaagta caagaagcc agattaaatg aaataacact ggcgaagttt | 300 |
| tagcaaggtg actctcatat aatgatcatt atcattacca cagttaaaag aaaagagttg | 360 |
| tttatgaaag gccatgtgtc tgcaatgaaa ctcaaaagag aaaagttaac aggtgcaara | 420 |
| ggtagtttta ttataaaagg agggtaggca acaagaatat gtttaatttt tcttcctttt | 480 | catgagtaag gacaagagtt tcatatatgt gaatattttt atttaattt aagtagaaat      540 ctgtttttaa aatatgggta tatgcttatt tgtgtaagtg taagaaacag aagtaagtac      600 agcaaaccag aaataggcca aacactcctg agcataattt                            640

<210> SEQ ID NO 335
<211> LENGTH: 919
<212> TYPE: DNA
<213> ORGANISM: Homo sapiens

<400> SEQUENCE: 335
tacacccagc acagcattt tggtctctat tttattctc ctctgaatgt aatgaggatt        60
cctagatggc tagccaattc gaatatttaa ggcaactgaa agttagaatg tttctgaaac      120
atagtgttgt tgccagagag tacgaaagtt ttcaagaata tcggcaatt ctgaaagtac       180 aaagaagcca gattaaatga aataacactg gcgaagtttt agcaaggtga ctctcatata      240
atgatcatta tcattaccac agttaaaaga aaagagttgt ttatgaaagg ccatgtgtct      300
gcaatgaaac tcaaaagaga aaagttaaca ggtgcaaaag gtagttttat tataaaagga     360
gggtaggcaa caagaatatg tttaattttt cttccttttc atgagtaagg acaagagtkt      420
catatatgtg aatattttta tttaatttta gtagaaatc tgttttaaaa atatgggtat      480
atgcttattt gtgtaagtgt aagaaacaga agtaagtaca gcaaaccaga aataggccaa      540
acactcctga gcataatttt acttggtaga ttattcctga aacttaagga atcatctttg      600
aactcttttc ctcacttgac ttccaggatt caccatgcac ttgtgatttt cctttcattt      660
cactctccgt tcctcctcag tctttttttc tcccccaggt cttttttgtt catcttaaac      720 tctaaattt agaatatccc aggggtctgc cttcggcctt ctcttttata tctacactgg       780
cctcatacat aatcttaacc aagtcattat tttaaatacc tacaatatac tgaaaacttc      840
taaatttgta tttaattct tgacttcttc catacagtct agatttgtat gtccataggc       900
tgacatcatt ggctgatac                                                   919

<210> SEQ ID NO 336
<211> LENGTH: 1001
<212> TYPE: DNA
<213> ORGANISM: Homo sapiens

<400> SEQUENCE: 336
ttactaaata ttctccaaca aatatatact tagtatatac tattagtgat gcatgctttc       60
aaatatttgg actatatcaa tgaatgaaac aaaaaattat ttgcccttaa ggagcttaga      120
ttctaacaga tggattcaga tgattttat gccttattc gtaggtttaa aagagcaatg        180
gggaaagggg aagaagagag ggattgaaaa tattgagaag gttgggagac ttagcaattt      240
taagtaaggt agtgagggta ggttttattg gcaaagtgat ttttcagcag agactgggaa      300
agatgaacgt ggtatcctgg aggaaagcct cccaggcaga gttaagctgc taacaaaagt     360
gcccttaggc tggagtgggc ttgtttgatt aaggaacaaa gaggtcagca tggttgcact      420
agagagaaaa aatcagatgg cgtaaggaga tgaaatcaga aagatacgag gctaggcaaa      480
ggggtactct atgtaatgaa yatgacctgg cagtactgac atctcctgag ggactgttag      540
aagtgcagac tcttgtatct tttctcaagt ctatgaaatc tagacttcat tttaacaaga      600
tgacccgata tttacataca cattaaagtt ccagaagcac tgatataaca cattgtaaga      660
tcgcacagga cttcaattct ttttctggtt tttagaggca gtcctttggg gtgttttgtg      720
tagagtataa tgacctgaaa tatctaggat cactctagct actatcttga ggaaagagtg      780

```
caataaggcg gaacagttca gaggcaatgg tggtcttcta aatgaaagac acacagcact      840
caaaccaggc agttgaggag ggatgggaag aagttgtcaa attctagaca tattttaaag      900
gtagtgtcca gagaatttcc ttagatgcgt aggaacatgg aggataggac atagggtgga      960
aataaacgaa ataagaaac tgaagctgat tctgacattt t                          1001
```

<210> SEQ ID NO 337
<211> LENGTH: 1576
<212> TYPE: DNA
<213> ORGANISM: Homo sapiens

<400> SEQUENCE: 337

```
ataccttta agtgacatcc tagtgaatct ccatttgtca cgagacctca agctttccag       60
ttctggcaca aagtgattac tcataccatc acttcaaaat gatgattatc ttcatttatt     120
ttagttatat tgaacaaaat atacatttaa aaaatctaat tactaaatat tctccaacaa     180
atatatactt agtatatact attagtgatg catgctttca aatatttgga ctatatcaat     240
gaatgaaaca aaaaattatt tgcccttaag gagcttagat tctaacagat ggattcagat     300
gatttttatg ccttatttcg taggtttaaa agagcaatgg ggaaaaggga agaagagagg     360
gattgaaaat attgagaagg ttgggagact tagcaatttt aagtaaggta gtgagggtag     420
gttttattgg caaagtgatt tttcagcaga gactgggaaa gatgaacgtg gtatcctgga     480
ggaaagcctc ccaggcagag ttaagctgct aacaaaagtg cccttaggct ggagtgggct     540
tgtttgatta aggaacaaag aggtcagcat ggttgcacta gagagaaaaa atcagatggc     600
gtaaggagat gaaatcagaa agatacgagg ctaggcaaag gggtactcta tgtaatgaac     660
atgacctggc agtactgaca tctcctgagg gactgttaga agtgcagact cttgtatctt     720
ttctcaartc tatgaaatct agacttcatt ttaacaagat gacccgatat ttacatacac     780
attaaagttc cagaagcact gatataacac attgtaagat cgcacaggac ttcaattctt     840
tttctggttt ttagaggcag tcctttgggg tgttttgtgt agagtataat gacctgaaat     900
atctaggatc actctagcta ctatcttgag gaaagagtgc aataaggcgg aacagttcag     960
aggcaatggt ggtcttctaa atgaaagaca cacagcactc aaaccaggca gttgaggagg    1020
gatgggaaga agttgtcaaa ttctagacat attttaaagg tagtgtccag agaatttcct    1080
tagatgcgta ggaacatgga ggataggaca tagggtggaa ataaacgaaa taagaaact    1140 gaagctgatt ctgacatttt agacctaaaa tctcaactaa agttgccaa gatgggaaaa    1200 actaggtgca tcttgtttgg tgagtggaaa tcagccttgt gaattaagac ttaaactgat    1260
gtctttaatc ccgtagaaat accatgaagg cagtagaaga tggctaaaga gaggtctaga    1320
ctgtaggtac aaatttaaaa gtcacttgca tttggatgct taaagtcagg atattgtgaa    1380
gtcaacagag gaataaataa atgcagagag gggaaagaaa aggcccatag actgagccat    1440
tgtctggttt atttacatat tagtatatat tttcttaaag atgtttgcta tataataatg    1500
agttacctaa agtgtgactt ttctaaattt atggggaatt ttctacattg tgttatggca    1560
ctactaaaaa taataa                                                    1576
```

<210> SEQ ID NO 338
<211> LENGTH: 1275
<212> TYPE: DNA
<213> ORGANISM: Homo sapiens

<400> SEQUENCE: 338

```
gtaaaactaa ttataattaa aatcaaaata tttactgaac ctacttactc ctataatttg      60
cgttgctggt taaaacccag ctataaaaat tttgatcaaa aattttattt ttgtaaatga     120
tctgacacag cataaatgtt aatcacattt ctttatttta tttgcagatt aatttgagta     180
atttgaaaaa ttattaatgt tacttaatta ctctcaacac cttacagtgt ctcctgtaag     240
cactattggt gatactgaat ttaagttaca tttaacaact atcagaaaat agttttaaa     300 gtaaaaatta tgatttggag tttaccaact aaatcttgtt agctttcact gcctctattg     360
agaagagcag cagttcttat cttcctcctt tttcttcttt aattaacaag agattatttg     420
tatcatagcc ataaaatcag ttcaggtatt acatgaacga caccctgac tgcaatggtg     480 tagtttattg tattagtcca ttttcatgct gctgataaag acatacataa gactgggtaa     540
tttataaaga aatagaagtt taacggactc acagttccat gtggctgggg aagcctcaca     600
atcatgatcg aaggcaaaag gcacatctta catggcaaca ggcaagagag aatgagagcc     660
aagtgaaagg agaaacccct tataaaacct tcagacctca tgagacttat tcactaccac     720
aagaacagta tgtgagaaac agtcccatga tccagttatc tccccactggg tccctcccac     780 cacacaaggg aattatggga actgcaattc aagatgaaat gtgggtggaa gcacaacgga     840
actatatcat gatcaaagca ttattgtttt ctctgataag ctgatctaga aagtgctgct     900
tgtgatcagc tttggtgacc atgatcagtg aaatggttaa ggaaatctac agattttgta     960
ggtttgtgcc ttgacagacg accggtatct gtttctcttt tcatgatgaa gtatctaaca    1020
aagctctgtc caaaattttg aatttctcgt taaawgcatc atgattatag aacagaggtt    1080
acaatcaatt attcagtcac acaatcactc tcatcagtca ttaaggtgca tacctggtgt    1140
tccagttatt cagtgtggta taacaaacta cctggaactt aatggcttga aatagtcacc    1200
attacattat gattgtccat tctctgcatc aataattagg atttggcaaa gagggaatgg    1260
tttgtttaca gacag                                                    1275
```

<210> SEQ ID NO 339
<211> LENGTH: 1275
<212> TYPE: DNA
<213> ORGANISM: Homo sapiens

<400> SEQUENCE: 339

```
gtaaaactaa ttataattaa aatcaaaata tttactgaac ctacttactc ctataatttg      60
cgttgctggt taaaacccag ctataaaaat tttgatcaaa aattttattt ttgtaaatga     120
tctgacacag cataaatgtt aatcacattt ctttatttta tttgcagatt aatttgagta     180
atttgaaaaa ttattaatgt tacttaatta ctctcaacac cttacagtgt ctcctgtaag     240
cactattggt gatactgaat ttaagttaca tttaacaact atcagaaaat agttttaaa     300 gtaaaaatta tgatttggag tttaccaact aaatcttgtt agctttcact gcctctattg     360
agaagagcag cagttcttat cttcctcctt tttcttcttt aattaacaag agattatttg     420
tatcatagcc ataaaatcag ttcaggtatt acatgaacga caccctgac tgcaatggtg     480 tagtttattg tattagtcca ttttcatgct gctgataaag acatacataa gactgggtaa     540
tttataaaga aatagaagtt taacggactc acagttccat gtggctgggg aagcctcaca     600
atcatgatcg aaggcaaaag gcacatctta catggcaaca ggcaagagag aatgagagcc     660
aagtgaaagg agaaacccct tataaaacct tcagacctca tgagacttat tcactaccac     720
aagaacagta tgtgagaaac agtcccatga tccagttatc tccccactggg tccctcccac     780 cacacaaggg aattatggga actgcaattc aagatgaaat gtgggtggaa gcacaacgga     840
```

```
actatatcat gatcaaagca ttattgtttt ctctgataag ctgatctaga aagtgctgct      900
tgtgatcagc tttggtgacc atgatcagtg aaatggttaa ggaaatctac agattttgta      960
ggtttgtgcc ttgacagacg accggtatct gtttctcttt tcatgatgaa gtatctaaca     1020
aagctctgtc caaaattttg aatttctcgt taaatgcatc atgattatag aacagaggtt     1080
acaatcaatt attcagtcac acaatcactc tcatcagtca ttaaggtgcr tacctggtgt     1140
tccagttatt cagtgtggta taacaaacta cctggaactt aatggcttga aatagtcacc     1200
attacattat gattgtccat tctctgcatc aataattagg atttggcaaa gagggaatgg     1260
tttgtttaca gacag                                                      1275

<210> SEQ ID NO 340
<211> LENGTH: 1001
<212> TYPE: DNA
<213> ORGANISM: Homo sapiens

<400> SEQUENCE: 340
gaaacaaaaa attgcttttt atatattgat attttttgcac ggatttctta ggattttcta     60
tgtacatgac catgtcatct gcaaatgaaa tagttttatt tctttatcaa tccggatgaa    120
tttattaaaa ttatcttgcc taatttccca aatagggcct ccatgttgaa cataagtggt    180
ggcaagggtg atctgttgct aatctcagtg gatgatattc agtgttttac aatgatcttc    240
gacagctctg gctgttaaat tatcatagtc tgtatggcct aaacaaacaa aatacttatg    300
attatggggg aggctgggat atccaagatc aagttgctgg caggtctagc aacctgccac    360
tgggaagccc tgcttcccag ttttcagatg gccaccttct tatagtatct tcaccaaaga    420
tagggcagag agagcaagca agctctctac cttctcatat aagggcacta atcccaccat    480
gaaggcgcca ctgtcatgac stgattatgt cacaaagacc ccggggcaaa tattaccact    540
gtgaggagta cagttttagc atgtgaattt tggaagaaca caaacattta gtacagagtg    600
actattaagt atgttattaa ctatggagtt tttgtaggca ttttttaaca cattgagaaa    660
gtttcctcta ttcctacttt tgttgagaag tttttatgat gacaaggcat tacattttat    720
ccaatgactt ttctgtgtgt attgagatga ctgatttgtt ctgccaattt aaatccattg    780
ttgattctct ctaggatttt ttttatttca gttattaaat ttttcaacag gagaattact    840
gtcttgttct tttttttgta atttctgtcc ccttactggt attccatatt taataaggca    900
tcataatagt actcttcttt agtttcttaa agatggtttt ctttagtttt taacatattt    960
atgtctattt agaagtcttt gttaagtctg acatctgagc t                       1001

<210> SEQ ID NO 341
<211> LENGTH: 1001
<212> TYPE: DNA
<213> ORGANISM: Homo sapiens

<400> SEQUENCE: 341
ggatttctta ggattttcta tgtacatgac catgtcatct gcaaatgaaa tagttttatt     60
tctttatcaa tccggatgaa tttattaaaa ttatcttgcc taatttccca aatagggcct    120
ccatgttgaa cataagtggt ggcaagggtg atctgttgct aatctcagtg gatgatattc    180
agtgttttac aatgatcttc gacagctctg gctgttaaat tatcatagtc tgtatggcct    240
aaacaaacaa aatacttatg attatggggg aggctgggat atccaagatc aagttgctgg    300
caggtctagc aacctgccac tgggaagccc tgcttcccag ttttcagatg gccaccttct    360
```

```
tatagtatct tcaccaaaga tagggcagag agagcaagca agctctctac cttctcatat        420
aagggcacta atcccaccat gaaggcgcca ctgtcatgac ctgattatgt cacaaagacc        480
ccggggcaaa tattaccact stgaggagta cagttttagc atgtgaattt tggaagaaca        540
caaacattta gtacagagtg actattaagt atgttattaa ctatggagtt tttgtaggca        600
ttttttaaca cattgagaaa gtttcctcta ttcctacttt tgttgagaag tttttatgat        660
gacaaggcat tacattttat ccaatgactt ttctgtgtgt attgagatga ctgatttgtt        720
ctgccaattt aaatccattg ttgattctct ctaggatttt tttatttca gttattaaat         780 ttttcaacag gagaattact gtcttgttct ttttttgta atttctgtcc ccttactggt          840
attccatatt aataaggca tcataatagt actcttcttt agtttcttaa agatggtttt          900
ctttagtttt taacatattt atgtctattt agaagtcttt gttaagtctg acatctgagc        960
tctctcaaag tttctgctga tttttttttt cctatgtttg g                           1001

<210> SEQ ID NO 342
<211> LENGTH: 701
<212> TYPE: DNA
<213> ORGANISM: Homo sapiens

<400> SEQUENCE: 342
ggaaaccctg gcctcttgat cacactttcc tggagtttag tccctctgc aatatgtacc           60 tgggagtcat aagaaatgcc agttacaaaa acttcctgta cagatatcct agcactcaac         120
tggaaaccgg ggagagtcac aattctgtct ttccagccat atgtaactga atggagatc          180 ttttcaccct gagccagggg tgatgggaaa gggagctggt catggctcaa tgtttagcct         240
tttcttggtc ttcaagattt catagacatt cttaaataca tgtttctttc aatgaagttt        300
gcccttagga caattcacag ctacattagg tacttttaa ataatacttt tgaccatccg         360
tggttatttc attgaagaaa atctatagag cacctcagcc atcattccag aagtgactat        420
cctcctcagt aatggttctt attctaattt taaatatcat tgatgtagaa cattctattt       480
cactattcct tcattttatt rttatgggaa attatataca gttctccaga ttttaaagc          540 cttgctaaca tgttttaagt cacacaaata ttcttctgtg ggaaaatgac agtaatttag         600
tgtgcaacaa ttatatagaa ctaттттттca actataaaa cgaagtgaaa ttctaaataa         660
aatcatttat caaacacaaa aatttgagcc agaataagga a                             701

<210> SEQ ID NO 343
<211> LENGTH: 701
<212> TYPE: DNA
<213> ORGANISM: Homo sapiens

<400> SEQUENCE: 343
aatgccagtt acaaaaactt cctgtacaga tatcctagca ctcaactgga aaccggggag          60
agtcacaatt ctgtctttcc agccatatgt aactgaaatg gagatctttt caccctgagc        120
caggggtgat gggaaaggga gctggtcatg gctcaatgtt tagccttttc ttggtcttca         180
agatttcata gacattctta aatacatgtt tctttcaatg aagtttgccc ttaggacaat         240
tcacagctac attaggtact ttttaaataa tactttgac catccgtggt tatttcattg          300
aagaaaatct atagagcacc tcagccatca ttccagaagt gactatcctc tcagtaatg          360 gttcttattc taattttaaa tatcattgat gtagaacatt ctatttcact attccttcat        420

tttattatta tgggaaatta tatacagttc tccagatttt taaagccttg ctaacatgtt        480

ttaagtcaca caaatattct yctgtgggaa aatgacagta atttagtgtg caacaattat         540
```

```
atagaactat ttttcaaact tataaacgaa gtgaaattct aaataaaatc atttatcaaa      600
cacaaaaatt tgagccagaa taaggaatgt aaattacaat ttaaacacag attataaact      660
atcttacttt taaaatgtta aaattcctaa cttgtttgaa a                          701
```

<210> SEQ ID NO 344
<211> LENGTH: 768
<212> TYPE: DNA
<213> ORGANISM: Homo sapiens

<400> SEQUENCE: 344

```
ctaaaatcta ccattatatg atatccttcc caatacataa attaaaaaaa aaaacactgt       60
agaggaaaaa gcaatatttt gaaatgatat gcttttcttt gtttgtcttc aaacaattac      120
atcttcatca taatggttgt attagtctgt tttacactg ctataaagaa ttgcctgaga       180
ctgagtaaca tataaagaaa aaagttttaa ttgaccacag tttcacaggc ttaataggaa      240
gcatgactgg gaaacttaga atcatggcag aagaggaagg ggaagcaagg atcttcttca      300
catggtagca ggagagagag cacaaagggg gacacgctac acactttcaa caacgagat       360 ctcctgagaa ctctatcggg agaacagcaa gagggaagtt caccccctatg attcaatcag     420 ctcccaccgg gcttctcccc tgacacatga ggaattacaa ttggatgaga gatttgggtg     480
gggacacaca gacaaaccat atcaactgtc atggacttaa acaattgtct ttgaattgtc     540 tttttttcata cttttatttg catctttyca ctaaaaagat gacacaaagt aatcctagtt     600
tacatttttt accatgtaat tccatattac ttttcctga aagttactta ttttaaatc       660 tcaaagctct tcatacttat ggtttgatct gcacttacaa ctggatctca gaaagattga     720
attctcccat cataccaagt tcatgtctct cactcttaat atttgttc                    768
```

<210> SEQ ID NO 345
<211> LENGTH: 701
<212> TYPE: DNA
<213> ORGANISM: Homo sapiens

<400> SEQUENCE: 345

```
aaatgatatg cttttctttg tttgtcttca aacaattaca tcttcatcat aatggttgta       60
ttagtctgtt tttacactgc tataaagaat tgcctgagac tgagtaacat ataaagaaaa      120
aagttttaat tgaccacagt ttcacaggct taataggaag catgactggg aaacttagaa      180
tcatggcaga agaggaaggg gaagcaagga tcttcttcac atggtagcag gagagagagc      240 acaaggggg acacgctaca cactttcaaa caacgagatc tcctgagaac tctatcggga      300
gaacagcaag agggaagttc accccctatga ttcaatcagc tcccaccggg cttctcccct      360
gacacatgag gaattacaat tggatgagag atttgggtgg ggacacacag acaaaccata      420
tcaactgtca tggacttaaa caattgtctt tgaattgtct tttttcatac ttttatttgc      480
atcttttcac taaaaagatg rcacaaagta atcctagttt acattttta ccatgtaatt      540 ccatattact ttttcctgaa agttactta ttttaaatct caaagctctt catacttatg       600
gtttgatctg cacttacaac tggatctcag aaagattgaa ttctcccatc ataccaagtt      660
catgtctctc actcttaata tttgttccca agacaacaat t                           701
```

<210> SEQ ID NO 346
<211> LENGTH: 6758
<212> TYPE: DNA
<213> ORGANISM: Homo sapiens

<400> SEQUENCE: 346

```
agagtgggcc attgttctga ctagtctggg gctccccaaa gaactggtat ctgtctcacc      60
tgactcagaa caatgataag gctgtagatc tttttggaag tctatgaaaa caggcacaat     120
gaaggcagca tgttagagat ataattccac aggaagatgc caggtaaaac aaaagagaaa     180
aagcaggaac aagctgatta ggaaatttgt gatgactaaa agtatataca caagcccaaa     240
taagatactc caaagatgtt tgataggttc tagatctcta gatatactgc tcaatgaaag     300
tgtcccctg aacaaagcca gtctgcaaag actgggtgag atgatttttt ttaaatgtca      360
agtctcagca acaacaaaaa tgacaagaca tgcacagaag caagaaaata taacacaatc     420
aaagaaaaaa aagccacaga atcagtcct agagaaaacy gatctatgag ctgcctgaca      480
ataattataa ataactatc ataaaaatgc ccagtgagat ataagaaaac acagacaact      540
aaatgaatca ggaaatgat gcatgaacaa atgggcata tcaacagaga tggaaatgac       600
aaagataaac aaacagaaat tttggagctt aaaaatacag taagtaaagt gaataattca     660
ctaaaaatat tcaatagcag actagatcag gcagaagaaa atatcaatga acttgaagac     720
agatcatcaa gtcagaggaa caacagcaac aaaaagaat gaaaaagtg aagacagcct       780
aagggactta ggagtcagta ccaaggaaat caatatatac gttatagatg tatcagaaga     840
aaaagggaga aaaatgaaaa gaaagcatat ttgaaaaaat aatagctgaa gaattctcaa     900
tttcaaagag agaaattgat atacaaattc aagaagttca aaagactcta gccataataa     960
atctaaagag actcacacta agacatatta tcatcaaact gtcaaaatca aagacaaaga    1020
attgtgaaat ctgccaagga aaagtgactc atcacacata agagatataa cataagattg    1080
tcacaggatt tctgaacaga cactttgcag gtcagaggga agtagggtga catattccag    1140
gtgctgaaag aagaaaacac cctgccaacc aagaatatgg catccagaaa aactttccta    1200
gaagaatgaa ggagaaattt agactttccc aaataaacaa agctgaggg agttcattac     1260
taccagacct gctctgcaaa atgctaaaga gaaaccttca ggtgaaacaa aaagatgcta    1320
gacagtaaca caaaaccact cataaataac ttcttcagta aaaataatac atcgacaaat    1380
atggtaacct gtattaatac tggtgcacaa attcactttc aaattttata ataagaatt     1440
taaggatga aacatctaa aactaactat aaatctatat aatgaatata caatatataa      1500
aaaaatttgt gatcacaata acataaaatg ggggaggtag agctgtatag gggtagagct    1560
tttgtatgca attgaaatta ccatcagttt aaactgaact gttataacat taagatgttt    1620
tatgtaattg caatggtaac tatattctat agaatatatt aaaagaaaa agaaaatagg     1680
aagggaatca aagcatgtcc ttgtaaaaaa gtcaatgaaa gcaaagaaa ggcagaaaga     1740
gtgaaaagga ggaataaaaa gttataagac ataaaaaaaa tgaaaatagt aatagtcctg    1800
ccatatcagt aattacatta aatataaatg gattaaactc cctaatcaaa tcatagattg    1860
gtttgcaaga actaacttta caattaaaga cacacagctg acggtgaagg gagaaaaaaa    1920
acttccatgc agtgaccaaa atagaggagg gtggctgtat tactgtcaga caaaataaaa    1980
tttaagtcaa aaactgttac aagagtaaaa gaagggcatt atacagttaa aaaagtaaat    2040
tcgccaggca gacacaacaa ttataaatat caatacataa aaataagagc tcctaaatat    2100
atgcagcaaa cagacataat tgaagaaaga aataaatagc taaaatggta gaagacttta    2160
ataccccac ttacaataat gtataaaata acaagacaga atgtaaataa aaatgtagag     2220
aatttgagca cacactgtaga ccaattggac ctaataaata tactcagaat aatccatcca    2280
accaaagcag aaacagaata tacattcttt tcaagtacac atttgacatt ctctgggatt    2340
```

```
aactacatgt tatgcaacaa acaagtctca acaatgttta aaagtctgat attacacaaa    2400
gtattgtttc tgatgacgat ggaaagaacc tagaagccaa tagcaaaaag aaaatagaaa    2460
atccacacat atgtggaaat taaactacat gcaattaagc aaagggccaa agaagaagaa    2520
gaaaaaagaa aacaccgtga aacaaataaa acaaaaata cagcatatga aaatgcatgg     2580
gatgcagcaa aagtgatggt aagagaaatg tttatagtta taaatgcaaa ccttaaaaaa    2640
gaagaaagaa aacaaaaata ctcaaattaa caactttaca agtcaagaag gtagagaaaa    2700
aagaacaaac tataccaaaa gctaacacag aaagaaaaga ataaagatta aaaacaaaaa    2760
caatttaaaa aatagcagaa ctaaaagttg gttctttgaa aagatcaaca gaattgacaa    2820
tttcttagct acattaagaa aaatacaaga ctcaaataac acaaatcagt ggtgaaaggg    2880
ggtattataa ctgatgccac agaaatacaa aaggatcata agggactact acaaattgta    2940
tgacaacaaa ttgagtaacc taggatacct tgataaattc caaaaaatgc acaatatact    3000
gaatcatgaa tacatgaccc ttataaatca agactaaatc ataagaaat agaaaatatc     3060 aacagaccaa taattagtaa ggagaataaa ctagtaatca gaaacctccc aacaaagaaa    3120
agcttaggac caaatggctt tactggagaa ttctaccaac cattaaaagg ataattaaga    3180
ccaatcttcc tcaaactttt aaaacaaatg ttaaagagga ggaaactctt tcaatctcat    3240
tcataaggtc agcattatcc ttataccaaa accagacaaa gacactatta aaaaactta    3300 gaccaatatc cctgatgaat ttcgatgcaa gaatcctcag caaaatacta tcaaacaatt    3360
caacagcata cttaaatgat tatatgctgt aatcaagatg catttattct ttgaatgcaa    3420
gtgtaattca acacataaaa ttcaatcaat gtaatacacc acattaacag aatgagagac    3480
aaaaaccaca taattatatc aactgatgca gaaaaaaatc tgacacagtt caacaccttt    3540
tgtgataaaa acactcaaca aactaggaaa agaaggaaac aactttaaca catcatatgc    3600
tcactgatga aaatctacaa gttctttata aaagatcagg aacaagacaa taatctgcat    3660
tgttaccact tctattatac gtagtattgg aagttctaat cagagcaaat taggcaagaa    3720
aaataaataa aaggcatcca agtggaaag gaagtaaaat aatctctttt tacagatgat    3780
ataaccttag aattagaaaa tcctaaaaat ttcacatacc aagaaaaagc gtgttaaaat    3840
taataagtaa attcagcaag ttgactgata caaaatcaac acagaaagct cagttgtgtg    3900
tctgtgtgtc tcatacacta acaatgaaca atctgaaaag gagattaaga aaacaatttc    3960
atttacaata gcatcaggaa aaaaaataaa tacttaggaa caaacttaac caaggggttg    4020
gaattcctgt atactgaaaa ctacaaatat tgccaaaaga aaataaagga gacacaaata    4080
agtgatatgt ttttaatatg tccacccaaa gtgatcttca gattcaatga atccctatc     4140 aaagttataa tggcattttt ctgcaggaat gtaaaaattt atcctaaaat tcatatagaa    4200
tctctaggta ccctgagggc caaacaattt tgagaaaaaa aaagaacaa aattggagga    4260 ctcacacttc cagattacaa gaatatttac aaattacata tttacaaaaa aaattacaaa    4320
gccacaataa tcaaaacaac gtgggatttg cataaaggca gatatataga ccagtggaat    4380
agtattgaga gtccagaaat aaaccctag gtatatcatc aaatgacatt tgacaaagtg    4440
ctggtaccac tcaatgggaa tgggacaatt tgttcaacaa atagagcaaa gaaaactaaa    4500
catccatgtg caaagaata atctggacc cttatattac actatagaca aaattaattc      4560
aaaatggatt aaagatctaa atgaaagatc taaaactata aaactcctag gagaaaacag    4620
aggaaaaatt tcatgctaat ttggcaacat tttgtgatgt gacaccaaaa gcagagtcaa    4680
```

```
taaaagcaaa aattagacag atggaaatcc atcatagttt ataacttttg gtcattaaag    4740
aacagtcaac agagtgaaaa ggcaatctat aaaatggggg aaaaacagaa atatgtgca    4800
aatcacagat atctgatagg ggattcatat ccagaataaa taaagaactc ctatatctca    4860
acaacaaaaa atctaatcca atcaaaaaat gggccaaggg agtgaagata catttctcca    4920
aagatgttat acaaatggcc aggaagcata tgaaaagatg ttcaatgtca ctaatcatca    4980
gagaaatgca atcaaaacc acagtgcaat atcacttcac attcattaga atggcttctg     5040
tcatgaacaa cagaaaataa caagtgttga tgagtgtgta gagaaattga gacctttata    5100
taattttggc agaaattcaa aatggtgcaa ccactataaa aaatgatatg gaggtcctca    5160
aaaaattaaa aatagaacta ccatatgatc cacaatccca cctctgggta catattcaaa    5220
agaattgaaa gcagggtgtt gaagatatat ttgcacactc tttatagcag cactgttcac    5280
aatagccaag agatgaaagt aacccaaagg ttcatgaagc aatgaataaa caaaatatat    5340
tatgtacata gagtaaaata ctgtgcagct ttaaagagaa aggaaatctt atactatgct    5400
acaacatgaa tggaacttta gggcattata gtaagtaaaa taagccagtt ttttttaaag    5460
gacaaataaa cactatacga ttctacttaa gtatttaatg ttgtcaaatt tataaatata    5520
gaatgtagaa tagtggttac cctgagctgg gggaaagggg caaaggggaa ttgttatttt    5580
aatgggtata gtttcagttc tgcaaaatga aaaggttctg gaaatctgtt tcacaatgtt    5640
gtaaatataa ttactctgaa attgtacact taaaaatggt taagatgaca aatagagttg    5700
tgatgtcttc ttttgttatt atatagaaaa acttttcat atgataatag tctttgtttt     5760
taagctgact ttgctgatat taatataatc cttccatttt tctttaaaat gctatatgct    5820
ttcacataat tttgctttac gttgatgtat ttatacataa ggtgggtttc ttatagatac    5880
cacgttgtgt gtctttttta tctaagttga tagacttgcc ttttgttagg gtatttaaat    5940
aatttatatt taatgtaatt attgatatag ttgagtgtgt tgattttgt tttctatttg     6000
ctccatctgt tgttggttct cattattcct ctgtttctac cttcttttgt actaattatt    6060
atattttatt attttttcatc tcaactgttg gcttattagc cacattgctt ttaaaatttt    6120
taatgattgc tctagggttt ataataaaca aaatgttagc attttctacc atcaaatatt    6180
tttacactat tcatgtatac ttcaatttct ttcttcccat cctttgaact atatcttcat    6240
acattttact ctacatttgt tataactcag tgctttgaaa gtcaattatt tttgtctttg    6300
acagtcaatg atttttaaag agtttaacag tgaaaaaaaa tggctttcat cttttttccat    6360
tagatttcat actccttctg cctgaagaat ttcttttaat agaccttgta ctgcgggtct    6420
caggcaagaa attctctcag cctttgttgg tttgaaaaac tgcttattac acctttgttt    6480
ttgaaagata ttttcactag gtatagaagt ctgggttgac agttctcatt gtttgtcaca    6540
gcattttttaa gatgcccatt caattgtctt gtcttgtata attttggatt agtctggtgt    6600
atttcttacc tttgttcctc tctgtgcaat gcttcaacca tcccacttca ggctgccttt    6660
aagatgttttt cttttccctt aatctttagt ttttagctgg ttgacagtga cgcatctaag    6720
tgtagtgtat gaggttgctt ttattgtcac tgttgttg                            6758
```

<210> SEQ ID NO 347
<211> LENGTH: 6758
<212> TYPE: DNA
<213> ORGANISM: Homo sapiens

<400> SEQUENCE: 347

```
agagtgggcc attgttctga ctagtctggg gctccccaaa gaactggtat ctgtctcacc      60
```

-continued

```
tgactcagaa caatgataag gctgtagatc ttttggaag tctatgaaaa caggcacaat      120
gaaggcagca tgttagagat ataattccac aggaagatgc caggtaaaac aaaagagaaa      180
aagcaggaac aagctgatta ggaaatttgt gatgactaaa agtatataca caagcccaaa      240
taagatactc caaagatgtt tgataggttc tagatctcta gatatactgc tcaatgaaag      300 tgtcccctg aacaaagcca gtctgcaaag actgggtgag atgatttttt ttaaatgtca       360
agtctcagca acaacaaaaa tgacaagaca tgcacagaag caagaaaata taacacaatc      420
aaagaaaaaa aagccacaga atcagtcct agagaaaact gatctatgag ctgcctgama       480
ataattataa aataactatc ataaaaatgc ccagtgagat ataagaaaac acagacaact      540
aaatgaatca ggaaaatgat gcatgaacaa aatgggcata tcaacagaga tggaaatgac      600
aaagataaac aaacagaaat tttggagctt aaaaatacag taagtaaagt gaataattca      660
ctaaaaatat tcaatagcag actagatcag gcagaagaaa atatcaatga acttgaagac      720
agatcatcaa gtcagaggaa caacagcaac aaaaagaat gaaaaaagtg aagacagcct      780
aagggactta ggagtcagta ccaaggaaat caatatatac gttatagatg tatcagaaga      840
aaaagggaga aaaatgaaaa gaaagcatat ttgaaaaaat aatagctgaa gaattctcaa      900
tttcaaagag agaaattgat atacaaattc aagaagttca aaagactcta gccataataa      960
atctaaagag actcacacta agacatatta tcatcaaact gtcaaaatca aagacaaaga     1020
attgtgaaat ctgccaagga aaagtgactc atcacacata agagatataa cataagattg     1080
tcacaggatt tctgaacaga cactttgcag gtcagaggga agtagggtga catattccag     1140
gtgctgaaag aagaaaacac cctgccaacc aagaatatgg catccagaaa aactttccta     1200
gaagaatgaa ggagaaattt agactttccc aaataaacaa aagctgaggg agttcattac     1260
taccagacct gctctgcaaa atgctaaaga gaaaccttca ggtgaaacaa aaagatgcta     1320
gacagtaaca caaaccact cataaataac ttcttcagta aaaataatac atcgacaaat      1380 atggtaaccct gtattaatac tggtgcacaa attcactttc aaatttata aataagaatt      1440 taaaggatga aaacatctaa aactaactat aaatctatat aatgaatata caatatataa     1500
aaaaatttgt gatcacaata acataaaatg ggggaggtag agctgtatag gggtagagct     1560
tttgtatgca attgaaatta ccatcagttt aaactgaact gttataacat taagatgttt     1620
tatgtaattg caatggtaac tatattctat agaatatatt aaaagaaaa agaaaatagg      1680 aagggaatca aagcatgtcc ttgtaaaaaa gtcaatgaaa gcaaagaaa ggcagaaaga      1740 gtgaaaagga ggaataaaaa gttataagac ataaaaaaa tgaaaatagt aatagtcctg      1800
ccatatcagt aattacatta aatataaatg gattaaactc cctaatcaaa tcatagattg     1860
gtttgcaaga actaacttta caattaaaga cacacagctg acggtgaagg gagaaaaaaa     1920
acttccatgc agtgaccaaa atagaggagg gtggctgtat tactgtcaga caaaataaaa     1980
tttaagtcaa aaactgttac aagagtaaaa gaagggcatt atacagttaa aaagtaaat      2040 tcgccaggca gacacaacaa ttataaatat caatacataa aaataagagc tcctaaatat     2100
atgcagcaaa cagacataat tgaagaaaga aataaatagc taaatggta gaagactta       2160 atacccccac ttcaataat gtataaaata acaagacaga atgtaaataa aaatgtagag      2220
aatttgagca acactgtaga ccaattggac ctaataaata tactcagaat aatccatcca     2280
accaaagcag aaacagaata tacattcttt tcaagtacac atttgacatt ctctgggatt     2340
aactacatgt tatgcaacaa acaagtctca acaatgttta aaagtctgat attacacaaa     2400
```

```
gtattgtttc tgatgacgat ggaaagaacc tagaagccaa tagcaaaaag aaaatagaaa    2460
atccacacat atgtggaaat taaactacat gcaattaagc aaagggccaa agaagaagaa    2520 gaaaaagaa  acaccgtga  acaaataaa  acaaaaata  cagcatatga  aaatgcatgg    2580
gatgcagcaa aagtgatggt aagagaaatg tttatagtta taaatgcaaa ccttaaaaaa    2640
gaagaaagaa acaaaaata  ctcaaattaa caactttaca agtcaagaag gtagagaaaa    2700
aagaacaaac tataccaaaa gctaacacag aagaaaaga  ataaagatta aaaacaaaaa    2760
caatttaaaa aatagcagaa ctaaagttg  gttctttgaa aagatcaaca gaattgacaa    2820
tttcttagct acattaagaa aaatacaaga ctcaaataac acaaatcagt ggtgaaaggg    2880
ggtattataa ctgatgccac agaaatacaa aaggatcata agggactact acaaattgta    2940
tgacaacaaa ttgagtaacc taggatacct tgataaattc caaaaaatgc acaatatact    3000
gaatcatgaa tacatgaccc ttataaatca agactaaatc ataaagaaat agaaaatatc    3060
aacagaccaa taattagtaa ggagaataaa ctagtaatca gaaacctccc aacaaagaaa    3120
agcttaggac caaatggctt tactggagaa ttctaccaac cattaaaagg ataattaaga    3180
ccaatcttcc tcaaactttt aaaacaaatg ttaaagagga ggaaactctt tcaatctcat    3240
tcataaggtc agcattatcc ttataccaaa accagacaaa gacactatta aaaaaactta    3300
gaccaatatc cctgatgaat ttcgatgcaa gaatcctcag caaaatacta tcaaacaatt    3360
caacagcata cttaaatgat tatatgctgt aatcaagatg catttattct ttgaatgcaa    3420
gtgtaattca acacataaaa ttcaatcaat gtaatacacc acattaacag aatgagagac    3480
aaaaaccaca taattatatc aactgatgca gaaaaaaatc tgacacagtt caacaccttt    3540
tgtgataaaa acactcaaca aactaggaaa agaaggaaac aactttaaca catcatatgc    3600
tcactgatga aaatctacaa gttctttata aaagatcagg aacaagacaa taatctgcat    3660
tgttaccact tctattatac gtagtattgg aagttctaat cagagcaaat taggcaagaa    3720
aaataaataa aaggcatcca aagtggaaag gaagtaaaat aatctctttt tacagatgat    3780
ataaccttag aattagaaaa tcctaaaaat ttcacatacc aagaaaagc  gtgttaaaat    3840 taataagtaa attcagcaag ttgactgata caaaatcaac acagaaagct cagttgtgtg    3900
tctgtgtgtc tcatacacta acaatgaaca atctgaaaag gagattaaga aaacaatttc    3960
atttacaata gcatcaggaa aaaaaataaa tacttaggaa caaacttaac caaggggttg    4020
gaattcctgt atactgaaaa ctacaaatat tgccaaaaga aaataaagga gacacaaata    4080
agtgatatgt ttttaatatg tccacccaaa gtgatcttca gattcaatga atccctatc     4140 aaagttataa tggcattttt ctgcaggaat gtaaaaattt atcctaaaat tcatatagaa    4200
tctctaggta ccctgagggc caaacaattt tgagaaaaaa aaagaacaa  aattggagga    4260 ctcacacttc cagattacaa gaatatttac aaattacata tttacaaaaa aaattacaaa    4320
gccacaataa tcaaacaac  gtgggatttg cataaaggca gatatataga ccagtggaat    4380
agtattgaga gtccagaaat aaaccccttag gtatatcatc aaatgacatt tgacaaagtg    4440
ctggtaccac tcaatgggaa tgggacaatt tgttcaacaa atagagcaaa gaaaactaaa    4500
catccatgtg caaagaata  aatctggacc cttatattac actatagaca aaattaattc    4560
aaaatggatt aaagatctaa atgaaagatc taaaactata aaactcctag agaaaacag     4620 aggaaaaatt tcatgctaat ttggcaacat tttgtgatgt gacaccaaaa gcagagtcaa    4680
taaaagcaaa aattagacag atggaaatcc atcatagttt ataactttg  gtcattaaag    4740 aacagtcaac agagtgaaaa ggcaatctat aaaatggggg aaaaacagaa aatatgtgca    4800
```

```
aatcacagat atctgatagg ggattcatat ccagaataaa taaagaactc ctatatctca    4860
acaacaaaaa atctaatcca atcaaaaaat gggccaaggg agtgaagata catttctcca    4920
aagatgttat acaaatggcc aggaagcata tgaaaagatg ttcaatgtca ctaatcatca    4980
gagaaatgca aatcaaaacc acagtgcaat atcacttcac attcattaga atggcttctg    5040
tcatgaacaa cagaaaataa caagtgttga tgagtgtgta gagaaattga gacctttata    5100
taattttggc agaaattcaa aatggtgcaa ccactataaa aaatgatatg gaggtcctca    5160
aaaaattaaa aatagaacta ccatatgatc cacaatccca cctctgggta catattcaaa    5220
agaattgaaa gcagggtgtt gaagatatat ttgcacactc tttatagcag cactgttcac    5280
aatagccaag agatgaaagt aacccaaagg ttcatgaagc aatgaataaa caaaatatat    5340
tatgtacata gagtaaaata ctgtgcagct ttaaagagaa aggaaatctt atactatgct    5400
acaacatgaa tggaacttta gggcattata gtaagtaaaa taagccagtt ttttttaaag    5460
gacaaataaa cactatacga ttctacttaa gtatttaatg ttgtcaaatt tataaatata    5520
gaatgtagaa tagtggttac cctgagctgg gggaaagggg caaggggaa ttgttatttt    5580 aatgggtata gtttcagttc tgcaaaatga aaaggttctg gaaatctgtt tcacaatgtt    5640
gtaaatataa ttactctgaa attgtacact taaaaatggt taagatgaca aatagagttg    5700
tgatgtcttc ttttgttatt atatagaaaa acttttcat atgataatag tctttgtttt    5760
taagctgact ttgctgatat taatataatc cttccatttt tctttaaaat gctatatgct    5820
ttcacataat tttgctttac gttgatgtat ttatacataa ggtgggtttc ttatagatac    5880
cacgttgtgt gtcttttta tctaagttga tagacttgcc ttttgttagg gtatttaaat    5940
aatttatatt taatgtaatt attgatatag ttgagtgtgt tgattttgt tttctatttg    6000 ctccatctgt tgttggttct cattattcct ctgtttctac cttcttttgt actaattatt    6060 atatttatt atttttcatc tcaactgttg gcttattagc cacattgctt ttaaaattttt    6120 taatgattgc tctagggttt ataataaaca aaatgttagc attttctacc atcaaatatt    6180
tttacactat tcatgtatac ttcaatttct ttcttcccat cctttgaact atatcttcat    6240 acatttact ctacatttgt tataactcag tgctttgaaa gtcaattatt tttgtctttg    6300
acagtcaatg attttaaag agtttaacag tgaaaaaaaaa tggctttcat ctttttccat    6360
tagatttcat actccttctg cctgaagaat ttcttttaat agaccttgta ctgcgggtct    6420
caggcaagaa attctctcag cctttgttgg tttgaaaaac tgcttattac acctttgttt    6480
ttgaaagata ttttcactag gtatagaagt ctgggttgac agttctcatt gtttgtcaca    6540
gcatttttaa gatgcccatt caattgtctt gtcttgtata attttggatt agtctggtgt    6600
atttcttacc tttgttcctc tctgtgcaat gcttcaacca tcccacttca ggctgccttt    6660
aagatgtttt ctttccctt aatctttagt ttttagctgg ttgacagtga cgcatctaag    6720
tgtagtgtat gaggttgctt ttattgtcac tgttgttg                             6758

<210> SEQ ID NO 348
<211> LENGTH: 501
<212> TYPE: DNA
<213> ORGANISM: Homo sapiens

<400> SEQUENCE: 348
gaccatgtta tgacatttta gtgcttgcta agcagtaaat actgacttac tttcctgcta      60
cactcttcag agcagaaaga gaaatctaca aaaagggcaa tgtagttggg atccaccaca     120
```

```
gccttgagac tgggccatgt tcctacagct tacccacatt ttaccccac tttctctgag      180 aaacaatgca aactggagaa caaggtcaga gaagttatct tggatggtag aagagaagaa      240
aggagaagaa rggataagca gaaaatcaaa aagggcataa aaaaattact ggggaaaata      300
attcttagtc actcaccatt tcttatgttt gtgaaaacag aaacgaggag caagtgttgt      360
tgtaagaatt gttcttgccc ctcccctcc accacccaca tctgtcaagc tatccctgtt      420
tcactgtttc ctctgcactc tctattaact tctttgtcct cctcttttct tttcctacag      480
caaagacttt ttgtcatgtt t                                                 501

<210> SEQ ID NO 349
<211> LENGTH: 501
<212> TYPE: DNA
<213> ORGANISM: Homo sapiens

<400> SEQUENCE: 349
tgacttactt tcctgctaca ctcttcagag cagaaagaga aatctacaaa aagggcaatg       60
tagttgggat ccaccacagc cttgagactg ggccatgttt ctacagctta cccacatttt      120 accccccactt tctctgagaa acaatgcaaa ctggagaaca aggtcagaga agttatcttg     180
gatggtagaa gagaagaaag gagaagaaag gataagcaga aatcaaaaa gggcataaaa       240 aaattactgg rgaaaataat tcttagtcac tcaccatttc ttatgtttgt gaaaacagaa      300
acgaggagca agtgttgttg taagaattgt tcttgcccct cccctccac acccacatc       360 tgtcaagcta tccctgtttc actgtttcct ctgcactctc tattaacttc tttgtcctcc      420
tcttttcttt tcctacagca aagacttttt gtcatgtttt gtttcttttt ctattgtttc      480
tttccctttt ctaatccttg a                                                 501

<210> SEQ ID NO 350
<211> LENGTH: 1148
<212> TYPE: DNA
<213> ORGANISM: Homo sapiens

<400> SEQUENCE: 350
tatgagattt aatgttaaga aataaaatgt aggatctaaa acgtaatcta tagcataatc       60
tcaaaaatgg tttagaaatg acataataat acagacattt gtgggtggta ggattatgca     120 tattttttata tattttttaaa tatatttttc aaaagcttcc tataaagaat gtaattctttt    180 cccaattcca aatctagctt aaacataatt ttacaaaaat tattctctca gaatgtaaac      240
tagtaccacc tctatggaaa acattatgga gatttcctaa agagttaaaa gtagatctac      300
catttgatcc agcaatctta atactgggta tctacccgga ggaaaagaag tcattgtatg     360
aaaaagacac ttgtacacat atgtttacag gaccacaatt cacaaatgca agatgcaga      420 accaacctaa gtggccastg actaatgaga ggataaagaa gatgtggcat atatatatca    480
gggactacta ctcagccatt acaaggaaca aaataatgtc ttttgcaaca acttggatag     540
agctggaggc cattattcta agtaaagtaa ttcaggaatt ggaaaaccaa aaaccgtatg     600
ttctctctta taagtgggaa ctaagttagg aataagcaaa ggcacacaga gggacatatt      660
ggactttaga gactcacgag gagagggta atagggact agggattaaa agaaaaacta     720
gacattaggt acaaggtacc ctacttaagt gcactaaaat ctcagaattc accactacgt      780
aattcaacta agtaacaaga aaccacttgt acccccaaaag ctactgaaat aaaaattatt    840
ctctcaaaaa tttaagccc taaacttcag ttcctattgt ttatatttac taagaaaaac     900
aacagaaaac actgttttaa aaatggtgga ttttttttaag gttaaaggta tataagacag      960
```

```
ctgcctaagg aaacgcagat acccctgtac cttgttgttg ttgttgtttt tcactttttt    1020
aaaaaacata gagatgggat ctccttatgc tgcccaggct tgtctcaaac tcctgagctc    1080
aagcaatcct ctgacctcag actctcaaag ttttgggact acaggcgaca gtcaccatgc    1140
cagccaat                                                             1148
```

<210> SEQ ID NO 351
<211> LENGTH: 1148
<212> TYPE: DNA
<213> ORGANISM: Homo sapiens

<400> SEQUENCE: 351

```
tatgagattt aatgttaaga aataaaatgt aggatctaaa acgtaatcta tagcataatc      60
tcaaaaatgg tttagaaatg acataataat acagacattt gtgggtggta ggattatgca     120 tattttata tatttttaaa tatatttttc aaaagcttcc tataaagaat gtaattcttt     180
cccaattcca aatctagctt aaacataatt ttacaaaaat tattctctca gaatgtaaac     240
tagtaccacc tctatggaaa acattatgga gatttcctaa agagttaaaa gtagatctac     300
catttgatcc agcaatctta atactgggta tctacccgga ggaaaagaag tcattgtatg     360
aaaaagacac ttgtacacat atgtttacag gaccacaatt cacaaatgca agatgcaga     420 accaacctaa gtggccactg actaatgaga ggataaagaa gatgtggcat atatayatca     480
gggactacta ctcagccatt acaaggaaca aaataatgtc ttttgcaaca acttggatag     540
agctggaggc cattattcta agtaaagtaa ttcaggaatt ggaaaaccaa aaaccgtatg     600
ttctctctta aagtgggaa ctaagttagg aataagcaaa ggcacacaga gggacatatt     660
ggactttaga gactcacgag gaggagggta ataggggact agggattaaa agaaaaacta     720
gacattaggt acaaggtacc ctacttaagt gcactaaaat ctcagaattc accactacgt     780
aattcaacta gtaacaaga aaccacttgt accccaaaag ctactgaaat aaaaattatt     840
ctctcaaaaa ttttaagccc taaacttcag ttcctattgt ttatatttac taagaaaaac     900
aacagaaaac actgttttaa aaatggtgga ttttttttaag gttaaaggta tataagacag     960
ctgcctaagg aaacgcagat acccctgtac cttgttgttg ttgttgtttt tcactttttt    1020
aaaaaacata gagatgggat ctccttatgc tgcccaggct tgtctcaaac tcctgagctc    1080
aagcaatcct ctgacctcag actctcaaag ttttgggact acaggcgaca gtcaccatgc    1140
cagccaat                                                             1148
```

<210> SEQ ID NO 352
<211> LENGTH: 1148
<212> TYPE: DNA
<213> ORGANISM: Homo sapiens

<400> SEQUENCE: 352

```
tatgagattt aatgttaaga aataaaatgt aggatctaaa acgtaatcta tagcataatc      60
tcaaaaatgg tttagaaatg acataataat acagacattt gtgggtggta ggattatgca     120 tattttata tatttttaaa tatatttttc aaaagcttcc tataaagaat gtaattcttt     180
cccaattcca aatctagctt aaacataatt ttacaaaaat tattctctca gaatgtaaac     240
tagtaccacc tctatggaaa acattatgga gatttcctaa agagttaaaa gtagatctac     300
catttgatcc agcaatctta atactgggta tctacccgga ggaaaagaag tcattgtatg     360
aaaaagacac ttgtacacat atgtttacag gaccacaatt cacaaatgca agatgcaga     420
```

```
accaacctaa gtggccactg actaatgaga ggataaagaa gatgtggcat atatayatca      480
gggactacta ctcagccatt acaaggaaca aaataatgtc ttttgcaaca acttggatag      540
agctggaggc cattattcta agtaaagtaa ttcaggaatt ggaaaaccaa aaaccgtatg      600
ttctctctta taagtgggaa ctaagttagg aataagcaaa ggcacacaga gggacatatt      660
ggactttaga gactcacgag gaggagggta ataggggact agggattaaa agaaaaacta      720
gacattaggt acaaggtacc ctacttaagt gcactaaaat ctcagaattc accactacgt      780
aattcaacta agtaacaaga aaccacttgt accccaaaag ctactgaaat aaaaattatt      840
ctctcaaaaa ttttaagccc taaacttcag ttcctattgt ttatatttac taagaaaaac      900
aacagaaaac actgttttaa aaatggtgga ttttttttaag gttaaaggta tataagacag      960
ctgcctaagg aaacgcagat accccctgtac cttgttgttg ttgttgtttt tcactttttt     1020
aaaaaacata gagatgggat ctccttatgc tgcccaggct tgtctcaaac tcctgagctc     1080
aagcaatcct ctgacctcag actctcaaag ttttgggact acaggcgaca gtcaccatgc     1140
cagccaat                                                              1148

<210> SEQ ID NO 353
<211> LENGTH: 1148
<212> TYPE: DNA
<213> ORGANISM: Homo sapiens

<400> SEQUENCE: 353
tatgagattt aatgttaaga aataaaatgt aggatctaaa acgtaatcta tagcataatc       60
tcaaaaatgg tttagaaatg acataataat acagacattt gtgggtggta ggattatgca      120 tattttata tattttttaaa tatattttttc aaaagcttcc tataaagaat gtaattcttt      180
cccaattcca aatctagctt aaacataatt ttacaaaaat tattctctca gaatgtaaac      240
tagtaccacc tctatggaaa acattatgga gatttcctaa agagttaaaa gtagatctac      300
catttgatcc agcaatctta atactgggta tctacccgga ggaaaagaag tcattgtatg      360
aaaaagacac ttgtacacat atgtttacag gaccacaatt cacaaatgca agatgcaga      420 accaacctaa gtggccactg actaatgaga ggataaagaa gatgtggcat atatatatca      480
gggactactr ctcagccatt acaaggaaca aaataatgtc ttttgcaaca acttggatag      540
agctggaggc cattattcta agtaaagtaa ttcaggaatt ggaaaaccaa aaaccgtatg      600
ttctctctta taagtgggaa ctaagttagg aataagcaaa ggcacacaga gggacatatt      660
ggactttaga gactcacgag gaggagggta ataggggact agggattaaa agaaaaacta      720
gacattaggt acaaggtacc ctacttaagt gcactaaaat ctcagaattc accactacgt      780
aattcaacta agtaacaaga aaccacttgt accccaaaag ctactgaaat aaaaattatt      840
ctctcaaaaa ttttaagccc taaacttcag ttcctattgt ttatatttac taagaaaaac      900
aacagaaaac actgttttaa aaatggtgga ttttttttaag gttaaaggta tataagacag      960
ctgcctaagg aaacgcagat accccctgtac cttgttgttg ttgttgtttt tcactttttt     1020
aaaaaacata gagatgggat ctccttatgc tgcccaggct tgtctcaaac tcctgagctc     1080
aagcaatcct ctgacctcag actctcaaag ttttgggact acaggcgaca gtcaccatgc     1140
cagccaat                                                              1148

<210> SEQ ID NO 354
<211> LENGTH: 611
<212> TYPE: DNA
<213> ORGANISM: Homo sapiens
```

<400> SEQUENCE: 354

```
caaaacctca accttccaga taagtctaag ggtgagaact tcacacaaga tgaataagaa      60
ccaatttctt ccagggcgat gttgaacctg gaaatgaaag ccaatctctc ttggaaggcc     120
tggtttgtag aaatgtcagt ctttgtttca agctgtggga gaatgagaag caagactttta    180
gggaagagg aataaaatag atgtgcagaa ataacagagt gagaaagtct tcagggtgtc      240
gctagcccta attgcaggca tccctgaatc ctagaccttg gattgcaaga gactccttaa     300
tatcttccca tgtccacatt tgcttcacat agtttgaatg tggcttctat tatatacaga    360
tacaagattc aaatccaacc tctaygatga ctggtcttgt gaataagcag aagaggcact     420
aacaatatga cgtgagggat tcagggaaga gcactttctt gagcacatat cttccctggt    480
ctgccagctg tagtttatga aattccacaa tgaggatgaa atggaatcac catttacaga    540
gtactctcca gatgtctaac cctaagctag gtaccttcaa aatattatct agtttagata    600
atcaacccctt t                                                         611
```

<210> SEQ ID NO 355
<211> LENGTH: 601
<212> TYPE: DNA
<213> ORGANISM: Homo sapiens

<400> SEQUENCE: 355

```
ttctctagtc caaagggttg attatctaaa ctagataata ttttgaaggt acctagctta      60
gggttagaca tctggagagt actctgtaaa tggtgattcc atttcatcct cattgtggaa    120
tttcataaac tacagctggc agaccaggga agatatgtgc tcaagaaagt gctcttccct    180
gaatccctca cgtcatattg ttagtgcctc ttctgcttat tcacaagacc agtcatcata    240
gaggttggat ttgaatcttg tatctgtata taatagaagc cacattcaaa ctatgtgaag    300
yaaatgtgga catgggaaga tattaaggag tctcttgcaa tccaaggtct aggattcagg    360
gatgcctgca attagggcta gcgacaccct gaagactttc tcactctgtt atttctgcac    420
atctatttta ttcctctttc cctaaagtct tgcttctcat tctcccacag cttgaaacaa    480
agactgacat ttctacaaac caggccttcc aagagagatt ggctttcatt tccaggttca    540
acatcgccct ggaagaaatt ggttcttatt catcttgtgt gaagttctca cccttagact    600
t                                                                     601
```

<210> SEQ ID NO 356
<211> LENGTH: 527
<212> TYPE: DNA
<213> ORGANISM: Homo sapiens

<400> SEQUENCE: 356

```
gctctagaat atggcattcc agaagtggga tgctacaaat agtctcattg agagtcaact      60
tgcacaatgt atcgtcctac ccttacatca atttctgaaa caacttctct ttgcacttcc    120
cctatagtta catgcataat aaattctgac aactcttatg aagtcatgga ataactttct    180
tcttatgttt cctatcaatg tcattagccc tttatcttgt ttgagtttcc atcagcaatg    240
ttttcaagtc ccaagatcat tcatgtatcc acaagcaatg atacgccaga tttggacaaa    300
taatactgaa tactatctta ttttcactgc catgatcaag gcagtgtgga ttgctgccaa    360
gtccaagaga agtgaggtca gcagctgcaa gccacctccg tcatttagaa aagcttcatg    420
atgtagtgtg tcgtttcgat gtgacactgt ctcacagagt taaaatgatg tgmaaggaac    480
```

```
tgttcaatgg aaatttagaa atttctcttt ttctcaattt tagtgta          527

<210> SEQ ID NO 357
<211> LENGTH: 601
<212> TYPE: DNA
<213> ORGANISM: Homo sapiens

<400> SEQUENCE: 357
gaacaagatt ttcctgcttt taaaaatact acattaaagc tgaaaattta ggccaaaatt    60
ttcaagtggt aatagttaca ggcaattcat ctttctggtc agaaagggt gttactgcag   120 ctatttctgc ctgaaactgg gtggcactac tactttttt tttttttttt taactgagca   180
gacattttcc ttacactaaa attgagaaaa agagaaattt ctaaatttcc attgaacagt   240
tccttgcaca tcattttaac tctgtgagac agtgtcacat cgaaacgaca cactacatca   300
ygaagctttt ctaaatgacg gaggtggctt gcagctgctg acctcacttc tcttggactt   360
ggcagcaatc cacactgcct tgatcatggc agtgaaaata agatagtatt cagtattatt   420
tgtccaaatc tggcgtatca ttgcttgtgg atacatgaat gatcttggga cttgaaaaca   480
ttgctgatgg aaactcaaac aagataaagg gctaatgaca ttgataggaa acataagaag   540
aaagttattc catgacttca taagagttgt cagaatttat tatgcatgta actacagggg   600
a                                                                  601

<210> SEQ ID NO 358
<211> LENGTH: 1001
<212> TYPE: DNA
<213> ORGANISM: Homo sapiens

<400> SEQUENCE: 358
gcttaatacc tgagtgatgg aatattctgt tcaacaaacc cctctgacat aggttttgcct    60 atataataaa cctgttcatg tactcctgaa cctaaaagtt taaaaagat tatgtagaaa   120 acccaaagga atctataaaa agtctactag agctagagtg atttaacaa gatttcaata   180 cacaaattca aatgtctttc tatatattaa tgacaatcaa caataaaatt ttaaaacatt   240
attaaagtat aatgaaaata tcaactgttt agggagaaat gtaacaagaa tggtgaagga   300
cctatacact aaaaagcttc aatatgttgt tgagattaac tgaagaaggt ctaaatagat   360 tttttttca tgtctcggaa gacttaatat gtgaagatac caattcttcc ccaaatgatc   420
aacaggtgaa atgcaatccc aatcaaaatc ccagcaatta ttttaagggg gaaattggca   480
atctgattct aaaattcata yggaaaaaaa caatggagtt agaataacta aaacaagtcc   540 gaaaagaaa aagaaatgga ggactaatgc tacctgattt caagtcttat cgtataaatc   600
tacatcaata aaggacaagt tggtattggg ttaaagatag ataaatacat cagtggaata   660
gaatattgaa tccagaataa atccacacat atatggataa aaataccaga caattcagtg   720
gagatggttt tgttttaca acaaatgtta ctggaacaaa ttgatatatg tattagtcag   780
atatggctgc cataacaaag aaccacaaac aggtggttta aataatgaa ataaatttcc   840 tcagaattct ggagtatgga agcccaagat caagttgctg ggaggattcg tttcttctga   900
gtgtctcttt ttttgatgac agatgactat cttttaccaa tgtcttcact tggttttccc   960
tctgtgtgtg cctaggtcct attctccaat tcctataagg a                     1001

<210> SEQ ID NO 359
<211> LENGTH: 1001
<212> TYPE: DNA
<213> ORGANISM: Homo sapiens
```

<400> SEQUENCE: 359

```
ctaaaagttt aaaaaagatt atgtagaaaa cccaaaggaa tctataaaaa gtctactaga      60
gctagagtga ttttaacaag atttcaatac acaaattcaa atgtcttttct atatattaat    120
gacaatcaac aataaaattt taaaacatta ttaaagtata atgaaaatat caactgttta    180
gggagaaatg taacaagaat ggtgaaggac ctatacacta aaaagcttca atatgttgtt    240
gagattaact gaagaaggtc taaatagatt ttttttttcat gtctcggaag acttaatatg    300
tgaagatacc aattcttccc caaatgatca acaggtgaaa tgcaatccca atcaaaatcc    360
cagcaattat tttaagggggg aaattggcaa tctgattcta aaattcatat ggaaaaaaac    420
aatggagtta gaataactaa aacaagtccg aaaagaaaaa agaaatggag gactaatgct    480
acctgatttc aagtcttatc rtataaatct acatcaataa aggacaagtt ggtattgggt    540
taaagataga taaatacatc agtggaatag aatattgaat ccagaataaa tccacacata    600
tatgagataaa aataccagac aattcagtgg agatggtttt gttttttacaa caaatgttac    660
tggaacaaat tgatatatgt attagtcaga tatggctgcc ataacaaaga accacaaaca    720
ggtggtttaa ataatggaaa taaatttcct cagaattctg gagtatggaa gcccaagatc    780
aagttgctgg gaggattcgt ttcttctgag tgtctctttt tttgatgaca gatgactatc    840
ttttaccaat gtcttcactt ggtttttccct ctgtgtgtgc ctaggtccta ttctccaatt    900
cctataagga aaccagtcat attggattag ggcccactct aatggcccca ttttacttgc    960
attatctctt taaagacact atctccagat gtagccacac t                        1001
```

<210> SEQ ID NO 360
<211> LENGTH: 1058
<212> TYPE: DNA
<213> ORGANISM: Homo sapiens

<400> SEQUENCE: 360

```
catgattagc tatgctactt tccactgctc ttagtatact gagaggcagc ataagtaaaa      60
ctaaaatatc tgaagatagc aatagactat ttaaagtaga agaagtatgc tattttttgtt    120
ttgttttcat ttcgaaggaa atatgcaaag gtttattgag tatttcagct tctcttacag    180
taggttttttt ttggattctt tctgtgtttg tctatgttga taaaacattg aaatgccata    240
tagctcaaag gtcattcact taagaaatct aagtactgat aacatcttag ccccgattct    300
tcataggcat tgttaagcct attataattt tggtwcagag agaaggtaaa ctatattcca    360
gacaggcata taaagcaatt tctcctataa ttggagttca cgaaaaattc acatatttct    420
ttttaatagt aactctcaca gcaagaacat atgtttgtaa ataatacatc acagaatctt    480
attggcagac aaggaaattc ctaaaatatt ttttactgcc acatcaatta agatatataa    540
aatacccttat atagaagatg tttgcaccca ggccaaacaa atcaaacaag aatagaagca    600
ctgacagtct tatttcaaaa ttggtttaac ttgtatttac aggatattgt agtaccttat    660
aaagttgatt gctgattggc cgtcttttac agaattctgt cagattgtta ttatttcttg    720
taaagattga ttcaaacaaa taaaaattgt caggattgga tatgtcctat agtgaggtgt    780
agttatgtca catgagattt ttaattacaa agaaatggaa aataaaatga gatagaatt    840
gagactcccc tgtcacctca caaatatgtt gaaatacaat gaaatttcca aagatgttaa    900
agcatataaa gttgaataat tcttattatg tattaaactt acagaaattt aatttctttaa    960
ctttataaga ggtagtgaaa atataaaatt aattatgaag acagagtagt cttagtcaga    1020
```

```
catggccta    taaagcatat  tcccattcgt  tacatcaa                    1058
```

<210> SEQ ID NO 361
<211> LENGTH: 1058
<212> TYPE: DNA
<213> ORGANISM: Homo sapiens

<400> SEQUENCE: 361

```
catgattagc  tatgctactt  tccactgctc  ttagtatact  gagaggcagc  ataagtaaaa    60
ctaaaatatc  tgaagatagc  aatagactat  ttaaagtaga  agaagtatgc  tattttttgtt   120
ttgttttcat  ttcgaaggaa  atatgcaaag  gtttattgag  tatttcagct  tctcttacag   180
taggttttt   ttggattctt  tctgtgtttg  tctatgttga  taaaacattg  aaatgccaya   240
tagctcaaag  gtcattcact  taagaaatct  aagtactgat  aacatcttag  ccccgattct   300
tcataggcat  tgttaagcct  attataattt  tggtacagag  agaaggtaaa  ctatattcca   360
gacaggcata  taaagcaatt  tctcctataa  ttggagttca  cgaaaaattc  acatatttct   420
ttttaatagt  aactctcaca  gcaagaacat  atgtttgtaa  ataatacatc  acagaatctt   480
attggcagac  aaggaaattc  ctaaaatatt  ttttactgcc  acatcaatta  agatatataa   540
aatacctta   atagaagatg  tttgcaccca  ggccaaacaa  atcaaacaag  aatagaagca   600
ctgacagtct  tatttcaaaa  ttggtttaac  ttgtatttac  aggatattgt  agtaccttat   660
aaagttgatt  gctgattggc  cgtcttttac  agaattctgt  cagattgtta  ttatttcttg   720
taaagattga  ttcaaacaaa  taaaaattgt  caggattgga  tatgtcctat  agtgaggtgt   780
agttatgtca  catgagattt  ttaattacaa  agaaatggaa  aataaaatga  aatagaatt    840
gagactcccc  tgtcacctca  caaatatgtt  gaaatacaat  gaaatttcca  aagatgttaa   900
agcatataaa  gttgaataat  tcttattatg  tattaaactt  acagaaattt  aatttcttta   960
ctttataaga  ggtagtgaaa  atataaaatt  aattatgaag  acagagtagt  cttagtcaga  1020
catggccta   taaagcatat  tcccattcgt  tacatcaa                          1058
```

<210> SEQ ID NO 362
<211> LENGTH: 956
<212> TYPE: DNA
<213> ORGANISM: Homo sapiens

<400> SEQUENCE: 362

```
aaaacaagga  acaaacaaac  aaaaatgtta  caaccgaaca  acagactttt  gagtcatgtt    60
tcaggccaag  aggtgatgag  ttactgtagt  tgcttgagct  ggttggtgaa  atattacctg   120
gcaacaaaac  tgaaatagaa  ggtggcttag  taaaatgcag  attcagaatg  agtgccttaa   180
ggttaaggca  tataagacca  aactgatttt  cttttttcacg  aggtcttcag  gtaaggccat   240
tgtagaagat  accttgtttg  cgaacttcag  taaattactt  cacttgtctc  atattttcat   300
tttcaggatg  gaggcttgag  attgaattgt  agtgcaatta  ggtaaatttt  tacccatttt   360
aaatataata  ttaaaatatt  aattataaat  taccttattt  gaatctggaa  taatatttat   420
tgcagggcat  ataatctaag  ctgtaaacgt  cctgtyagaa  gacaacatat  tcatcttgct   480
aaggtataag  ctatatgact  ggcactgtgc  tcaactcaga  gtcattgaat  gaacagtatt   540
tatttaatct  atgaatgaga  gcacttcaag  tatacagaaa  gatatctcaa  aagattcagc   600
cttacattgc  tcataacttc  aatgacttag  atgaaaacct  cctgaacatt  tttatcagtt   660
gtataggtac  cccaaatcat  aagggaatgt  ttatcaatta  gatgatgaaa  tggggatgca   720
actacatcat  ggcaggctaa  agcaatagaa  tgactttgac  aagaggaaat  tacatagagg   780
```

```
cacctgagtc tcctaaacca atttcaaagg tatgagaggg gggtgatata aataaatagt    840
tgatagatga aaaaactcag aagttatagt tgacagcaat tttaatataa tatgaaaaat    900
gtggttggac ttttagggaa aaaaacctaa taaaatctaa tggaaattag tggtcc        956

<210> SEQ ID NO 363
<211> LENGTH: 956
<212> TYPE: DNA
<213> ORGANISM: Homo sapiens

<400> SEQUENCE: 363
caaccgaaca acagactttt gagtcatgtt tcaggccaag aggtgatgag ttactgtagt     60
tgcttgagct ggttggtgaa atattacctg gcaacaaaac tgaaatagaa ggtggcttag    120
taaaatgcag attcagaatg agtgccttaa ggttaaggca tataagacca aactgatttt    180 cttttttcacg aggtcttcag gtaaggccat tgtagaagat accttgtttg cgaacttcag   240
taaattactt cacttgtctc atattttcat tttcaggatg gaggcttgag attgaattgt    300
agtgcaatta ggtaaatttt tacccatttt aaatataata ttaaaatatt aattataaat    360 taccttatttt gaatctggaa taatatttat tgcaggcat ataatctaag ctgtaaacgt    420
cctgtcagaa gacaacatat tcatcttgct aaggtrtaag ctatatgact ggcactgtgc    480
tcaactcaga gtcattgaat gaacagtatt tatttaatct atgaatgaga gcacttcaag    540
tatacagaaa gatatctcaa aagattcagc cttacattgc tcataacttc aatgacttag    600
atgaaaacct cctgaacatt tttatcagtt gtataggtac cccaaatcat aagggaatgt    660
ttatcaatta gatgatgaaa tggggatgca actacatcat ggcaggctaa agcaatagaa    720
tgactttgac aagaggaaat tacatagagg cacctgagtc tcctaaacca atttcaaagg    780
tatgagaggg gggtgatata aataaatagt tgatagatga aaaaactcag aagttatagt    840
tgacagcaat tttaatataa tatgaaaaat gtggttggac ttttagggaa aaaaacctaa    900
taaaatctaa tggaaattag tggtccactc atttctccac ctaggatgtt aaaaat        956

<210> SEQ ID NO 364
<211> LENGTH: 601
<212> TYPE: DNA
<213> ORGANISM: Homo sapiens

<400> SEQUENCE: 364
gtaaaacaca tagatcgctg tatccttgtt cagtaagcta caacatactc gtatctcctg     60
aaatcctggg cttaaatcga ggtctcaaag gctttgtttt gttttgttgt atggttgtat    120
ggtgagtgtg tgtgtgtgtg tgtgtgtgtg tgtttattct cctgaaattc tcctcctcac    180
ttgacttaag ctaaaagata aacgtcctct tcctttcagc cacagatggt gatggataaa    240
ttgaatgtca ttcacattat tcccttaaaa taaactctct ccctcccctc tccgtctca    300 wccttgtccc tttctttata taatgggtaa tgcgttaatg tcagcagaat agttttgggg    360
ccataatggc aagtatcacg tggatggttt agcattgttt ttagaatgct gtgaatttgg    420
gtatatgtga gttttgggga aagttttgca actatatgtt tgttaattaa atgaggacta    480
taaagtaata taaaattatg tttctggaac atattttgga agctataaag tcatctgtat    540
ttattatcca cagacataat gtcattgttc aggtcctgca accttcttat aatcaacata    600
c                                                                    601

<210> SEQ ID NO 365
```

<211> LENGTH: 601
<212> TYPE: DNA
<213> ORGANISM: Homo sapiens

<400> SEQUENCE: 365

```
agtaagctac aacatactcg tatctcctga atcctgggc ttaaatcgag gtctcaaagg    60
ctttgttttg ttttgttgta tggttgtatg gtgagtgtgt gtgtgtgtgt gtgtgtgtgt   120
gtttattctc ctgaaattct cctcctcact tgacttaagc taaaagataa acgtcctctt   180
cctttcagcc acagatggtg atggataaat tgaatgtcat tcacattatt cccttaaaat   240
aaactctctc cctcccctct cccgtctcat ccttgtccct ttctttatat aatgggtaat   300
kcgttaatgt cagcagaata gttttggggc cataatggca agtatcacgt ggatggttta   360
gcattgtttt tagaatgctg tgaatttggg tatatgtgag ttttggggaa agttttgcaa   420
ctatatgttt gttaattaaa tgaggactat aaagtaatat aaaattatgt ttctggaaca   480
tattttggaa gctataaagt catctgtatt tattatccac agacataatg tcattgttca   540
ggtcctgcaa ccttcttata atcaacatac gtgggcccag ggattttatg tatcttcgcc   600
t                                                                  601
```

<210> SEQ ID NO 366
<211> LENGTH: 1079
<212> TYPE: DNA
<213> ORGANISM: Homo sapiens

<400> SEQUENCE: 366

```
gaatttatgg tctgatggag aagggaatca ttaaagttct atgtagtgag atatccccaa    60
ggggtgtatt aggcttacca ccactggaat ctggatagat gaagacagag tggcagggaa   120
gtcgtattaa ggttctgttt ctgctgggag ccacaggtcc tcaggaagca acaagtactg   180
ggcagattga tactgtagct rggctctagc tctatacctc tagaataaag gttacaaact   240
agcaacttga aagctaaacc tggcccacag atatgtttta tttggctctt acactgttt    300
aaaaaatatt accaacattt aaaactggga agttttatga aaaacccag acttctggat   360
tctgttgaaa aaaaaaatca gaagatctgg caatactgag ctgacattcc tatatgacaa   420
caattggctg gatctatgca gcttctctcc aaaaagcaaa gaatgtgttc ttgcttaaca   480
cagtccccac cactccctca tattctccaa tcctggacct gagcgtcatt tgctatgtat   540
cgccatttgc catgaagttt tacactctac agaaatataa ttttttgta gaagactatg    600
ctttaatcaa gatcaggata atataaagtg agatctgaaa gtggaaaaaa gataaatgtc   660
caacaatgat agactggatt aagaaaatgt ggcacatata caccgtggag tactatgcag   720
ccaaaaaaaa cgatgagttc atgtcctttg tagggacatg gatgaagctg gaaaccacca   780
ttctcagcaa actatcgcaa ggacaaaaaa ccaaacgccg catgttctca ctcataggtg   840
ggaattgaac aatgagaaca cttgggcaca ggaaggggaa catcacacac cgggccctgt   900
tgtggggtgg ggggaggagg gagggatagc atttggagat atacctaatg ttaaatgact   960
agtttctggg tgcagcacac catcatggca catgtataca tatgtaacta acctgcacat  1020
tgtgcacatg taccctaaaa cttaaagtat aattttaaa aaaagatatt ttcttatct   1079
```

<210> SEQ ID NO 367
<211> LENGTH: 501
<212> TYPE: DNA
<213> ORGANISM: Homo sapiens

<400> SEQUENCE: 367

```
ataaatttc tcttccctca agaatttatg gtctgatgga gaagggaatc attaaagttc     60
tatgtagtga gatatcccca aggggtgtat taggcttacc accactggaa tctggataga    120
tgaagacaga gtggcaggga agtcgtatta aggttctgtt tctgctggga gccacaggtc    180
ctcaggaagc aacaagtact gggcagattg atactgtagc tgggctctag ctctatacct    240
ctagaataaa kgttacaaac tagcaacttg aaagctaaac ctggcccaca gatatgtttt    300
atttggctct tacactgttt taaaaaatat taccaacatt taaaactggg aagttttatg    360
aaaaaaccca gacttctgga ttctgttgaa aaaaaaaatc agaagatctg gcaatactga    420
gctgacattc ctatatgaca acaattggct ggatctatgc agcttctctc caaaaagcaa    480
agaatgtgtt cttgcttaac a                                              501
```

```

<210> SEQ ID NO 368
<211> LENGTH: 1001
<212> TYPE: DNA
<213> ORGANISM: Homo sapiens

<400> SEQUENCE: 368
tgaagaagcc gcctggcttc ttgtttcttc tcatagcaaa atgcaatgag aaagagataa     60
tttgagaaaa gaaccgttta aacaaaaaga aaccaagaca taatgatttt ggaaattctc    120
agtttattca gactgcaaaa gatattaaaa taaagaaact cagtaacagg gatagataat    180
ctaaagaaaa agcctaggac acggctgtag taaccttctg tttttatacc tcagcaattt    240
gctaatgcct caaaaagatc aaaagtactc aaatataaag ggctctttga agagattaga    300
tttcctcaat caaaccaaag agcatcgagg aagcttaagg ttactgtccc tcacatatct    360
cagcagaagg caaaaataga agactgatta tctaagaaag atctctgaaa gagtctcata    420
ttatggagtg aacccctgtg gcatacatgg gagacccact tggttcttga gaattttata    480
tcaggagaaa cactgtcagt ytgtattgaa aggaacagag aaaatacgaa attaaagaag    540
actattaaac ctccaaaatt ctggcaggaa agaagcttac acagctactc agttgcaaag    600
atctgccact tttcatatac atgaaaggac tcagaggagg aagccacagg tttagaagga    660
aaagctaaaa gcaacatcgt attagtcttg gatctaggaa cctaatttct ctagcagaat    720
ctagaaatgg cttgggacaa gtgattgttt ttttacctag gattttctcc ctcttgaaaa    780
caggactgtc tgtaactatt atcctatgcc tgccctacca tcatatttca gaaacaggta    840
acttatgttt tcactttcaa agattcacaa taaagagaaa ttgtacctca gaatggatta    900
taccagagct ttcctcatgc ataaattaaa taatttaggt tatgtgattt gaagcttttg    960
agtgggtgag gtgacatttt ggatgctgag ttggtgccgt a                       1001
```

```

<210> SEQ ID NO 369
<211> LENGTH: 1001
<212> TYPE: DNA
<213> ORGANISM: Homo sapiens

<400> SEQUENCE: 369
tcttctcata gcaaaatgca atgagaaaga gataatttga gaaaagaacc gtttaaacaa     60
aaagaaacca agacataatg attttggaaa ttctcagttt attcagactg caaaagatat    120
taaaataaag aaactcagta acagggatag ataatctaaa gaaaaagcct aggacacggc    180
tgtagtaacc ttctgttttt atacctcagc aatttgctaa tgcctcaaaa agatcaaaag    240
tactcaaata taaagggctc tttgaagaga ttagatttcc tcaatcaaac caaagagcat    300
```

```
cgaggaagct taaggttact gtccctcaca tatctcagca gaaggcaaaa atagaagact      360
gattatctaa gaaagatctc tgaaagagtc tcatattatg gagtgaaccc ctgtggcata      420
catgggagac ccacttggtt cttgagaatt ttatatcagg agaaacactg tcagtctgta      480
ttgaaaggaa cagagaaaat rcgaaattaa agaagactat taaacctcca aaattctggc      540
aggaaagaag cttacacagc tactcagttg caaagatctg ccacttttca tatacatgaa      600
aggactcaga ggaggaagcc acaggtttag aaggaaaagc taaaagcaac atcgtattag      660
tcttggatct aggaacctaa tttctctagc agaatctaga aatggcttgg acaagtgat       720
tgttttttta cctaggattt tctccctctt gaaaacagga ctgtctgtaa ctattatcct      780
atgcctgccc taccatcata tttcagaaac aggtaactta tgttttcact ttcaaagatt      840
cacaataaag agaaattgta cctcagaatg gattatacca gagctttcct catgcataaa      900
ttaaataatt taggttatgt gatttgaagc ttttgagtgg gtgaggtgac attttggatg      960
ctgagttggt gccgtagtga gtccagaatt ctgcggaact t                         1001

<210> SEQ ID NO 370
<211> LENGTH: 601
<212> TYPE: DNA
<213> ORGANISM: Homo sapiens

<400> SEQUENCE: 370
ctctagactc ctcctgtatt ttaatttagc cacttttta  gggcctacaa ttttagatct       60
ccacagggct cttgaaactt cttgaacctc atcagtaaca tgtccattag tggcatgacc      120
caagagttct agaacatcta ttcagcaagt gtgtatctgg taagtgaata ttccttctat      180
gtgttccctt ttgcatcaaa ctacacactg tcattcctcc tttatctcca aaagcttgaa      240
aattcctcac ttgtatctca ttctttctct cttagaaaac tgatcacctc tgatgaatta      300
raacggaatg accaagcttt gggagaggca aagaatctc  ggtgttaaag actcagagtt      360
taagaagcaa caaaaagatt atacagatgt gaatatgtga ccttcctcca ccagggcatg      420
ttgccttgga gtaagataat ctaagcacac acttcatagc ctgagaacaa ttttggaagt      480
ctttgcttta tggatattta cataaagcaa atatggatat ttacctaaag gctggaccaa      540
ggcctaattc ctctagagcc ccttgatcat gaacaccatt cctgtcatga ttcttaaggt      600
c                                                                      601

<210> SEQ ID NO 371
<211> LENGTH: 601
<212> TYPE: DNA
<213> ORGANISM: Homo sapiens

<400> SEQUENCE: 371
acaagctcca gccatggacg caattccttc tagaagcaaa atttatctct agactcctcc       60
tgtattttaa tttagccact tttaggggc  ctacaatttt agatctccac agggctcttg      120
aaacttcttg aacctcatca gtaacatgtc cattagtggc atgacccaag agttctagaa      180
catctattca gcaagtgtgt atctggtaag tgaatattcc ttctatgtgt tcccttttgc      240
atcaaactac acactgtcat tcctccttta tctccaaaag cttgaaaatt cctcacttgt      300
rtctcattct ttctctctta gaaaactgat cacctctgat gaattagaac ggaatgacca      360
agctttggga gaggcaaaag aatctcggtg ttaaagactc agagtttaag aagcaacaaa      420
aagattatac agatgtgaat atgtgacctt cctccaccag gcatgttgc  cttggagtaa      480
gataatctaa gcacacactt catagcctga gaacaatttt ggaagtcttt gctttatgga      540
```

```
tatttacata aagcaaatat ggatatttac ctaaaggctg gaccaaggcc taattcctct    600
a                                                                   601
```

<210> SEQ ID NO 372
<211> LENGTH: 701
<212> TYPE: DNA
<213> ORGANISM: Homo sapiens

<400> SEQUENCE: 372

```
gaagatgcac tctaatgttt tttcccagaa gctctgtagg tttagctttt acctttctgg    60
gtttgttttg ttttgttttt tgagatggag tcccactcgt gtcacccagg ctggagtaca   120
atggtgcaat ctcggttcac tgcaacctcc acctcccggg ttcaagcaat tccctgtct   180
ccacctctcg agtagctggg atgggaggcg cctgccacca tacctggcta attttcatat   240
ttttagtaaa gatagggttt caccatgtta gccaggctgg tctcgaactc ctgacctcaa   300
gtgatccacc cgcctcagct tcccaaagtg ctgggattac aggcgtgagc cactgcgccc   360
agccctagct ttttggtcta tgattcctcc caaattaatt tctgtgaacc attaccttaa   420
gatgttgaga tttaatgtcc agaatctcat ttgttcacct ttgaaaatta agaaaccctg   480
gcacagtgtt gactggagcc wcttaccttta atagaaaata aagctcacat atatccataa   540
tgaaaagcag agaccagcac aaccatagtc acctgacagt tttaaaatcc aaggccagga   600
tcttctcaac tcaggcccac tcacttactc cacaacatac ttcttctttc ctcagcatct   660
actacttgtg ctgggacctt ggtcttccca ttgttcatgt c                        701
```

<210> SEQ ID NO 373
<211> LENGTH: 701
<212> TYPE: DNA
<213> ORGANISM: Homo sapiens

<400> SEQUENCE: 373

```
agatggagtc ccactcgtgt cacccaggct ggagtacaat ggtgcaatct cggttcactg    60
caacctccac ctcccgggtt caagcaattc cctgtctcc acctctcgag tagctgggat   120
gggaggcgcc tgccaccata cctggctaat tttcatattt ttagtaaaga tagggtttca   180
ccatgttagc caggctggtc tcgaactcct gacctcaagt gatccacccg cctcagcttc   240
ccaaagtgct gggattacag gcgtgagcca ctgcgcccag ccctagcttt ttggtctatg   300
attcctccca aattaatttc tgtgaaccat taccttaaga tgttgagatt taatgtccag   360
aatctcattt gttcaccttt gaaaattaag aaaccctggc acagtgttga ctggagccac   420
ttaccttaat agaaaataaa gctcacatat atccataatg aaaagcagag accagcacaa   480
ccatagtcac ctgacagttt waaaatccaa ggccaggatc ttctcaactc aggcccactc   540
acttactcca acatactt cttctttcct cagcatctac tacttgtgct gggaccttgg   600
tcttcccatt gttcatgtca ttcttttcct cacagttccc attctttcct ccctgaaata   660
aagaaatttc aaaatatacc atgtttcatg aaaaagacaa a                        701
```

<210> SEQ ID NO 374
<211> LENGTH: 701
<212> TYPE: DNA
<213> ORGANISM: Homo sapiens

<400> SEQUENCE: 374

```
gatttccacc ctcaggtgat ggggatggtt gaacatccaa cacctgaaac aggacagacg    60
```

```
atattgacag tacttgttag ttgcatataa tcacagacca gtggaaacag atgaaccaca      120
cagggccaca gcggggtttc actggggaac agagtgaaca atcaggaggt gtgggaggca      180
ggtttagtag tttaaagagg ttgaggtgtc ccctggatc  ccatgggagg atcacattgg      240
ctcatttgaa ttatcatacg gactggcagg gaactgaaat cttctactca gggataagca      300
gaaactgtcc ctggtttcct tgataaaaag ggttgtttga taggggacct tatccatggg      360
aggaaagtga ggagggaaat ttgtggctaa gccattcaag gccctcccag ttttactaga      420
tgtcaaggca gcacacgtaa tattgggact taatttagc  cacataacta ataaatttgt      480
aagtatgtgc aacggctcac rcttgcttcc agaatggcac ctaaaaaaca gatttacctc      540
tccccaaatt cagatatgga attaaatgta atgtcaggaa aattgtctaa gagttggaaa      600
tgggaaaaaa atgttctttt ggtggagtta tggactccag aggttatcag attctattga      660
ataacgtact tttgattgta tttgtaacaa ttaggctatt t                          701

<210> SEQ ID NO 375
<211> LENGTH: 1001
<212> TYPE: DNA
<213> ORGANISM: Homo sapiens

<400> SEQUENCE: 375
gcatataatc acagaccagt ggaaacagat gaaccacaca gggccacagc ggggtttcac       60
tggggaacag agtgaacaat caggaggtgt gggaggcagg tttagtagtt taaagaggtt      120
gaggtgtccc cctggatccc atgggaggat cacattggct catttgaatt atcatacgga      180
ctggcaggga actgaaatct tctactcagg ataagcaga  aactgtccct ggtttccttg      240
ataaaaaggg ttgtttgata ggggaccttt ccatgggag  gaaagtgagg agggaaattt      300
gtggctaagc cattcaaggc cctcccagtt ttactagatg tcaaggcagc acacgtaata      360
ttgggactta attttagcca cataactaat aaatttgtaa gtatgtgcaa cggctcacac      420
ttgcttccag aatggcacct aaaaaacaga tttacctctc cccaaattca gatatggaat      480
taaatgtaat gtcaggaaaa ytgtctaaga gttggaaatg ggaaaaaaat gttcttttgg      540
tggagttatg gactccagag gttatcagat tctattgaat aacgtacttt tgattgtatt      600
tgtaacaatt aggctatttg tgaactcggt aggggtagaa atcgagttgt agaaaatgga      660
tggtaatgca agtgattttt gaccatatca atgcaaatga attctgttgg tagaaatatt      720
catttccaca ctgtagatga ccctaaacat atgtcattac attatatttt attgccttat      780
agactattaa ccaattttga atcatacagt agcaaattta tttcagcatt cttgtgtgta      840
tgtgtttata tatacacgtg catatgtatt taagatatat aattgtatat tcttcaaatt      900 cttcttgaa caggttttgaa cctcttatta gtttcctcat taaggaattt aataagacct      960
ttaatgcatg tttgtatttt catgagagtc attattttac c                         1001

<210> SEQ ID NO 376
<211> LENGTH: 695
<212> TYPE: DNA
<213> ORGANISM: Homo sapiens

<400> SEQUENCE: 376
tgctccttca ttagtgcaat ggaacagcaa atcaggatac tttcacagtt ctcttaagtg       60
agcctagaag tggggagctg cttgttcaca aacttgaagc ctgaatatgt taatattctt      120
tcagtggccg gacgcggtgg ctcatgcctg taatcccaac actttgggag gccgaggtag      180
gcagatcaac ctgaagtcag gagttcgagg ccagcctggc caacatggtg aaaccccacc      240
```

```
tgttggtctg tactaaaaat agaaaaatta gctgggcatg gtggcgcatg cctgtaatcc    300
cagctactca ggaggctgtg cagaagaat cgcctgcacc tgggaggcag aggttgcttt     360
gagttgatat cgtgtcactg cactccagcc tgggcaacag agtgagatcc tttcagaaac    420
ctgctgtctg tatttggata caattaaaaa aaaaaaaaag atgagacagg caggtgcgaa    480
agaaataaaa gtcamaactg atccagttgg gaaactcaga attgacagtt acgtgtcctt    540
tcatttattg atattttgag attcacaggg gtttaaactt tattttttcca agactgaata   600 gttcccacct ccttccata tataaaattt gagtagctgg ggagatttaa aagaggctcc    660
ccataaactc agaagttaaa agagacaagg gtccc                               695
```

<210> SEQ ID NO 377
<211> LENGTH: 601
<212> TYPE: DNA
<213> ORGANISM: Homo sapiens

<400> SEQUENCE: 377

```
aaccccacct gttggtctgt actaaaaata gaaaaattag ctgggcatgg tggcgcatgc    60
ctgtaatccc agctactcag gaggctgtgg cagaagaatc gcctgcacct gggaggcaga   120
ggttgctttg agttgatatc gtgtcactgc actccagcct gggcaacaga gtgagatcct   180
ttcagaaacc tgctgtctgt atttggatac aattaaaaaa aaaaaaaaga tgagacaggc   240
aggtgcgaaa gaaataaaag tcacaactga tccagttggg aaactcagaa ttgacagtta   300
sgtgtccttt catttattga tattttgaga ttcacagggg tttaaacttt attcttccaa   360
gactgaatag ttcccacctc ccttccatat ataaaatttg agtagctggg gagatttaaa   420
agaggctccc cataaactca gaagttaaaa gagacaaggg tcccagtaaa tacaaaatga   480 ttgggggttga ggaggcagat tttctgtcct cagtgaagtt tgttggttgg ttggttggtt   540
ggttggttaa ttggttggtt tttgagtcag ggtctcactt tgtcacccaa gctggagtgc   600
a                                                                   601
```

<210> SEQ ID NO 378
<211> LENGTH: 663
<212> TYPE: DNA
<213> ORGANISM: Homo sapiens

<400> SEQUENCE: 378

```
tgtagcaaca ggagggatga gacccaaagg tctgaaaagc cagtatttta agaagtcttg    60
gaaaatgtgg aggttgaaaa atctaacagg agtgcttgct tcagcagcaa tttagagtag   120
attagcatgg cctctgcgcc aggatgacat gcacattcct aaaagtgttc cgtgttttaa   180 aaaaagaga gagacagaat ctaagggat gtgtacattt gctagagcta ctataacaaa    240
gtaccagagg cagggtcact tcaacaacag aaatttattt ctcacagttc tggaggctag   300
acgtccaaga ttaaggtgtt gactgggttg aattcagccc ataacaggaa ataaggagtt   360
aaataaagca cttgcttcta ttgtttgtac ctaaacttaa cagaayacag taagtaacaa   420
gtcattggga tgcagaaaag aaaaagaga gtgaaggaag gagagaaggt gaagggagaa   480
tggaagagag gaagggaggg aggaaagaaa agtttgatga atgattgcag tctaaactgg   540
ttcaaacaag agatcttgtt taattaagga attcatccca tctctgccta ttaggaggag   600
gaaaaagtct aaaatagaag atggtgaaag ttggatgacc ccaggcatta aggccattca   660
tct                                                                 663
```

<210> SEQ ID NO 379
<211> LENGTH: 662
<212> TYPE: DNA
<213> ORGANISM: Homo sapiens

<400> SEQUENCE: 379

```
ttaagaagtc ttggaaaatg tggaggttga aaaatctaac aggagtgctt gcttcagcag      60
caatttagag tagattagca tggcctctgc gccaggatga catgcacatt cctaaaagtg     120
ttccgtgttt taaaaaaaag agagagacag aatctaaggg gatgtgtaca tttgctagag     180
ctactataac aaagtaccag aggcagggtc acttcaacaa cagaaattta tttctcacag     240
ttctggaggc tagacgtcca agattaaggt gttgactggg ttgaattcag cccataacag     300
gaaataagga gttaaataaa gcacttgctt ctattgtttg tacctaaact taacagaaca     360
cagtaagtaa caagtcattg ggatgcagaa aagaaaaaag agagtgaagg aaggagaraa     420
ggtgaaggga gaatggaaga gaggaaggga gggaggaaag aaaagtttga tgaatgattg     480
cagtctaaac tggttcaaac aagagatctt gtttaattaa ggaattcatc ccatctctgc     540
ctattaggag gaggaaaaag tctaaaatag aagatggtga agttggatg accccaggca      600
ttaaggccat tcatctttaa ctgttatgct tggatcatgc aaatgtgtct ggtagctaca     660
ag                                                                     662
```

<210> SEQ ID NO 380
<211> LENGTH: 615
<212> TYPE: DNA
<213> ORGANISM: Homo sapiens

<400> SEQUENCE: 380

```
ttccatacat tccttccaca ccattgccct taacctttca aattcctgct taaaactaat      60
cccattttta tggctgacct caccctgtat caaaaactcc gacatccctt tacgacagag     120
agcacaaact agtggtccaa aatgtcatgg gggtcttctc agagttgttt tttcaatcag     180
gaaatttcac ataaaaatat ggatttctga tttctctttt aaaaacagaa aaacgagcca     240
ccagtgggag cactgcaggt atctgtgtga gaccygtact tcacaactcc tgctttccct     300
ccataaagta gcttgcattt tccacattga ctttgcagtt ctttggtatc tgtattggtt     360
ttaagataat ttctactata tcacatatct cctcacagta caaagatatc attttcttc      420
cctttctttt ttaaaaaatt tgtattttta attttgtgg gtacacagta gatatttatg     480
gggcatatga ggtattttat aggcatataa tatgtactag ggtaagtggg gtattcatca     540
cctcaagcat ttatcctttc tttgtgtaaa atatagcatt ttctgaacac tatgaatact     600
taagtacaag gatca                                                       615
```

<210> SEQ ID NO 381
<211> LENGTH: 994
<212> TYPE: DNA
<213> ORGANISM: Homo sapiens

<400> SEQUENCE: 381

```
tcaaagtgta acaaatttcc tttcctcata aactagcaga cattctatcc cctcattatt      60
gtaacacatt tctaatatct ttctcaaatt gtcttcctgt attacaatgc actcaccttg     120
gcttagaatg tctgagacaa gaaaatctat tcaccattcc cacagatgac tccctcactc     180
tcctcccaag tcttccatac attccttcca caccattgcc cttaaccttt caattcctg     240
cttaaaacta atcccatttt tatggctgac ctcaccctgt atcaaaaact ccgacatccc     300
```

```
tttacgacag agagcacaaa ctagtggtcc aaaatgtcat gggggtcttc tcagagttgt    360
tttttcaatc aggaaatttc acataaaaat atggatttct gatttctctt ttaaaaacag    420
aaaaacgagc caccagtggg agcactgcag gtatctgtgt gagacctgta cttcacaact    480
cctgctttcc ctccataaag yagcttgcat tttccacatt gactttgcag ttctttggta    540
tctgtattgg ttttaagata atttctacta tatcacatat ctcctcacag tacaaagata    600
tcattttctt tccctttttct ttttaaaaaa tttgtatttt taattttttgt gggtacacag    660
tagatattta tggggcatat gaggtatttt ataggcatat aatatgtact agggtaagtg    720
gggtattcat cacctcaagc atttatcctt tctttgtgta aaatatagca ttttctgaac    780
actatgaata cttaagtaca aggatcaagt cataggatttt ggaattgatt tttaaaatat    840
gttgaccaaa gtgctcttat catcaaactt aacatcacta atgaaggatg aacatcccaa    900
atctgaaaat ccaaaatcca aaatgctcca taatctaaaa cttgttgagc accaacatga    960
tgcttaaagg aaatgctcct ggagcatttc agat                                994
```

<210> SEQ ID NO 382
<211> LENGTH: 1001
<212> TYPE: DNA
<213> ORGANISM: Homo sapiens

<400> SEQUENCE: 382

```
ctatgagaaa tattttaaaa gtggttagga acaattcata gcactgacat gttatcagta     60
aaaatagaag aaaataaatt aatattatga aatattaatt atatttcatt aattatgtaa    120
tatgaattat gttttagctc aaatatttcc caagggacaa ttaagtaaat gaaaaataca    180
cacagattaa aataataaat agagaaggag atattaatga ggtacaaaaa gaaaaaatac    240
atgtaatcac atgaaatgct attatttgaa agattaacaa aacttgtaaa ctacctgcta    300
acttgatcaa agaaaaaaat cgagaaacca tatgcgcaat taatagtaag agggaaataa    360
acattgaaac agaagacatt tgaaatacca tataagactg ggtttcagag ctctatgtac    420
gtaaattgat aatgtcctgg agaagtgcag atgaccaaaa tggacaccctt tcaacttaga    480
aatcataaac agattcattt ycttaaagtt aatgaaaaga attaacagac cctcctcaaa    540
aaagacatat atgcggccta caatcatatg aaaaaaagtt caacattact gttcattaga    600
gaaatgcaaa tcaaaaccac aatgagatac catctcacac cagtcagaat ggctattatt    660
aagaagtcaa aaaataaaag atgctggcga ggttgtggag aaaaaagaat gcttttatac    720
acttggtggg aatgtaaatt agttcagtca ttgtggaaga ctttgatgat tcctagaaga    780
cctaaataca gaactactat ttgacccaac aatcccatta ctgggtatat actcaaatga    840
ctataaatca ttctattata aagacacatg catggatatg ttcattacag cactatgcac    900
aatagcaaag acttggaatc aacatgaatg tccatcaatg atagactaga taagaaaat    960
gtggtacaca tataccatgg aatactatgc agccataaaa a                       1001
```

<210> SEQ ID NO 383
<211> LENGTH: 1001
<212> TYPE: DNA
<213> ORGANISM: Homo sapiens

<400> SEQUENCE: 383

```
tcagtaaaaa tagaagaaaa taaattaata ttatgaaata ttaattatat ttcattaatt     60
atgtaatatg aattatgttt tagctcaaat atttcccaag ggacaattaa gtaaatgaaa    120
```

| | |
|---|---|
| aatacacaca gattaaaata ataaatagag aaggagatat taatgaggta caaaaagaaa | 180 |
| aaatacatgt aatcacatga aatgctatta tttgaaagat taacaaaact tgtaaactac | 240 |
| ctgctaactt gatcaaagaa aaaaatcgag aaaccatatg cgcaattaat agtaagaggg | 300 |
| aaataaacat tgaaacagaa gacatttgaa ataccatata agactgggtt tcagagctct | 360 |
| atgtacgtaa attgataatg tcctggagaa gtgcagatga ccaaaatgga caccttttcaa | 420 |
| cttagaaatc ataaacagat tcatttcctt aaagttaatg aaaagaatta acagaccctc | 480 |
| ctcaaaaaag acatatatgc rgcctacaat catatgaaaa aaagttcaac attactgttc | 540 |
| attagagaaa tgcaaatcaa aaccacaatg agataccatc tcacaccagt cagaatggct | 600 |
| attattaaga agtcaaaaaa taaaagatgc tggcgaggtt gtggagaaaa aagaatgctt | 660 |
| ttatacactt ggtgggaatg taaattagtt cagtcattgt ggaagacttt gatgattcct | 720 |
| agaagaccta aatacagaac tactatttga cccaacaatc ccattactgg gtatatactc | 780 |
| aaatgactat aaatcattct attataaaga cacatgcatg gatatgttca ttacagcact | 840 |
| atgcacaata gcaaagactt ggaatcaaca tgaatgtcca tcaatgatag actagataaa | 900 |
| gaaaatgtgg tacacatata ccatggaata ctatgcagcc ataaaatga aggagatcat | 960 |
| gccctttgca gggacacgaa tagaggtgga ggccattatc c | 1001 |

<210> SEQ ID NO 384
<211> LENGTH: 501
<212> TYPE: DNA
<213> ORGANISM: Homo sapiens

<400> SEQUENCE: 384

| | |
|---|---|
| agttgcttga aagcaaagtt ctcgcagtag ctctctatct agaaggaggc attttattta | 60 |
| tgtaaggaag tcacctaaaa gaaaattcat ttgttatggt gtggctttaa gagttactta | 120 |
| cttttaatgg aatccccag ataataataa attctgaaaa aaaaaaatca gaatcatggc | 180 |
| atgttaaaac tggatacatt cctagaaata gatggaaact gctcttgcaa aaagcttagc | 240 |
| acatgttaaa rcattttaga aacaatttgc caaagtttat ttagtctagt gatttcgaca | 300 |
| ggttaaatgg acccttttgag atctttttttc ctcaagtaca aaggctcact tgcttaatga | 360 |
| acacagtccc agaaaagcag ggggctgaac cttggctcta ccatcttacc taagattcta | 420 |
| gagttagcaa agggtttcca caagcccaaa ttattatgtt taatcttttc aattatctgt | 480 |
| gaagcattag gttggtgcaa a | 501 |

<210> SEQ ID NO 385
<211> LENGTH: 501
<212> TYPE: DNA
<213> ORGANISM: Homo sapiens

<400> SEQUENCE: 385

| | |
|---|---|
| gaggcatttt atttatgtaa ggaagtcacc taaaagaaaa ttcatttgtt atggtgtggc | 60 |
| tttaagagtt acttactttt aatggaatcc cccagataat aataaattct gaaaaaaaaa | 120 |
| aatcagaatc atggcatgtt aaaactggat acattcctag aaatagatgg aaactgctct | 180 |
| tgcaaaaagc ttagcacatg ttaaagcatt ttagaaacaa tttgccaaag tttatttagt | 240 |
| ctagtgattt ygacaggtta aatggaccct ttgagatctt ttttcctcaa gtacaaaggc | 300 |
| tcacttgctt aatgaacaca gtcccagaaa agcaggggc tgaaccttgg ctctaccatc | 360 |
| ttacctaaga ttctagagtt agcaaagggt ttccacaagc ccaaattatt atgtttaatc | 420 |
| ttttcaatta tctgtgaagc attaggttgg tgcaaaagta actgcaggtt ttgacattaa | 480 |

```
aactggcaaa aactgcaata a                                              501
```

<210> SEQ ID NO 386
<211> LENGTH: 703
<212> TYPE: DNA
<213> ORGANISM: Homo sapiens

<400> SEQUENCE: 386

```
gacaccagtt agcatattgt cgcggggggag aggggtggga aaggcgagag aacagcatgt    60
ggtccagagg ccatacccag atggaggctg cagtcagctc cccagtcaaa ggcaaagccc   120
aagtcaaagc catgcttccc tcttgcccac ctgctccaat gccacccaca gagagtgcgc   180
cacagctcac aggatgcagg tctggttgaa tcttaacaat aactttgtaa gggaggtgtc   240
attagctcca ttctcctggc aggaggatga ggctcaaggc agctaaaggc ttttgctgaa   300
catcaagtgg tgagccagga ctcaawgcca gatcttcttg tttccctgtt aggtgtatgt   360
agcacaactg gtatctgcag actatgctgc tggaagggct agccgtcact gttatcacag   420
cgactgctgc ctgagatatg ccaggtactg ctgcaagaag tttacaaata taagctcact   480
tgatcttcat aacatactac ctaggtacaa tcattatatt tatttgacag atacagagac   540
agaggggaca cagaaaggat tagtaacttg ccccaaacca cacagccagc aaggtgtaag   600
tgagcacctg cagtctagat gagacaccac tcaaaacgtc attttctgg cagccccgtg    660
cagttaccac agtggtcacc ccagtggtca gctaaaggcc aag                     703
```

<210> SEQ ID NO 387
<211> LENGTH: 704
<212> TYPE: DNA
<213> ORGANISM: Homo sapiens

<400> SEQUENCE: 387

```
gcatattgtc gcgggggaga ggggtgggaa aggcgagaga acagcatgtg gtccagaggc    60
catacccaga tggaggctgc agtcagctcc ccagtcaaag gcaaagccca agtcaaagcc   120
atgcttccct cttgcccacc tgctccaatg ccacccacag agagtgcgcc acagctcaca   180
ggatgcaggt ctggttgaat cttaacaata actttgtaag ggaggtgtca ttagctccat   240
tctcctggca ggaggatgag gctcaaggca gctaaaggct tttgctgaac atcaagtggt   300
gagccaggac tcaatgccag atcttcttgt ttccctgtta ggtgtwtgta gcacaactgg   360
tatctgcaga ctatgctgct ggaagggcta gccgtcactg ttatcacagc gactgctgcc   420
tgagatatgc caggtactgc tgcaagaagt ttacaaatat aagctcactt gatcttcata   480
acatactacc taggtacaat cattatattt atttgacaga tacagagaca gaggggacac   540
agaaaggatt agtaacttgc cccaaaccac acagccagca aggtgtaagt gagcacctgc   600
agtctagatg agacaccact caaaacgtca ttttctggc agccccgtgc agttaccaca    660
gtggtcaccc cagtggtcag ctaaaggcca agcccaccgt ttct                    704
```

<210> SEQ ID NO 388
<211> LENGTH: 975
<212> TYPE: DNA
<213> ORGANISM: Homo sapiens

<400> SEQUENCE: 388

```
gacttaagac aagggggtct taatttgatt attttttttct gttttatatg atttctatga    60
aaactacaac aaaataaagt taattctatt taagtgactt tttaatgaat tgcctttgtt   120
```

| | |
|---|---|
| agaaaaaaaa ttaagtgttt ttgtctcact ctgtcaccca ggctggagca cagtggtgtg | 180 |
| atcatggctt actgcagcca tgacctcccg ggctcaggtg atcctcccac ctcagcttcc | 240 |
| caaatagatg ggactacagt tgtgtgccac aacgcctggc taattttgt atttttttgt | 300 |
| agagacaggg tctcaccagg ttgcccaggc tgatcttgaa ctccttggct caagcgatcc | 360 |
| acccacctca gcctccctga gtgctgggat tacaggcatg agccagcgca cccagccaga | 420 |
| attacatttt tttaaatggt actgtcctag aaaatccagg atgtgcagtg atcaygtatg | 480 |
| aatgcatgga cctgcacaca caggagtgaa caaaagaccc accctgcca ggtcaccact | 540 |
| catatctcac cccagcccac gctagctcac actcctcccc acacaccact gacctcatca | 600 |
| ttgctaggta cccacttgac ttctcaacag gttcaagaca attggccttc ctcgtctctt | 660 |
| ctagaaacac cctctttct gggctttgtg taacacctgg tctttctccc ctctctggcc | 720 |
| acttctcagc ttttcttttt ctttctttct tttttttttt ttttttttg ccacttcctc | 780 |
| ttcctctaca tcaagcttgt ccaacccaca gcccaggaca gctttgaatg cagcctaaca | 840 |
| caaattcgta agctttctta aaacattatg agatgtgtgt gtgtgtgtgt gtgtgtgtgt | 900 |
| gtgtgtgtgt gtgtgtgt gtttagctca tcagctatcg ttattgttag tgtattttat | 960 |
| gtgtggccca agaca | 975 |

<210> SEQ ID NO 389
<211> LENGTH: 976
<212> TYPE: DNA
<213> ORGANISM: Homo sapiens

<400> SEQUENCE: 389

| | |
|---|---|
| gacttttaa tgaattgcct tgttagaaa aaaaattaag tgttttgtc tcactctgtc | 60 |
| acccaggctg gagcacagtg gtgtgatcat ggcttactgc agccatgacc tcccgggctc | 120 |
| aggtgatcct cccacctcag cttcccaaat agatgggact acagttgtgt gccacaacgc | 180 |
| ctggctaatt tttgtatttt tttgtagaga cagggtctca ccaggttgcc caggctgatc | 240 |
| ttgaactcct tggctcaagc gatccaccca cctcagcctc cctgagtgct gggattacag | 300 |
| gcatgagcca gcgcacccag ccagaattac attttttaa atggtactgt cctagaaaat | 360 |
| ccaggatgtg cagtgatcac gtatgaatgc atggacctgc acacacagga gtgaacaaaa | 420 |
| gacccacccc tgccaggtca ccactcatat ctcaccccag cccacgctag ctcacrctcc | 480 |
| tccccacaca ccactgacct catcattgct aggtacccac ttgacttctc aacaggttca | 540 |
| agacaattgg ccttcctcgt ctcttctaga aacaccctct tttctgggct tgtgtaaca | 600 |
| cctggtcttt ctccctctc tggccacttc tcagcttttc ttttctttc tttctttttt | 660 |
| tttttttt ttttgccact tcctcttcct ctacatcaag cttgtccaac ccacagccca | 720 |
| ggacagcttt gaatgcagcc taacacaaat tcgtaagctt tcttaaaaca ttatgagatg | 780 |
| tgtgtgtg tgtgtgtg tgtgtgtgtg tgtgtgtg tgtgttta gctcatcagc | 840 |
| tatcgttatt gttagtgtat tttatgtgtg cccaagaca tttcttcttc cagtgtggcc | 900 |
| cagggaagcc aaaagattgg acaccctgc tctacaacat ctcaatatag gcctttttca | 960 |
| tgtttcattc tagatt | 976 |

<210> SEQ ID NO 390
<211> LENGTH: 801
<212> TYPE: DNA
<213> ORGANISM: Homo sapiens

<400> SEQUENCE: 390

```
atccagacgg tgcccatact ccctgctctg tctagatggt gtccacattc cctgctccgt    60
ctagactgtg cccatattcg ctgctggctg caaatgcgag gagttgacag cagcctcccc   120
tttacaaggc aggaggtgcc actgttcgcc attgtctcca cctagggctt cacttgcttt   180
ctatctgcag acatcagagg gacccacatc tctctgttct gacacgctgt gtgttgatgg   240
cagagtttaa ttatccacat gcaatcttac tttccttatt cccaagtccg tggggctgcc   300
tcatcaaagc attgtaagaa actgataacca tcttctagaa gtatcatagt gatattaaga   360
acacacatca cagatcatag taaatggctt taattttta rcgaaatctc actactgcaa   420
atgcattgtt gtcctagcta atgaatgcat agagtattgc ctgcaaaata ataattgaga   480
ttctatttt aagaagctta gaacagtaca tggtgcatag caaagactct gtgtatgtga   540
agccagattt taaatatgg taacaagtgt ctgaaaatat gtggctcaat ttgtctcccg   600
gttactttc cctctccccc tttaaaatgt agaggaagga gaagaagaga taagaggttt   660
gtgagtgaag acaagggccc tttaaggcct gggaagacta acgccatagg gatctccctc   720
tgccttaaaa ggcacaggaa tcttagtggg gaaaaagaag tggtgataaa tagccagtcc   780
gtgtgcctgg aatatcaaag t                                            801

<210> SEQ ID NO 391
<211> LENGTH: 801
<212> TYPE: DNA
<213> ORGANISM: Homo sapiens

<400> SEQUENCE: 391
ccctgctccg tctagactgt gcccatattc gctgctggct gcaaatgcga ggagttgaca    60
gcagcctccc ctttacaagg caggaggtgc cactgttcgc cattgtctcc acctagggct   120
tcacttgctt tctatctgca gacatcagag ggacccacat ctctctgttc tgacacgctg   180
tgtgttgatg gcagagtttta attatccaca tgcaatctta ctttccttat tcccaagtcc   240
gtggggctgc ctcatcaaag cattgtaaga actgataacc atcttctaga agtatcatag   300
tgatattaag aacacacatc acagatcata gtaaatggct ttaatttttt agcgaaatct   360
cactactgca aatgcattgt tgtcctagct aatgaatgca yagagtattg cctgcaaaat   420
aataattgag attctatttt taagaagctt agaacagtac atggtgcata gcaaagactc   480
tgtgtatgtg aagccagatt ttaaaatatg gtaacaagtg tctgaaaata tgtggctcaa   540
tttgtctccc ggttactttt ccctctcccc ctttaaaatg tagaggaagg agaagaagag   600
ataagaggtt tgtgagtgaa gacaagggcc ctttaaggcc tgggaagact aacgccatag   660
ggatctccct ctgccttaaa aggcacagga atcttagtgg ggaaaaagaa gtggtgataa   720
atagccagtc cgtgtgcctg gaatatcaaa gtcagtgcgt gccagggatc acactgcggg   780
tcacgtgcac tctgggtctc t                                            801

<210> SEQ ID NO 392
<211> LENGTH: 601
<212> TYPE: DNA
<213> ORGANISM: Homo sapiens

<400> SEQUENCE: 392
ttggcctggg gctgattcct ccaaagcaat gtgtctcttc gcagagtctc ttagagctgc    60
aaggcagtat gggatcatca gagaggatgc taggaagctt cagaaatgga ggtcctggta   120
gaaagggtcc tttggcgtgg cctctgaaga gtccaaatgt gggacaagac cctccgaaag   180
```

| | |
|---|---|
| cggtggcctg gggagccaca ggtggggcag ccagcacgga agagggtggc tttgctacca | 240 |
| ttgggaaaac ttatcctcca catcctcatg aggcaaacac ctttcctacc ttaccgctcc | 300 |
| ycagtggcct ccctgttgcc ttcttattca agactaagac cctctagaat gttctttatc | 360 |
| ctgagtccag ctgattgtct atactaatat cagtacgggg tgtagatgag gacaaccagt | 420 |
| gtgcctggct gccaggcacc ccctccccaa accccaggag tttctggaac attccaactc | 480 |
| tgcttgaggg tatccatgca gcatctacta ctgtgagcag gtggtctgat ctgtggaaaa | 540 |
| cttctatgat tcacctgagg gtaactgccc tttgtgattt gaaagaatga tgctaacaga | 600 |
| a | 601 |

<210> SEQ ID NO 393
<211> LENGTH: 601
<212> TYPE: DNA
<213> ORGANISM: Homo sapiens

<400> SEQUENCE: 393

| | |
|---|---|
| gcagagtctc ttagagctgc aaggcagtat gggatcatca gagaggatgc taggaagctt | 60 |
| cagaaatgga ggtcctggta gaaagggtcc tttggcgtgg cctctgaaga gtccaaatgt | 120 |
| gggacaagac cctccgaaag cggtggcctg gggagccaca ggtggggcag ccagcacgga | 180 |
| agagggtggc tttgctacca ttgggaaaac ttatcctcca catcctcatg aggcaaacac | 240 |
| ctttcctacc ttaccgctcc tcagtggcct ccctgttgcc ttcttattca agactaagac | 300 |
| yctctagaat gttctttatc ctgagtccag ctgattgtct atactaatat cagtacgggg | 360 |
| tgtagatgag gacaaccagt gtgcctggct gccaggcacc ccctccccaa accccaggag | 420 |
| tttctggaac attccaactc tgcttgaggg tatccatgca gcatctacta ctgtgagcag | 480 |
| gtggtctgat ctgtggaaaa cttctatgat tcacctgagg gtaactgccc tttgtgattt | 540 |
| gaaagaatga tgctaacaga agtgttgtc atttctgaac ttttctgaac tctgcagcga | 600 |
| g | 601 |

<210> SEQ ID NO 394
<211> LENGTH: 1001
<212> TYPE: DNA
<213> ORGANISM: Homo sapiens

<400> SEQUENCE: 394

| | |
|---|---|
| agatttggat ggggacacaa aaccaaacca tatcataggt taaattgtgt ctcccacccc | 60 |
| aaaaatgtgt atgttgaagt cctaaccttc agtactcaga atgtgacatt atttggaaat | 120 |
| agggtcattg cagatggagt tagttaagat gaggtcatta ggatgagtcc ctaatccaat | 180 |
| atgactggtg ctcttacaaa aaggggaagt ttggacacag agccatgcac atgggtggga | 240 |
| agaatcccaa atgaacggat aggcagaggg ttggagagat gcatcaacaa ggaacaccaa | 300 |
| agattgccag caaccccag aagctggggg agaggcctgg aacagattct ccctcacagc | 360 |
| ctgagaggaa ccaagctggc tgacaccttg atctcaggtt accggccttg agaactgaga | 420 |
| gaccctgggt ttctgttgtt taagcctctc agggtgcagc actttattat ggaagcctga | 480 |
| gctgactaat acaggtgtct ytatatctca ctgagggaaa gtgacaggaa agtaagaacc | 540 |
| atttatgtcc aagagtccag aggagtcaac cagattctgg gggaaaagaa ggtacaatgc | 600 |
| tggcctctcc atgcagccta gtccccaaca cttgtagggc ccagggcaag atctaaagca | 660 |
| ctctctcacc tatgcatcta tatgctgtaa ctcagataaa caaactatta aataatatat | 720 |
| gtgtcttgcc tctcaatctg acaattacac ctttataata gcaacatagg aaaataacta | 780 |

-continued

| | | |
|---|---|---|
| aaactatggt tttaggcaa ccaaatacca gcaaaatgta ataattccta ttattagata | 840 |
| tgtttaagtg ttctgctggt gggtcagcat ctttggtaga gtcataaaat taaaatgtac | 900 |
| ataattaatt aaatattata tgtttattcc ctaacattta tttctgtcat ttcttttttc | 960 |
| ttttttcag acagtctcac tcttttgccc aggccggagt g | 1001 |

<210> SEQ ID NO 395
<211> LENGTH: 1001
<212> TYPE: DNA
<213> ORGANISM: Homo sapiens

<400> SEQUENCE: 395

| | | |
|---|---|---|
| ttgtgtctcc caccccaaaa atgtgtatgt tgaagtccta accttcagta ctcagaatgt | 60 |
| gacattattt ggaaataggg tcattgcaga tggagttagt taagatgagg tcattaggat | 120 |
| gagtccctaa tccaatatga ctggtgctct tacaaaaagg ggaagtttgg acacagagcc | 180 |
| atgcacatgg gtgggaagaa tcccaaatga acggataggc agagggttgg agagatgcat | 240 |
| caacaaggaa caccaaagat tgccagcaac ccccagaagc tgggggagag gcctggaaca | 300 |
| gattctccct cacagcctga gaggaaccaa gctggctgac accttgatct caggttaccg | 360 |
| gccttgagaa ctgagagacc ctgggtttct gttgtttaag cctctcaggg tgcagcactt | 420 |
| tattatggaa gcctgagctg actaatacag gtgtctctat atctcactga gggaaagtga | 480 |
| caggaaagta agaaccattt rgtccaaga gtccagagga gtcaaccaga ttctggggga | 540 |
| aaagaaggta caatgctggc ctctccatgc agcctagtcc ccaacacttg tagggcccag | 600 |
| ggcaagatct aaagcactct ctcacctatg catctatatg ctgtaactca gataaacaaa | 660 |
| ctattaaata atatatgtgt cttgcctctc aatctgacaa ttacaccttt ataatagcaa | 720 |
| cataggaaaa taactaaaac tatggttttt aggcaaccaa ataccagcaa aatgtaataa | 780 |
| ttcctattat tagatatgtt taagtgttct gctggtgggt cagcatcttt ggtagagtca | 840 |
| taaaattaaa atgtacataa ttaattaaat attatatgtt tattccctaa catttatttc | 900 |
| tgtcatttct ttttcttttt tttcagacag tctcactctt ttgcccaggc cggagtgcag | 960 |
| tggcgtgatc tcagctcact gcaacctccg cctcccaggt t | 1001 |

<210> SEQ ID NO 396
<211> LENGTH: 1218
<212> TYPE: DNA
<213> ORGANISM: Homo sapiens

<400> SEQUENCE: 396

| | | |
|---|---|---|
| gataaagaaa ggtcatcctc aatttcaatt tactttatat attctttgag aggtaaccgt | 60 |
| gtcttatctc cccccaaaat tccttttaaa aggaaatttc caaagatgct ctattctgtg | 120 |
| aataaagcat tgtgccacag ccgagaggat ccagcaatga acatgagatt gcccttgatt | 180 |
| cataaggtct acaagctagt aaggatagag aacactttaa aataaaaaaa atagtttt | 240 |
| ggtatattta tattgtgtat ttggtataat tgagttttct acattctcat atatgtattt | 300 |
| catattttga agaatatgca gaaaataatc aagcttccaa ataaacattt ttttttaaga | 360 |
| actgcacaag tgagaattta ggagaacaga agatcagagg gctgcacrgg ctaaactaga | 420 |
| caatgagccc atgcaagtaa gttaagagga gaagcgggta agtatgcacc tgctttgtct | 480 |
| aggtgaccag caagcattta gcaatagtct tttcaaaaca acagctcctt atattgtcaa | 540 |
| atctcaagaa gtaatatttta tggttaaaaa aatctcagac ccaacagaaa atccatgagg | 600 |

```
gagatggttt tggaaacgca gaattttcag ctatgatatc cttttataaa caagcagata      660 cttteeccaa atataattca atgcetcagt ctacctcctg ctgaaaccac taacaccacc      720
actaaagctc gactatatgg gaaaatttag gtgtcacttt caaaatatgt cctagcataa      780
aggcaattaa aaaatgtaaa gcaccaaaga tgcaagagag acataaatga ataaaatatc      840
tggcacgaaa gttttcaaaa gcttgggaat ctgattcaaa aaaaataaaa atcagccaag      900
cagtgttagt aagttagcca atcaggtttc aagaaggcag aaagacaaaa tcaacatcac      960
cagcatttga caccgctact gggggaaaaa aggggggatgg agttcgttta tggcctttttt     1020 aaaaatgcca ttacttggac aagagtcata acagagaagc actgcttatt tcagttctgt     1080
taactgtaaa tatcagagcc aacacccaga aaaagttcac cattagccaa ttggtttttgc    1140 ctggccaatt ggagatggta ataggcctgc tatggatgac attctttctg atataagttg     1200
tttcttgctt tttctccc                                                   1218

<210> SEQ ID NO 397
<211> LENGTH: 1218
<212> TYPE: DNA
<213> ORGANISM: Homo sapiens

<400> SEQUENCE: 397
gataaagaaa ggtcatcctc aatttcaatt tactttatat attctttgag aggtaaccgt       60
gtcttatctc cccccaaaat tccttttaaa aggaaatttc caaagatgct ctattctgtg      120
aataaagcat tgtgccacag ccgagaggat ccagcaatga acatgagatt gcccttgatt      180
cataaggtct acaagctagt aaggatagag aacactttaa aataaaaaaa atagtttttt     240
ggtatattta tattgtgtat ttggtataat tgagttttct acattctcat atatgtattt      300
catattttga agaatatgca gaaaataatc aagcttccaa ataaacattt tttttaagaa     360
actgcacaag tgagaattta ggagaacaga agatcagagg gctgcacggg ctaaactaga      420
caatgagccc atgcaagtaa gttaagagga gaagcgggta agtatgcacc tgctttgtct      480
aggwgaccag caagcattta gcaatagtct tttcaaaaca acagctcctt atattgtcaa      540
atctcaagaa gtaatattta tggttaaaaa aatctcagac ccaacagaaa atccatgagg      600
gagatggttt tggaaacgca gaattttcag ctatgatatc cttttataaa caagcagata      660 cttteeccaa atataattca atgcetcagt ctacctcctg ctgaaaccac taacaccacc      720
actaaagctc gactatatgg gaaaatttag gtgtcacttt caaaatatgt cctagcataa      780
aggcaattaa aaaatgtaaa gcaccaaaga tgcaagagag acataaatga ataaaatatc      840
tggcacgaaa gttttcaaaa gcttgggaat ctgattcaaa aaaaataaaa atcagccaag      900
cagtgttagt aagttagcca atcaggtttc aagaaggcag aaagacaaaa tcaacatcac      960
cagcatttga caccgctact gggggaaaaa aggggggatgg agttcgttta tggcctttttt     1020 aaaaatgcca ttacttggac aagagtcata acagagaagc actgcttatt tcagttctgt     1080
taactgtaaa tatcagagcc aacacccaga aaaagttcac cattagccaa ttggtttttgc    1140 ctggccaatt ggagatggta ataggcctgc tatggatgac attctttctg atataagttg     1200
tttcttgctt tttctccc                                                   1218

<210> SEQ ID NO 398
<211> LENGTH: 1072
<212> TYPE: DNA
<213> ORGANISM: Homo sapiens

<400> SEQUENCE: 398
```

```
cacttaaaag ctctggaaac ctacgagatt atctttaaaa tcgtggggac caaatggctg    60
gccaaggact tgtttctgta caggtgcgat tgcttctctg ctgtgttcct ttttattacc   120
caagtaaccg gtatttcagc tcacaagatg agaaaatgac aaacaggcaa aataagcgta   180
gggctgtgtg tgcaacagtt watcataaag ccatcaccag gagacgtcac tgggcgcctt   240
ctggagtcta tccgtcctaa ctttgctttc tttctttttt tttttaaatt taagttctag   300
ggtacatatg cacaacgtgc aggtttgtca cacatgtata catgtgccat gttggtgtgc   360
tgcacccatt aactcgtcat ttacattagg tgtatctcct agtgctatcc ctccccactc   420
ccccgacccc atgacaggcc ccagtgtgtg atgttcccct tcctgtgtcc aagtgttctc   480
attgttcaat ccccacctat gagtgagaac atgccatgtt tggtttttg tccttgcgat    540 agtttgctga gaatgatggt ttccagcttc atccatgtcc ctacaaagga catgaactca   600
tcctttttta tggctacata gtattccatg gtgtatatgt gccacatttt cttaatccag   660
tctatcatcg atggacattt gggttggttc caagtctttg ctattgtgac tagtgttgca   720
ataaatatac gtgtggatgt gtctttatag cagtttgatt tataatcctt tgggtatata   780
cccagtaacg ggatggctgg gtcaaatggt atttctagtt ctagatcctt gaggaatcgc   840
cacactgact tccacaatgg ttgaactagt taacagtccc accaacagtg tgaaagtgtt   900
cctatttctc cacatcctct ccagcacccc attttgactt tgctataagg gaactttagc   960
atctgaacgt gcggacagct tcattgctgg cttgttacgt aacagtgttt tgtgaccatc  1020
tcatgtcata cccacacatc gaaaccagca gtttaaatgg ccagctgttt gc          1072
```

<210> SEQ ID NO 399
<211> LENGTH: 1072
<212> TYPE: DNA
<213> ORGANISM: Homo sapiens

<400> SEQUENCE: 399

```
agattatctt taaaatcgtg gggaccaaat ggctggccaa ggacttgttt ctgtacaggt    60
gcgattgctt ctctgctgtg ttccttttta ttacccaagt aaccggtatt tcagctcaca   120
agatgagaaa atgacaaaca ggcaaaataa gcgtagggct gtgtgtgcaa cagtttatca   180
taaagccatc accaggagac rtcactgggc gccttctgga gtctatccgt cctaactttg   240
ctttctttct ttttttttt aaatttaagt tctagggtac atatgcacaa cgtgcaggtt   300
tgtcacacat gtatacatgt gccatgttgg tgtgctgcac ccattaactc gtcatttaca   360
ttaggtgtat ctcctagtgc tatccctccc cactccccg acccatgac aggcccagt      420 gtgtgatgtt cccttcctg tgtccaagtg ttctcattgt tcaatcccca cctatgagtg   480
agaacatgcc atgtttggtt ttttgtcctt gcgatagttt gctgagaatg atggtttcca   540
gcttcatcca tgtccctaca aggacatga actcatcctt ttttatggct acatagtatt   600
ccatggtgta tatgtgccac attttcttaa tccagtctat catcgatgga catttgggtt   660
ggttccaagt ctttgctatt gtgactagtg ttgcaataaa tatacgtgtg gatgtgtctt   720
tatagcagtt tgatttataa tcctttgggt atatacccag taacgggatg gctgggtcaa   780
atggtatttc tagttctaga tccttgagga tcgccacac tgacttccac aatggttgaa    840
ctagttaaca gtcccaccaa cagtgtgaaa gtgttcctat ttctccacat cctctccagc   900
accccatttt gactttgcta taagggaact ttagcatctg aacgtgcgga cagcttcatt   960
gctggcttgt tacgtaacag tgttttgtga ccatctcatg tcatacccac acatcgaaac  1020
```
cagcagttta aatggccagc tgtttgcttg tgaaaactcc cctcggctgg ct          1072

<210> SEQ ID NO 400
<211> LENGTH: 948
<212> TYPE: DNA
<213> ORGANISM: Homo sapiens

<400> SEQUENCE: 400

| aaattttctt | tgctgaagtg | tcttttcaaa | ttttttgcctt | ttaaaaaaat | tgagttgtct | 60 |
| taatattgag | tcgtaaggtt | ctttatatat | tctggctata | tgtcctttgt | cagatatatg | 120 |
| tcttgcaaat | attttctccc | agtctgtggc | ttacctttc | cattttaaa | ctgtgtttta | 180 |
| taaaaaaag | aagttttttt | agatcaaagt | ccattttaat | cattttttct | tttatagttc | 240 |
| atgcttttg | tgtctcattt | aagaaatctt | tccctactcc | aatgtcacaa | atatattctc | 300 |
| tgagaagctt | aacagttttt | gcaactaaat | ttaggtctat | gatccgtttt | gacttaattt | 360 |
| ttccatatgg | tgtcatgtaa | cagttgagat | tttttttccta | tgcaggcaga | tattcaatgg | 420 |
| ttcaagtacc | atttattgaa | atggctatct | tttctccact | gaatgacctt | ggcacttta | 480 |
| tcaaacatca | actggccaca | yacaggtgag | tctacttctg | gacacttacc | ctgttccatt | 540 |
| catctgtata | tctctatcct | tacaccaaca | cgcatagtct | tgaatactag | ggcaagttaa | 600 |
| ttttaagatg | tctcctggat | atgtaaaaat | tatatctgag | ttgaactaca | gtttatttat | 660 |
| atatccaggc | agcaaataaa | tgtgagaatc | tggaggtgag | ggaagagatc | agagatacca | 720 |
| ccttggaaac | catcaattta | gagatgattc | ttaaggcagg | ggactaaggg | acactctgta | 780 |
| ggacacagac | atagagaagg | gaaggggctg | cggcctgaac | accccacctg | catgctcact | 840 |
| cacatacttt | cgtcggcctg | tgttaacgaa | gtgctgggtc | tccccagcct | ctctcatctg | 900 |
| taagcagtgc | caacaacgtc | caacacagtt | ccatccaatt | tggatctg |  | 948 |

<210> SEQ ID NO 401
<211> LENGTH: 920
<212> TYPE: DNA
<213> ORGANISM: Homo sapiens

<400> SEQUENCE: 401

| aattttgcc | ttttaaaaaa | attgagttgt | cttaatattg | agtcgtaagg | ttctttatat | 60 |
| attctggcta | tatgtccttt | gtcagatata | tgtcttgcaa | atattttctc | ccagtctgtg | 120 |
| gcttaccttt | tccatttta | aactgtgttt | tataaaaaaa | agaagttttt | ttagatcaaa | 180 |
| gtccatttta | atcatttttt | cttttatagt | tcatgcttt | tgtgtctcat | ttaagaaatc | 240 |
| tttccctact | ccaatgtcac | aaatatattc | tctgagaagc | ttaacagttt | ttgcaactaa | 300 |
| atttaggtct | atgatccgtt | ttgacttaat | ttttccatat | ggtgtcatgt | aacagttgag | 360 |
| attttttttcc | tatgcaggca | gatattcaat | ggttcaagta | ccatttattg | aaatggctat | 420 |
| cttttctcca | ctgaatgacc | ttggcacttt | tatcaaacat | caactggcca | cacacaggtg | 480 |
| agtctacttc | tggacactta | ycctgttcca | ttcatctgta | tatctctatc | cttacaccaa | 540 |
| cacgcatagt | cttgaatact | agggcaagtt | aattttaaga | tgtctcctgg | atatgtaaaa | 600 |
| attatatctg | agttgaacta | cagtttattt | atatatccag | gcagcaaata | aatgtgagaa | 660 |
| tctggaggtg | agggaagaga | tcagagatac | caccttggaa | accatcaatt | tagagatgat | 720 |
| tcttaaggca | ggggactaag | ggacactctg | taggacacag | acatagagaa | gggaaggggc | 780 |
| tgcggcctga | acaccccacc | tgcatgctca | ctcacatact | ttcgtcggcc | tgtgttaacg | 840 |
| aagtgctggg | tctccccagc | ctctctcatc | tgtaagcagt | gccaacaacg | tccaacacag | 900 |

```
ttccatccaa tttggatctg                                                 920

<210> SEQ ID NO 402
<211> LENGTH: 701
<212> TYPE: DNA
<213> ORGANISM: Homo sapiens

<400> SEQUENCE: 402
tgtgctgctt ccattccata ggcacctgat cctaagtgtt aaccaatccc agaactctcc     60
ccttatttct tgctgcatgt tttgaattga tgtgataaac aatgtgattc gagcgtctta    120
actcagccta tgagcctctc tattctgtga ctgctggaat aggctgcttg gccatgttct    180
tggaagctac caccatatca rgtaatttc ccacacaaca ttccagcccc tgctttcccc     240
tctggcctta tctagggcca ttccccaact caggtgaatg cagactccaa atgtactgag    300
ctgtgtgcag gggccaggtg caaatgcttt ctgtgcatct gcacatgctg ttctacctgg    360
gaagtccttt cctcctttca cctatttta ccttaaacct cagacatcat ctaccctgga    420
aagtccttcc tgacctcacg catctaagta ggtcccccc ataatcccta tccatgcctt     480
ctatagtact aacatggtg accttaatt gttcatttac ttagctctct gctctcccac      540
actgtgaact ccttacaaac agggaatgtc atctctgaat gaatctttca tctccatgta    600
acacatgcct ccaaccctac ctagcacaca atctggcata taacaggcac tcaataaacc    660
ttcaatgaat gccttgatca agtacaagga acataagcaa a                        701

<210> SEQ ID NO 403
<211> LENGTH: 701
<212> TYPE: DNA
<213> ORGANISM: Homo sapiens

<400> SEQUENCE: 403
ttaaccaatc ccagaactct ccccttattt cttgctgcat gttttgaatt gatgtgataa     60
acaatgtgat tcgagcgtct taactcagcc tatgagcctc tctattctgt gactgctgga    120
ataggctgct tggccatgtt cttggaagct accaccatat cagggtaatt cccacacaa     180 cattccagcc cctgctttcc yctctggcct tatctagggc cattccccaa ctcaggtgaa    240
tgcagactcc aaatgtactg agctgtgtgc aggggccagg tgcaaatgct ttctgtgcat    300
ctgcacatgc tgttctacct gggaagtcct ttcctccttt cacctatttt taccttaaac    360
ctcagacatc atctaccctg gaaagtcctt cctgacctca cgcatctaag taggtccccc    420
ccataatccc tatccatgcc ttctatagta cttaacatgg tgacctttaa ttgttcattt    480
acttagctct ctgctctccc acactgtgaa ctccttacaa acagggaatg tcatctctga    540
atgaatcttt catctccatg taacacatgc ctccaaccct acctagcaca caatctggca    600
tataacaggc actcaataaa ccttcaatga atgccttgat caagtacaag gaacataagc    660
aaatttcctg tggaaaaaaa gaattgtatt aagttctttg g                        701

<210> SEQ ID NO 404
<211> LENGTH: 601
<212> TYPE: DNA
<213> ORGANISM: Homo sapiens

<400> SEQUENCE: 404
atgttcactt acacatcttt cttcacttac attgaatcct ttatttttgt cttagaatct     60
tctgaatatt gaaacagag aactatactg gaagaacata gtgtattaag actcatggag     120
```

```
agggagatgt gatactgtgt cactgaggtc gttccagtca taggagaaat gttaccactg    180
gattgaggtc tggtacattt taaaagatga tttaattcta tgatatgtgt tcaacttgca    240
ctaggatagt ttttactttc acctttgttc catgcaccgc gcaaatacct gggaaccctt    300
rttgcccaac tcaagagcca gagtcctctg tcatcatttt gcctctctcc taagtgacag    360
gactgagtgc agacttggtg tttgtgggtg aggcatgtgg actgacaggc aggcttcagt    420
ttatttagcg agtgtgagcc ctggcaggaa gattctcttt ctctgcttgc caggttgagg    480
aggcctcatt aagcagtttg aacttgtggt tttggcgtgt ctagtcctgg tgcaggtggc    540
ttggtatcct cacaggcatt tctttggcct cacccttggg gtgactgttc acttgtgttt    600
g                                                                    601
```

<210> SEQ ID NO 405
<211> LENGTH: 601
<212> TYPE: DNA
<213> ORGANISM: Homo sapiens

<400> SEQUENCE: 405

```
tcttctgaat attgaaaaca gagaactata ctggaagaac atagtgtatt aagactcatg     60
gagagggaga tgtgatactg tgtcactgag gtcgttccag tcataggaga aatgttacca    120
ctggattgag gtctggtaca ttttaaaaga tgatttaatt ctatgatatg tgttcaactt    180
gcactaggat agttttttact ttcacctttg ttccatgcac cgcgcaaata cctgggaacc    240
cttgttgccc aactcaagag ccagagtcct ctgtcatcat tttgcctctc tcctaagtga    300
saggactgag tgcagacttg gtgtttgtgg gtgaggcatg tggactgaca ggcaggcttc    360
agtttattta gcgagtgtga gccctggcag gaagattctc tttctctgct tgccaggttg    420
aggaggcctc attaagcagt ttgaacttgt ggttttggcg tgtctagtcc tggtgcaggt    480
ggcttggtat cctcacaggc atttctttgg cctcacccct ggggtgactg ttcacttgtg    540
tttgagcggc tgggactcag taggttcact ggagtaggta tttctttaga gccactggcg    600
g                                                                    601
```

<210> SEQ ID NO 406
<211> LENGTH: 701
<212> TYPE: DNA
<213> ORGANISM: Homo sapiens

<400> SEQUENCE: 406

```
cagctccttg gcaagcctgc tccttcccca gcaaatggaa acaccattct gaacacctgg     60
gcattgtctc tgatgtccct tttcatctcc ctactctcac acaatccagc tgcctctctg    120
ccttccacgg atattaagaa cgtccaccat ctcctgagtc caagcccttc tcactcacct    180 cttttcttgaa ctaatttctt yctgttttttt tccagtcctc ccttctgttc atgtctctcc    240
tctgcacact tccatttttct ggttcagaaa atgtcaccgt cccagtcaca cttgccttat    300
ggctgttgtg tcataaatac agttgacact tgaacaacat gggtttgaac tgcatggatt    360
cacttataca catatttttt caatacaaat atatttaaaa attttggaga tttgcaacaa    420
tttgaaaaaa cttgcagatg aacagcatag catagaaata ttgaaaaatt aagaaaaagg    480
tatgtcatga atgcataaaa catatgcaga tactagtcta ttttaacctt tactgccata    540
aaatatacac aaatctatta taaaggtta agtttatca agcttatgc acacaaacac    600 ttatagacca tataggggagc cattcagtag agagaaatgt aagcgaacgt aaaggtgtgc    660
tatttaatca caactgcata cacactgtac cactgcacta a                        701
```

<210> SEQ ID NO 407
<211> LENGTH: 701
<212> TYPE: DNA
<213> ORGANISM: Homo sapiens

<400> SEQUENCE: 407

```
gggcattgtc tctgatgtcc cttttcatct ccctactctc acacaatcca gctgcctctc    60
tgccttccac ggatattaag aacgtccacc atctcctgag tccaagccct tctcactcac   120
ctctttcttg aactaatttc tttctgtttt tttccagtcc tcccttctgt tcatgtctct   180
cctctgcaca cttccatttt stggttcaga aaatgtcacc gtcccagtca cacttgcctt   240
atggctgttg tgtcataaat acagttgaca cttgaacaac atgggtttga actgcatgga   300
ttcacttata cacatatttt ttcaatacaa atatatttaa aaattttgga gatttgcaac   360
aatttgaaaa aacttgcaga tgaacagcat agcatagaaa tattgaaaaa ttaagaaaaa   420
ggtatgtcat gaatgcataa acatatgca gatactagtc tattttaacc tttactgcca   480
taaaatatac acaaatctat tataaaaggt taaagtttat caaagcttat gcacacaaac   540
acttatagac catataggga gccattcagt agagagaaat gtaagcgaac gtaaaggtgt   600
gctatttaat cacaactgca tacacactgt accactgcac taatttcaga gccacctcct   660
gttgtgattg tggtgagccc aagtgttgtg aggatctgct t                       701
```

<210> SEQ ID NO 408
<211> LENGTH: 501
<212> TYPE: DNA
<213> ORGANISM: Homo sapiens

<400> SEQUENCE: 408

```
caggtagggt aagcaaatga acacaaattc aaactcggaa ttcaaaacca gcctctgtgt    60
attcctgagg accatactgt ctgctaagtg tagagaaagg cacatcctgg ttcaacagca   120
gagaaagcaa acaggaggca ctttctgtga gtcatctcca ccacagggcc ctctcttttg   180
tgatccagcg atacttgttc acagtcaaag cccaggaaga gtggaaagat taacctttgt   240
gagccaaacc rtgtgacact tgattacttg acagaactaa tccttctgtc ctgatgacag   300
aaattcaact acacaggtac atgcaagcta atatctgttg taatgcctcc cagtttctct   360
ggagaattcc ttagttttcct ggacatctct gaaatgcaaa gttttggcaa cgagtctctg   420
aattaacctc tgaaaatctc acccagccaa gatggccttc ttgagaagac tgaagaacat   480
ggttggtttc aggctgagct g                                             501
```

<210> SEQ ID NO 409
<211> LENGTH: 604
<212> TYPE: DNA
<213> ORGANISM: Homo sapiens

<400> SEQUENCE: 409

```
cactttctgt gagtcatctc caccacaggg ccctctcttt tgtgatccag cgatacttgt    60
tcacagtcaa agcccaggaa gagtggaaag attaaccttt gtgagccaaa ccgtgtgaca   120
cttgattact tgacagaact aatccttctg tcctgatgac agaamttcaa ctacacaggt   180
acatgcaagc taatatctgt tgtaatgcct cccagtttct ctggagaatt ccttagtttc   240
ctggacatct ctgaaatgca agttttggc aacgagtctc tgaattaacc tctgaaaatc   300
tcacccagcc aagatggcct tcttgagaag actgaagaac atggttggtt tcaggctgag   360
```

| | |
|---|---|
| ctggaagtgg tttacctccc aggagaggtt ccccacagtg gtgtttaagg catggggtgg | 420 |
| accaacacca ggaagactca gacatcacac cacccacctt caactcagtc acatccacct | 480 |
| acattttctg aaaacaaaag gcagtctccc caaaaagcac tgagactctt gtgtaggtaa | 540 |
| tctgagcaga caccaacttc ccagggcttc cttttatcca ggagagcttg gctgttcttt | 600 |
| ttaa | 604 |

<210> SEQ ID NO 410
<211> LENGTH: 701
<212> TYPE: DNA
<213> ORGANISM: Homo sapiens

<400> SEQUENCE: 410

| | |
|---|---|
| ctccttccgc catggttgta agtttcctga cgcctcccag tcatgcttcc cgtacagcct | 60 |
| gcagaactgc gagtcaatga aatccctttt ctccacaaat tacccagtct caggtagttc | 120 |
| cttacagcag cgtgggaaca gactcaagag ctgaagcaag caaggccgtt agcaaggagc | 180 |
| gggctgggga gagcactcca ggcagaggga acagccaggg ccaggccctt gagacagacg | 240 |
| tgagccagga tatctgagga acagcagaga agccagtgtg gccgcagcta aatgaggaac | 300 |
| aatgtgtgag ttccctgggg cggccaaaac aaacaccacg gacgggggcc ttcaaccaca | 360 |
| gacaccgatt tcctcacagc tctggaggcg aaaagtccaa gaaaactgca cggagtatct | 420 |
| atgaggccct gatggagacc tgacctggtc cacacccatg gcctggcaag ctagatgggg | 480 |
| tgaattttca cctgccacag ycgcaagtca aagccaccgg cttctctctt ctccctccca | 540 |
| ttgctcctga cagccagggt taatattttg cctcatgtaa acaggaggc atccacccga | 600 |
| gaatctcccc tcagcccaca taagctctgc agagagggct gtgttgctcc agttcccacc | 660 |
| tggacatgag cactttgaag ggcagcttcc ctcccggggt c | 701 |

<210> SEQ ID NO 411
<211> LENGTH: 612
<212> TYPE: DNA
<213> ORGANISM: Homo sapiens

<400> SEQUENCE: 411

| | |
|---|---|
| gggctgggga gagcactcca ggcagaggga acagccaggg ccaggccctt gagacagacg | 60 |
| tgagccagga tatctgagga acagcagaga agccagtgtg gccgcagcta aatgaggaac | 120 |
| aatgtgtgag ttccctgggg cggccaaaac aaacaccacg gacgggggcc ttcaaccaca | 180 |
| gacaccgatt tcctcacagc tctggaggcg aaaagtccaa gaaaactgca cggagtatct | 240 |
| atgaggccct gatggagacc tgacctggtc cacacccatg gcctggcaag ctagatgggg | 300 |
| tgaattttca cctgccacag tcgcaagtca aagccaccgg cttctctctt ctccctccca | 360 |
| ttgctcctga cagccagggt taatattttg cctcatgtaa acaggaggc ayccacccga | 420 |
| gaatctcccc tcagcccaca taagctctgc agagagggct gtgttgctcc agttcccacc | 480 |
| tggacatgag cactttgaag ggcagcttcc ctcccggggt ctggctgagc tcagggtagg | 540 |
| cgtcagtctg catggattgg atggaggaag gctgtgcgtg gcaggagatg acactgccct | 600 |
| tgggctgtgt gg | 612 |

<210> SEQ ID NO 412
<211> LENGTH: 1001
<212> TYPE: DNA
<213> ORGANISM: Homo sapiens

<400> SEQUENCE: 412

```
ttggggaagg aagcactggg gggaaggaag cactgggctt gggacagggc tgggcgctgc      60
ctcttcactg gaccatgaca aggttgttac ctcaccaagg agaggtgcaa aaagcttagg    120
ggcttggatt tctagatttc agtgccaact atgccactta ctggctttat ccttggggaa    180
tttatctact ctgtgaccct cagttttttt atcttaatta ttaatacata cctcataatg    240
tgactgtgag gattcactta ataatatatg gaaaaccata gaatagtgcc cagcatctag    300
gaagtgccac agccccttc agaagctagt gaaacctgca gaccacttt cagagtgata      360 ttattatttt tttctaggtt tactgagtta taattgaaaa aataaaaatg gaatatagat    420
gtacaacatg aagctctgat gcatatatcc attgtgaaat gatgaccaca atcaagctaa    480
ttaatgttat ctatcacttc wcatagttca accttttttt gtggtgagag tactgaagat    540
ctactctctt agcaattttc aaatctaaaa tacattatta ttaacacagt cactgtgccg    600
tacgttagct ctgaggacct tattcatttt atacctaaaa gtctgtatcc tttaaccaac    660
ctctcctaat ttcccactgt catccctact gccacctctg gtaaccagcc ttctgctctg    720
tttctgagtc caaccttctt agattccaca tatgagtgag atcatgctgt gcagtgtttg    780
tttttctgtg tctggcttgc tttcacttag cataatgtcc tccaggtcca cccatgttgt    840
tgcaaatggc agaatcttct tcttgttaaa gactgaataa tatccctgtg tgtgcgtgca    900
tgtgtgtgtg tgtttgtgtg tgtgtgtgta tcacattttc ttcatccatt catccatcaa    960
tggacactaa gcactaaggt tgattccgta tcttggctat t                       1001

<210> SEQ ID NO 413
<211> LENGTH: 2480
<212> TYPE: DNA
<213> ORGANISM: Homo sapiens

<400> SEQUENCE: 413
aacattactt ggggaaggaa gcactggggg gaaggaagca ctgggcttgg gacagggctg      60
ggcgctgcct cttcactgga ccatgacaag gttgttacct caccaaggag aggtgcaaaa    120
agcttagggg cttggatttc tagatttcag tgccaactat gccacttact ggctttatcc    180
ttggggaatt tatctactct gtgaccctca gttttttat cttaattatt aatacatacc     240
tcataatgtg actgtgagga ttcacttaat aatatatgga aaaccataga atagtgccca    300
gcatctagga agtgccacag ccccttcag aagctagtga aacctgcaga ccacttttca     360
gagtgatatt attatttttt tctaggttta ctgagttata attgaaaaaa taaaaatgga    420
atatagatgt acaacatgaa gctctgatgc atatatccat tgtgaaatga tgaccacaat    480
caagctaatt aatgttatct atcacttcac atagttcaac cttttttgt ggtgagagta     540 ctgaagatct actctcttag caattttcaa atctaaaata cattattatt aacacagtca    600
ctgtgccrta cgttagctct gaggaccttta ttcatttat acctaaaagt ctgtatcctt    660
taaccaacct cctaatttt cccactgtca tccctactgc cacctctggt aaccagcctt     720
ctgctctgtt tctgagtcca accttcttag attccacata tgagtgagat catgctgtgc    780
agtgtttgtt tttctgtgtc tggcttgctt tcacttagca taatgtcctc caggtccacc    840
catgttgttg caaatggcag aatcttcttc ttgttaaaga ctgaataata tccctgtgtg    900
tgcgtgcatg tgtgtgtgtg tttgtgtgtg tgtgtgtatc acattttctt catccattca    960
tccatcaatg acactaagc actaaggttg attccgtatc ttggctattg tgaataatgc    1020
tgcaataaac atatgagtcc agatacctct tcaagatact gatttcattt cctttaaata   1080
```

```
tatgcccaga agtgggattg ctggatcata tggtagttct atatttagta tcttgaggaa    1140
tttccatact gttttttcata atgattgtag caatctatat tcccatcaac agtgtacaag    1200
ggttccattt tctacatggc cttaccaacg tttgttatca cttatctttt tgataataga    1260
tattctagca ggtgtgaggt ggtatctcat tgtggtttta atttgcattt tcctgatgat    1320
tagtggtgta gagcatcttt tcatattccc attggtaatt cgtatatctt cctttgagaa    1380
atatttattc agatcttttg cccattgtta gctgagttat atgtgagttg gtttggttt    1440 gttgttgttt tttgtttttg ctattgagct gagttccttg tatattttgg atattaaatc    1500
cttctcagct gtatggttga cagatacatt cttgcattct gtaagttgca tctgtaggtt    1560
gcaacagagt ctcttttactc tgttgattgc ttgctttact gtgtgaaagc ttttttagct    1620
tgatgtaatt gtgtttgtct atttttgctt tgttgcttg tacttttagt gtcatatcca    1680
aaaagttatt gcccagacca gtgtcatccc ctatgttttc ttctagtaat tttaaagttt    1740
caggtcttat gtctatgtct ttaatccatt ttgagttaat ttttgtgtag ggtttaagat    1800
aagaatccaa ttttattttt atttttttgta tatggatatc caatttcccc aacaccattt    1860
attgaaaatt ctatcctttc tttgttgtgt attaacatca gaataatatt tttaaataca    1920
taaaattcag aagatgacaa aggaaaccaa ttacattgaa atgcatacag agttataatt    1980
ctgaaagagc aatatatgtg cctctttgta aacacatcat atatcaaact gcagtgaccg    2040
ttctaacaac tattgcaatt tcaaagtcat gttgagtagg aggagtactt tgagattctg    2100
aaacaacgtt cttgtgctat gaaatatcca tgattttgat tggtgatggt atcccaggtc    2160
ttgttaatgc tgctgtaatc tgttgcttcc attccatagt tgaataaaat gcttgatatc    2220
tgttggaaat tagtaaaaat aaaaacgtat tttttttccat ccaagttcat tctcagaccc    2280
tgaagagtca cttctctgga ttctgcagca aagttcccag ctggggcagc aagatttagg    2340
caattgaaaa gaacatacac cttgttctca gtggcaaacc acatggaaag ctttaaatgt    2400
cagagaagaa ttctgccatt ttgctgactt ttttgtagtt ctcctaataa acaagtgtta    2460
agtgacaagc ttttcagagg                                                 2480
```

<210> SEQ ID NO 414
<211> LENGTH: 601
<212> TYPE: DNA
<213> ORGANISM: Homo sapiens

<400> SEQUENCE: 414

```
ccccccccccc ccccgcagat ctcaggtggg cattttttgaa cttaactaga taacaaaaca      60
cagctaagac aagtcctttt ctccagcaaa gatggcaatg ctctaataac tctgagcata     120
ttaaagattc tccaagactc tagcctctgc tgcaaaaaca catacaaata cctactacta     180
ctgctgctgt gatgatgatg atgacagcaa tagtgagaat attttaaata tgccaggcac     240
ggtggcaact gctttccaaa tattatcata tttaatctga tcattgccct atgaggtagg     300
ragtattctg attcccattt tataaataag gaacccgagg cttagagagc atcggtgact     360
tgttcaaggt cacccacagc tgtcaagtga cagaacttcg ataaaaatcc agactccttt     420
aatggagtat ggagggaggt cagaaaacat aggaagtaag ggattgtgat tgacaatgtg     480
tccttgcaaa gggacaggtt aagagacaca agggcagctg tctgaggtgt gccattcacc     540
agcttcagga gagaagtggc aggctacctc cagctatcca gccctatcca gccaaggaag     600
c                                                                     601
```

<210> SEQ ID NO 415
<211> LENGTH: 601
<212> TYPE: DNA
<213> ORGANISM: Homo sapiens

<400> SEQUENCE: 415

```
caaaacacag ctaagacaag tccttttctc cagcaaagat ggcaatgctc taataactct      60
gagcatatta aagattctcc aagactctag cctctgctgc aaaaacacat acaaatacct     120
actactactg ctgctgtgat gatgatgatg acagcaatag tgagaatatt ttaaatatgc     180
caggcacggt ggcaactgct ttccaaatat tatcatattt aatctgatca ttgccctatg     240
aggtagggag tattctgatt cccatttat aaataaggaa cccgaggctt agagagcatc      300
rgtgacttgt tcaaggtcac ccacagctgt caagtgacag aacttcgata aaaatccaga     360
ctcctttaat ggagtatgga gggaggtcag aaaacatagg aagtaaggga ttgtgattga     420
caatgtgtcc ttgcaaaggg acaggttaag agacacaagg gcagctgtct gaggtgtgcc     480
attcaccagc ttcaggagag aagtggcagg ctacctccag ctatccagcc ctatccagcc     540
aaggaagctt gggagacatg ttagttcccg ccttcatttc catcagcaac ctcaaagcca     600
c                                                                    601
```

<210> SEQ ID NO 416
<211> LENGTH: 5823
<212> TYPE: DNA
<213> ORGANISM: Homo sapiens

<400> SEQUENCE: 416

```
tatttcaggc tttcttcttt ctatggataa gaaagctcct caggtggcaa caaaggccat      60
ttctttggaa gcaggcatgg catgtgacga aaaaaagaca tctcagaaaa gagccaagaa     120
taagactgga gagccactgt cagagaacag aaactgggct taatcaagga acatctcttg     180
ttcccagagt aggaggctgg caatattttc tcactgaaat ttcagaattg ttatggacca     240
gtgactgctc tatgtgttca atttgttccc ttttcaaatg gaagcattta ttgcagacga     300
cctgcctctg tcccaccatt gtgtattagg tttgtagagy gtagacaact tgccttttta     360
gtttgtaggt ttctgtatca agagaagatg tgtgtgggcc taacctagat tacaggatcc     420
tggacttcaa gtctgatata atgactggat gagactttga ctgtcctaga attgggatga     480
acatattttg ccggtgggag ggcgtgagta attgcggtta gagggcagac tgtccctcac     540
acctattcct tttcatggtg ccttcccaaa ctgcctctgg aggtggccac acaaatggct     600
ttggccattg tgaccatggg aaacttgatg cagaggctgg aaaaagcact tgcatgtttc     660
tgtctcctct cttgttcctc tacaatcaca agaaatgtct aggcaggtct gagcaggccc     720
aggctcatct gccatggaag aagaatggca catggaagag ggtcacattg tcccaaccaa     780
gacgatccta gaccagccag gccccagttc atggttcaag acacatgaac atagttgcac     840
gaaccaagat tagttgtgta tggcccagac tagcagcagc acccatccaa cctacagact     900
ctgagaaata aatactagtt gtcttaagct tccaagtttc agtgtgagca ttaggtagta     960
acagttaatg aataagacag ataatcattt tatctgtctg gatacttata caatgatttc    1020
tattttttat tgatacataa tatttacat attgctgggg tacatgtgac attttgctac    1080
atacatagaa tgtgtaatga tccagtcagg atatctgagg tgtccatcac tttgagaatt    1140
tctcacttct gtgtgttggg aacaattcaa gtcgtctctt ctagttattt taaaatatac    1200
aatacattgt taactgtagt ctttttatt gaatgacagg acttgtacct tttatctaac    1260
```

```
tgtatgtttg tatctattaa gctagttctc tttatccctg cccctccta cccactcact    1320
cttcccaacc tctaacatgt atcatcctat tctatatctc catgagatca acttctttag    1380
ctcccacata tgagcaaaaa catatgatgt tgtctttct gtgcccggtt tatttcactt    1440
atgacctcca tttccatcca tgttactata aatgacagga tttcattctt tttgtggcca    1500
aacagtattt cattgtgtat atatactaca ttttcttat ccattcatcc attgatgaac    1560
acttacgttg attccatatc tttgctattg tgaatggtgc tgcaataaac atgcacgtgc    1620
agttatccct ttgatacact gatttatttt cctttggata aatacccagt agtgagattg    1680
ctggatcata cggtagttct acttttagtt tttgagacat ttccatactt ttccagtgtt    1740
tgtattaatt tacattccca tcaacaatgt ataagatttc cctttcctcc acatcctcac    1800
cagcatctgc tattttttgt ctttttaata atagtcattc taactggggt gagaggatat    1860
ctcgctatgg ttttgatttg catttccctg atatttaatg atattgagca tttcttcata    1920
taacctattg gccatttgtg tgtcttttt ttttttttt tttttttga gaattgtcta    1980
ctcatttttg gctttttaaa agatttattt tttgttgttg ttgagtttag tgcatatcct    2040
ggatattagt ctcttatctg atgaagagtt tgccaatatt ttctcccatt caacaggttg    2100
tctcttcatt ctgttgactg tttcccttgc tgtgcagaag cactttatat acagtcccat    2160
ttgtctattt tttagtagtc tatgcattta aggtctcagc cacaaaatct ttgcctagac    2220
cagtcctaaa gtgtttcccc tatattttct tctagtagtt ttattgtttc atgtcttata    2280
tttaagtcta taatccattg tgagttgatt tttgtatatg gtgagatagg ggccttgttt    2340
cattcctctg catatagata tttaattttc tcagcaccat ttattgaagg tgtccttccc    2400
tattgtatgt tcttggtgcc tttgtcaaaa ttcagttggc tataaatatg tgaatttatt    2460
tctgggttct ctatgtggtt ccattagtct atgtgtctat ttttatacca atatcatgct    2520
gttttgatta ccatagccct gtaatatatt ttgaagtcag gtagtgtgat gcctccagct    2580
ttgttctttt tgctcaggat tgctgtgcat actctggctt tttggttaca tacaaatttc    2640
aggattttg tatttctgtg aaaaatggca ttagtatttt gataggaatt gcactggatc    2700
tgtatattgt cctggacaac atggtcattt taacaatatt aattcttcta atctatgagt    2760
atgagacgtc ttcccacttg tttgtgtcct cttcaatttc tttcattggt gtttcataat    2820
ctcccttcta caggcctttc acctccttgg ttaaattaat tcctaggtat ttttttgtag    2880
ctactgtaaa tgggactgcc ttctttctca gctagttcat ttttggtgca tagaaaccct    2940
attttttgtat gttcatttc tatcctgcaa cattaccaaa tttgcttatc agctttaagt    3000
gtgtatttg ctttgcttgt agagtcttct ggtttctcta aatgtaagac gatgtcatct    3060
gcaaacgggg acaatttgac ttcctcttaa aaatctgtat gccttttatt cctttctctt    3120
gcctgattgc tctggctcta cctccagtac tatactgaat aaaagtggta aaagtgagca    3180
tccttccttg tcttgctcta gttccttagag gaaatacttt cagtttttcc ccactcagta    3240
tgatgttagc tgtgggtcat atatagccct tattatgtta agatatgttt cttctgtacc    3300
tggtttgttg acagctttt atcataaaag gatgtagaat tttatcaaat gttttttctg    3360
catctgttga gataatcata tggttttgt cattccttct actgttgtga tgtatcatgt    3420
ttattgattt gtgtatgtta aaccatcctt gtgtccttgg tataaattat acttggtcat    3480
ggtgtattat cttttggca tcctgtcgaa ttgtttgcta gctttttgtt ttgttctttt    3540
tgagaatttt tatgtctagg ttccttagaa acactggcct gtagttctct ttttgtgtgt    3600
gtgtccttgt ctagtttggt gtcagggaaa tggtggtctt gtagaatgag ttgttttttc    3660
```

```
tttgattttt ttgcaagagt ttgaggagaa tgggtattag ttcttcttta tgtggttggt    3720
caaattggca gtgaattcat tcagtcatga gcttttcttt ttttgggagg gttctcatta    3780
ctgagttaat cacactgctc attactgatc tgttcagatt ttctatttct tctggaatct    3840
cagtagttgt atgtttccag caatttatcc atttcctcta ggttttctag tttggtagta    3900
tatagctatt cataatagtc tctgatgatc ttttgtattt ctgtgatatc agttgtaatg    3960
tcttttcat ttcctatttt atttgggtct tttcttgttt agtctagcaa ggggtttatc     4020
tattttatct ttttgaagaa ccaacttttt gtttcattga ccctttctac gtctttagtc    4080
tttatttcat ttagatttgc tctgaacttt actatgtctt tccttctaat tttgggtttg    4140
gtttgttctt ttctagttcc ttgaggtgca tcattgaatt gtttctttga tatctatcta    4200
ctcatttgat gtaggtgttt attgctatac actctcccct cctagagctc cttttgttgt    4260
gtcccatagg tcttggtatg ttgtttctat tttcatttgt ttcaaacatt ttatttccat    4320
attaatttt atcattcagg aggagcatat tatttaattc ccatgtattt gtatagtttc     4380
caaagttcct cttatttcta tttttactcc attgtggtct gagaagatac ttcatatgat    4440
ttcaattttt aaaaatttgt caagacttgt tttttgtcct aacatatggt ctatcctgga    4500
gaatgttcca tgtgctgatg agaaaaatgt gtactcagca gttgttgagt aacatgttct    4560
acaaatatct gttagatcca tttggtctaa agtctagttt aaatccaatg agttttgtt     4620
aattttgtct agatgatcat gatctgagac tgaggtgaag tccccaacaa ttatcgtgtt    4680
ggagtctacc tctcttttta aatctagaaa tatttgcttt ataaatccgg gtggtctagt    4740
gttgggtgca tatatttagt tgttatttcc tcattagatt gatctcttta ctattatata    4800
ataactgttt actgcttctg gcataaagtc tgttttatgt aagtacagcc attcctgctt    4860
gagtttagta ccatgttgac aaagggatgc atagagagtt ggtaaagcat gatttctggg    4920
tgtctgtgtg aaggtgtttt gagaagagtt tagcatgagt ctgtggagtg agtgggaaga    4980
ttctccctca atgtcagcag gaaccatcca tccactgggg gcccaggtag aaaaagatga    5040
agaaatggtg aattctctct ctctcctgga gctgggtcac ccttcttctg cccttgaaca    5100
ggacatcaca actccaggct ctccagcctt tggactccaa gactgacacc agtgcccctc    5160
cccaattacc ccaggccctc aggcctttgg cctaggattg agacttacac catcagcttc    5220
cctggttctg aggcttctgg acttgcactg ggccatacta ccagcatccc agggtctcca    5280
gcttgcagag agcctgttgt gggacttttc agcctccata atcaagtaag ccaatttccc    5340
tggtatctat atagatatac aatcatgttt tgcttaccag cctgaaaaat gtatcgctag    5400
atgagtctgt cattgcataa acatcatagt gtacttacac aaacctagat tctatagcct    5460
actacacacc tagtctataa acatgtacag catgttactg tactgaatat tgtaggcaac    5520
tgtaacacaa tggtgaatat ttgcatattt aaacatatct tatcattaaa aagatacagt    5580
aaacataagg tataaaagac aaaaaccggc acacctatat agggcactta ccataaatgc    5640
agcttgcagg actagaagtc actcagggtg agtcagtgag cgaacgtgaa ggcctaggtt    5700
attactgtcc actacggtag actttatcaa cactgtacac aggctacact aaatttattt    5760
tttaaaaatt tgctctccaa taataaatta atcttcgcat ccttttttg ttgttcactg     5820
tgg                                                                  5823
```

<210> SEQ ID NO 417
<211> LENGTH: 5823
<212> TYPE: DNA

<213> ORGANISM: Homo sapiens

<400> SEQUENCE: 417

```
tatttcaggc tttcttcttt ctatggataa gaaagctcct caggtggcaa caaaggccat      60
ttctttggaa gcaggcatgg catgtgacga aaaaaagaca tctcagaaaa gagccaagaa     120
taagactgga gagccactgt cagagaacag aaactgggct taatcaagga acatctcttg     180
ttcccagagt aggaggctgg caatattttc tcactgaaat ttcagaattg ttatggacca     240
gtgactgctc tatgtgttca atttgttccc ttttcaaatg gaagcattta ttgcagacga     300
cctgcctctg tcccaccatt gtgtattagg tttgtagagt gtagacaact tgcctttta      360
gtttgtaggt ttctgtatca agagaagatg tgtgtrggcc taacctagat tacaggatcc     420
tggacttcaa gtctgatata atgactggat gagactttga ctgtcctaga attgggatga     480
acatattttg ccggtgggag ggcgtgagta attgcggtta gagggcagac tgtccctcac     540
acctattcct tttcatggtg ccttcccaaa ctgcctctgg aggtggccac acaaatggct     600
ttggccattg tgaccatggg aaacttgatg cagaggctga aaaagcact tgcatgtttc      660
tgtctcctct cttgttcctc tacaatcaca agaaatgtct aggcaggtct gagcaggccc     720
aggctcatct gccatggaag aagaatggca catggaagag ggtcacattg tcccaaccaa     780
gacgatccta gaccagccag gccccagttc atggttcaag acacatgaac atagttgcac     840
gaaccaagat tagttgtgta tggcccagac tagcagcagc acccatccaa cctacagact     900
ctgagaaata aatactagtt gtcttaagct tccaagtttc agtgtgagca ttaggtagta     960
acagttaatg aataagacag ataatcattt tatctgtctg atacttata caatgatttc      1020
tatttttat tgatacataa tattttacat attgctgggg tacatgtgac attttgctac     1080
atacataga tgtgtaatga tccagtcagg atatctgagg tgtccatcac tttgagaatt     1140
tctcacttct gtgtgttggg aacaattcaa gtcgtctctt ctagttattt taaaatatac     1200
aatacattgt taactgtagt cttttttatt gaatgacagg acttgtacct tttatctaac     1260
tgtatgtttg tatctattaa gctagttctc tttatccctg cccctccta cccactcact     1320
cttcccaacc tctaacatgt atcatcctat tctatatctc catgagatca acttctttag     1380
ctcccacata tgagcaaaaa catatgatgt tgtctttct gtgcccggtt tatttcactt      1440
atgacctcca tttccatcca tgttactata aatgacagga tttcattctt tttgtggcca     1500
aacagtattt cattgtgtat atatactaca ttttctttat ccattcatcc attgatgaac     1560
acttacgttg attccatatc tttgctattg tgaatggtgc tgcaataaac atgcacgtgc     1620
agttatccct ttgatacact gatttattt cctttggata aatacccagt agtgagattg     1680
ctggatcata cggtagttct actttagtt tttgagacat ttccatactt ttccagtgtt     1740
tgtattaatt tacattccca tcaacaatgt ataagatttc cctttcctcc acatcctcac     1800
cagcatctgc tatttttgt cttttaata atagtcattc taactggggt gagaggatat     1860
ctcgctatgg ttttgatttg catttccctg atatttaatg atattgagca tttcttcata     1920
taacctattg gccatttgtg tgtctttttt tttttttttt tttttttga gaattgtcta     1980
ctcatttttg gcttttaaa agattattt ttgttgttg ttgagtttag tgcatatcct      2040
ggatattagt ctcttatctg atgaagagtt tgccaatatt ttctcccatt caacaggttg     2100
tctcttcatt ctgttgactg tttccttttgc tgtgcagaag cactttatat acagtcccat     2160
ttgtctattt tttagtagtc tatgcattta aggtctcagc cacaaaatct ttgcctagac     2220
cagtcctaaa gtgtttcccc tatatttct tctagtagtt ttattgtttc atgtcttata     2280
```

```
tttaagtcta taatccattg tgagttgatt tttgtatatg gtgagatagg ggccttgttt    2340
cattcctctg catatagata tttaattttc tcagcaccat ttattgaagg tgtccttccc    2400
tattgtatgt tcttggtgcc tttgtcaaaa ttcagttggc tataaatatg tgaatttatt    2460
tctgggttct ctatgtggtt ccattagtct atgtgtctat ttttatacca atatcatgct    2520
gttttgatta ccatagcctt gtaatatatt ttgaagtcag gtagtgtgat gcctccagct    2580
ttgttctttt tgctcaggat tgctgtgcat actctggctt tttggttaca tacaaatttc    2640 aggattttg tatttctgtg aaaaatggca ttagtatttt gataggaatt gcactggatc     2700
tgtatattgt cctggacaac atggtcattt taacaatatt aattcttcta atctatgagt    2760
atgagacgtc ttcccacttg tttgtgtcct cttcaatttc tttcattggt gtttcataat    2820
ctcccttcta caggcctttc acctccttgg ttaaattaat tcctaggtat ttttttgtag    2880
ctactgtaaa tgggactgcc ttctttctca gctagttcat ttttggtgca tagaaaccct    2940 attttgtat gttcattttc tatcctgcaa cattaccaaa tttgcttatc agctttaagt     3000
gtgtattttg ctttgcttgt agagtcttct ggtttctcta aatgtaagac gatgtcatct    3060
gcaaacgggg acaatttgac ttcctcttaa aaatctgtat gccttttatt cctttctctt    3120
gcctgattgc tctggctcta cctccagtac tatactgaat aaaagtggta aaagtgagca    3180
tccttccttg tcttgctcta gttcttagag gaaatacttt cagttttcc ccactcagta     3240 tgatgttagc tgtgggtcat atatagcctt tattatgtta agatatgttt cttctgtacc    3300
tggtttgttg acagcttttt atcataaaag gatgtagaat tttatcaaat gttttttctg    3360
catctgttga gataatcata tggttttgt cattccttct actgttgtga tgtatcatgt     3420
ttattgattt gtgtatgtta aaccatcctt gtgtccttgg tataaattat acttggtcat    3480
ggtgtattat ctttttggca tcctgtcgaa ttgtttgcta gcttttgtt ttgttctttt     3540 tgagaatttt tatgtctagg ttccttagaa acactggcct gtagtctct ttttgtgtgt     3600 gtgtccttgt ctagtttggt gtcagggaaa tggtggtctt gtagaatgag ttgttttttc    3660
tttgattttt ttgcaagagt ttgaggagaa tgggtattag ttcttcttta tgtggttggt    3720
caaattggca gtgaattcat tcagtcatga gctttctttt ttttgggagg ttctcatta    3780 ctgagttaat cacactgctc attactgatc tgttcagatt ttctatttct tctggaatct    3840
cagtagttgt atgtttccag caattatcc atttcctcta ggttttctag tttggtagta     3900
tatagctatt cataatagtc tctgatgatc ttttgtattt ctgtgatatc agttgtaatg    3960 tcttttcat ttcctatttt atttgggtct tttcttgtt agtctagcaa ggggtttatc      4020
tattttatct ttttgaagaa ccaacttttt gtttcattga ccctttctac gtctttagtc    4080
tttatttcat ttagatttgc tctgaacttt actatgtctt tccttctaat tttgggtttg    4140
gtttgttctt ttctagttcc ttgaggtgca tcattgaatt gtttctttga tatctatcta    4200
ctcatttgat gtaggtgttt attgctatac actctcccct cctagagctc cttttgttgt    4260
gtcccatagg tcttggtatg ttgtttctat tttcatttgt ttcaaacatt ttatttccat    4320
attaattttt atcattcagg aggagcatat tatttaattc ccatgtattt gtatagtttc    4380
caaagttcct cttatttcta tttttactcc attgtggtct gagaagatac ttcatatgat    4440
ttcaattttt aaaaatttgt caagacttgt tttttgtcct aacatatggt ctatcctgga    4500
gaatgttcca tgtgctgatg agaaaaatgt gtactcagca gttgttgagt aacatgttct    4560
acaaatatct gttagatcca tttggtctaa agtctagttt aaatccaatg agtttttgtt    4620
```

```
aattttgtct agatgatcat gatctgagac tgaggtgaag tccccaacaa ttatcgtgtt    4680
ggagtctacc tctctttta aatctagaaa tatttgcttt ataaatccgg gtggtctagt     4740
gttgggtgca tatatttagt tgttatttcc tcattagatt gatctcttta ctattatata    4800
ataactgttt actgcttctg gcataaagtc tgttttatgt aagtacagcc attcctgctt    4860
gagtttagta ccatgttgac aaagggatgc atagagagtt ggtaaagcat gatttctggg    4920
tgtctgtgtg aaggtgtttt gagaagagtt tagcatgagt ctgtggagtg agtgggaaga    4980
ttctccctca atgtcagcag gaaccatcca tccactgggg gcccaggtag aaaaagatga    5040
agaaatggtg aattctctct ctctcctgga gctgggtcac ccttcttctg cccttgaaca    5100
ggacatcaca actccaggct ctccagcctt tggactccaa gactgacacc agtgcccctc    5160
cccaattacc ccaggccctc aggcctttgg cctaggattg agacttacac catcagcttc    5220
cctggttctg aggcttctgg acttgcactg ggccatacta ccagcatccc agggtctcca    5280
gcttgcagag agcctgttgt gggacttttc agcctccata atcaagtaag ccaatttccc    5340
tggtatctat atagatatac aatcatgttt tgcttaccag cctgaaaaat gtatcgctag    5400
atgagtctgt cattgcataa acatcatagt gtacttacac aaacctagat tctatagcct    5460
actacacacc tagtctataa acatgtacag catgttactg tactgaatat tgtaggcaac    5520
tgtaacacaa tggtgaatat ttgcatattt aaacatatct tatcattaaa aagatacagt    5580
aaacataagg tataaaagac aaaaaccggc acacctatat agggcactta ccataaatgc    5640
agcttgcagg actagaagtc actcagggtg agtcagtgag cgaacgtgaa ggcctaggtt    5700
attactgtcc actacggtag actttatcaa cactgtacac aggctacact aaatttattt    5760
tttaaaaatt tgctctccaa taataaatta atcttcgcat cctttttttg ttgttcactg    5820
tgg                                                                  5823

<210> SEQ ID NO 418
<211> LENGTH: 707
<212> TYPE: DNA
<213> ORGANISM: Homo sapiens

<400> SEQUENCE: 418
aacggtgtca gctggagtga actcctgtgt gtgcaaggcc tgggtctcct ggtcagacta     60
ctttctatgg gaaaggcata gtgtatagtc tatatactat acatagggt gctgggagga    120 actggggttt tcacagccag cttttggtttt cattaggttt gtttagtttc cattgcttca   180
ggggtgttag ttttgtgttc mcaactagat tataaactcc tcttgcattc ctgatggcag    240
tgacttgaag gcatttattt gaagaataat agacatacag aaaggggcgc atgtcataaa    300
ggtacagctg gacgacttt cacaaagtga gcacatttgt atgatcgatg ttgagaccaa     360
gagcattcag tggacaactc ctttccagtt actccacccc actcccagtg accatcattc    420
tgacttctaa ctgtgtagac atgttttgct tgttttgtac tttacaaaca tatctactct    480
attttaggtg gctagacaat gtgttttaca atgctggcca tgacagtgtt tgaaagaata    540
aaatggaatc aaatagaatg ggcagtatca gagtgtgttg cctgcctaag aaatgttttg    600
tgacattttg gctttgggtc tatttacaca ttaaatctaa gagcaccaga atgtggtgtc    660
aaaatgtgtt tggggatgaa gatattctaa agtcctgtag taagcaa                  707

<210> SEQ ID NO 419
<211> LENGTH: 712
<212> TYPE: DNA
<213> ORGANISM: Homo sapiens
```

<400> SEQUENCE: 419

```
cagactactt tctatgggaa aggcatagtg tatagtctat atactataca tagggggtgct      60
gggaggaact gggggttttca cagccagctt tggttttcat taggtttgtt tagtttccat     120
tgcttcaggg gtgttagttt tgtgttccca actagattat aaactcctct tgcattcctg     180
atggcagtga cttgaaggca tttatttgaa gaataataga catacagaaa ggggcrcatg     240
tcataaaggt acagctggac gacttttcac aaagtgagca catttgtatg atcgatgttg     300
agaccaagag cattcagtgg acaactcctt tccagttact ccaccccact cccagtgacc     360
atcattctga cttctaactg tgtagacatg ttttgcttgt tttgtacttt acaaacatat     420
ctactctatt ttaggtggct agacaatgtg ttttacaatg ctggccatga cagtgtttga     480
aagaataaaa tggaatcaaa tagaatgggc agtatcagag tgtgttgcct gcctaagaaa     540
tgttttgtga cattttggct ttgggtctat ttacacatta aatctaagag caccagaatg     600
tggtgtcaaa atgtgtttgg ggatgaagat attctaaagt cctgtagtaa gcaatgcaaa     660
acgttctgga ggtgttatt aaacatttgt ttgtagaatg gagaggaaga ca             712
```

<210> SEQ ID NO 420
<211> LENGTH: 1210
<212> TYPE: DNA
<213> ORGANISM: Homo sapiens

<400> SEQUENCE: 420

```
aaagcagcac tgctctgcat tcagccttgc tacgtctcct tcagatgggc gcactagata      60
ctgagtgatg atcatgcctt gtctaggatc tcaccaagac agttcatgaa agagacagtg     120
cagctcatgg aggagatggt gcagctcaca gagaggatgg tgccatcatg gaaagcatgg     180
ggcagtcatg gagatgacgg rgtagctcat ggagaatata atgccatcat ggaaggcata     240
gtgcagtcat ggagatgatg gtgcagctca tggagaagat ggtgccatca tggaaggcat     300
ggtgcaatca tggagtagac agtgcagctg gccaagatt ctccctgact aagctcttct     360
caggcacctc tgagccgtcg tcttaactag gcctccagct tggcttgtga aaactgcaga     420
ctctcagcac aaatgatttg cctcctacat taagagactt aaataaacac ttgcatggct     480
gtgtttattt aaacagctca aggctgtgtc cctgggatga caatgactcc agcccctaaa     540
attcctgctt gtgaaagctc attgctgaca gaaggatcta ccatttgttc cagccaacac     600
ctggtggcag gcagataggc cctgagcccc atttaagagc agttccttta gaaagcttgc     660
aattgtaaat cttttctctg cccatttgag atgtaaatct tctaccacct agaactgtct     720
tctcaaggac ctgtgagctg actcactgaa atgcaaacat tcaggagat aactccactc     780
ctgtccccat gcgacggcga ggccctgact ttggtgggca ccttgctctt atttgcacca     840
ccacctcctg tcctaaagac atgagacgtt tgtctctcct ctggataagt gcctattaac     900
caacccaggt gtcctggtca catgaaccag tccagcctag cacctggcac tgcctttccc     960
tcagcacact ccagtctgta aaagtctcct tatggttgtt ttggcaaagt tgagcttagt    1020
taatgctaga ccccttctct actgcaatag ttactgctga ataaagtcta tccttaccac    1080
tttaactagt gttgggcttt gtttctcttt cataagctca tggagaagac aatgcagttc    1140
catcaagttt ctggctctta cactgctaac agtcagctct ggggtccctg agagggacag    1200
actcacacca                                                            1210
```

<210> SEQ ID NO 421

```
<211> LENGTH: 1194
<212> TYPE: DNA
<213> ORGANISM: Homo sapiens

<400> SEQUENCE: 421
gcattcagcc ttgctacgtc tccttcagat gggcgcacta gatactgagt gatgatcatg    60
ccttgtctag gatctcacca agacagttca tgaaagagac agtgcagctc atggaggaga   120
tggtgcagct cacagagagg atggtgccat catggaaagc atggggcagt catggagatg   180
acggagtagc tcatggagaa kataatgcca tcatggaagg catagtgcag tcatggagat   240
gatggtgcag ctcatggaga agatggtgcc atcatggaag gcatggtgca atcatggagt   300
agacagtgca gctgggccaa gattctccct gactaagctc ttctcaggca cctctgagcc   360
gtcgtcttaa ctaggcctcc agcttggctt gtgaaaactg cagactctca gcacaaatga   420
tttgcctcct acattaagag acttaaataa acacttgcat ggctgtgttt atttaaacag   480
ctcaaggctg tgtccctggg atgacaatga ctccagcccc taaaattcct gcttgtgaaa   540
gctcattgct gacagaagga tctaccattt gttccagcca cacctggtg gcaggcagat    600 aggccctgag ccccatttaa gagcagttcc tttagaaagc ttgcaattgt aaatcttttc   660
tctgcccatt tgagatgtaa atcttctacc acctagaact gtcttctcaa ggacctgtga   720
gctgactcac tgaaatgcaa acattcaggg agataactcc actcctgtcc ccatgcgacg   780
gcgaggccct gactttggtg ggcaccttgc tcttatttgc accaccacct cctgtcctaa   840
agacatgaga cgtttgtctc tcctctggat aagtgcctat taaccaaccc aggtgtcctg   900
gtcacatgaa ccagtccagc ctagcacctg gcactgcctt ccctcagca cactccagtc    960 tgtaaaagtc tccttatggt tgttttggca agttgagct tagttaatgc tagacccctt    1020
ctctactgca atagttactg ctgaataaag tctatcctta ccactttaac tagtgttggg   1080 cttttgtttct ctttcataag ctcatggaga agacaatgca gttccatcaa gtttctggct   1140
cttacactgc taacagtcag ctctggggtc cctgagaggg acagactcac acca          1194

<210> SEQ ID NO 422
<211> LENGTH: 1194
<212> TYPE: DNA
<213> ORGANISM: Homo sapiens

<400> SEQUENCE: 422
gcattcagcc ttgctacgtc tccttcagat gggcgcacta gatactgagt gatgatcatg    60
ccttgtctag gatctcacca agacagttca tgaaagagac agtgcagctc atggaggaga   120
tggtgcagct cacagagagg atggtgccat catggaaagc atggggcagt catggagatg   180
acggagtagc tcatggagaa kataatgcca tcatggaagg catagtgcag tcatggagat   240
gatggtgcag ctcatggaga agatggtgcc atcatggaag gcatggtgca atcatggagt   300
agacagtgca gctgggccaa gattctccct gactaagctc ttctcaggca cctctgagcc   360
gtcgtcttaa ctaggcctcc agcttggctt gtgaaaactg cagactctca gcacaaatga   420
tttgcctcct acattaagag acttaaataa acacttgcat ggctgtgttt atttaaacag   480
ctcaaggctg tgtccctggg atgacaatga ctccagcccc taaaattcct gcttgtgaaa   540
gctcattgct gacagaagga tctaccattt gttccagcca cacctggtg gcaggcagat    600 aggccctgag ccccatttaa gagcagttcc tttagaaagc ttgcaattgt aaatcttttc   660
tctgcccatt tgagatgtaa atcttctacc acctagaact gtcttctcaa ggacctgtga   720
gctgactcac tgaaatgcaa acattcaggg agataactcc actcctgtcc ccatgcgacg   780
```

```
gcgaggccct gactttggtg ggcaccttgc tcttatttgc accaccacct cctgtcctaa        840
agacatgaga cgtttgtctc tcctctggat aagtgcctat taaccaaccc aggtgtcctg        900
gtcacatgaa ccagtccagc ctagcacctg gcactgcctt tccctcagca cactccagtc        960
tgtaaaagtc tccttatggt tgttttggca aagttgagct tagttaatgc tagacccctt       1020
ctctactgca atagttactg ctgaataaag tctatcctta ccactttaac tagtgttggg       1080 cttttgtttct ctttcataag ctcatggaga agacaatgca gttccatcaa gtttctggct      1140
cttacactgc taacagtcag ctctggggtc cctgagaggg acagactcac acca             1194
```

<210> SEQ ID NO 423
<211> LENGTH: 1118
<212> TYPE: DNA
<213> ORGANISM: Homo sapiens

<400> SEQUENCE: 423

```
accaagacag ttcatgaaag agacagtgca gctcatggag gagatggtgc agctcacaga         60
gaggatggtg ccatcatgga aagcatgggg cagtcatgga gatgacggag tagctcatgg        120
agaagataat gccatcatgg aaggcatagt gcagtcatgg agatgatggt gcagctcatg        180
gagaagatgg tgccatcatg raaggcatgg tgcaatcatg gagtagacag tgcagctggg       240
ccaagattct ccctgactaa gctcttctca ggcacctctg agccgtcgtc ttaactaggc        300
ctccagcttg gcttgtgaaa actgcagact ctcagcacaa atgatttgcc tcctacatta       360
agagacttaa ataaacactt gcatggctgt gtttatttaa acagctcaag gctgtgtccc        420
tgggatgaca atgactccag cccctaaaat tcctgcttgt gaaagctcat tgctgacaga        480
aggatctacc atttgttcca gccaacacct ggtggcaggc agataggccc tgagccccat        540
ttaagagcag ttcctttaga aagcttgcaa ttgtaaatct tttctctgcc catttgagat        600
gtaaatcttc taccacctag aactgtcttc tcaaggacct gtgagctgac tcactgaaat        660
gcaaacattc agggagataa ctccactcct gtccccatgc gacggcgagg ccctgacttt        720
ggtgggcacc ttgctcttat ttgcaccacc acctcctgtc ctaaagacat gagacgtttg        780
tctctcctct ggataagtgc ctattaacca acccaggtgt cctggtcaca tgaaccagtc        840
cagcctagca cctggcactg cctttccctc agcacactcc agtctgtaaa agtctcctta        900
tggttgtttt ggcaaagttg agcttagtta atgctagacc ccttctctac tgcaatagtt        960
actgctgaat aaagtctatc cttaccactt taactagtgt tgggctttgt ttctctttca       1020
taagctcatg gagaagacaa tgcagttcca tcaagtttct ggctcttaca ctgctaacag       1080
tcagctctgg ggtccctgag agggacagac tcacacca                               1118
```

<210> SEQ ID NO 424
<211> LENGTH: 601
<212> TYPE: DNA
<213> ORGANISM: Homo sapiens

<400> SEQUENCE: 424

```
gtagggcac tgtctatact ggctgcactc tggccagtgc tgtcccaacg ctgacccctc         60
tggaagctaa tctggcttat aatgaggatg ctttctttag aggggactct ccatgcacag       120
cagaaaatcc caatggagtg gttcttccct atgtccccaa gggactggga atattctttc       180
agtaacaatg gccattggg ggaagaagga tgaaagtggg gtgagagacg tgaaatttgg        240
agaggtccct caaagattgt gatgtgcctc tcttgttcca atcacaggac aggggtataa       300
```

```
yggctttcct ttgaaacacg gggatgaatt taactattca cttcccaggt agattcatca    360
gggtctagag cttcagctaa cagcatgagg aagattccaa atgtgccccc atcagcatag    420
gaactgggta tgttgagtct atggtctcat aaaaccagaa gaaggacaag ggattgtggc    480
tccaggcttg ggagcacctt ttccttacca tgggctacag tatttattta gggtaaagga    540
aggaaactcc tgaggtgcta tggggtgcca gcaatttgga gcatcagtaa ttcaatgtcc    600
c                                                                   601

<210> SEQ ID NO 425
<211> LENGTH: 601
<212> TYPE: DNA
<213> ORGANISM: Homo sapiens

<400> SEQUENCE: 425
acgctgaccc ctctggaagc taatctggct tataatgagg atgctttctt tagaggggac     60
tctccatgca cagcagaaaa tcccaatgga gtggttcttc cctatgtccc caagggactg    120
ggaatattct ttcagtaaca atggcccatt ggggaagaa ggatgaaagt ggggtgagag     180
acgtgaaatt tggagaggtc cctcaaagat tgtgatgtgc ctctcttgtt ccaatcacag    240
gacagggta taacggcttt cctttgaaac acggggatga atttaactat tcacttccca     300
rgtagattca tcagggtcta gagcttcagc taacagcatg aggaagattc caaatgtgcc    360
cccatcagca taggaactgg gtatgttgag tctatggtct cataaaacca gaagaaggac    420
aagggattgt ggctccaggc ttgggagcac cttttcctta ccatgggcta cagtatttat    480
ttagggtaaa ggaaggaaac tcctgaggtg ctatggggtg ccagcaattt ggagcatcag    540
taattcaatg tcccttcagc catgtgtatt caactcctgc tgtgggtgtg gacttggtgc    600
a                                                                   601

<210> SEQ ID NO 426
<211> LENGTH: 701
<212> TYPE: DNA
<213> ORGANISM: Homo sapiens

<400> SEQUENCE: 426
ttcctgggca tcgtcatatt ctgtaaaaca aggaagctca gcccagtgtg ttctaacatg     60
acctcctttc tacatcctta ggtgttgtta tgcgtgaatc acgtccccc aaaagacatg     120
ttcatgtcct aaccccagg acctcagaat gtgtgatctg gtttggaaat aaggtcatca    180
cagatgaaat tagctaagac aaggtcatat tggaataggg ttggcccta atccactgtg    240
actggtgtcc ttttaagaag aggacacaga cacaggaggg gagagggcca tgggatgatg    300
caggtggaga ctggagtgct acagctgcaa gcaaatacat ttctgtgctg tgaagccacc    360
catttggtgg tactacgtta aaacagctct aggaaattaa tacagatgtt gcctgtattt    420
ttgtttctca tattactact cattgtttta atgatgactg ttttattcat taagttgaaa    480
gctcctaaag cagagggacc rtattttat gtcccaactc tccttaaggc cttgcctatg    540
atagcacatc tcttcaatag aattgtccta actttaacag agacaacttg ggttatttaa    600
tatggagaac aaagggttaa gctggtgcca gatgggtttc attttctcta aatctggaac    660
caaaggcagc aagtctatgg ggtggacgga gttcttagct c                        701

<210> SEQ ID NO 427
<211> LENGTH: 701
<212> TYPE: DNA
<213> ORGANISM: Homo sapiens
```

```
<400> SEQUENCE: 427
caaggaagct cagcccagtg tgttctaaca tgacctcctt tctacatcct taggtgttgt      60
tatgcgtgaa tcacgtcccc ccaaaagaca tgttcatgtc ctaaccccca ggacctcaga     120
atgtgtgatc tggtttggaa ataaggtcat cacagatgaa attagctaag acaaggtcat     180
attggaatag ggttggccct taatccactg tgactggtgt ccttttaaga agaggacaca     240
gacacaggag gggagagggc catgggatga tgcaggtgga gactggagtg ctacagctgc     300
aagcaaatac atttctgtgc tgtgaagcca cccatttggt ggtactacgt taaaacagct     360
ctaggaaatt aatacagatg ttgcctgtat ttttgtttct catattacta ctcattgttt     420
taatgatgac tgttttattc attaagttga aagctcctaa agcagaggga ccatattttt     480
atgtcccaac tctccttaag sccttgccta tgatagcaca tctcttcaat agaattgtcc     540
taactttaac agagacaact tgggttattt aatatggaga acaaagggtt aagctggtgc     600
cagatgggtt tcattttctc taaatctgga accaaaggca gcaagtctat ggggtggacg     660
gagttcttag ctcaaccctt tggtgaggta agaagaagga t                         701
```

SIMULTANEOUS DETERMINATION OF ANEUPLOIDY AND FETAL FRACTION

CROSS REFERENCE

This Application is a continuation of, and claims priority to, U.S. patent application Ser. No. 15/664,008 entitled "Simultaneous Determination of Aneuploidy and Fetal Fraction", filed on Jul. 31, 2017, which is a continuation of U.S. patent application Ser. No. 13/365,240 entitled "Simultaneous Determination of Aneuploidy and Fetal Fraction", filed on Feb. 2, 2012, which is a continuation of U.S. patent application Ser. No. 12/958,356 entitled "Simultaneous Determination of Aneuploidy and Fetal Fraction", filed on Dec. 1, 2010, which claims priority to U.S. Provisional Application Ser. No. 61/296,358 entitled "Methods for Determining Fraction of Fetal Nucleic Acids in Maternal Samples", filed on Jan. 19, 2010; U.S. Provisional Application Ser. No. 61/360,837 entitled "Methods for Determining Fraction of Fetal Nucleic Acids in Maternal Samples", filed on Jul. 1, 2010; U.S. Provisional Application Ser. No. 61/407,017 entitled "Method for Determining Copy Number Variations", filed on Oct. 26, 2010; and U.S. Provisional Application Ser. No. 61/455,849 entitled "Simultaneous determination of Aneuploidy and Fetal Fraction", filed on Oct. 26, 2010; each of which are incorporated herein by reference in their entirety.

SEQUENCE LISTING

The sequence listing submitted via EFS, in compliance with C.F.R. § 1.52(e), is incorporated herein by reference. The sequence listing text file submitted via EFS, in U.S. patent application Ser. No. 13/365,240, contains the file "Seq_List_0119_301.txt" created on Mar. 7, 2012, which is 238,557 bytes in size.

FIELD OF THE INVENTION

The invention relates generally to the field of diagnostics, and provides a method that is applicable to the practice of noninvasive prenatal diagnostics.

BACKGROUND OF THE INVENTION

Prenatal diagnosis to determine potential fetal abnormalities provides an opportunity for necessary care and management during pregnancy, the neonatal period and delivery. Imaging techniques such as ultrasonography, magnetic resonance imaging and fetal echocardiography are useful for the identification of structural abnormalities of the fetus. Amniocentesis, chronic villus sampling and fetal blood sampling provide fetal cells and tissues for the analysis of chromosomal, genetic and biochemical abnormalities, but are invasive and pose great risk to the pregnancy.

The existence of circulating cell-free DNA in maternal blood (Lo et al., Lancet 350:485-487 [1997]) is being exploited for developing noninvasive processes that use fetal nucleic acids from a maternal peripheral blood sample to determine fetal chromosomal abnormalities (Fan H C and Quake S R Anal Chem 79:7576-7579 [2007]; Fan et al., Proc Natl Acad Sci 105:16266-16271 [2008]).

These methods provide a paradigm shift in prenatal diagnosis, as they could effectively pronounce the end of invasive procedures. However, the sensitivity of fetal aneuploidy determination largely depends on the fetal DNA fraction, which has been determined to be <10% of the total circulating cell-five DNA (cfDNA) (Lo et al., *Am J Hum Genet* 62:768-775 [1998]). Given the relatively low concentration of fetal circulating nucleic acids, false negative results can arise if there is insufficient starting nucleic acid for analysis. Accordingly, assays for the noninvasive determination of fetal DNA fraction have been developed, but typically rely on comparing the amount of fetal-specific locus (such as the SRY locus on chromosome Y in male pregnancies) to that of a locus on any autosome that is common to both the mother and the fetus (Dahllan et al., Lancet 369:474-481 [2007]; Li et al., Clin Chem 1002-1011 [2004]; Fan et al., Proc Natl Acad Sci 105:16266-16271 [2008]). In addition, the assays used for quantifying fetal fraction are performed independently of the assays being developed for determining the presence or absence of aneuploidies in circulating cfDNA.

Therefore, it would be desirable to provide a prenatal test that affords an internal control to measure the adequacy of input fetal nucleic acids and avoid incorrect diagnoses of fetal chromosomal abnormalities.

The present invention provides compositions and methods that enable the simultaneous determination of fetal fraction and the determination of the presence or absence of aneuploidy from a single diagnostic sequencing process. The method allows for determining fetal fraction in a gender-independent manner, which relies on quantification of alleles on multiple chromosomes. The noninvasive diagnostic method encompasses the use of next generation sequencing (NGS) technology that can be implemented in a streamlined and cost-effective process to provide noninvasive prenatal diagnoses of fetal aneuploidies with greater confidence.

SUMMARY OF THE INVENTION

The invention provides compositions and methods for simultaneously determining the presence or absence of fetal aneuploidy and the relative amount of fetal nucleic acids in a sample obtained from a pregnant female. The method encompasses the use of sequencing technologies and exploits the occurrence of polymorphisms to provide a streamlined noninvasive process applicable to the practice of prenatal diagnostics.

In one embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids; (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy.

In another embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids; wherein enriching comprises amplifying a plurality of polymorphic target nucleic acids in a portion of said mixture; (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy.

In another embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids; wherein enriching comprises amplifying a plurality of polymorphic target nucleic acids in a portion of a purified mixture of fetal and maternal nucleic acids; (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy.

In another embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids; wherein enriching comprises combining at least a portion of a first sequencing library of said mixture of fetal and maternal nucleic acid molecules with at least a portion of a second sequencing library of amplified polymorphic target nucleic acids; (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy.

In one embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids; wherein each of the plurality of polymorphic target nucleic acids comprises at least one single nucleotide polymorphism (SNP); (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy. In some embodiments, the at least one SNP, is a single SNP selected from each of said plurality of polymorphic target nucleic acids comprises a SNP selected from rs560681, rs1109037, rs9866013, rs13182883, rs13218440, rs7041158, rs740598, rs10773760, rs4530059, rs7205345, rs8078417, rs576261, rs2567608, rs430046, rs9951171, rs338882, rs10776839, rs9905977, rs1277284, rs258684, rs1347696, rs508485, rs9788670, rs8137254, rs3143, rs2182957, rs3739005, and rs530022. Alternatively, the at least one SNP is a set of two tandem SNPs selected from sets rs7277033-rs2110153; rs2822654-rs1882882; rs368657-rs376635; rs2822731-rs2822732; rs1475881-rs7275487; rs1735976-rs2827016; rs447340-rs2824097; rs418989-rs13047336; rs987980-rs987981; rs4143392-rs4143391; rs1691324-rs13050434; rs11909758-rs9980111; rs2826842-rs232414; rs1980969-rs1980970; rs9978999-rs9979175; rs1034346-rs12481852; rs7509629-rs2828358; rs4817013-rs7277036; rs9981121-rs2829696; rs455921-rs2898102; rs2898102-rs458848; rs961301-rs2830208; rs2174536-rs458076; rs11088023-rs11088024; rs1011734-rs1011733; rs2831244-rs9789838; rs8132769-rs2831440; rs8134080-rs2831524; rs4817219-rs4817220; rs2250911-rs2250997; rs2831899-rs2831900; rs2831902-rs2831903; rs11088086-rs2251447; rs2832040-rs11088088; rs2832141-rs2246777; rs2832959-rs9980934; rs2833734-rs2833735; rs933121-rs933122; rs2834140-rs12626953; rs2834485-rs3453; rs9974986-rs2834703; rs2776266-rs2835001; rs1984014-rs1984015; rs7281674-rs2835316; rs13047304-rs13047322; rs2835545-rs4816551; rs2835735-rs2835736; rs13047608-rs2835826; rs2836550-rs2212596; rs2836660-rs2836661; rs465612-rs8131220; rs9980072-rs8130031; rs418359-rs2836926; rs7278447-rs7278858; rs385787-rs367001; rs367001-rs386095; rs2837296-rs2837297; and rs2837381-rs4816672.

In one embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids; wherein each of the plurality of polymorphic target nucleic acids comprises at least one single nucleotide polymorphism (SNP); (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy. The step of enriching comprises amplifying a plurality of polymorphic target nucleic acids in a portion of said mixture. In some embodiments, the at least one SNP, is a single SNP selected from each of said plurality of polymorphic target nucleic acids comprises a SNP selected from rs560681, rs1109037, rs9866013, rs13182883, rs13218440, rs7041158, rs740598, rs10773760, rs4530059, rs7205345, rs8078417, rs576261, rs2567608, rs430046, rs9951171, rs338882, rs10776839, rs9905977, rs1277284, rs258684, rs1347696, rs508485, rs9788670, rs8137254, rs3143, rs2182957, rs3739005, and rs530022. Alternatively, the at least one SNP is a set of two tandem SNPs selected from sets rs7277033-rs2110153; rs2822654-rs1882882; rs368657-rs376635; rs2822731-rs2822732; rs1475881-rs7275487; rs1735976-rs2827016; rs447340-rs2824097; rs418989-rs13047336; rs987980-rs987981; rs4143392-rs4143391; rs1691324-rs13050434; rs11909758-rs9980111; rs2826842-rs232414; rs1980969-rs1980970; rs9978999-rs9979175; rs1034346-rs12481852; rs7509629-rs2828358; rs4817013-rs7277036; rs9981121-rs2829696; rs455921-rs2898102; rs2898102-rs458848; rs961301-rs2830208; rs2174536-rs458076; rs11088023-rs11088024; rs1011734-rs1011733; rs2831244-rs9789838; rs8132769-rs2831440; rs8134080-rs2831524; rs4817219-rs4817220; rs2250911-rs2250997; rs2831899-rs2831900; rs2831902-rs2831903; rs11088086-rs2251447; rs2832040-rs11088088; rs2832141-rs2246777; rs2832959-rs9980934; rs2833734-rs2833735; rs933121-rs933122; rs2834140-rs12626953; rs2834485-rs3453; rs9974986-rs2834703; rs2776266-rs2835001; rs1984014-rs1984015; rs7281674-rs2835316; rs13047304-rs13047322; rs2835545-rs4816551; rs2835735-rs2835736; rs13047608-rs2835826; rs2836550-rs2212596; rs2836660-rs2836661; rs465612-rs8131220; rs9980072-rs8130031; rs418359-rs2836926; rs7278447-rs7278858; rs385787-rs367001; rs367001-rs386095; rs2837296-rs2837297; and rs2837381-rs4816672.

In one embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids; wherein each of the plurality of polymorphic target nucleic acids comprises at least one single nucleotide polymorphism (SNP); (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy. The step of enriching comprises amplifying a plurality of polymorphic target nucleic acids in a portion of a purified mixture of fetal and maternal nucleic acids. In some embodiments, the at least one SNP, is a single SNP selected from rs560681, rs1109037, rs9866013, rs13182883, rs13218440, rs7041158, rs740598, rs10773760, rs 4530059, rs7205345, rs8078417, rs576261, rs2567608, rs430046, rs9951171, rs338882, rs10776839, rs9905977, rs1277284, rs258684, rs1347696, rs508485, rs9788670, rs8137254, rs3143, rs2182957, rs3739005, and rs530022. Alternatively, the at least one SNP is a set of two tandem SNPs selected from sets rs7277033-rs2110153; rs2822654-rs1882882; rs368657-rs376635; rs2822731-rs2822732; rs1475881-rs7275487; rs1735976-rs2827016; rs447340-rs2824097; rs418989-rs13047336; rs987980-rs987981; rs4143392-rs4143391; rs1691324-rs13050434; rs11909758-rs9980111; rs2826842-rs232414; rs1980969-rs1980970; rs9978999-rs9979175; rs1034346-rs12481852; rs7509629-rs2828358; rs4817013-rs7277036; rs9981121-rs2829696; rs455921-rs2898102; rs2898102-rs458848; rs961301-rs2830208; rs2174536-rs458076; rs11088023-rs11088024; rs1011734-rs1011733; rs2831244-rs9789838; rs8132769-rs2831440; rs8134080-rs2831524; rs4817219-rs4817220; rs2250911-rs2250997; rs2831899-rs2831900; rs2831902-rs2831903; rs11088086-rs2251447; rs2832040-rs11088088; rs2832141-rs2246777; rs2832959-rs9980934; rs2833734-rs2833735; rs933121-rs933122; rs2834140-rs12626953; rs2834485-rs3453; rs9974986-rs2834703; rs2776266-rs2835001; rs1984014-rs1984015; rs7281674-rs2835316; rs13047304-rs13047322; rs2835545-rs4816551; rs2835735-rs2835736; rs13047608-rs2835826; rs2836550-rs2212596; rs2836660-rs2836661; rs465612-rs8131220; rs9980072-rs8130031; rs418359-rs2836926; rs7278447-rs7278858; rs385787-rs367001; rs367001-rs386095; rs2837296-rs2837297; and rs2837381-rs4816672.

In one embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids; wherein each of the plurality of polymorphic target nucleic acids comprises at least one single nucleotide polymorphism (SNP); (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy. The step of enriching comprises combining at least a portion of a first sequencing library of said mixture of fetal and maternal nucleic acid molecules with at least a portion of a second sequencing library of amplified polymorphic target nucleic acids. In some embodiments, the at least one SNP, is a single SNP selected from each of said plurality of polymorphic target nucleic acids comprises a SNP selected from rs560681, rs1109037, rs9866013, rs13182883, rs13218440, rs7041158, rs740598, rs10773760, rs4530059, rs7205345, rs8078417, rs576261, rs2567608, rs430046, rs9951171, rs338882, rs10776839, rs9905977, rs1277284, rs258684, rs1347696, rs508485, rs9788670, rs8137254, rs3143, rs2182957, rs3739005, and rs530022. Alternatively, the at least one SNP is a set of two tandem SNPs selected from sets rs7277033-rs2110153; rs2822654-rs1882882; rs368657-rs376635; rs2822731-rs2822732; rs1475881-rs7275487; rs1735976-rs2827016; rs447340-rs2824097; rs418989-rs13047336; rs987980-rs987981; rs4143392-rs4143391; rs1691324-rs13050434; rs11909758-rs9980111; rs2826842-rs232414; rs1980969-rs1980970; rs9978999-rs9979175; rs1034346-rs12481852; rs7509629-rs2828358; rs4817013-rs7277036; rs9981121-rs2829696; rs455921-rs2898102; rs2898102-rs458848; rs961301-rs2830208; rs2174536-rs458076; rs11088023-rs11088024; rs1011734-rs1011733; rs2831244-rs9789838; rs8132769-rs2831440; rs8134080-rs2831524; rs4817219-rs4817220; rs2250911-rs2250997; rs2831899-rs2831900; rs2831902-rs2831903; rs11088086-rs2251447; rs2832040-rs11088088; rs2832141-rs2246777; rs2832959-rs9980934; rs2833734-rs2833735; rs933121-rs933122; rs2834140-rs12626953; rs2834485-rs3453; rs9974986-rs2834703; rs2776266-rs2835001; rs1984014-rs1984015; rs7281674-rs2835316; rs13047304-rs13047322; rs2835545-rs4816551; rs2835735-rs2835736; rs13047608-rs2835826; rs2836550-rs2212596; rs2836660-rs2836661; rs465612-rs8131220; rs9980072-rs8130031; rs418359-rs2836926; rs7278447-rs7278858; rs385787-rs367001; rs367001-rs386095; rs2837296-rs2837297; and rs2837381-rs4816672.

In another embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids, wherein each of the plurality of polymorphic target nucleic acids comprises at least one short tandem repeat (STR); (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy. In some embodiments, the at least one STR is less than about 200 base pairs. In other embodiments, each of said plurality of polymorphic target nucleic acids comprises an STR selected from CSF1PO, FGA, TH01, TPOX, vWA, D3S1358, D5S818, D7S820, D8S1179, D13S317, D16S539, D18S51, D21S11, D2S1338, PentaD, PentaE, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627 and D1GATA113.

In another embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids, wherein each of the plurality of polymorphic target nucleic acids comprises at least one short tandem repeat (STR); (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy. The step of enriching comprises amplifying a plurality of polymorphic target nucleic acids in a portion of the mixture. In some embodiments, the at least one STR is less than about 200 base pairs. In other embodiments, each of said plurality of polymorphic target nucleic acids comprises an STR selected from CSF1PO, FGA, TH01, TPOX, vWA, D3S1358, D5S818, D7S820, D8S1179, D13S317, D16S539, D18S51, D21S11, D2S1338, PentaD, PentaE, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627 and D1GATA113.

In another embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids, wherein each of the plurality of polymorphic target nucleic acids comprises at least one short tandem repeat (STR); (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy. The step of enriching comprises amplifying a plurality of polymorphic target nucleic acids in a portion of a purified mixture of fetal and maternal nucleic acids. In some embodiments, the at least one STR is less than about 200 base pairs. In other embodiments, each of said plurality of polymorphic target nucleic acids comprises an STR selected from CSF1PO, FGA, TH01, TPOX, vWA, D3S1358, D5S818, D7S820, D8S1179, D13S317, D16S539, D18S51, D21S11, D2S1338, PentaD, PentaE, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627 and D1GATA113.

In another embodiment, a method is provided for simultaneously determining aneuploidy and fetal fraction in a maternal sample comprising a mixture of fetal and maternal nucleic acid molecules, the method comprising: (a) enriching said mixture for a plurality of polymorphic target nucleic acids, wherein each of the plurality of polymorphic target nucleic acids comprises at least one short tandem repeat (STR); (b) sequencing at least a portion of the enriched mixture obtained in step (a), wherein sequencing comprises providing a plurality of sequence tags; and (c) based on the sequencing, simultaneously determining the fetal fraction and the presence or absence of the fetal aneuploidy. The step of enriching comprises combining at least a portion of a first sequencing library of said mixture of fetal and maternal nucleic acid molecules with at least a portion of a second sequencing library of amplified polymorphic target nucleic acids. In some embodiments, the at least one STR is less than about 200 base pairs. In other embodiments, each of said plurality of polymorphic target nucleic acids comprises an STR selected from CSF1PO, FGA, TH01, TPOX, vWA, D3S1358, D5S818, D7S820, D8S1179, D13S317, D16S539, D18S51, D21S11, D2S1338, PentaD, PentaE, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627 and D1GATA113.

In the embodiments of the method summarized above and described in further detail below, the maternal sample is a biological sample that can be chosen from but is not limited to blood, plasma, serum, urine and saliva. Preferably, the fetal and maternal nucleic acid molecules in the maternal sample are cell-free DNA (cfDNA) molecules. The polymorphic target nucleic acids can be on the same or on different chromosomes.

In the embodiments of the method summarized above and described in further detail below, the aneuploidy that is determined can be a chromosomal or a partial aneuploidy. In some embodiments, the aneuploidy is a chromosomal aneuploidy that is selected from trisomy 8, trisomy 13, trisomy 15, trisomy 16, trisomy 18, trisomy 21, trisomy 22, monosomy X, and XXX. In some embodiments, determining the aneuploidy comprises calculating a chromosome dose based on the number of said sequence tags for a chromosome of interest and for a normalizing chromosome, and comparing said dose to a threshold value, while determining the fetal fraction comprises identifying at least one informative polymorphic site in said enriched mixture, and calculating the fetal fraction from the amount of fetal and maternal polymorphic sites in said enriched sample.

In the embodiments of the method summarized above and described in further detail below, sequencing that can be used for the simultaneous determination is performed using next generation (NGS) sequencing. In some embodiments, sequencing is massively parallel sequencing using sequencing-by-synthesis with reversible dye terminators. In other embodiments, sequencing is sequencing-by-ligation. In yet other embodiments, sequencing is single molecule sequencing. The sequencing of the enriched mixture can further comprise an amplification.

In another embodiment, a composition comprising at least one set of primers for amplifying at least one SNP in a maternal sample e.g. a plasma sample, comprising a mixture of nucleic acid molecules is provided. Nucleic acid molecules can be cfDNA molecules. In one embodiment, the composition comprises at least one set of primers for amplifying at least one SNP selected from rs560681, rs1109037, rs9866013, rs13182883, rs13218440, rs7041158, rs740598, rs10773760, rs4530059, rs7205345, rs8078417, rs576261, rs2567608, rs430046, rs9951171, rs338882, rs10776839, rs9905977, rs1277284, rs258684, rs1347696, rs508485, rs9788670, rs8137254, rs3143, rs2182957, rs3739005, and rs530022. In one embodiment, the at least one set of primers is selected from primer sets of SEQ ID NOs:57-112.

In another embodiment, a composition comprising at least one set of primers for amplifying at least one STR in a maternal sample e.g. a plasma sample, comprising a mixture of nucleic acid molecules is provided. Nucleic acid molecules can be cfDNA molecules. In one embodiment, the composition comprises at least one set of primers for amplifying at least one STR selected from CSF1PO, FGA, TH01, TPOX, vWA, D3S1358, D5S818, D7S820, D8S1179, D13S317, D16S539, D18S51, D21S11, D2S1338, PentaD, PentaE, D22S1045, D20S1082, D20S482, D18S853, D17S1301, D17S974, D1451434, D12ATA63, D11S4463, D1051435, D1051248, D9S2157, D9S1122, D8S1115, D6S1017, D6S474, D5S2500, D4S2408, D4S2364, D3S4529, D3S3053, D2S1776, D2S441, D1S1677, D1S1627 and D1GATA113. In one embodiment, the at least one set of STR primers is selected from primer sets of SEQ ID NOs:113-196.

In another embodiment, a kit for preparing a sequencing library for massively parallel sequencing of fetal and maternal nucleic acid molecules in a maternal sample is provided. In some embodiments, the maternal sample is a plasma sample. The kit comprises a composition comprising at least one set of primers for amplifying at least one polymorphic nucleic acid in the mixture of fetal and maternal nucleic acid molecules. The polymorphic nucleic acid sequences each comprise at least one SNP or an STR. Sequences comprising tandem SNPs are encompassed in the kit of the invention. In some embodiments, sequencing is single molecule sequencing. In some embodiments, the massively parallel sequencing is sequencing-by-synthesis with reversible dye terminators. In other embodiments, the massively parallel sequencing is sequencing-by-ligation.

Preferably, the fetal and maternal nucleic acid molecules are cfDNA molecules. In some embodiments, the maternal sample is a plasma sample. The kit comprises a composition comprising at least one set of primers for amplifying at least one polymorphic nucleic acid comprised in the fetal and maternal nucleic acid molecules. In some embodiments, the polymorphic nucleic acid comprises a SNP. In other embodiment, the polymorphic nucleic acid comprises an STR.

INCORPORATION BY REFERENCE

All patents, patent applications, and other publications, including all sequences disclosed within these references, referred to herein are expressly incorporated by reference, to the same extent as if each individual publication, patent or patent application was specifically and individually indicated to be incorporated by reference. All documents cited are, in relevant part, incorporated herein by reference. However, the citation of any document is not to be construed as an admission that it is prior art with respect to the present invention.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
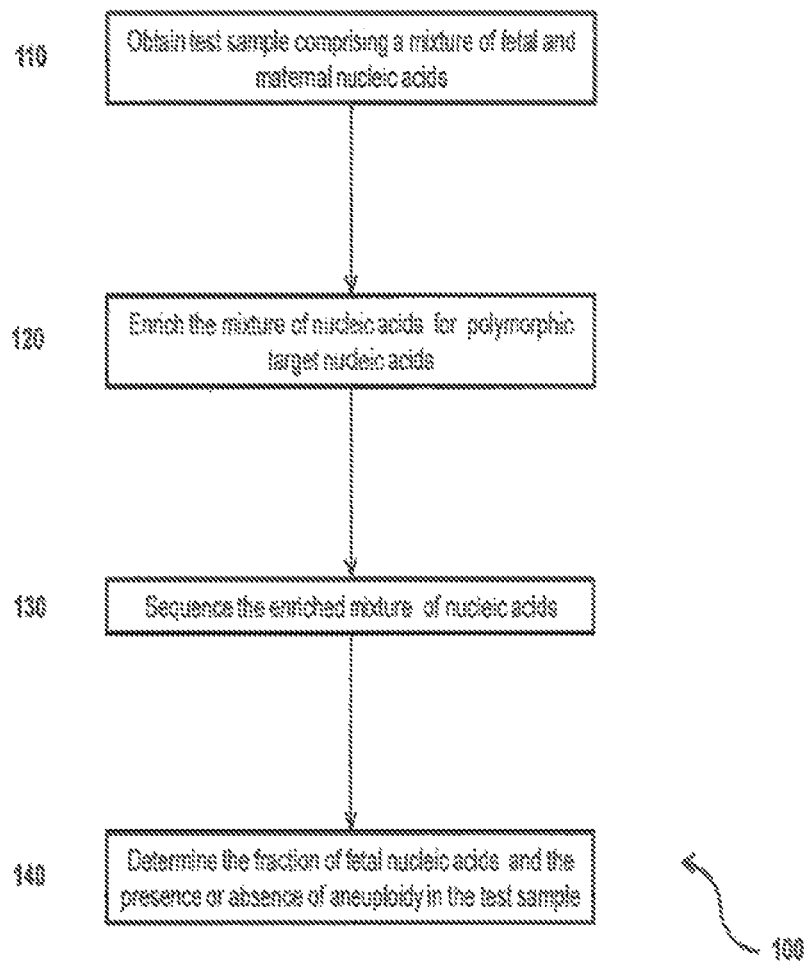
FIG. 1 is a flowchart of a method 100 for simultaneously determining the presence or absence of aneuploidy and the fetal fraction in a maternal test sample comprising a mixture of fetal and maternal nucleic acids.
Figure 2:
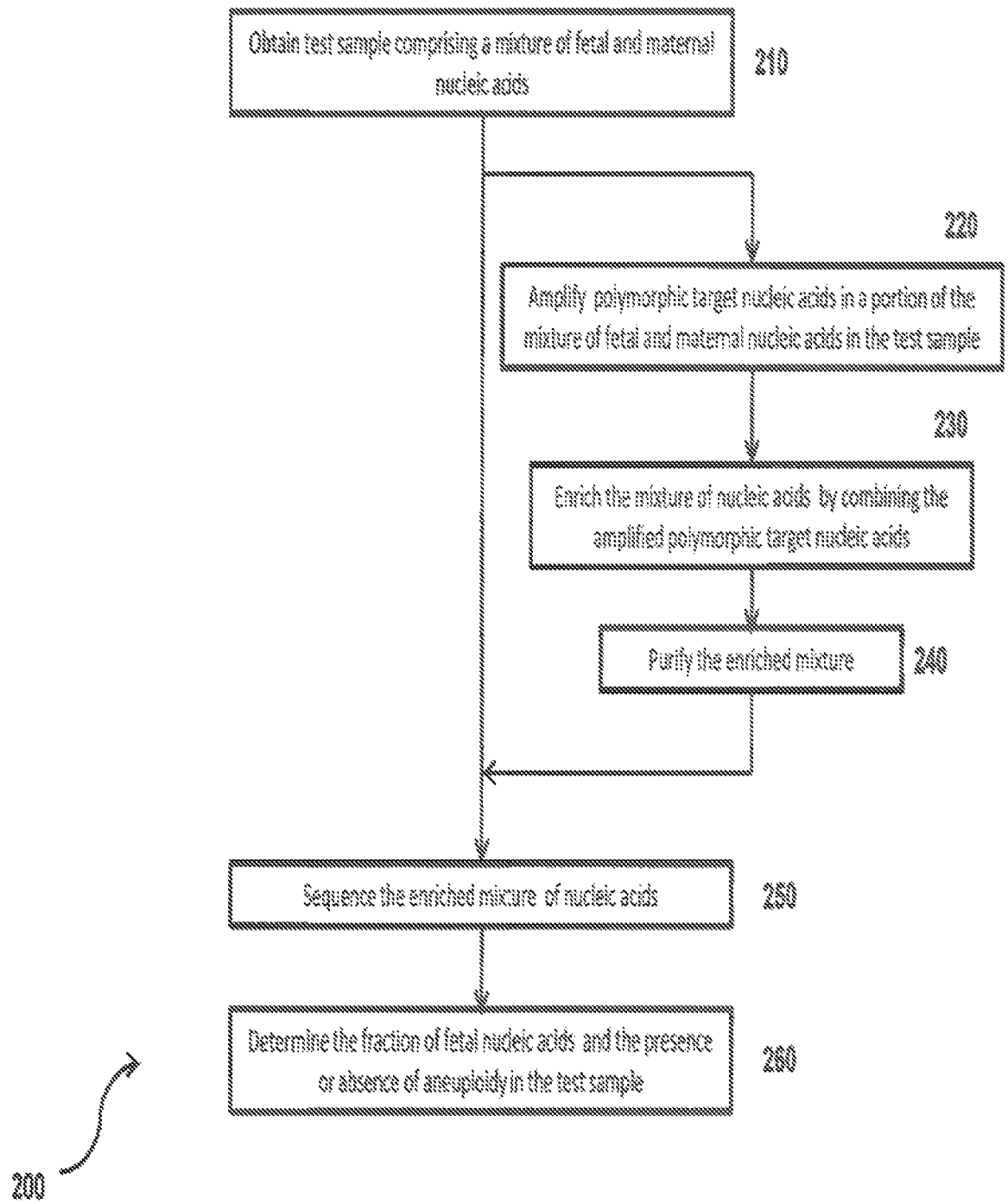
FIG. 2 is a flowchart of a method 200 for simultaneously determining the presence or absence of fetal aneuploidy and the fetal fraction in a maternal plasma test sample enriched for polymorphic nucleic acids.
Figure 3:
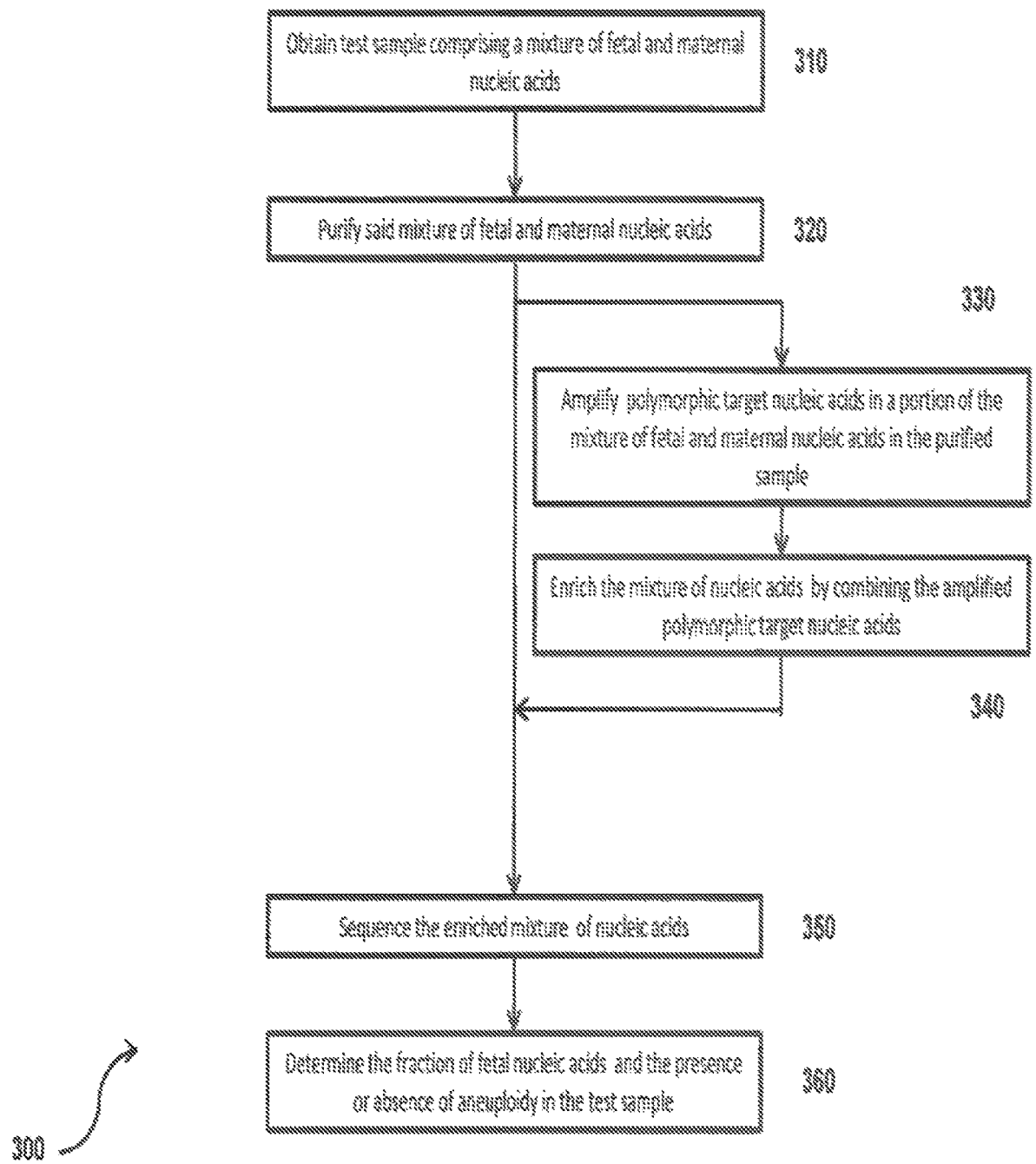
FIG. 3 is a flowchart of a method 300 for simultaneously determining the presence or absence of fetal aneuploidy and the fetal fraction in a maternal purified cfDNA test sample that has been enriched with polymorphic nucleic acids.

The invention provides compositions and methods for simultaneously determining the presence or absence of fetal aneuploidy and the relative amount of fetal nucleic acids in a sample obtained from a pregnant female. The method encompasses the use of sequencing technologies e.g. next generation sequencing, and exploits the occurrence of polymorphisms to provide a streamlined noninvasive process applicable to the practice of prenatal diagnostics.

Unless otherwise indicated, the practice of the present invention involves conventional techniques commonly used in molecular biology, microbiology, protein purification, protein engineering, protein and DNA sequencing, and recombinant DNA fields, which are within the skill of the art. Such techniques are known to those of skill in the art and are described in numerous standard texts and reference works. All patents, patent applications, articles and publications mentioned herein are hereby expressly incorporated herein by reference in their entirety.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not limitations of the various aspects or embodiments of the invention which can be had by reference to the Specification as a whole. Accordingly, as indicated above, the terms defined immediately below are more fully defined by reference to the specification as a whole.

Unless defined otherwise herein, all technical and scientific terms used herein have the same meaning as commonly understood by one of ordinary skill in the art to which this invention belongs. Various scientific dictionaries that include the terms included herein are well known and available to those in the art. Although any methods and materials similar or equivalent to those described herein find use in the practice or testing of the present invention, some preferred methods and materials are described. Accordingly, the terms defined immediately below are more fully described by reference to the Specification as a whole. It is to be understood that this invention is not limited to the particular methodology, protocols, and reagents described, as these may vary, depending upon the context they are used by those of skill in the art.

Definitions

As used herein, the singular terms "a", "an," and "the" include the plural reference unless the context clearly indicates otherwise. Unless otherwise indicated, nucleic acids are written left to right in 5' to 3' orientation and amino acid sequences are written left to right in amino to carboxy orientation, respectively.

The term "assessing" herein refers to characterizing the status of a chromosomal aneuploidy by one of three types of calls: "normal", "affected", and "no-call". For example, in the presence of trisomy the "normal" call is determined by the value of a parameter e.g. a test chromosome dose that is below a user-defined threshold of reliability, the "affected" call is determined by a parameter e.g. a test chromosome dose, that is above a user-defined threshold of reliability, and the "no-call" result is determined by a parameter e.g. a test chromosome dose, that lies between the a user-defined thresholds of reliability for making a "normal" or an "affected" call.

The term "copy number variation" herein refers to variation in the number of copies of a nucleic acid sequence that is 1 kb or larger present in a test sample in comparison with the copy number of the nucleic acid sequence present in a qualified sample. A "copy number variant" refers to the 1 kb or larger sequence of nucleic acid in which copy-number differences are found by comparison of a sequence of interest in test sample with that present in a qualified sample. Copy number variants/variations include deletions, including microdeletions, insertions, including microinsertions, duplications, multiplications, inversions, translocations and complex multi-site variants. CNV encompass chromosomal aneuploidies and partial aneuplodies.

The term "aneuploidy" herein refers to an imbalance of genetic material caused by a loss or gain of a whole chromosome, or part of a chromosome.

The term "chromosomal aneuploidy" herein refers to an imbalance of genetic material caused by a loss or gain of a whole chromosome, and includes germline aneuploidy and mosaic aneuploidy.

The term "partial aneuploidy" herein refers to an imbalance of genetic material caused by a loss or gain of part of a chromosome e.g. partial monosomy and partial trisomy, and encompasses imbalances resulting from translocations, deletions and insertions.

The term "tandem SNPs" herein refers to two or more SNPs that are present within a polymorphic target nucleic acid sequence.

The terms "polymorphic target nucleic acid", "polymorphic sequence", "polymorphic target nucleic acid sequence" and "polymorphic nucleic acid" are used interchangeably herein to refer to a nucleic acid sequence e.g. a DNA sequence, that comprises one or more polymorphic sites.

The term "polymorphic site" herein refers to a single nucleotide polymorphism (SNP), a small-scale multi-base deletion or insertion, a Multi-Nucleotide Polymorphism (MNP) or a Short Tandem Repeat (STR).

The term "plurality" is used herein in reference to a number of nucleic acid molecules or sequence tags that is sufficient to identify significant differences in copy number variations (e.g. chromosome doses) in test samples and qualified samples using in the methods of the invention. In some embodiments, at least about $3 \times 10^6$ sequence tags, at least about $5 \times 10^6$ sequence tags, at least about $8 \times 10^6$ sequence tags, at least about $10 \times 10^6$ sequence tags, at least about $15 \times 10^6$ sequence tags, at least about $20 \times 10^6$ sequence tags, at least about $30 \times 10^6$ sequence tags, at least about $40 \times 10^6$ sequence tags, or at least about $50 \times 10^6$ sequence tags comprising between 20 and 40 bp reads are obtained for each test sample.

The terms "polynucleotide", "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next, include sequences of any form of nucleic acid, including, but not limited to RNA, DNA and cfDNA molecules. The term "polynucleotide" includes, without limitation, single- and double-stranded polynucleotide.

The term "portion" when used in reference to the amount of sequence information of fetal and maternal nucleic acid molecules in a biological sample herein refers to the amount of sequence information of fetal and maternal nucleic acid molecules in a biological sample that in sum amount to less than the sequence information of <1 human genome.

The term "test sample" herein refers to a sample comprising a mixture of nucleic acids comprising at least one nucleic acid sequence whose copy number is suspected of having undergone variation. Nucleic acids present in a test sample are referred to as "test nucleic acids".

The term "qualified sample" herein refers to a sample comprising a mixture of nucleic acids that are present in a known copy number to which the nucleic acids in a test sample are compared, and it is a sample that is normal i.e. not aneuploid, for the sequence of interest e.g. a qualified sample used for identifying a normalizing chromosome for chromosome 21 is a sample that is not a trisomy 21 sample.

The term "enrich" herein refers to the process of amplifying polymorphic target nucleic acids contained in a portion of a maternal sample, and combining the amplified product with the remainder of the maternal sample from which the portion was removed.

The term "qualified nucleic acid" is used interchangeably with "qualified sequence" is a sequence against which the amount of a test sequence or test nucleic acid is compared. A qualified sequence is one present in a biological sample preferably at a known representation i.e. the amount of a qualified sequence is known. A "qualified sequence of interest" is a qualified sequence for which the amount is known in a qualified sample, and is a sequence that is associated with a difference in sequence representation in an individual with a medical condition.

The term "sequence of interest" herein refers to a nucleic acid sequence that is associated with a difference in sequence representation in healthy versus diseased individuals. A sequence of interest can be a sequence on a chromosome that is misrepresented i.e. over- or under-represented, in a disease or genetic condition. A sequence of interest may also be a portion of a chromosome, or a chromosome. For example, a sequence of interest can be a chromosome that is over-represented in an aneuploidy condition, or a gene encoding a tumor-suppressor that is under-represented in a cancer. Sequences of interest include sequences that are over- or under-represented in the total population, or a subpopulation of cells of a subject. A "qualified sequence of interest" is a sequence of interest in a qualified sample. A "test sequence of interest" is a sequence of interest in a test sample.

The term "plurality of polymorphic target nucleic acids" herein refers to a number of nucleic acid sequences each comprising at least one polymorphic site e.g. one SNP, such that at least 1, 2, 3, 4, 5, 6, 7, 8, 9, 10, 15, 20, 25, 30, 40 or more different polymorphic sites are amplified from the polymorphic target nucleic acids to identify and/or quantify fetal alleles present in maternal samples comprising fetal and maternal nucleic acids.

The term "normalizing sequence" herein refers to a sequence that displays a variability in the number of sequence tags that are mapped to it among samples and sequencing runs that best approximates that of the sequence of interest for which it is used as a normalizing parameter, and/or that can best differentiate an affected sample from one or more unaffected samples. A "normalizing chromosome" is an example of a "normalizing sequence".

The term "differentiability" herein refers to the characteristic of a normalizing chromosome that enables to distinguish one or more unaffected i.e. normal, samples from one or more affected i.e. aneuploid, samples.

The term "group of chromosomes" herein refers to two or more chromosomes.

The term "sequence dose" herein refers to a parameter that relates the sequence tag density of a sequence of interest to the tag density of a normalizing sequence. A "test sequence dose" is a parameter that relates the sequence tag density of a sequence of interest e.g. chromosome 21, to that of a normalizing sequence e.g. chromosome 9, determined in a test sample. Similarly, a "qualified sequence dose" is a parameter that relates the sequence tag density of a sequence of interest to that of a normalizing sequence determined in a qualified sample.

The term "sequence tag density" herein refers to the number of sequence reads that are mapped to a reference genome sequence e.g. the sequence tag density for chromosome 21 is the number of sequence reads generated by the sequencing method that are mapped to chromosome 21 of the reference genome. The term "sequence tag density ratio" herein refers to the ratio of the number of sequence tags that are mapped to a chromosome of the reference genome e.g. chromosome 21, to the length of the reference genome chromosome 21.

The term "parameter" herein refers to a numerical value that characterizes a quantitative data set and/or a numerical relationship between quantitative data sets. For example, a ratio (or function of a ratio) between the number of sequence tags mapped to a chromosome and the length of the chromosome to which the tags are mapped, is a parameter.

The terms "threshold value" and "qualified threshold value" herein refer to any number that is calculated using a qualifying data set and serves as a limit of diagnosis of a copy number variation e.g. an aneuploidy, in an organism. If a threshold is exceeded by results obtained from practicing the invention, a subject can be diagnosed with a copy number variation e.g. trisomy 21.

The term "read" refers to a DNA sequence of sufficient length (e.g., at least about 30 bp) that can be used to identify a larger sequence or region, e.g. that can be aligned and specifically assigned to a chromosome or genomic region or gene.

The term "sequence tag" is herein used interchangeably with the term "mapped sequence tag" to refer to a sequence read that has been specifically assigned i.e. mapped, to a larger sequence e.g. a reference genome, by alignment. Mapped sequence tags are uniquely mapped to a reference genome i.e. they are assigned to a single location to the reference genome. Tags that can be mapped to more than one location on a reference genome i.e. tags that do not map uniquely, are not included in the analysis.

The terms "aligned", "alignment", or "aligning" refer to one or more sequences that are identified as a match in terms of the order of their nucleic acid molecules to a known sequence from a reference genome. Such alignment can be done manually or by a computer algorithm, examples including the Efficient Local Alignment of Nucleotide Data (ELAND) computer program distributed as part of the Illumina Genomics Analysis pipeline. The matching of a sequence read in aligning can be a 100% sequence match or less than 100% (non-perfect match).

The term "reference genome" refers to any particular known genome sequence, whether partial or complete, of any organism or virus which may be used to reference identified sequences from a subject. For example, a reference genome used for human subjects as well as many other organisms is found at the National Center for Biotechnology Information at www.ncbi.nlm.nih.gov. A "genome" refers to the complete genetic information of an organism or virus, expressed in nucleic acid sequences.

The term "artificial target sequences genome" herein refers to a grouping of known sequences that encompass alleles of known polymorphic sites. For example, a "SNP reference genome" is an artificial target sequences genome comprising a grouping of sequences that encompass alleles of known SNPs.

The term "clinically-relevant sequence" herein refers to a nucleic acid sequence that is known or is suspected to be associated or implicated with a genetic or disease condition. Determining the absence or presence of a clinically-relevant sequence can be useful in determining a diagnosis or confirming a diagnosis of a medical condition, or providing a prognosis for the development of a disease.

The term "derived" when used in the context of a nucleic acid or a mixture of nucleic acids, herein refers to the means whereby the nucleic acid(s) are obtained from the source from which they originate. For example, in one embodiment, a mixture of nucleic acids that is derived from two different genomes means that the nucleic acids e.g. cfDNA, were naturally released by cells through naturally occurring processes such as necrosis or apoptosis. In another embodiment, a mixture of nucleic acids that is derived from two different genomes means that the nucleic acids were extracted from two different types of cells from a subject.

The term "maternal sample" herein refers to a biological sample obtained from a pregnant subject e.g. a woman.

The term "original maternal sample" herein refers to a biological sample obtained from a pregnant subject e.g. a woman, who serves as the source from which a portion is removed to amplify polymorphic target nucleic acids. The "original sample" can be any sample obtained from a pregnant subject, and the processed fractions thereof e.g. a purified cfDNA sample extracted from a maternal plasma sample.

The term "biological fluid" herein refers to a liquid taken from a biological source and includes, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

The terms "maternal nucleic acids" and "fetal nucleic acids" herein refer to the nucleic acids of a pregnant female subject and the nucleic acids of the fetus being carried by the pregnant female, respectively.

The term "corresponding to" herein refers to a nucleic acid sequence e.g. a gene or a chromosome, that is present in the genome of different subjects, and which does not necessarily have the same sequence in all genomes, but serves to provide the identity rather than the genetic information of a sequence of interest e.g. a gene or chromosome.

The term "substantially cell free" herein refers to preparations of the desired sample from which components that are normally associated with it are removed. For example, a plasma sample is rendered essentially cell free by removing blood cells e.g. white blood cells, which are normally associated with it. In some embodiments, substantially free samples are processed to remove cells that would otherwise contribute to the desired genetic material that is to be tested for an aneuploidy.

As used herein, the term "fetal fraction" refers to the fraction of fetal nucleic acids present in a sample comprising fetal and maternal nucleic acid.

As used herein the term "chromosome" refers to the heredity-bearing gene carrier of a living cell which is derived from chromatin and which comprises DNA and protein components (especially histones). The conventional internationally recognized individual human genome chromosome numbering system is employed herein.

As used herein, the term "polynucleotide length" refers to the absolute number of nucleic acid molecules (nucleotides) in a sequence or in a region of a reference genome. The term "chromosome length" refers to the known length of the chromosome given in base pairs e.g. provided in the NCBI36/hg18 assembly of the human chromosome found on the world wide web at genome.ucsc.edu/cgi-bin/hgTracks?hgsid=167155613&chromInfoPage=

The term "subject" herein refers to a human subject as well as a non-human subject such as a mammal, an invertebrate, a vertebrate, a fungus, a yeast, a bacteria, and a virus. Although the examples herein concern human cells and the language is primarily directed to human concerns, the concept of this invention is applicable to genomes from any plant or animal, and is useful in the fields of veterinary medicine, animal sciences, research laboratories and such.

The term "condition" herein refers to "medical condition" as a broad term that includes all diseases and disorders, but can include injuries and normal health situations, such as pregnancy, that might affect a person's health, benefit from medical assistance, or have implications for medical treatments.

Description

The method described herein is a sequencing method that enables the simultaneous determination of the fraction of the minor fetal nucleic acid component in a sample comprising a mixture of fetal and maternal nucleic acids. In particular, the method enables the determination of the fraction of cfDNA contributed by a fetus to the mixture of fetal and maternal cfDNA in a maternal sample e.g. a plasma sample. The difference between the maternal and fetal fraction is determined by the relative contribution of a polymorphic allele derived from the fetal genome to the contribution of the corresponding polymorphic allele derived from the maternal genome. Polymorphic sequences can be used in conjunction with clinically-relevant diagnostic tests as a positive control for the presence of cfDNA in order to highlight false-negative or false-positive results stemming from low levels of cfDNA below the identification limit. The method described is useful across a range of gestational ages.

Exemplary embodiments of the method of the invention are illustrated in FIGS. 1-4 as follows.

FIG. 1 provides a flow diagram of one embodiment of method of the invention 100 for simultaneously determining a fetal aneuploidy and the fraction of fetal nucleic acids in a maternal biological sample. In step 110 a test sample comprising a mixture of fetal and maternal nucleic acids is obtained from a subject. The sample is a maternal sample that is obtained from a pregnant female, for example a pregnant woman. Any maternal biological sample can be used a source of fetal and maternal nucleic acids which are contained in cells or that are "cell-free". In some embodiments, it is advantageous to obtain a maternal sample that comprises cell-free nucleic acids e.g. cfDNA. Preferably, the maternal biological sample is a biological fluid sample. A biological fluid includes, as non-limiting examples, blood, plasma, serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples. In some embodiments, the biological fluid sample is a sample that is easily obtainable by non-invasive procedures e.g. blood, plasma, serum, sweat, tears, sputum, urine, sputum, ear flow, and saliva. In some embodiments, the biological sample is a peripheral blood sample, or the plasma and/or the serum fractions thereof. In another embodiment, the sample is a mixture of two or more biological samples e.g. a biological sample can comprise two or more of a biological fluid samples. As used herein, the terms "blood," "plasma" and "serum" expressly encompass fractions or processed portions thereof. In some embodiments, the biological sample is processed to obtain a sample fraction e.g. plasma, that contains the mixture of fetal and maternal nucleic acids. In some embodiments, the mixture of fetal and maternal nucleic acids is further processed from the sample fraction e.g. plasma, to obtain a sample comprising a purified mixture of fetal and maternal nucleic acids e.g. cfDNA. Cell-free nucleic acids, including cell-free DNA, can be obtained by various methods known in the art from biological samples including but not limited to plasma, serum and urine (Fan et al., Proc Natl Acad Sci 105:16266-16271 [2008]; Koide et al., Prenatal Diagnosis 25:604-607 [2005]; Chen et al., Nature Med. 2: 1033-1035 [1996]; Lo et al., Lancet 350: 485-487 [1997]). To separate cfDNA from cells, fractionation, centrifugation (e.g., density gradient centrifugation), DNA-specific precipitation, or high-throughput cell sorting and/or separation methods can be used. Commercially available kits for manual and automated separation of cfDNA are available (Roche Diagnostics, Indianapolis, IN, Qiagen, Valencia, CA, Macherey-Nagel, Duren, DE). In some instances, it can be advantageous to fragment the nucleic acid molecules in the nucleic acid sample. Fragmentation can be random, or it can be specific, as achieved, for example, using restriction endonuclease digestion. Methods for random fragmentation are well known in the art, and include, for example, limited DNAse digestion, alkali treatment and physical shearing. In one embodiment, sample nucleic acids are obtained from as cfDNA, which is not subjected to fragmentation. In other embodiments, the sample nucleic acids are obtained as genomic DNA, which is subjected to fragmentation into fragments of approximately 500 or more base pairs, and to which NGS methods can be readily applied.

In step 120 (FIG. 1) the mixture of nucleic acids present in the sample is enriched for polymorphic target nucleic acids each comprising a polymorphic site. In some embodiments, the nucleic acids that are enriched are cfDNA. Target nucleic acids are segments of genetic material that are known to comprise at least one polymorphic site. In some embodiments, the target nucleic acids comprise a SNP. In other embodiments, the target nucleic acid comprises an STR. Enrichment of a mixture of fetal and maternal nucleic acids comprises amplifying target sequences from a portion of nucleic acids contained in the original maternal sample, and combining part or the entire amplified product with the remainder of the original maternal sample. In step 130, at least a portion of the enriched mixture is sequenced, sequence differences stemming from the polymorphic nature of the target sequences are identified, and the relative contribution of polymorphic sequences derived from the fetal genome i.e. the fetal fraction, is determined in step 140. In some embodiments, the original maternal sample is a biological fluid sample e.g. plasma. In other embodiments, the original maternal sample is a processed fraction of plasma comprising purified fetal and maternal cfDNA.

Polymorphic sites that are contained in the target nucleic acids include without limitation single nucleotide polymorphisms (SNPs), tandem SNPs, small-scale multi-base deletions or insertions, called IN-DELS (also called deletion insertion polymorphisms or DIPs), Multi-Nucleotide Polymorphisms (MNPs) and Short Tandem Repeats (STRs). The polymorphic sites that are encompassed by the method of the invention are located on autosomal chromosomes, thereby enabling the determination of fetal fraction independently of sex of the fetus. Any polymorphic site that can be encompassed by the reads generated by the sequencing methods described herein can be used to determine simultaneously the fetal fraction and the presence or absence of an aneuploidy in a maternal sample.

In one embodiment, the mixture of fetal and maternal nucleic acids in the sample is enriched for target nucleic acids that comprise at least one SNP. In some embodiments, each target nucleic acid comprises a single i.e. one SNP. Target nucleic acid sequences comprising SNPs are available from publicly accessible databases including, but not limited to Human SNP Database at world wide web address wi.mit.edu, NCBI dbSNP Home Page at world wide web address ncbi.nlm.nih.gov, world wide web address lifesciences.perkinelmer.com, Celera Human SNP database at world wide web address celera.com, the SNP Database of the Genome Analysis Group (GAN) at world wide web address gan.iarc.fr. In one embodiment, the SNPs chosen for enriching the fetal and maternal cfDNA are selected from the group of 92 individual identification SNPs (IISNPs) described by Pakstis et al. (Pakstis et al. Hum Genet 127: 315-324 [2010]), which have been shown to have a very small variation in frequency across populations ($F_{st}$<0.06), and to be highly informative around the world having an average heterozygosity ≥0.4. SNPs that are encompassed by the method of the invention include linked and unlinked SNPs. Each target nucleic acid comprises at least one polymorphic site e.g. a single SNP, that differs from that present on another target nucleic acid to generate a panel of polymorphic sites e.g. SNPs, that contain a sufficient number of polymorphic sites of which at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40 or more are informative. For example, a panel of SNPs can be configured to comprise at least one informative SNP. In one embodiment, the SNPs that are targeted for amplification are selected from rs560681, rs1109037, rs9866013, rs13182883, rs13218440, rs7041158, rs740598, rs10773760, rs4530059, rs7205345, rs8078417, rs576261, rs2567608, rs430046, rs9951171, rs338882, rs10776839, rs9905977, rs1277284, rs258684, rs1347696, rs508485, rs9788670, rs8137254, rs3143, rs2182957, rs3739005, and rs530022.

In other embodiments, each target nucleic acid comprises two or more SNPs i.e. each target nucleic acid comprises tandem SNPs. Preferably, each target nucleic acid comprises two tandem SNPs. The tandem SNPs are analyzed as a single unit as short haplotypes, and are provided herein as sets of two SNPs. To identify suitable tandem SNP sequences, the International HapMap Consortium database can be searched (The International HapMap Project, Nature 426:789-796 [2003]). The database is available on the world wide web at hapmap.org. In one embodiment, tandem SNPs that are targeted for amplification are selected from the following sets of tandem pairs of SNPS rs7277033-rs2110153; rs2822654-rs1882882; rs368657-rs376635; rs2822731-rs2822732; rs1475881-rs7275487; rs1735976-rs2827016; rs447340-rs2824097; rs418989-rs13047336; rs987980-rs987981; rs4143392-rs4143391; rs1691324-rs13050434; rs11909758-rs9980111; rs2826842-rs232414; rs1980969-rs1980970; rs9978999-rs9979175; rs1034346-rs12481852; rs7509629-rs2828358; rs4817013-rs7277036; rs9981121-rs2829696; rs455921-rs2898102; rs2898102-rs458848; rs961301-rs2830208; rs2174536-rs458076; rs11088023-rs11088024; rs1011734-rs1011733; rs2831244-rs9789838; rs8132769-rs2831440; rs8134080-rs2831524; rs4817219-rs4817220; rs2250911-rs2250997; rs2831899-rs2831900; rs2831902-rs2831903; rs11088086-rs2251447; rs2832040-rs11088088; rs2832141-rs2246777; rs2832959-rs9980934; rs2833734-rs2833735; rs933121-rs933122; rs2834140-rs12626953; rs2834485-rs3453; rs9974986-rs2834703; rs2776266-rs2835001; rs1984014-rs1984015; rs7281674-rs2835316; rs13047304-rs13047322; rs2835545-rs4816551; rs2835735-rs2835736; rs13047608-rs2835826; rs2836550-rs2212596; rs2836660-rs2836661;

rs465612-rs8131220; rs9980072-rs8130031; rs418359-rs2836926; rs7278447-rs7278858; rs385787-rs367001; rs367001-rs386095; rs2837296-rs2837297; and rs2837381-rs4816672.

In another embodiment, the mixture of fetal and maternal nucleic acids in the sample is enriched for target nucleic acids that comprise at least one STR. STR loci are found on almost every chromosome in the genome and may be amplified using a variety of polymerase chain reaction (PCR) primers. Tetranucleotide repeats have been preferred among forensic scientists due to their fidelity in PCR amplification, although some tri- and pentanucleotide repeats are also in use. A comprehensive listing of references, facts and sequence information on STRs, published PCR primers, common multiplex systems, and related population data are compiled in STRBase, which may be accessed via the World Wide Web at ibm4.carb.nist.gov:8800/dna/home.htm. Sequence information from GenBank® (http://www2.ncbi.nlm.nih.gov/cgi-bin/genbank) for commonly used STR loci is also accessible through STRBase. The polymorphic nature of tandem repeated DNA sequences that are widespread throughout the human genome have made them important genetic markers for gene mapping studies, linkage analysis, and human identity testing. Because of the high polymorphism of STRs, most individuals will be heterozygous i.e. most people will possess two alleles (versions) of each—one inherited from each parent—with a different number of repeats. Therefore, the non-maternally inherited fetal STR sequence will differ in the number of repeats from the maternal sequence. Amplification of these STR sequences will result in two major amplification products corresponding to the maternal alleles (and the maternally inherited fetal allele) and one minor product corresponding to the non-maternally inherited fetal allele. This technique was first reported in 2000 (Pertl et al., Human Genetics 106:45-49 [2002]) and has subsequently been developed using simultaneous identification of multiple different STR regions using real-time PCR (Liu et al., Acta Obset Gyn Scand 86:535-541 [2007]). Thus, the fraction of fetal nucleic acid in a maternal sample can also be determined by sequencing polymorphic target nucleic acids comprising STRs, which vary among individuals in the number of tandem repeated units between alleles. In one embodiment, simultaneous determination of aneuploidy and fetal fraction comprises sequencing at least a portion of fetal and maternal nucleic acids present in a maternal sample that has been enriched for polymorphic sequences comprising STRs. Given that the size of fetal cfDNA is between X and Y bp, the polymorphic sequences comprise miniSTR, which can be amplified to generate amplicons that are of lengths about the size of the circulating fetal DNA fragments. The method can use one or a combination of any number of informative miniSTRs to determine the fraction of fetal nucleic acid. For example, any one or a combination of any number of miniSTRs, for example the miniSTRs disclosed in Table 15, can be used. In one embodiment, the fraction of fetal nucleic acid in a maternal sample is performed using a method that includes determining the number of copies of the maternal and fetal nucleic acid present in the maternal sample by amplifying at least one autosomal miniSTR chosen from CSF1PO, FGA, TH01, TPOX, vWA, D3S1358, D5S818, D7S820, D8S1179, D13S317, D16S539, D18S51, D21S11, Penta D, Penta E, D2S1338, D1S1677, D2S441, D4S2364, D10S1248, D14S1434, D22S1045, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D5S2500, D4S2408, D4S2364, D3S4529, D3S3053, D2S1776, D2S441, D1S1677, D1S1627, and D1GATA113. In another embodiment, the at least one autosomal miniSTR is the group of miniSTRs CSF1PO, FGA, D13S317, D16S539, D18S51, D2S1338, D21S11 and D7S820.

Enrichment of the sample for the target nucleic acids is accomplished by methods that comprise specifically amplifying target nucleic acid sequences that comprise the polymorphic site. Amplification of the target sequences can be performed by any method that uses PCR or variations of the method including but not limited to asymmetric PCR, helicase-dependent amplification, hot-start PCR, qPCR, solid phase PCR, and touchdown PCR. Alternatively, replication of target nucleic acid sequences can be obtained by enzyme-independent methods e.g. chemical solid-phase synthesis using the phosphoramidites. Amplification of the target sequences is accomplished using primer pairs each capable of amplifying a target nucleic acid sequence comprising the polymorphic site e.g. SNP, in a multiplex PCR reaction. Multiplex PCR reactions include combining at least 2, at least three, at least 3, at least 5, at least 10, at least 15, at least 20, at least 25, at least 30, at least 35, at least 40 or more sets of primers in the same reaction to quantify the amplified target nucleic acids comprising at least two, at least three, at least 5, at least 10, at least 15, at least 20, at least 25, at least 30, at least 35, at least 40 or more polymorphic sites in the same sequencing reaction. Any panel of primer sets can be configured to amplify at least one informative polymorphic sequence.

Amplification of SNPs

A number of nucleic acid primers are already available to amplify DNA fragments containing the SNP polymorphisms and their sequences can be obtained, for example, from the above-identified databases. Additional primers can also be designed, for example, using a method similar to that published by Vieux, E. F., Kwok, P-Y and Miller, R. D. in BioTechniques (June 2002) Vol. 32. Supplement: "SNPs: Discovery of Marker Disease, pp. 28-32. In one embodiment, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40 or more sets of primers is chosen to amplify a target nucleic acid comprising at least one informative SNPs in a portion of a mixture of fetal and maternal cfDNA. In one embodiment, the sets are of primers comprise forward and reverse primers that encompass at least one informative SNP selected from rs560681, rs1109037, rs9866013, rs13182883, rs13218440, rs7041158, rs740598, rs10773760, rs4530059, rs7205345, rs8078417, rs576261, rs2567608, rs430046, rs9951171, rs338882, rs10776839, rs9905977, rs1277284, rs258684, rs1347696, rs508485, rs9788670, rs8137254, rs3143, rs2182957, rs3739005, and rs530022. Exemplary sets of primers that are used to amplify the tandem SNPs provided in Example 5 (Tables 5 and 6) and disclosed herein as SEQ ID NOs:57-112 to amplify a target nucleic acid comprising at least one informative SNP in a portion of a mixture of fetal and maternal cfDNA. In another embodiment, the group of 13 sets of primers SEQ ID NOs:1-26 is used to amplify a target nucleic acid each comprising at least one SNP e.g. a single SNP, in a portion of a mixture of fetal and maternal cfDNA.

In yet another embodiment, at least one set of primers is used to amplify a target nucleic acid each comprising at least one SNP e.g. a set of two tandem SNPs, in a portion of a mixture of fetal and maternal cfDNA. In one embodiment, the sets are of primers comprise forward and reverse primers that encompass at least one informative tandem SNP selected from rs7277033-rs2110153; rs2822654-rs1882882; rs368657-rs376635; rs2822731-rs2822732; rs1475881-rs7275487; rs1735976-rs2827016; rs447340-rs2824097; rs418989-rs13047336; rs987980-rs987981; rs4143392-rs4143391; rs1691324-rs13050434; rs11909758-rs9980111; rs2826842-rs232414; rs1980969-rs1980970; rs9978999-rs9979175; rs1034346-rs12481852; rs7509629-rs2828358; rs4817013-rs7277036; rs9981121-rs2829696; rs455921-rs2898102; rs2898102-rs458848; rs961301-rs2830208; rs2174536-rs458076; rs11088023-rs11088024; rs1011734-rs1011733; rs2831244-rs9789838; rs8132769-rs2831440; rs8134080-rs2831524; rs4817219-rs4817220; rs2250911-rs2250997; rs2831899-rs2831900; rs2831902-rs2831903; rs11088086-rs2251447; rs2832040-rs11088088; rs2832141-rs2246777; rs2832959-rs9980934; rs2833734-rs2833735; rs933121-rs933122; rs2834140-rs12626953; rs2834485-rs3453; rs9974986-rs2834703; rs2776266-rs2835001; rs1984014-rs1984015; rs7281674-rs2835316; rs13047304-rs13047322; rs2835545-rs4816551; rs2835735-rs2835736; rs13047608-rs2835826; rs2836550-rs2212596; rs2836660-rs2836661; rs465612-rs8131220; rs9980072-rs8130031; rs418359-rs2836926; rs7278447-rs7278858; rs385787-rs367001; rs367001-rs386095; rs2837296-rs2837297; and rs2837381-rs4816672.

The primers used for amplifying the target sequences comprising the tandem SNPs are designed to encompass both SNP sites. Exemplary sets of primers that are used to amplify the tandem SNPs disclosed herein are provided in Example 10 and disclosed as SEQ ID NNos:197-310.

Amplification of the target nucleic acids is performed using sequence-specific primers that allow for sequence specific amplification. For example, the PCR primers are designed to discriminate against the amplification of similar genes or paralogs that are on other chromosomes by taking advantage of sequence differences between the target nucleic acid and any paralogs from other chromosomes. The forward or reverse PCR primers are designed to anneal close to the SNP site and to amplify a nucleic acid sequence of sufficient length to be encompassed in the reads generated by massively parallel sequencing methods. In some embodiments, some massively parallel sequencing methods require that nucleic acid sequence have a minimum length (bp) to enable bridging amplification that may optionally be used prior to sequencing. Thus, the PCR primers used for amplifying target nucleic acids are designed to amplify sequences that are of sufficient length to be bridge amplified and to identify SNPs that are encompassed by the sequence reads. In some embodiments, the first of two primers in the primer set comprising the forward and the reverse primer for amplifying the target nucleic acid is designed to identify a single SNP present within a sequence read of about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances in massively parallel sequencing technologies will enable single-end reads of greater than 500 bp. In one embodiment, one of the PCR primers is designed to amplify SNPs that are encompassed in sequence reads of 36 bp. The second primer is designed to amplify the target nucleic acid as an amplicon of sufficient length to allow for bridge amplification. In one embodiment, the exemplary PCR primers are designed to amplify target nucleic acids that contain a single SNP selected from SNPs rs560681, rs1109037, rs9866013, rs13182883, rs13218440, rs7041158, rs740598, rs10773760, rs4530059, rs7205345, rs8078417, rs576261, rs2567608, rs430046, rs9951171, rs338882, rs10776839, rs9905977, rs1277284, rs258684, rs1347696, rs508485, rs9788670, rs8137254, rs3143, rs2182957, rs3739005 and rs530022. In other embodiments, the forward and reverse primers are each designed for amplifying target nucleic acids each comprising a set of two tandem SNPs, each being present within a sequence read of about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In one embodiment, at least one of the primers is designed to amplify the target nucleic acid comprising a set of two tandem SNPs as an amplicon of sufficient length to allow for bridge amplification.

The SNPs, single or tandem SNPs, are contained in amplified target nucleic acid amplicons of at least about 100 bp, at least about 150 bp, at least about 200 bp, at least about 250 bp, at least about 300 bp, at least about 350 bp, or at least about 400 bp. In one embodiment, target nucleic acids comprising a polymorphic site e.g. a SNP, are amplified as amplicons of at least about 110 bp, and that comprise a SNP within 36 bp from the 3' or 5' end of the amplicon. In another embodiment, target nucleic acids comprising two or more polymorphic sites e.g. two tandem SNPs, are amplified as amplicons of at least about 110 bp, and that comprise the first SNP within 36 bp from the 3' end of the amplicon, and/or the second SNP within 36 bp from the 5' end of the amplicon.

Amplification of STRs

A number of nucleic acid primers are already available to amplify DNA fragments containing the STRs and their sequences can be obtained, for example, from the above-identified databases. Various sized PCR amplicons have been used to discern the respective size distributions of circulating fetal and maternal DNA species, and have shown that the fetal DNA molecules in the plasma of pregnant women are generally shorter than maternal DNA molecules (Chan et al., Clin Chem 50:8892 [2004]). Size fractionation of circulating fetal DNA has confirmed that the average length of circulating fetal DNA fragments is <300 bp, while maternal DNA has been estimated to be between about 0.5 and 1 Kb (Li et al., Clin Chem, 50: 1002-1011 [2004]). These findings are consistent with those of Fan et al., who determined using NGS that fetal cfDNA is rarely >340 bp (Fan et al., Clin Chem 56:1279-1286 [2010]). The method of the invention encompasses determining the fraction of fetal nucleic acid in a maternal sample that has been enriched with target nucleic acids each comprising one miniSTR comprising quantifying at least one fetal and one maternal allele at a polymorphic miniSTR, which can be amplified to generate amplicons that are of lengths about the size of the circulating fetal DNA fragments.

In one embodiment, the method comprises determining the number of copies of at least one fetal and at least one maternal allele at least at one polymorphic miniSTR that is amplified to generate amplicons that are less than about 300 bp, less than about 250 bp, less than about 200 bp, less than about 150 bp, less than about 100 bp, or less than about 50 bp. In another embodiment, the amplicons that are generated by amplifying the miniSTRs are less than about 300 bp. In another embodiment, the amplicons that are generated by amplifying the miniSTRs are less than about 250 bp. In another embodiment, the amplicons that are generated by amplifying the miniSTRs are less than about 200 bp. Amplification of the informative allele includes using miniSTR primers, which allow for the amplification of reduced-size amplicons to discern STR alleles that are less than about 500 bp, less than about 450 bp, less than about 400 bp, less than about 350 bp, less than about 300 base pairs (bp), less than about 250 bp, less than about 200 bp, less than about 150 bp, less than about 100 bp, or less than about 50 bp. The reduced-size amplicons generated using the miniSTR primers are known as miniSTRs that are identified according to the marker name corresponding to the locus to which they have been mapped. In one embodiment, the miniSTR primers include mini STR primers that have permitted the maximum size reduction in amplicon size for all 13 CODIS STR loci in addition to the D2S1338, Penta D, and pentaE found in commercially available STR kits (Butler et al., J Forensic Sci 48:1054-1064 [2003]), miniSTR loci that are unlinked to the CODIS markers as described by Coble and Butler (Coble and Butler, J Forensic Sci 50:43-53 [2005]), and other minSTRs that have been characterized at NIST. Information regarding the miniSTRs characterized at NIST is accessible via the world wide web at cstl.nist.gov/biotech/strbase/newSTRs.htm. Any one pair or a combination of two or more pairs of miniSTR primers can be used to amplify at least one miniSTR. For example, at least one set of primers is selected from set CSF1PO_F (SEQ ID NO:81) and CSF1PO_R (SEQ ID NO:82), set FGA_F (SEQ ID NO:83) and FGA_R (SEQ ID NO:84), set TH01_F (SEQ ID NO:85) and TH01_R (SEQ ID NO:86), set TPOX_F (SEQ ID NO:87) and TPOX_R (SEQ ID NO:88), set vWA_F (SEQ ID NO:89) and vWA_R (SEQ ID NO:90), set D3S1358_F (SEQ ID NO:91) and D3S1358_R (SEQ ID NO:92), set D5S818_F (SEQ ID NO:93) and D5S818_R (SEQ ID NO:94), set D7S820_F (SEQ ID NO:95) and D7S820_R (SEQ ID NO:96), set D7S820_F (SEQ ID NO:97) and D7S820_R (SEQ ID NO:98), set D13S317_F (SEQ ID NO:99) and D13S317_R (SEQ ID NO:100), set D16S539_F (SEQ ID NO:101) and D16S539_R (SEQ ID NO:102), set D18S51_F (SEQ ID NO:103) and D18S51_R (SEQ ID NO:104), set D21S11_F (SEQ ID NO:105) and D21S11_R (SEQ ID NO:106), set D2S1338_F (SEQ ID NO:107) and D2S1338_R (SEQ ID NO:108), set Penta D_F (SEQ ID NO:109) and Penta D_R (SEQ ID NO:110), set Penta E _F (SEQ ID NO:111) and Penta E _R (SEQ ID NO:112), set (D22S1045_F; SEQ ID NO:113) and D22S1045_F (SEQ ID NO:114), set D20S1082_R (SEQ ID NO:115) and D20S1082_F (SEQ ID NO:116), set D20S482_R (SEQ ID NO:117) and D20S482_F (SEQ ID NO:118), set D18S853_R (SEQ ID NO:119) and D18S853_F (SEQ ID NO:120), set D17S1301_F (SEQ ID NO:121) and D17S1301_R (SEQ ID NO:122), set D17S974_F (SEQ ID NO:123) and D17S974_R (SEQ ID NO:124), set D14S1434_F (SEQ ID NO:125) and D14S1434_R (SEQ ID NO:126), set D12ATA63_F (SEQ ID NO:127) and D12ATA63_R (SEQ ID NO:128), D11S4463_F (SEQ ID NO:129) and D11S4463_R(SEQ ID NO:130), set D10S1435_F (SEQ ID NO:131) and D10S1435_R (SEQ ID NO:132), set D10S1248_F (SEQ ID NO:133) and D10S1248_R (SEQ ID NO:134), set D9S2157_F (SEQ ID NO:135) and D9S2157_R (SEQ ID NO:136), set D9S1122_F (SEQ ID NO:137) and D9S1122_R (SEQ ID NO:138), set D8S1115_F (SEQ ID NO:139) and D8S1115_R (SEQ ID NO:140), set D6S1017_F (SEQ ID NO:141) and D6S1017_R (SEQ ID NO:142), D6S474_F (SEQ ID NO:143) and D6S474_R (SEQ ID NO:144), set D5S2500_F (SEQ ID NO:145) and D5S2500_R (SEQ ID NO:146), set D4S2408_F (SEQ ID NO:147) and D4S2408_R (SEQ ID NO:148), set D4S2364U_F (SEQ ID NO:149) and D4S2364U_R (SEQ ID NO:150), set D3S452_F (SEQ ID NO:151) and D3S452_R (SEQ ID NO:152), set D3S3053_F (SEQ ID NO:153) and D3S3053_R (SEQ ID NO:154), set D2S1776_F (SEQ ID NO:155) and D2S1776_R (SEQ ID NO:156), set D2S441_F (SEQ ID NO:157) and D2S441_R (SEQ ID NO:158), set D1S1677_F (SEQ ID NO:159) and D1S1677_R (SEQ ID NO:160), set D1S1627_F (SEQ ID NO:161) and D1S1627_R (SEQ ID NO:162), and set D1GATA113_F (SEQ ID NO:163) and D1GATA113_R (SEQ ID NO:164).

Enrichment of the sample is obtained by amplifying target nucleic acids contained in a portion of the mixture of fetal and maternal nucleic acids in the original sample, and combining at least a portion or all of the amplified product with the remainder of the original unamplified sample. Enrichment comprises amplifying the target nucleic acids that are contained in a portion of biological fluid sample. In one embodiment, the sample that is enriched is the plasma fraction of a blood sample (See FIG. 2). For example, a portion of an original maternal plasma sample is used for amplifying target nucleic acid sequences. Subsequently, some or all of the amplified product is combined with the remaining unamplified original plasma sample thereby enriching it (see Example 8). In another embodiment, the sample that is enriched is the sample of purified cfDNA that is extracted from plasma (See FIG. 3). For example, enrichment comprises amplifying the target nucleic acids that are contained in a portion of an original sample of purified mixture of fetal and maternal nucleic acids e.g. cfDNA that has been purified from a maternal plasma sample, and subsequently combining some or all of the amplified product with the remaining unamplified original purified sample (see Example 7). In yet another embodiment, the sample that is enriched is a sequencing library sample prepared from a purified mixture of fetal and maternal nucleic acids (see FIG. 4). For example, enrichment comprises amplifying the target nucleic acids that are contained in a portion of an original sample of purified mixture of fetal and maternal nucleic acids e.g. cfDNA that has been purified from a maternal plasma sample, preparing a first sequencing library of unamplified nucleic acid sequences, preparing a second sequencing library of amplified polymorphic target nucleic acids, and subsequently combining some or all of the second sequencing library with some or all of the first sequencing library (see Example 6). The amount of amplified product that is used to enrich the original sample is selected to obtain sufficient sequencing information for determining both the presence or absence of aneuploidy and the fetal fraction from the same sequencing run. At least about 3%, at least about 5%, at least about 7%, at least about 10%, at least about 15%, at least about 20%, at least about 25%, at least about 30% or more of the total number of sequence tags obtained from sequencing are mapped to determine the fetal fraction.

In step 130 (FIG. 1), the enriched mixture of fetal and maternal nucleic acids is sequenced. Sequence information that is needed for the simultaneous determination of aneuploidy and fetal fraction can be obtained using any of the known DNA sequencing methods. In one embodiment, the method described herein employs next generation sequencing technology (NGS) in which clonally amplified DNA templates or single DNA molecules are sequenced in a massively parallel fashion within a flow cell (e.g. as described in Volkerding et al. Clin Chem 55:641-658 [2009]; Metzker M Nature Rev 11:31-46 [2010]). In addition to high-throughput sequence information, NGS provides digital quantitative information, in that each sequence read is a countable "sequence tag" representing an individual clonal DNA template or a single DNA molecule. This quantification allows NGS to expand the digital concept of counting cell-free DNA molecules (Fan et al., Proc Natl Acad Sci USA 105:16266-16271 [2008]; Chiu et al., Proc Natl Acad Sci USA 2008; 105:20458-20463 [2008]). The sequencing technologies of NGS include pyrosequencing, sequencing-by-synthesis with reversible dye terminators, sequencing by oligonucleotide probe ligation and real time sequencing.

Some of the sequencing technologies are available commercially, such as the sequencing-by-hybridization platform from Affymetrix Inc. (Sunnyvale, CA) and the sequencing-by-synthesis platforms from 454 Life Sciences (Bradford, CT), Illumina/Solexa (Hayward, CA) and Helicos Biosciences (Cambridge, MA), and the sequencing-by-ligation platform from Applied Biosystems (Foster City, CA), as described below. In addition to the single molecule sequencing performed using sequencing-by-synthesis of Helicos Biosciences, other single molecule sequencing technologies are encompassed by the method of the invention and include the SMRT™ technology of Pacific Biosciences, the Ion Torrent™ technology, and nanopore sequencing being developed for example, by Oxford Nanopore Technologies.

While the automated Sanger method is considered as a 'first generation' technology, Sanger sequencing including the automated Sanger sequencing, can also be employed by the method of the invention. Additional sequencing methods that comprise the use of developing nucleic acid imaging technologies e.g. atomic force microscopy (AFM) or transmission electron microscopy (TEM), are also encompassed by the method of the invention. Exemplary sequencing technologies are described below.

In one embodiment, the DNA sequencing technology that is used in the method of the invention is the Helicos True Single Molecule Sequencing (tSMS) (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step.

In one embodiment, the DNA sequencing technology that is used in the method of the invention is the 454 sequencing (Roche) (e.g. as described in Margulies, M. et al. Nature 437:376-380 [2005]). 454 sequencing involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is discerned and analyzed.

In one embodiment, the DNA sequencing technology that is used in the method of the invention is the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In one embodiment, the DNA sequencing technology that is used in the method of the invention is the single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength identifiers (ZMW identifiers) that obtain sequence information while phospolinked nucleotides are being incorporated into the growing primer strand. A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Identification of the corresponding fluorescence of the dye indicates which base was incorporated. The process is repeated.

In one embodiment, the DNA sequencing technology that is used in the method of the invention is nanopore sequencing (e.g. as described in Soni G V and Meller A. Clin Chem 53: 1996-2001 [2007]). Nanopore sequencing DNA analysis techniques are being industrially developed by a number of companies, including Oxford Nanopore Technologies (Oxford, United Kingdom). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence.

In one embodiment, the DNA sequencing technology that is used in the method of the invention is the chemical-sensitive field effect transistor (chemFET) array (e.g., as described in U.S. Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In one embodiment, the DNA sequencing technology that is used in the method of the invention is the Halcyon Molecular's method that uses transmission electron microscopy (TEM). The method, termed Individual Molecule Placement Rapid Nano Transfer (IMPRNT), comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445. The method allows for sequencing complete human genomes in less than ten minutes.

In one embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be identified by Ion Torrent's ion sensor. The sequencer—essentially the world's smallest solid-state pH meter—calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct identification allows recordation of nucleotide incorporation in seconds.

Other sequencing methods include digital PCR and sequencing by hybridization. Digital polymerase chain reaction (digital PCR or dPCR) can be used to directly identify and quantify nucleic acids in a sample. Digital PCR can be performed in an emulsion. Individual nucleic acids are separated, e.g., in a microfluidic chamber device, and each nucleic can is individually amplified by PCR. Nucleic acids can be separated such there is an average of approximately 0.5 nucleic acids/well, or not more than one nucleic acid/well. Different probes can be used to distinguish fetal alleles and maternal alleles. Alleles can be enumerated to determine copy number. In sequencing by hybridization, the hybridization comprises contacting the plurality of polynucleotide sequences with a plurality of polynucleotide probes, wherein each of the plurality of polynucleotide probes can be optionally tethered to a substrate. The substrate might be flat surface comprising an array of known nucleotide sequences. The pattern of hybridization to the array can be used to determine the polynucleotide sequences present in the sample. In other embodiments, each probe is tethered to a bead, e.g., a magnetic bead or the like. Hybridization to the beads can be identified and used to identify the plurality of polynucleotide sequences within the sample.

In one embodiment, the method employs massively parallel sequencing of millions of DNA fragments using Illumina's sequencing-by-synthesis and reversible terminator-based sequencing chemistry (e.g. as described in Bentley et al., Nature 6:53-59 [2009]). Template DNA can be genomic DNA e.g. cfDNA. In some embodiments, genomic DNA from isolated cells is used as the template, and it is fragmented into lengths of several hundred base pairs. In other embodiments, cfDNA is used as the template, and fragmentation is not required as cfDNA exists as short fragments. For example fetal cfDNA circulates in the bloodstream as fragments of <300 bp, and maternal cfDNA has been estimated to circulate as fragments of between about 0.5 and 1 Kb (Li et al., Clin Chem, 50: 1002-1011 [2004]). Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchors. Under limiting-dilution conditions, adapter-modified, single-stranded template DNA is added to the flow cell and immobilized by hybridization to the anchors. Attached DNA fragments are extended and bridge amplified to create an ultra-high density sequencing flow cell with hundreds of millions of clusters, each containing ~1,000 copies of the same template. In one embodiment, the randomly fragmented genomic DNA e.g. cfDNA, is amplified using PCR before it is subjected to cluster amplification. Alternatively, an amplification-free genomic library preparation is used, and the randomly fragmented genomic DNA e.g. cfDNA is enriched using the cluster amplification alone (Kozarewa et al., Nature Methods 6:291-295 [2009]). The templates are sequenced using a robust four-color DNA sequencing-by-synthesis technology that employs reversible terminators with removable fluorescent dyes. High-sensitivity fluorescence identification is achieved using laser excitation and total internal reflection optics. Short sequence reads of about 20-40 bp e.g. 36 bp, are aligned against a repeat-masked reference genome and genetic differences are called using specially developed data analysis pipeline software. After completion of the first read, the templates can be regenerated in situ to enable a second read from the opposite end of the fragments. Thus, either single-end or paired end sequencing of the DNA fragments is used according to the method. Partial sequencing of DNA fragments present in the sample is performed, and sequence tags comprising reads of predetermined length e.g. 36 bp, that are mapped to a known reference genome are counted. In one embodiment, the reference genome sequence is the NCBI36/hg18 sequence, which is available on the world wide web at genome.ucsc.edu/cgi-bin/hgGateway?org=Human&db=hg18&hgsid=166260105). Other sources of public sequence information include GenBank, dbEST, dbSTS, EMBL (the European Molecular Biology Laboratory), and the DDBJ (the DNA Databank of Japan). A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al., Genome Biology 10:R25.1-R25.10 [2009]), or ELAND (Illumina, Inc., San Diego, CA, USA). In one embodiment, one end of the clonally expanded copies of the plasma cfDNA molecules is sequenced and processed by bioinformatic alignment analysis for the Illumina Genome Analyzer, which uses the Efficient Large-Scale Alignment of Nucleotide Databases (ELAND) software.

The length of the sequence read is associated with the particular sequencing technology. NGS methods provide sequence reads that vary in size from tens to hundreds of base pairs. In some embodiments of the method described herein, the sequence reads are about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the sequence reads are 36 bp. Other sequencing methods that can be employed by the method of the invention include the single molecule sequencing methods that can sequence nucleic acids molecules >5000 bp. The massive quantity of sequence output is transferred by an analysis pipeline that transforms primary imaging output from the sequencer into strings of bases. A package of integrated algorithms performs the core primary data transformation steps: image analysis, intensity scoring, base calling, and alignment.

In one embodiment, partial sequencing of DNA fragments present in the sample is performed, and sequence tags comprising reads of predetermined length e.g. 36 bp, that map to a known reference genome are counted. Only sequence reads that uniquely align to the reference genome are counted as sequence tags. In one embodiment, the reference genome is the human reference genome NCBI36/hg18 sequence, which is available on the world wide web at genome.ucsc.edu/cgi-bin/hgGateway?org=Human&db=hg18&hgsid=166260105). Other sources of public sequence information include GenBank, dbEST, dbSTS, EMBL (the European Molecular Biology Laboratory), and the DDBJ (the DNA Databank of Japan). In another embodiment, the reference genome comprises the human reference genome NCBI36/hg18 sequence and an artificial target sequences genome, which includes the target polymorphic sequences e.g. a SNP genome. Mapping of the sequence tags is achieved by comparing the sequence of the tag with the sequence of the reference genome to determine the chromosomal origin of the sequenced nucleic acid (e.g. cfDNA) molecule, and specific genetic sequence information is not needed. A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al., Genome Biology 10:R25.1-R25.10 [2009]), or ELAND (Illumina, Inc., San Diego, CA, USA). In one embodiment, one end of the clonally expanded copies of the plasma cfDNA molecules is sequenced and processed by bioinformatic alignment analysis for the Illumina. Genome Analyzer, which uses the Efficient Large-Scale Alignment of Nucleotide Databases (ELAND) software. Analysis of sequencing information for the determination of aneuploidy may allow for a small degree of mismatch (0-2 mismatches per sequence tag) to account for minor polymorphisms that may exist between the reference genome and the genomes in the mixed sample. Analysis of sequencing information for the determination of fetal fraction may allow for a small degree of mismatch depending on the polymorphic sequence. For example, a small degree of mismatch may be allowed if the polymorphic sequence is an STR. In cases when the polymorphic sequence is a SNP, all sequence that match exactly to either of the two alleles at the SNP site are counted first and filtered from the remaining reads, for which a small degree of mismatch may be allowed.

In step 140, the sequencing information obtained in step 130 is analyzed and the simultaneous determination of the fetal fraction and determination of the presence or absence of aneuploidy is made.

A plurality of sequence tags are obtained per sample. In some embodiments, at least about $3 \times 10^6$ sequence tags, at least about $5 \times 10^6$ sequence tags, at least about $8 \times 10^6$ sequence tags, at least about $10 \times 10^6$ sequence tags, at least about $15 \times 10^6$ sequence tags, at least about $20 \times 10^6$ sequence tags, at least about $30 \times 10^6$ sequence tags, at least about $40 \times 10^6$ sequence tags, or at least about $50 \times 10^6$ sequence tags comprising between 20 and 40 bp reads are obtained from mapping the reads to the reference genome per sample. In one embodiment, all the sequence reads are mapped to all regions of the reference genome. In one embodiment, the tags comprising reads that have been mapped to all regions e.g. all chromosomes, of the human reference genome are counted, and the fetal aneuploidy i.e. the over- or under-representation of a sequence of interest e.g. a chromosome or portion thereof, in the mixed DNA sample is determined, and the tags comprising reads that are mapped to the artificial target sequences genome are counted to determine the fetal fraction. The method does not require differentiation between the maternal and fetal genomes.

Determination of Aneuploidy

Figure 5:
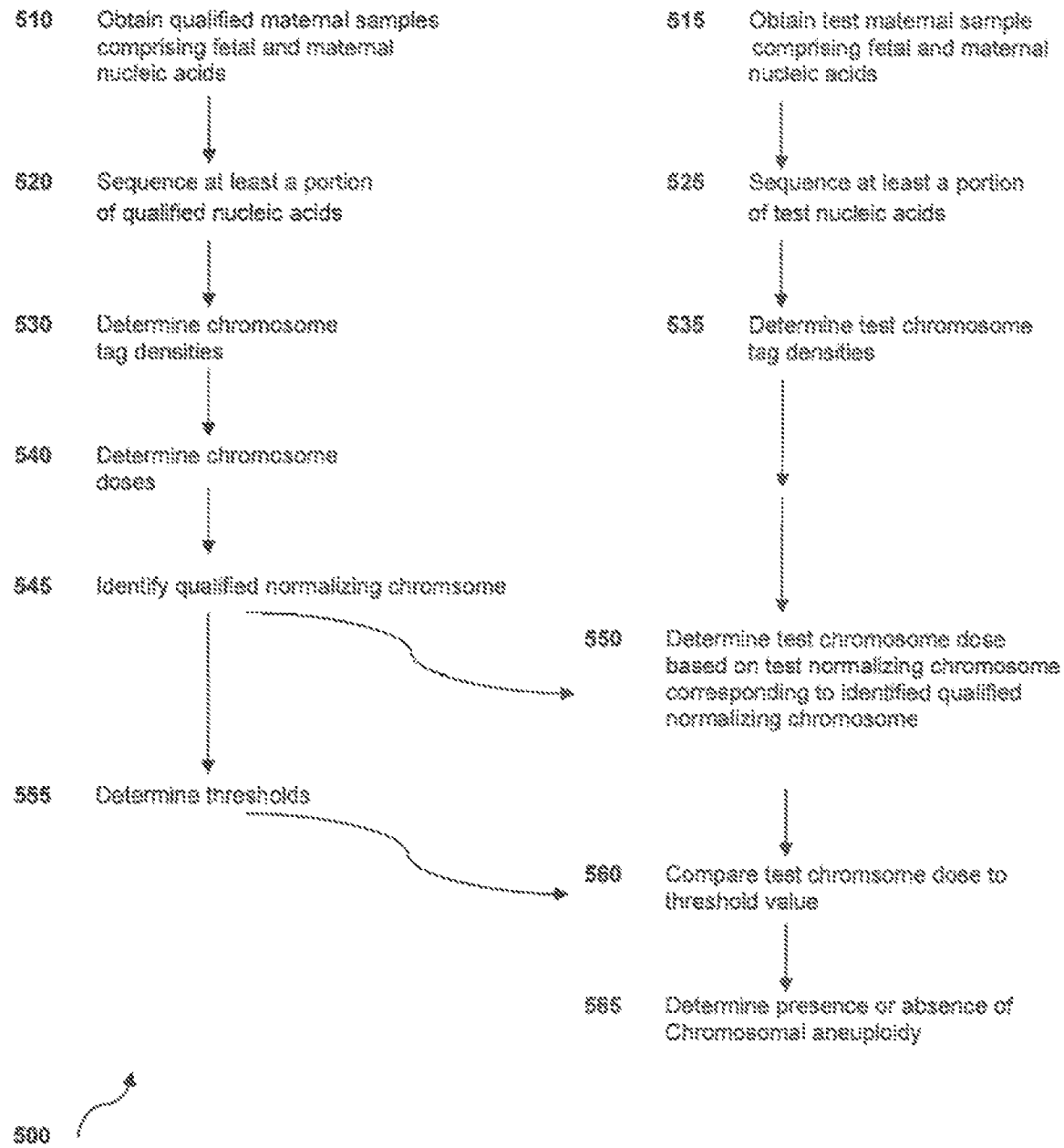
FIG. 5 is a flowchart of a method 500 for determining the presence or absence of a copy number variation in a test sample comprising a mixture of nucleic acids.

The accuracy required for correctly determining whether an aneuploidy is present or absent in a sample, is predicated in part on the variation of the number of sequence tags that map to the reference genome among samples within a sequencing run (inter-chromosomal variability), and the variation of the number of sequence tags that map to the reference genome in different sequencing runs (inter-sequencing variability). For example, the variations can be particularly pronounced for tags that map to GC-rich or GC-poor reference sequences. In one embodiment, the method uses sequencing information to calculate chromosome dose, which intrinsically account for the accrued variability stemming from interchromosomal, inter-sequencing and platform-dependent variability. Chromosome doses are determined from sequencing information i.e. the number of sequence tags, for the sequence of interest e.g. chromosome 21, and the number of sequence tags for a normalizing sequence. Identification of a normalizing sequence is performed in a set of qualified samples known not to contain an aneuploidy of the sequence of interest. The flow chart provided in FIG. 5 shows the process 500 whereby normalizing sequences e.g. normalizing chromosomes, are identified, and the presence or absence of an aneuploidy is determined. In step 510, a set of qualified maternal samples is obtained to identify qualified normalizing sequences e.g. normalizing chromosomes, and to provide variance values for use in determining statistically meaningful identification of an aneuploidy in test samples. In step 510, a plurality of biological qualified samples are obtained from a plurality of subjects known to comprise cells having a normal copy number for any one sequence of interest e.g. a chromosome of interest such as a chromosome associated with an aneuploidy. In one embodiment, the qualified samples are obtained from mothers pregnant with a fetus that has been confirmed using cytogenetic means to have a normal copy number of chromosomes relative to the chromosome of interest. The biological qualified maternal samples may be biological fluid samples e.g. plasma samples, or any suitable sample as described above that contains a mixture of fetal and maternal cfDNA molecules.

In step 520, at least a portion of each of all the qualified nucleic acids contained in the qualified maternal samples are sequenced to generate sequence reads of between 20 and 40 bp e.g. 36 bp, which are aligned to a reference genome, e.g. hg18. In some embodiments, the sequence reads comprise about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130 bp, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the sequence reads comprise 36 bp. Sequence reads are aligned to a human reference genome, and the reads that are uniquely mapped to the human reference genome are counted as sequence tags. In one embodiment, at least about $3 \times 10^6$ qualified sequence tags, at least about $5 \times 10^6$ qualified sequence tags, at least about $8 \times 10^6$ qualified sequence tags, at least about $10 \times 10^6$ qualified sequence tags, at least about $15 \times 10^6$ qualified sequence tags, at least about $20 \times 10^6$ qualified sequence tags, at least about $30 \times 10^6$ qualified sequence tags, at least about $40 \times 10^6$ qualified sequence tags, or at least about $50 \times 10^6$ qualified sequence tags comprising between 20 and 40 bp reads are obtained from reads that map uniquely to a reference genome.

In step 530, all the tags obtained from sequencing the nucleic acids in the qualified maternal samples are counted to determine a qualified sequence tag density. In one embodiment the sequence tag density is determined as the number of qualified sequence tags mapped to the sequence of interest on the reference genome. In another embodiment, the qualified sequence tag density is determined as the number of qualified sequence tags mapped to a sequence of interest normalized to the length of the qualified sequence of interest to which they are mapped. Sequence tag densities that are determined as a ratio of the tag density relative to the length of the sequence of interest are herein referred to as tag density ratios. Normalization to the length of the sequence of interest is not required, and may be included as a step to reduce the number of digits in a number to simplify it for human interpretation. As all qualified sequence tags are mapped and counted in each of the qualified samples, the sequence tag density for a sequence of interest e.g. chromosome of interest, in the qualified samples is determined, as are the sequence tag densities for additional sequences from which normalizing sequences e.g. chromosomes, are identified subsequently. In one embodiment, the sequence of interest is a chromosome that is associated with a chromosomal aneuploidy e.g. chromosome 21, and the qualified normalizing sequence is a chromosome that is not associated with a chromosomal aneuploidy and whose variation in sequence tag density best approximates that of chromosome 21. For example, a qualified normalizing sequence is a sequence that has the smallest variability. In some embodiments, the normalizing sequence is a sequence that best distinguishes one or more qualified, samples from one or more affected samples i.e. the normalizing sequence is a sequence that has the greatest differentiability. The level of differentiability can be determined as a statistical difference between the chromosome doses in a population of qualified samples and the chromosome dose(s) in one or more test samples. In another embodiment, the sequence of interest is a segment of a chromosome associated with a partial aneuploidy, e.g. a chromosomal deletion or insertion, or unbalanced chromosomal translocation, and the normalizing sequence is a chromosomal segment that is not associated with the partial aneuploidy and whose variation in sequence tag density best approximates that of the chromosome segment associated with the partial aneuploidy.

In step 540, based on the calculated qualified tag densities, a qualified sequence dose for a sequence of interest is determined as the ratio of the sequence tag density for the sequence of interest and the qualified sequence tag density for additional sequences from which normalizing sequences are identified subsequently. In one embodiment, doses for the chromosome of interest e.g. chromosome 21, is determined as a ratio of the sequence tag density of chromosome 21 and the sequence tag density for each of all the remaining chromosomes i.e. chromosomes 1-20, chromosome 22, chromosome X, and chromosome Y.

In step 545, a normalizing sequence e.g. a normalizing chromosome, is identified for a sequence of interest e.g. chromosome 21, in a qualified sample based on the calculated sequence doses. The method identifies sequences that inherently have similar characteristics and that are prone to similar variations among samples and sequencing runs, and which are useful for determining sequence doses in test samples. In some embodiments, the normalizing sequence is one that best differentiates an affected sample i.e. an aneuploid sample, from one or more qualified samples. In other embodiments, a normalizing sequence is a sequence that displays a variability in the number of sequence tags that are mapped to it among samples and sequencing runs that best approximates that of the sequence of interest for which it is used as a normalizing parameter, and/or that can best differentiate an affected sample from one or more unaffected samples.

In some embodiments, more than one normalizing sequence is identified. For example, the variation e.g. coefficient of variation, in chromosome dose for chromosome of interest 21 is least when the sequence tag density of chromosome 14 is used. In other embodiments, two, three, four, five, six, seven, eight or more normalizing sequences are identified for use in determining a sequence dose for a sequence of interest in a test sample.

In one embodiment, the normalizing sequence for chromosome 21 is selected from chromosome 9, chromosome 1, chromosome 2, chromosome 3, chromosome 4, chromosome 5, chromosome 6, chromosome 7, chromosome 8, chromosome 10, chromosome 11, chromosome 12, chromosome 13, chromosome 14, chromosome 15, chromosome 16, and chromosome 17. Preferably, the normalizing sequence for chromosome 21 is selected from chromosome 9, chromosome 1, chromosome 2, chromosome 11, chromosome 12, and chromosome 14. Alternatively, the normalizing sequence for chromosome 21 is a group of chromosomes selected from chromosome 9, chromosome 1, chromosome 2, chromosome 3, chromosome 4, chromosome 5, chromosome 6, chromosome 7, chromosome 8, chromosome 10, chromosome 11, chromosome 12, chromosome 13, chromosome 14, chromosome 15, chromosome 16, and chromosome 17. In other embodiments, the normalizing sequence for chromosome 21 is a group of chromosomes selected from chromosome 9, chromosome 1, chromosome 2, chromosome 11, chromosome 12, and chromosome 14.

In one embodiment, the normalizing sequence for chromosome 18 is selected from chromosome 8, chromosome 2, chromosome 3, chromosome 4, chromosome 5, chromosome 6, chromosome 7, chromosome 9, chromosome 10, chromosome 11, chromosome 12, chromosome 13, and chromosome 14. Preferably, the normalizing sequence for chromosome 18 is selected chromosome 8, chromosome 2, chromosome 3, chromosome 5, chromosome 6, chromosome 12, and chromosome 14. Alternatively, the normalizing sequence for chromosome 18 is a group of chromosomes selected from chromosome 8, chromosome 2, chromosome 3, chromosome 4, chromosome 5, chromosome 6, chromosome 7, chromosome 9, chromosome 10, chromosome 11, chromosome 12, chromosome 13, and chromosome 14. In other embodiments, the normalizing sequence for chromosome 18 is a group of chromosomes selected from chromosome 8, chromosome 2, chromosome 3, chromosome 5, chromosome 6, chromosome 12, and chromosome 14.

In one embodiment, the normalizing sequence for chromosome X is selected from chromosome 1, chromosome 2, chromosome 3, chromosome 4, chromosome 5, chromosome 6, chromosome 7, chromosome 8, chromosome 9, chromosome 10, chromosome 11, chromosome 12, chromosome 13, chromosome 14, chromosome 15, and chromosome 16. Preferably, the normalizing sequence for chromosome X is selected from chromosome 2, chromosome 3, chromosome 4, chromosome 5, chromosome 6, and chromosome 8. Alternatively, the normalizing sequence for chromosome X is a group of chromosomes selected from chromosome 1, chromosome 2, chromosome 3, chromosome 4, chromosome 5, chromosome 6, chromosome 7, chromosome 8, chromosome 9, chromosome 10, chromosome 11, chromosome 12, chromosome 13, chromosome 14, chromosome 15, and chromosome 16. In other embodiments, the normalizing sequence for chromosome X is a group of chromosomes selected from chromosome 2, chromosome 3, chromosome 4, chromosome 5, chromosome 6, and chromosome 8

In one embodiment, the normalizing sequence for chromosome 13 is a chromosome selected from chromosome 2, chromosome 3, chromosome 4, chromosome 5, chromosome 6, chromosome 7, chromosome 8, chromosome 9, chromosome 10, chromosome 11, chromosome 12, chromosome 14, chromosome 18, and chromosome 21. Preferably, the normalizing sequence for chromosome 13 is selected from chromosome 2, chromosome 3, chromosome 4, chromosome 5, chromosome 6, and chromosome 8. In another embodiment, the normalizing sequence for chromosome 13 is a group of chromosomes selected from chromosome 2, chromosome 3, chromosome 4, chromosome 5, chromosome 6, chromosome 7, chromosome 8, chromosome 9, chromosome 10, chromosome 11, chromosome 12, chromosome 14, chromosome 18, and chromosome 21. In other embodiments, the normalizing sequence for chromosome 13 is a group of chromosomes selected from chromosome 2, chromosome 3, chromosome 4, chromosome 5, chromosome 6, and chromosome 8.

The variation in chromosome dose for chromosome Y is greater than 30 independently of which normalizing chromosome is used in determining the chromosome Y dose. Therefore, any one chromosome, or a group of two or more chromosomes selected from chromosomes 1-22 and chromosome X can be used as the normalizing sequence for chromosome Y. In one embodiment, the at least one normalizing chromosome is a group of chromosomes consisting of chromosomes 1-22, and chromosome X. In another embodiment, the at least one normalizing chromosome is a group of chromosomes selected from chromosome 2, chromosome 3, chromosome 4, chromosome 5 and chromosome 6.

Based on the identification of the normalizing sequence(s) in qualified samples, a sequence dose is determined for a sequence of interest in a test sample comprising a mixture of nucleic acids derived from genomes hat differ in one or more sequences of interest.

In step 515, a test sample e.g. plasma sample, comprising fetal and maternal nucleic acids e.g. cfDNA, is obtained from a pregnant subject e.g. a pregnant woman, for which the presence or absence of a fetal aneuploidy needs to be determined.

In step 525, at least a portion of the test nucleic acids in the test sample is sequenced to generate millions of sequence reads comprising between 20 and 500 bp e.g. 36 bp. As in step 520, the reads generated from sequencing the nucleic acids in the test sample are uniquely mapped to a human reference genome and are counted. As described in step 520, at least about $3\times10^6$ qualified sequence tags, at least about $5\times10^6$ qualified sequence tags, at least about $8\times10^6$ qualified sequence tags, at least about $10\times10^6$ qualified sequence tags, at least about $15\times10^6$ qualified sequence tags, at least about $20\times10^6$ qualified sequence tags, at least about $30\times10^6$ qualified sequence tags, at least about $40\times10^6$ qualified sequence tags, or at least about 50×10⁶ qualified sequence tags comprising between 20 and 40 bp reads are obtained from reads that map uniquely to the human reference genome.

In step 535, all the tags obtained from sequencing the nucleic acids in the test samples are counted to determine a test sequence tag density. In one embodiment, the number of test sequence tags mapped to a sequence of interest is normalized to the known length of a sequence of interest to which they are mapped to provide a test sequence tag density. As described for the qualified samples, normalization to the known length of a sequence of interest is not required, and may be included as a step to reduce the number of digits in a number to simplify it for human interpretation. As all the mapped test sequence tags are counted in the test sample, the sequence tag density for a sequence of interest e.g. a clinically-relevant sequence such as chromosome 21, in the test samples is determined, as are the sequence tag densities for additional sequences that correspond to at least one normalizing sequence identified in the qualified samples.

In step 550, based on the identity of at least one normalizing sequence in the qualified samples, a test sequence dose is determined for a sequence of interest in the test sample. The sequence dose e.g. chromosome dose, for a sequence of interest in a test sample is a ratio of the sequence tag density determined for the sequence of interest in the test sample and the sequence tag density of at least one normalizing sequence determined in the test sample, wherein the normalizing sequence in the test sample corresponds to the normalizing sequence identified in the qualified samples for the particular sequence of interest. For example, if the normalizing sequence identified for chromosome 21 in the qualified samples is determined to be chromosome 14, then the test sequence dose for chromosome 21 (sequence of interest) is determined as the ratio of the sequence tag density for chromosome 21 in and the sequence tag density for chromosome 14 each determined in the test sample. Similarly, chromosome doses for chromosomes 13, 18, X, Y, and other chromosomes associated with chromosomal aneuploidies are determined. As described previously, a sequence of interest can be part of a chromosome e.g. a chromosome segment. Accordingly, the dose for a chromosome segment can be determined as the ratio of the sequence tag density determined for the segment in the test sample and the sequence tag density for the normalizing chromosome segment in the test sample, wherein the normalizing segment in the test sample corresponds to the normalizing segment identified in the qualified samples for the particular segment of interest.

In step 555, threshold values are derived from standard deviation values established for a plurality of qualified sequence doses. Accurate classification depends on the differences between probability distributions for the different classes i.e. type of aneuploidy. Preferably, thresholds are chosen from empirical distribution for each type of aneuploidy e.g. trisomy 21. Possible threshold values that were established for classifying trisomy 13, trisomy 18, trisomy 21, and monosomy X aneuploidies as described in the Examples, which describe the use of the method for determining chromosomal aneuploidies by sequencing cfDNA extracted from a maternal sample comprising a mixture of fetal and maternal nucleic acids.

In step 560, the copy number variation of the sequence of interest e.g. chromosomal or partial aneuploidy, is determined in the test sample by comparing the test sequence dose for the sequence of interest to at least one threshold value established from the qualified sequence doses.

In step 560, the calculated dose for a test sequence of interest is compared to that set as the threshold values that are chosen according to a user-defined threshold of reliability to classify the sample as a "normal" an "affected" or a "no call" in step 565. The "no call" samples are samples for which a definitive diagnosis cannot be made with reliability.

Another embodiment of the invention provides a method for providing prenatal diagnosis of a fetal chromosomal aneuploidy in a biological sample comprising fetal and maternal nucleic acid molecules. The diagnosis is made based on receiving the data from sequencing at least a portion of the mixture of the fetal and maternal nucleic acid molecules derived from a biological test sample e.g. a maternal plasma sample, computing from the sequencing data a normalizing chromosome dose for one or more chromosomes of interest, determining a statistically significant difference between the normalizing chromosome dose for the chromosome of interest in the test sample and a threshold value established in a plurality of qualified (normal) samples, and providing the prenatal diagnosis based on the statistical difference. As described in step 565 of the method, a diagnosis of normal or affected is made. A "no call" is provided in the event that the diagnosis for normal or affected cannot be made with confidence.

Quantification of the number of sequence reads aligning to each chromosome for determining chromosomal aneuploidies can also be achieved by normalizing the median number of sequence tags for a chromosome of interest to the median number of tags for each of the other autosomes (Fan et al., Proc Natl Acad Sci 105:16266-16271 [2008]). Alternatively, the number of unique reads aligning to each chromosome is compared to the total number of reads aligning to all chromosomes to derive a percent genomic representation for each chromosome. A "z score" is generated to represent the difference between the percent genomic representation of the chromosome of interest and the mean percent representation for the same chromosome between a euploid control group, divided by the standard deviation (Chiu et al., Clin Chem 56:459-463 [2010].

Determination of Fetal Fraction

The determination of the fetal fraction is based on the total number of tags that map to the first allele and the total number of tags that map to second allele at an informative polymorphic site e.g. a SNP, contained in a reference genome. For example, the reference genome is the human reference genome NCBI36/hg18 sequence, or the reference genome comprises the human reference genome NCBI36/hg18 sequence and an artificial target sequences genome, which includes the target polymorphic sequences. For example, the artificial target genome encompasses polymorphic sequences that comprise SNPs rs560681, rs1109037, rs9866013, rs13182883, rs13218440, rs7041158, rs740598, rs10773760, rs4530059, rs7205345, rs8078417, rs576261, rs2567608, rs430046, rs9951171, rs338882, rs10776839, rs9905977, rs1277284, rs258684, rs1347696, rs508485, rs9788670, rs8137254, rs3143, rs2182957, rs3739005, and rs530022. In another example, the artificial genome includes the polymorphic target sequences of SEQ ID NOs:1-56 (see Example 5). In another example, the artificial genome comprises polymorphic sequences that comprise tandem SNPs r s7277033-rs2110153; rs2822654-rs1882882; rs368657-rs376635; rs2822731-rs2822732; rs1475881-rs7275487; rs1735976-rs2827016; rs447340-rs2824097; rs418989-rs13047336; rs987980-rs987981; rs4143392-rs4143391; rs1691324-rs13050434; rs11909758-rs9980111;

rs2826842-rs232414; rs1980969-rs1980970; rs9978999-rs9979175; rs1034346-rs12481852; rs7509629-rs2828358; rs4817013-rs7277036; rs9981121-rs2829696; rs455921-rs2898102; rs2898102-rs458848; rs961301-rs2830208; rs2174536-rs458076; rs11088023-rs11088024; rs1011734-rs1011733; rs2831244-rs9789838; rs8132769-rs2831440; rs8134080-rs2831524; rs4817219-rs4817220; rs2250911-rs2250997; rs2831899-rs2831900; rs2831902-rs2831903; rs11088086-rs2251447; rs2832040-rs11088088; rs2832141-rs2246777; rs2832959-rs9980934; rs2833734-rs2833735; rs933121-rs933122; rs2834140-rs12626953; rs2834485-rs3453; rs9974986-rs2834703; rs2776266-rs2835001; rs1984014-rs1984015; rs7281674-rs2835316; rs13047304-rs13047322; rs2835545-rs4816551; rs2835735-rs2835736; rs13047608-rs2835826; rs2836550-rs2212596; rs2836660-rs2836661; rs465612-rs8131220; rs9980072-rs8130031; rs418359-rs2836926; rs7278447-rs7278858; rs385787-rs367001; rs367001-rs386095; rs2837296-rs2837297; and rs2837381-rs4816672. In another example, the artificial target genome encompasses polymorphic sequences that comprise STRs selected from CSF1PO, FGA, TH01, TPOX, vWA, D351358, D5S818, D7S820, D8S1179, D135317, D165539, D18S51, D21511, Penta D, Penta E, D2S1338, D1S1677, D2S441, D4S2364, D1051248, D1451434, D22S1045, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D5S2500, D4S2408, D4S2364, D3S4529, D3S3053, D2S1776, D2S441, D1S1677, D1S1627, and D1GATA113. The composition of the artificial target sequences genome will vary depending on the polymorphic sequences that are used for determining the fetal fraction. Accordingly, an artificial target sequences genome is not limited to the SNP or STR sequences exemplified herein.

Figure 6:
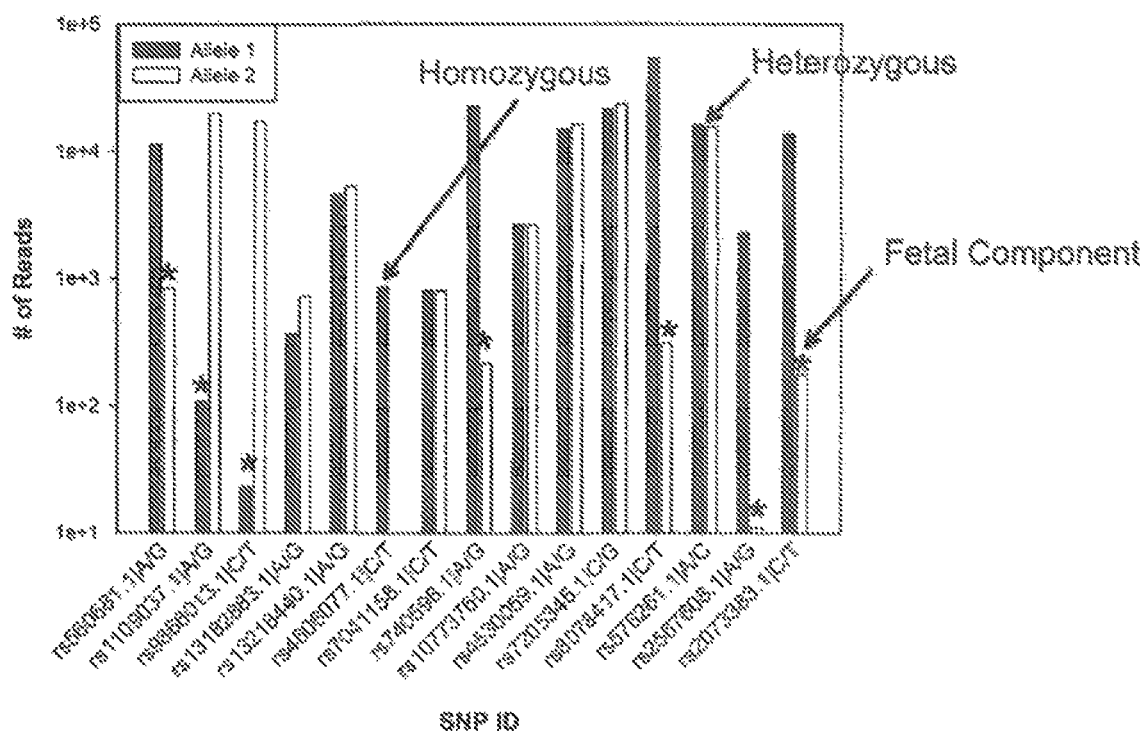
FIG. 6 is a bar diagram showing the identification of fetal and maternal polymorphic sequences (SNPs) used to determine fetal fraction in a test sample. The total number of sequence reads (Y-axis) mapped to the SNP sequences identified by rs numbers (X-axis), and the relative level of fetal nucleic acids (*) are shown.
Figure 7A:
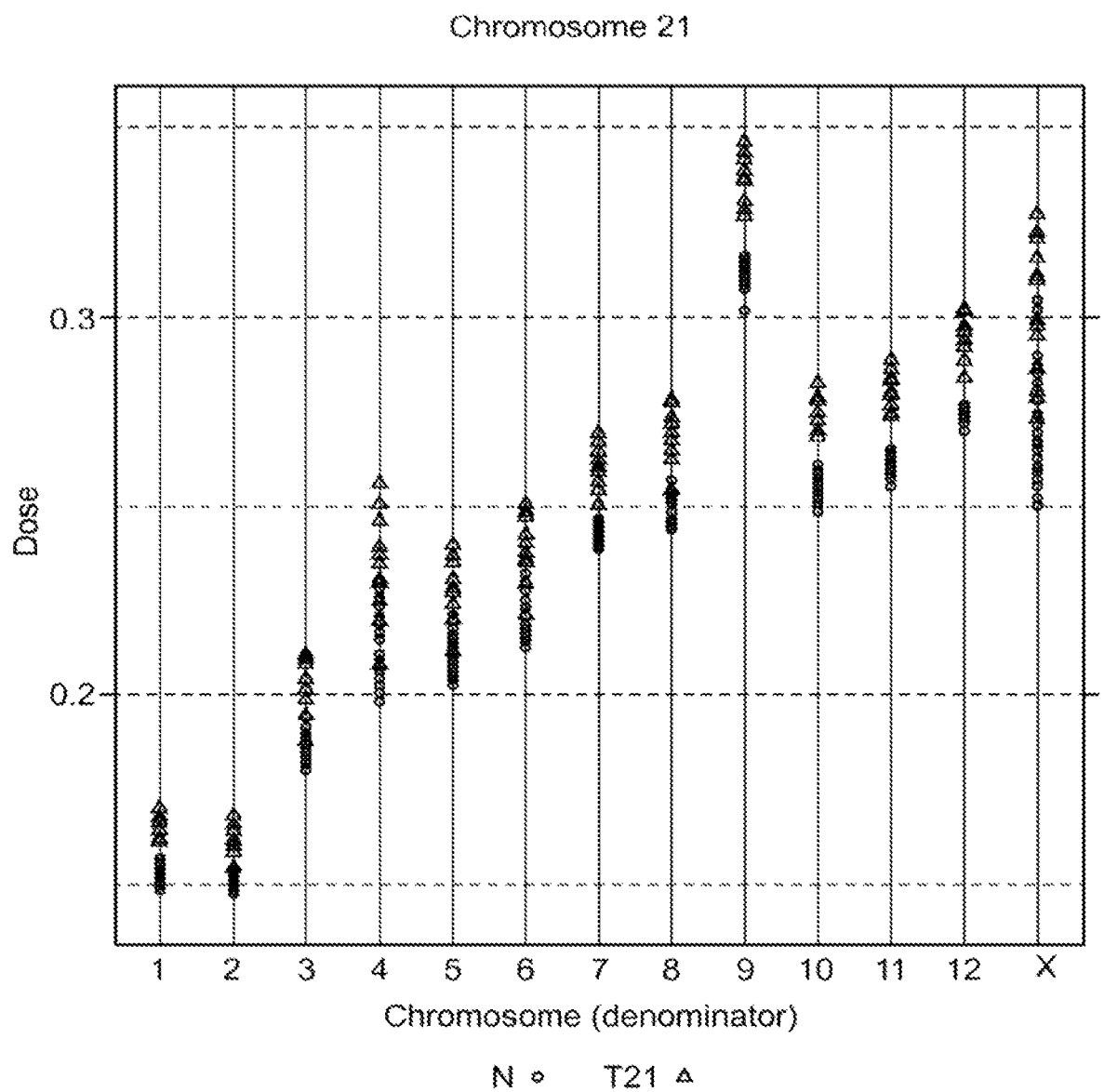
FIGS. 7A and 7B illustrate the distribution of the chromosome dose for chromosome 21 determined from sequencing cfDNA extracted from a set of 48 blood samples obtained from human subjects pregnant with male or female fetuses. Chromosome 21 doses for qualified i.e. normal for chromosome 21 (O), and trisomy 21 test samples are shown (Δ) for chromosomes 1-12 and X (FIG. 7A), and for chromosomes 1-22 and X (FIG. 7B).
Figure 7B:
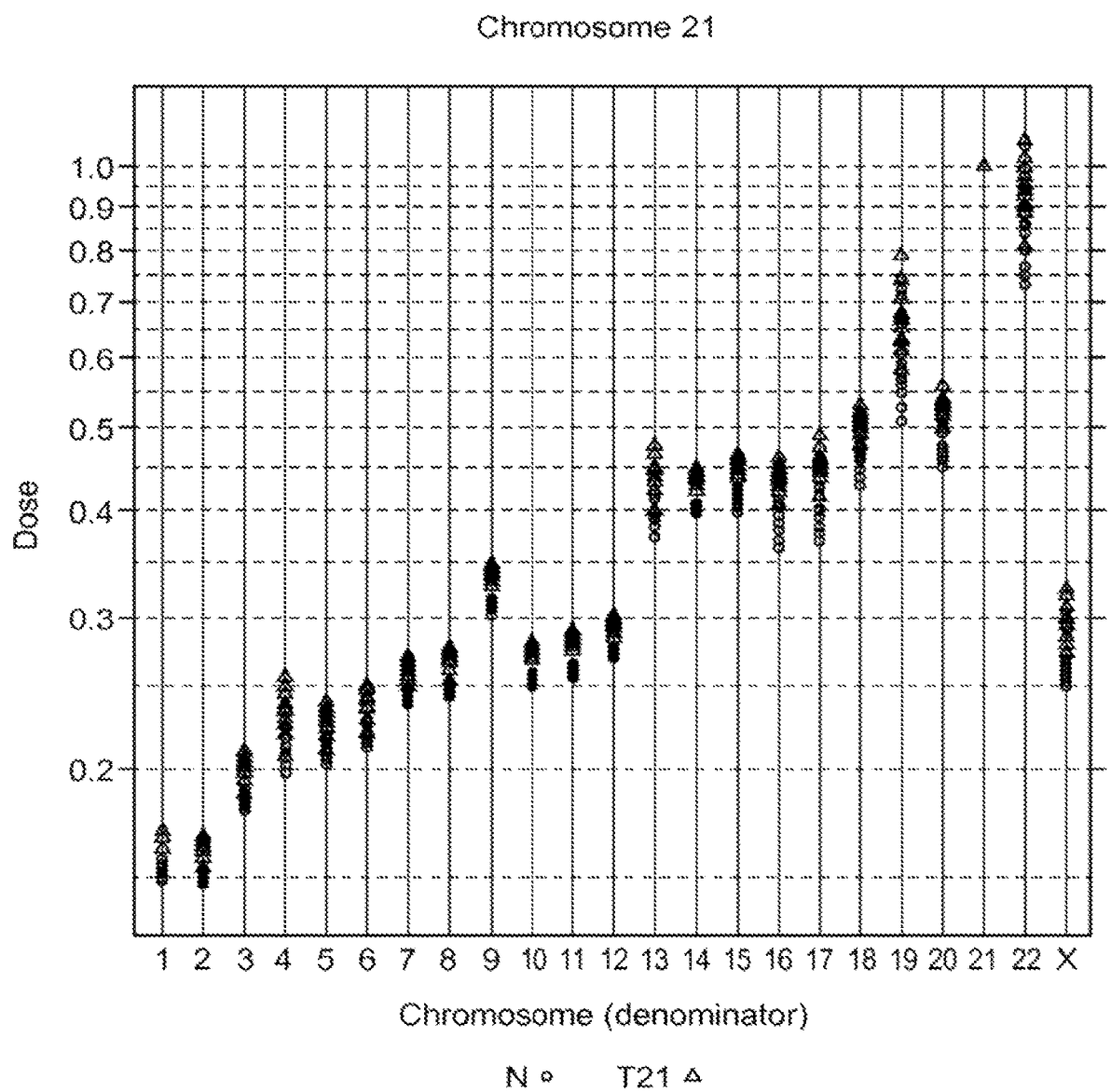
Figure 8A:
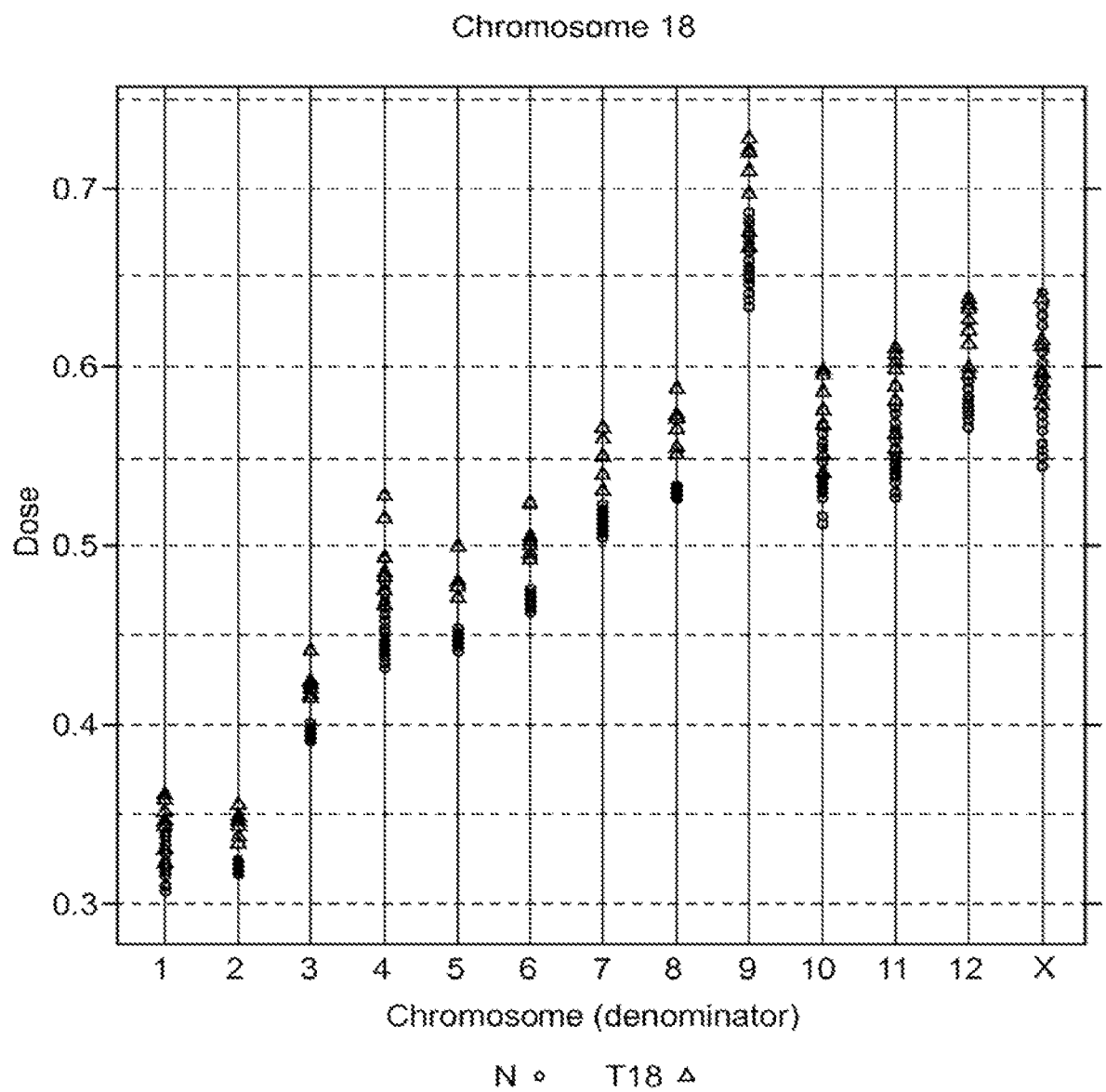
FIGS. 8A and 8B illustrate the distribution of the chromosome dose for chromosome 18 determined from sequencing cfDNA extracted from a set of 48 blood samples obtained from human subjects pregnant with male or female fetuses. Chromosome 18 doses for qualified i.e. normal for chromosome 18 (O), and trisomy 18 (Δ) test samples are shown for chromosomes 1-12 and X (FIG. 8A), and for chromosomes 1-22 and X (FIG. 8B).
Figure 8B:
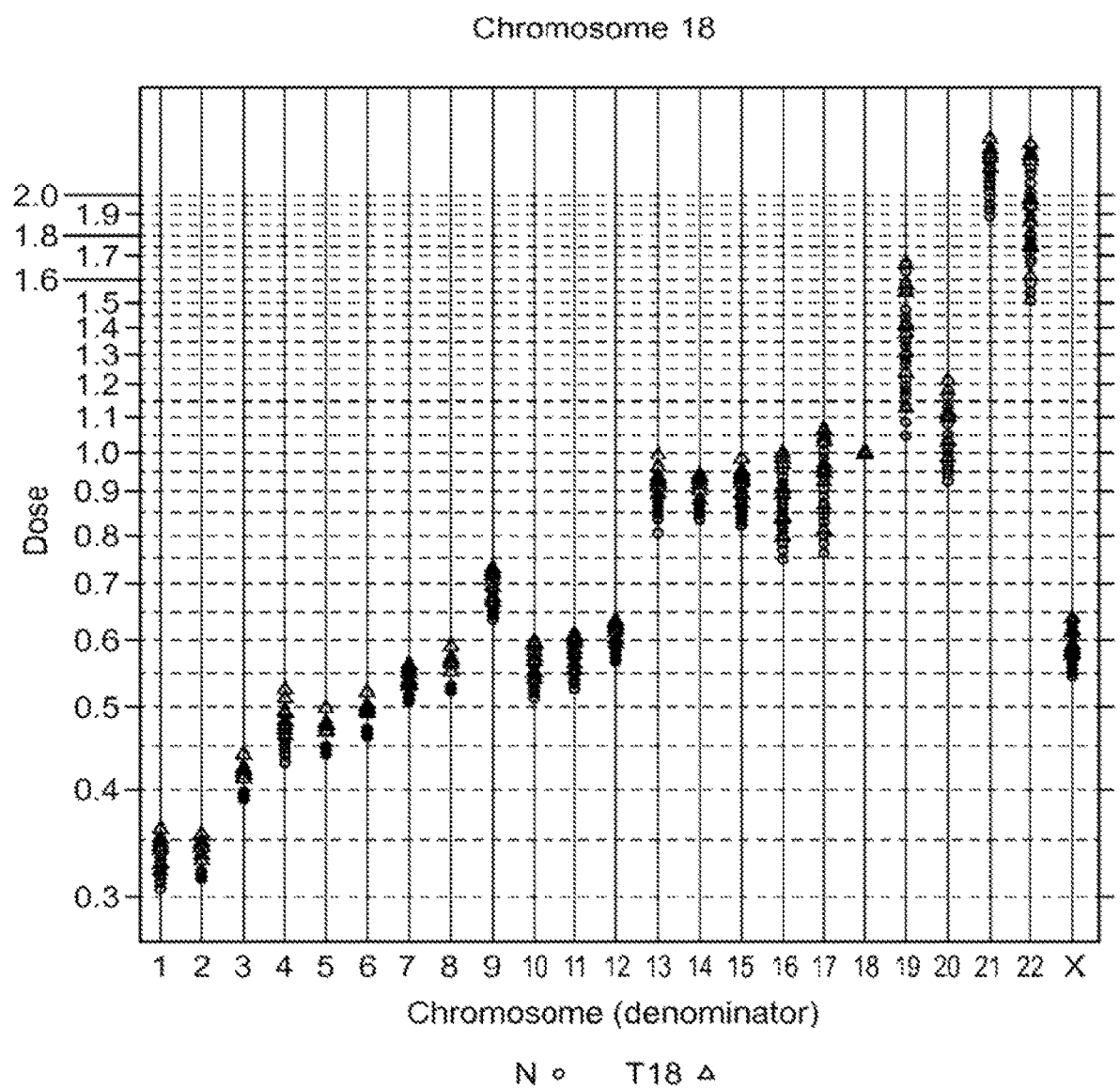
Figure 9A:
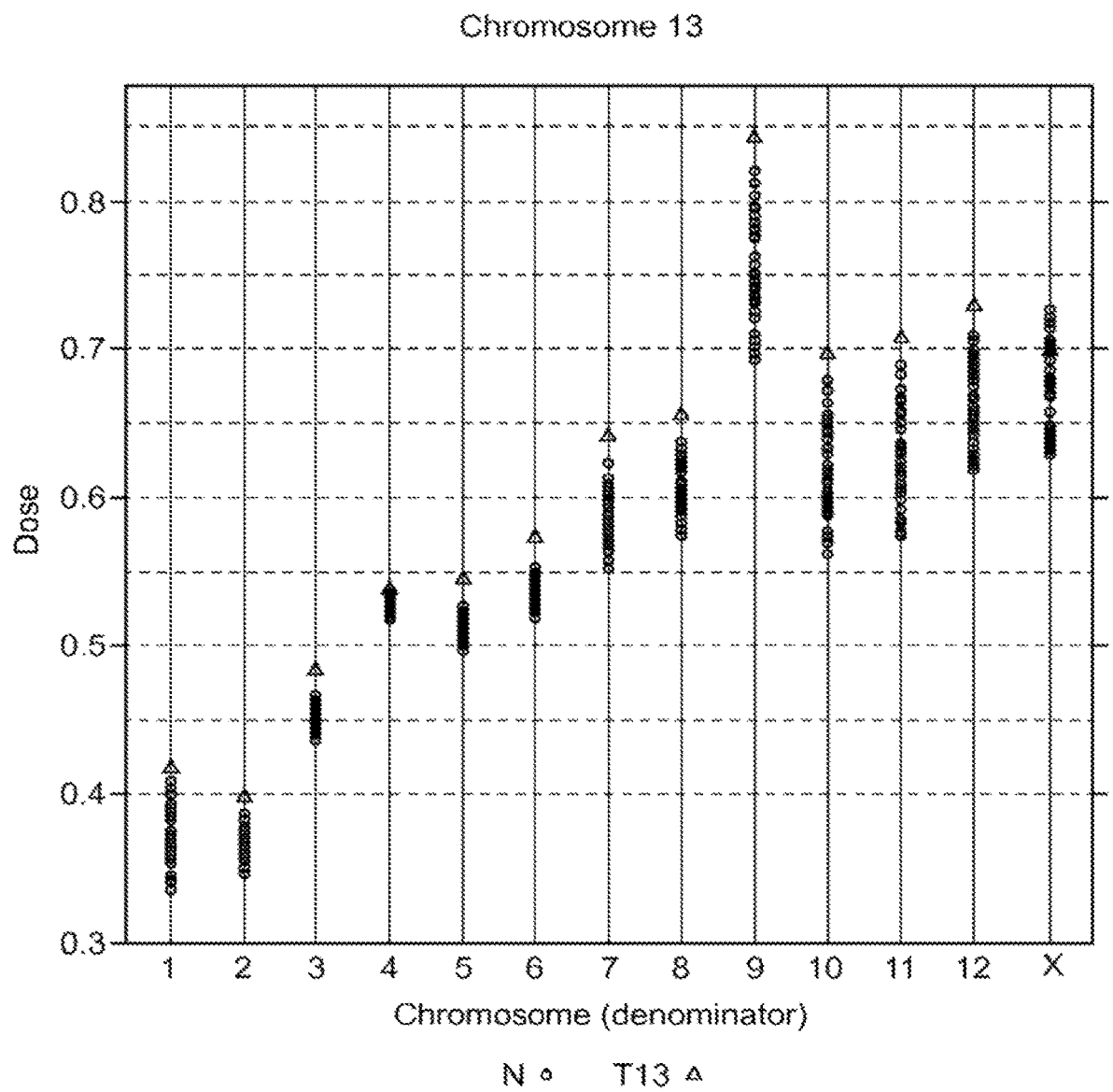
FIGS. 9A and 9B illustrate the distribution of the chromosome dose for chromosome 13 determined from sequencing cfDNA extracted from a set of 48 blood samples obtained from human subjects pregnant with male or female fetuses. Chromosome 13 doses for qualified i.e. normal for chromosome 13 (O), and trisomy 13 (Δ) test samples are shown for chromosomes 1-12 and X (FIG. 9A), and for chromosomes 1-22 and X (FIG. 9B).
Figure 9B:
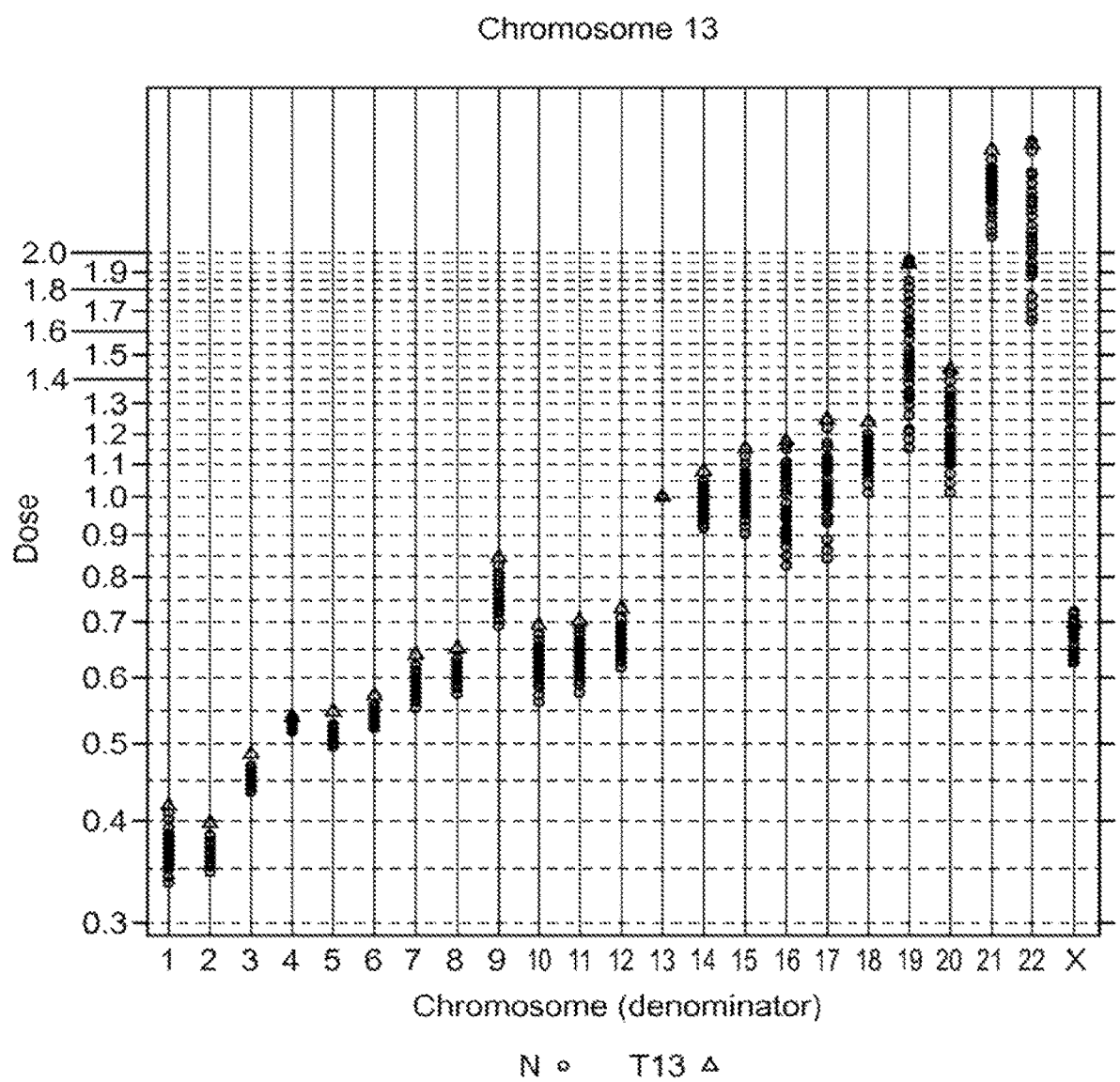
Figure 10A:
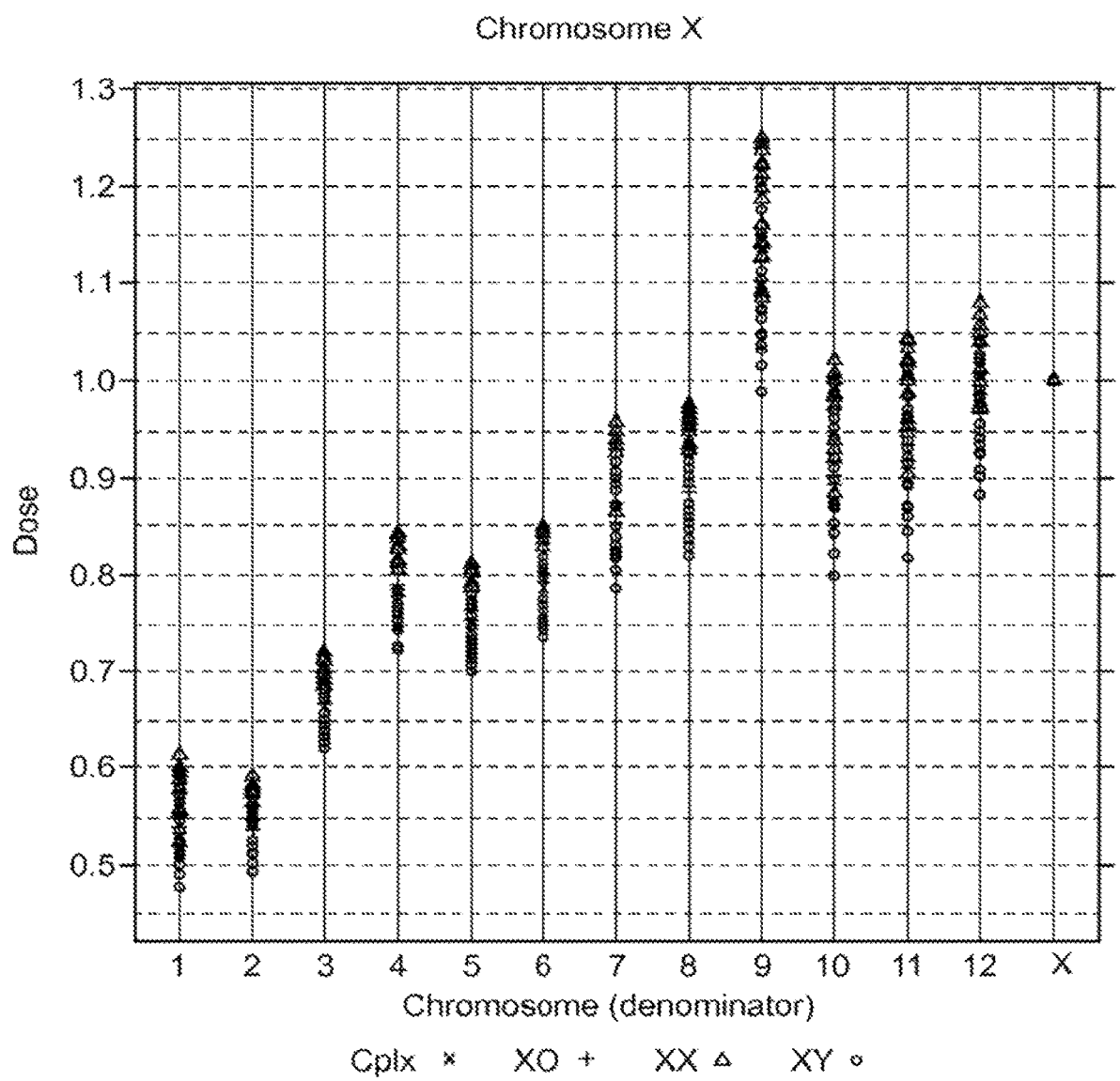
FIGS. 10A and 10B illustrate the distribution of the chromosome doses for chromosome X determined from sequencing cfDNA extracted from a set of 48 test blood samples obtained from human subjects pregnant with either male or female fetuses. Chromosome X doses for males (46,XY; (O)), females (46,XX; (Δ)); monosomy X (45,X; (+)), and complex karyotypes (Cplx (X)) samples are shown for chromosomes 1-12 and X (FIG. 10A), and for chromosomes 1-22 and X (FIG. 10B).
Figure 10B:
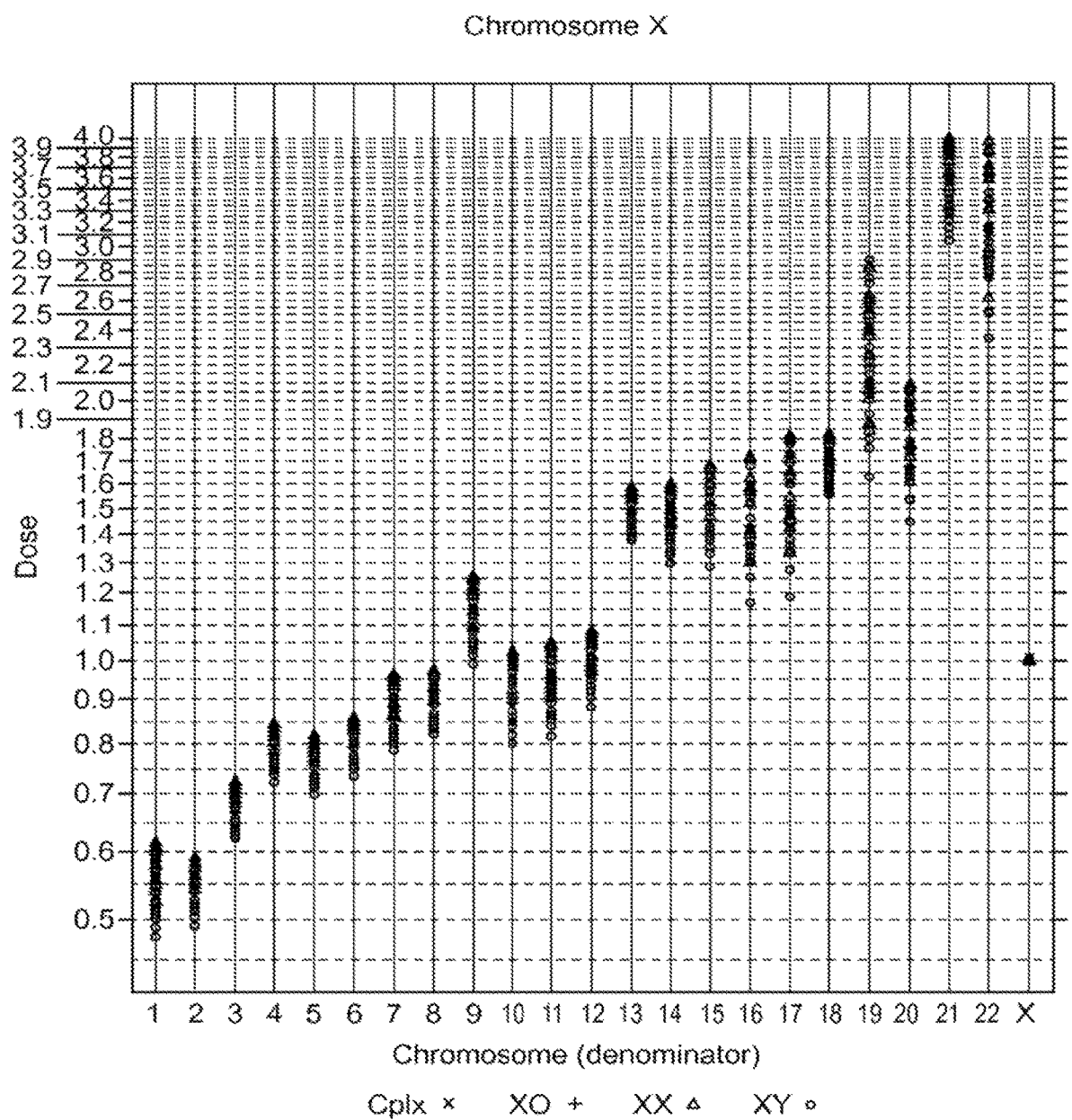
Figure 11A:
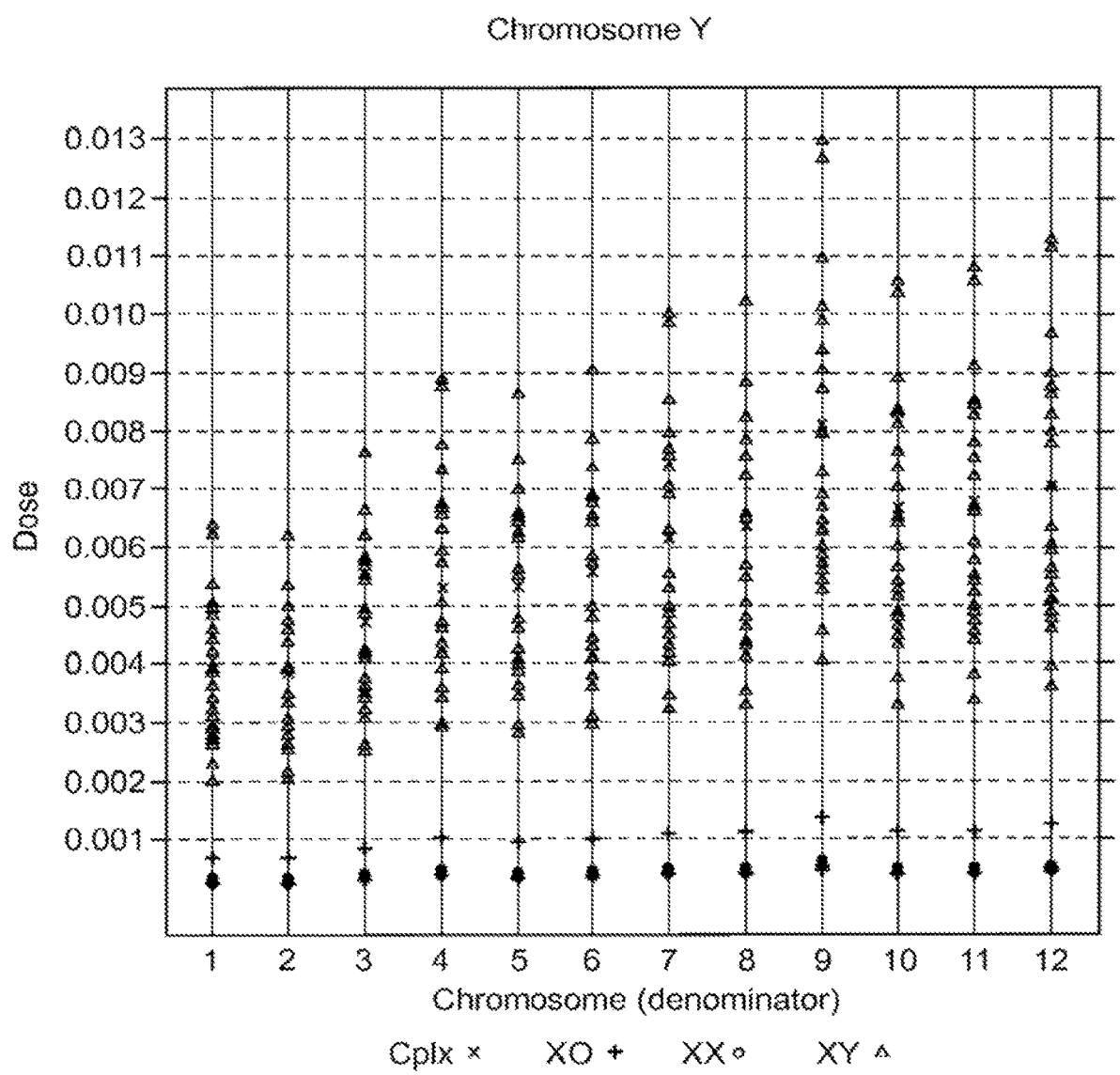
FIGS. 11A and 11B illustrate the distribution of the chromosome doses for chromosome Y determined from sequencing cfDNA extracted from a set of 48 test blood samples obtained from human subjects pregnant with either male or female fetuses. Chromosome Y doses for males (46,XY; (Δ)), females (46,XX; (O)); monosomy X (45,X; (+)), and complex karyotypes (Cplx (X)) samples are shown for chromosomes 1-12 (FIG. 11A), and for chromosomes 1-22 (FIG. 11B).
Figure 11B:
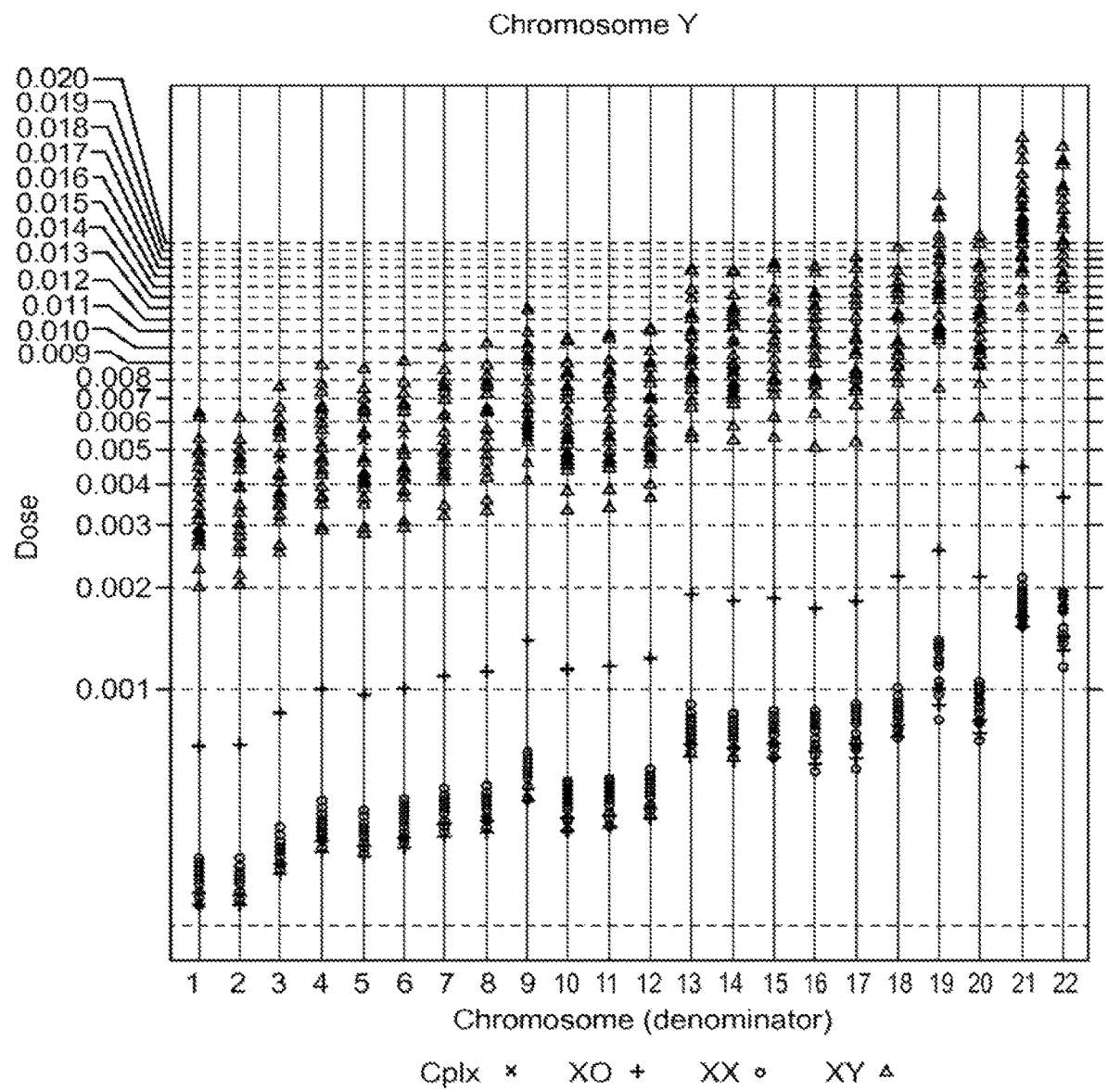

The informative polymorphic site e.g. SNP, is identified by the difference in the allelic sequences and the amount of each of the possible alleles. Fetal cfDNA is present at a concentration that is <10% of the maternal cfDNA. Thus, the presence of a minor contribution of an allele to the mixture of fetal and maternal nucleic acids relative to the major contribution of the maternal allele can be assigned to the fetus. Alleles that are derived from the maternal genome are herein referred to as major alleles, and alleles that are derived from the fetal genome are herein referred to as minor alleles. Alleles that are represented by similar levels of mapped sequence tags represent maternal alleles. The results of an exemplary multiplex amplification of target nucleic acids comprising SNPs and derived from a maternal plasma sample is shown in FIG. 6. Informative SNPs are discerned from the single nucleotide change at a predetermined polymorphic site, and fetal alleles are discerned by their relative minor contribution to the mixture of fetal and maternal nucleic acids in the sample when compared to the major contribution to the mixture by the maternal nucleic acids. Accordingly, the relative abundance of fetal cfDNA in the maternal sample is determined as a parameter of the total number of unique sequence tags mapped to the target nucleic acid sequence on a reference genome for each of the two alleles of the predetermined polymorphic site. In one embodiment, the fraction of fetal nucleic acids in the mixture of fetal and maternal nucleic acids is calculated for each of the informative allele (allele$_x$) as follows:

% fetal fraction allele$_x$=(($\Sigma$Fetal sequence tags for allele$_x$)/($\Sigma$Maternal sequence tags for allele$_x$))×100, and fetal fraction for the sample is calculated as the average of the fetal fraction of all of the informative alleles. Optionally, the fraction of fetal nucleic acids in the mixture of fetal and maternal nucleic acids is calculated for each of the informative allele (allele$_x$) as follows:

% fetal fraction allele$_x$=((2×$\Sigma$Fetal sequence tags for allele$_x$)/(Maternal sequence tags for allele$_x$))×100, to compensate for the presence of 2 fetal alleles, one being masked by the maternal background.

The percent fetal fraction is calculated for at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40 or more informative alleles. In one embodiment, the fetal fraction is the average fetal fraction determined for at least 3 informative alleles.

In one embodiment, the step of enriching the mixture of fetal and maternal nucleic acids for polymorphic target nucleic acids comprises amplifying the target nucleic acids in a portion of a test sample e.g. a plasma test sample, and combining all or a portion of the amplified product with the remaining plasma test sample. The embodiment of the method 200 is depicted in flowchart provided in FIG. 2. In step 210, a test sample e.g. a biological fluid sample such as a blood sample, is obtained from a pregnant woman, and in step 220 a portion of the cfDNA contained in the plasma fraction of the blood sample is used for amplifying target nucleic acids comprising polymorphic sites e.g. SNPs. In one embodiment, at least about 1%, at least about 1.5%, at least about 2% at least about 10% of the maternal plasma was used to amplify the target nucleic acids. In step 230, a portion or all of the amplified target nucleic acids is combined with the mixture of fetal and maternal cfDNA present in the maternal sample, and the combined cfDNA and amplified nucleic acids are purified in step 240, and used for preparing a library that was sequenced in step 250. The library was prepared from purified cfDNA and comprising at least about 10%, at least about 15%, at least about 20%, at least about 25%, at least about 30%, at least about 35%, at least about 40%, at least about 45%, or at least about 50% amplified product. In step 260, the data from the sequencing runs is analyzed and the simultaneous determination of the fetal fraction and presence or absence of aneuploidy is made.

In one embodiment, the step of enriching the mixture of fetal and maternal nucleic acids for polymorphic target nucleic acids comprises a plurality of polymorphic target nucleic acids in a portion of a mixture of fetal and maternal nucleic acids purified from a maternal test sample. In one embodiment, a portion of a mixture of fetal and maternal nucleic acids e.g. cfDNA, purified from a maternal plasma sample is used for amplifying polymorphic nucleic acid sequences, and a portion of the amplified product is combined with the unamplified mixture of purified fetal and maternal nucleic acids e.g. cfDNA (see FIG. 3). The embodiment of the method 300 is depicted in flowchart provided in FIG. 3. In step 310, a test sample e.g. a biological fluid sample such as a blood sample, comprising a mixture of fetal and maternal nucleic acids is obtained from a pregnant woman, and the mixture of fetal and maternal nucleic acids is purified from the plasma fraction in step 320. As described above, methods for the separation of cell-free DNA from plasma are well-known. In step 330, a portion of the cfDNA contained in the purified sample is used for amplifying target nucleic acids comprising polymorphic sites e.g. SNPs. At least about 5%, at least about 10%, at least about 15%, at least about 20%, at least about 25%, at least about 30%, at least about 35%, at least about 40%, at least about 45%, or at least about 50% of purified cfDNA is used for amplifying the target nucleic acids. Preferably, amplification of the target sequences can be performed by any method that uses PCR or variations of the method including but not limited to asymmetric PCR, helicase-dependent amplification, hot-start PCR, qPCR, solid phase PCR, and touchdown PCR. In step 340, a portion e.g. at least about 0.01% of the amplified product is combined with the unamplified purified cfDNA sample, and the mixture of amplified and unamplified fetal and maternal nucleic acids is sequenced in step 350. In one embodiment, sequencing is performed using any one of the NGS technologies. In step 360, the data from the sequencing runs is analyzed and the simultaneous determination of the fetal fraction and presence or absence of aneuploidy is made as described in step 140 of the embodiment depicted in FIG. 1.

Figure 4:
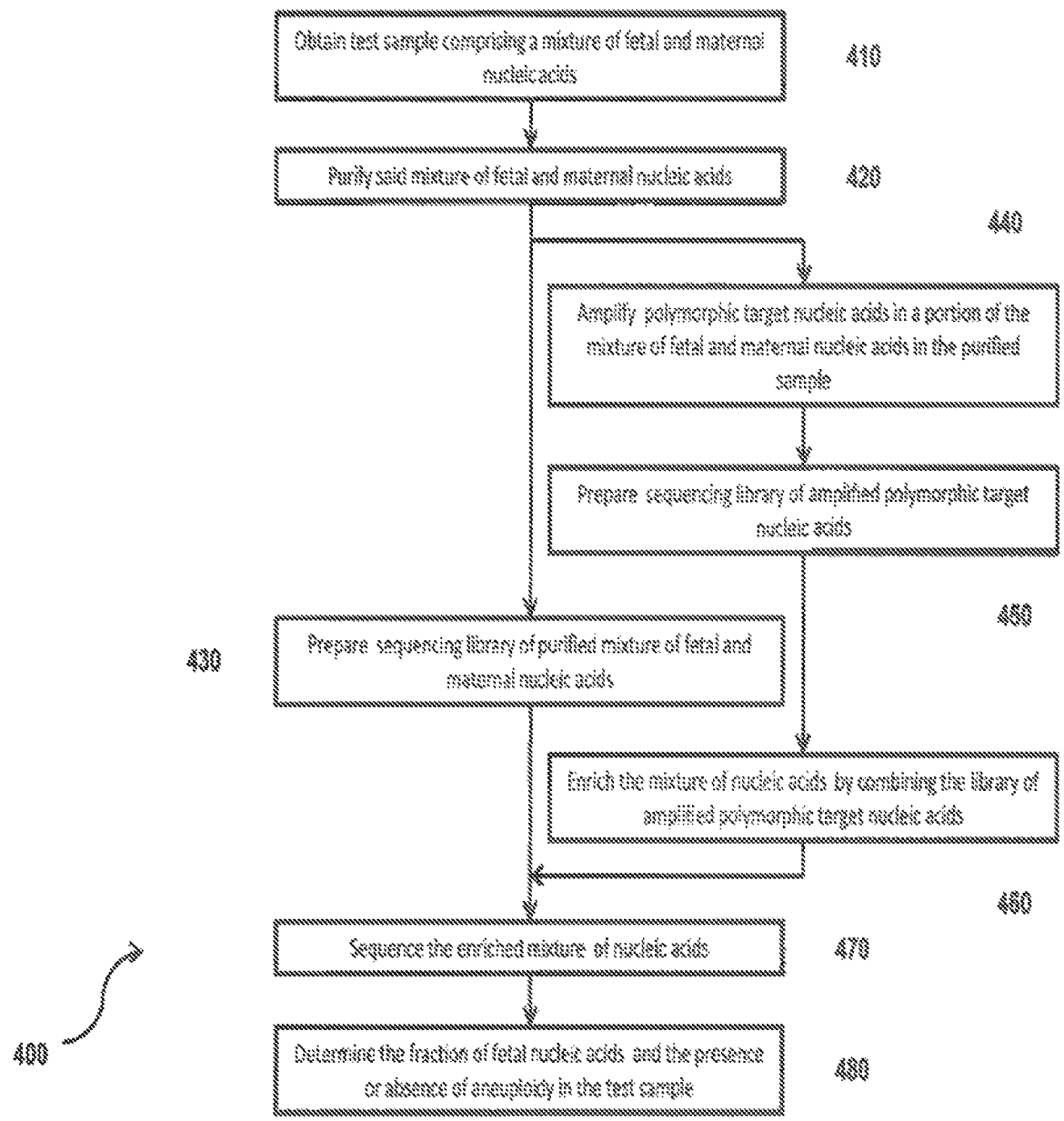
FIG. 4 is a flowchart of a method 400 for simultaneously determining the presence or absence of fetal aneuploidy and the fetal fraction in a sequencing library constructed from fetal and maternal nucleic acids derived from a maternal test sample and enriched with polymorphic nucleic acids.

In another embodiment, the step 120 of enriching the mixture of fetal and maternal nucleic acids for polymorphic target nucleic acids comprises combining at least a portion of a first sequencing library of unamplified fetal and maternal nucleic acid molecules with at least a portion of a second sequencing library of amplified polymorphic target nucleic acids. Thus, the sample that is enriched is the library sample that is prepared for sequencing (FIG. 4). Enrichment of the library sample for the target nucleic acids is accomplished by methods that comprise specifically amplifying the nucleic acid sequences that comprise the polymorphic site. In step 410, a test sample e.g. a biological fluid sample such as a blood sample, comprising a mixture of fetal and maternal nucleic acids is obtained from a pregnant woman, and the mixture of fetal and maternal nucleic acids is purified from the plasma fraction in step 420. In step 430, a portion of the cfDNA contained in the purified sample is used for amplifying target nucleic acids comprising polymorphic sites e.g. SNPs. At least about 5%, at least about 10%, at least about 15%, at least about 20%, at least about 25%, or at least about 30% of the purified cfDNA is used for amplifying target nucleic acid sequences. Preferably, amplification of the target sequences can be performed by any method that uses PCR or variations of the method including but not limited to asymmetric PCR, helicase-dependent amplification, hot-start PCR, qPCR, solid phase PCR, and touchdown PCR. In step 440, the amplified target nucleic acids comprising the polymorphic sites e.g. SNPs, are used to prepare a target nucleic acid sequencing library. Similarly, the portion of purified unamplified cfDNA is used to prepare a primary sequencing library in step 450. In step 460, a portion of the target library is combined with the primary library generated from the unamplified mixture of nucleic acids, and the mixture of fetal and maternal nucleic acids comprised in the two libraries is sequenced in step 470. The enriched library comprises at least about 5%, at least about 10%, at least about 15%, at least about 20%, or at least about 25% of the target library. In step 480, the data from the sequencing runs is analyzed and the simultaneous determination of the fetal fraction and presence or absence of aneuploidy is made as described in step 140 of the embodiment depicted in FIG. 1.

Determination of Aneuploidies for Prenatal Diagnoses

Cell-free fetal DNA and RNA circulating in maternal blood can be used for the early non-invasive prenatal diagnosis (NIPD) of an increasing number of genetic conditions, both for pregnancy management and to aid reproductive decision-making. The presence of cell-free DNA circulating in the bloodstream has been known for over 50 years. More recently, presence of small amounts of circulating fetal DNA was discovered in the maternal bloodstream during pregnancy (Lo et al., Lancet 350:485-487 [1997]). Thought to originate from dying placental cells, cell-free fetal DNA (cfDNA) has been shown to consists of short fragments typically fewer than 200 bp in length (Chan et al., Clin Chem 50:88-92 [2004]), which can be discerned as early as 4 weeks gestation (Illanes et al., Early Human Dev 83:563-566 [2007]), and known to be cleared from the maternal circulation within hours of delivery (Lo et al., Am J Hum Genet 64:218-224 [1999]). In addition to cfDNA, fragments of cell-free fetal RNA (cfRNA) can also be discerned in the maternal bloodstream, originating from genes that are transcribed in the fetus or placenta. The extraction and subsequent analysis of these fetal genetic elements from a maternal blood sample offers novel opportunities for NIPD.

The present method is a polymorphism-independent method that for use in NIPD and that does not require that the fetal cfDNA be distinguished from the maternal cfDNA to enable the determination of a fetal aneuploidy. In some embodiments, the aneuploidy is a complete chromosomal trisomy or monosomy, or a partial trisomy or monosomy. Partial aneuploidies are caused by loss or gain of part of a chromosome, and encompass chromosomal imbalances resulting from unbalanced translocations, unbalanced inversions, deletions and insertions. By far, the most common known aneuploidy compatible with life is trisomy 21 i.e. Down Syndrome (DS), which is caused by the presence of part or all of chromosome 21. Rarely, DS can be cause by an inherited or sporadic defect whereby an extra copy of all or part of chromosome 21 becomes attached to another chromosome (usually chromosome 14) to form a single aberrant chromosome. DS is associated with intellectual impairment, severe learning difficulties and excess mortality caused by long-term health problems such as heart disease. Other aneuploidies with known clinical significance include Edward syndrome (trisomy 18) and Patau Syndrome (trisomy 13), which are frequently fatal within the first few months of life. Abnormalities associated with the number of sex chromosomes are also known and include monosomy X e.g. Turner syndrome (XO), and triple X syndrome (XXX) in female births and Kleinefelter syndrome (XXY) and XYY syndrome in male births, which are all associated with various phenotypes including sterility and reduction in intellectual skills. The method of the invention can be used to diagnose these and other chromosomal abnormalities prenatally.

According to embodiments of the present invention the trisomy determined by the present invention is selected from trisomy 21 (T21; Down Syndrome), trisomy 18 (T18; Edward's Syndrome), trisomy 16 (T16), trisomy 22 (T22; Cat Eye Syndrome), trisomy 15 (T15; Prader Willi Syndrome), trisomy 13 (T13; Patau Syndrome), trisomy 8 (T8; Warkany Syndrome) and the XXY (Kleinefelter Syndrome), XYY, or XXX trisomies. It will be appreciated that various other trisomies and partial trisomies can be determined in fetal cfDNA according to the teachings of the present invention. These include, but not limited to, partial trisomy 1q32-44, trisomy 9 p, trisomy 4 mosaicism, trisomy 17p, partial trisomy 4q26-qter, trisomy 9, partial 2p trisomy, partial trisomy 1q, and/or partial trisomy 6p/monosomy 6q.

The method of the present invention can be also used to determine chromosomal monosomy X, and partial monosomies such as, monosomy 13, monosomy 15, monosomy 16, monosomy 21, and monosomy 22, which are known to be involved in pregnancy miscarriage. Partial monosomy of chromosomes typically involved in complete aneuploidy can also be determined by the method of the invention. Monosomy 18p is a rare chromosomal disorder in which all or part of the short arm (p) of chromosome 18 is deleted (monosomic). The disorder is typically characterized by short stature, variable degrees of mental retardation, speech delays, malformations of the skull and facial (craniofacial) region, and/or additional physical abnormalities. Associated craniofacial defects may vary greatly in range and severity from case to case. Conditions caused by changes in the structure or number of copies of chromosome 15 include Angelman Syndrome and Prader-Willi Syndrome, which involve a loss of gene activity in the same part of chromosome 15, the 15q11-q13 region. It will be appreciated that several translocations and microdeletions can be asymptomatic in the carrier parent, yet can cause a major genetic disease in the offspring. For example, a healthy mother who carries the 15q11-q13 microdeletion can give birth to a child with Angelman syndrome, a severe neurodegenerative disorder. Thus, the present invention can be used to identify such a deletion in the fetus. Partial monosomy 13q is a rare chromosomal disorder that results when a piece of the long arm (q) of chromosome 13 is missing (monosomic). Infants born with partial monosomy 13q may exhibit low birth weight, malformations of the head and face (craniofacial region), skeletal abnormalities (especially of the hands and feet), and other physical abnormalities. Mental retardation is characteristic of this condition. The mortality rate during infancy is high among individuals born with this disorder. Almost all cases of partial monosomy 13q occur randomly for no apparent reason (sporadic). 22q11.2 deletion syndrome, also known as DiGeorge syndrome, is a syndrome caused by the deletion of a small piece of chromosome 22. The deletion (22 q11.2) occurs near the middle of the chromosome on the long arm of one of the pair of chromosome. The features of this syndrome vary widely, even among members of the same family, and affect many parts of the body. Characteristic signs and symptoms may include birth defects such as congenital heart disease, defects in the palate, most commonly related to neuromuscular problems with closure (velo-pharyngeal insufficiency), learning disabilities, mild differences in facial features, and recurrent infections. Microdeletions in chromosomal region 22q11.2 are associated with a 20 to 30-fold increased risk of schizophrenia. In one embodiment, the method of the invention is used to determine partial monosomies including but not limited to monosomy 18p, partial monosomy of chromosome 15 (15q11-q13), partial monosomy 13q, and partial monosomy of chromosome 22 can also be determined using the method.

The method of the invention can be also used to determine any aneuploidy if one of the parents is a known carrier of such abnormality. These include, but not limited to, mosaic for a small supernumerary marker chromosome (SMC); t(11; 14)(p15; p13) translocation; unbalanced translocation t(8; 11)(p23.2; p15.5); 11q23 microdeletion; Smith-Magenis syndrome 17p11.2 deletion; 22q13.3 deletion; Xp22.3 microdeletion; 10p14 deletion; 20p microdeletion, DiGeorge syndrome [del(22)(q11.2q11.23)], Williams syndrome (7q11.23 and 7q36 deletions); 1p36 deletion; 2p microdeletion; neurofibromatosis type 1 (17q11.2 microdeletion), Yq deletion; Wolf-Hirschhorn syndrome (WHS, 4p16.3 microdeletion); 1p36.2 microdeletion; 11q14 deletion; 19q13.2 microdeletion; Rubinstein-Taybi (16 p13.3 microdeletion); 7p21 microdeletion; Miller-Dieker syndrome (17p13.3), 17p11.2 deletion; and 2q37 microdeletion.

Compositions and Kits

Compositions comprising primers for amplifying polymorphic sites are provided to enable the quantification of fetal fraction and aneuploidy by sequencing mixtures of fetal and maternal nucleic acids e.g. cfDNA, present in a sample. Preferably, the sample is a maternal blood plasma sample. In one embodiment, the composition includes primers for amplifying polymorphic target nucleic acids that each comprise at least one SNP. The at least one SNP is selected from SNPs rs560681, rs1109037, rs9866013, rs13182883, rs13218440, rs7041158, rs740598, rs10773760, rs4530059, rs7205345, rs8078417, rs576261, rs2567608, rs430046, rs9951171, rs338882, rs10776839, rs9905977, rs1277284, rs258684, rs1347696, rs508485, rs9788670, rs8137254, rs3143, rs2182957, rs3739005, and rs530022. The corresponding sets of primers for amplifying the SNPs are PROVIDED IN Example 3 and disclosed as SEQ ID NOs; 57-112.

In another embodiment, the composition includes primers for amplifying polymorphic target nucleic acids that each comprise at least one tandem SNP. In one embodiment, the composition includes primers for amplifying the exemplary tandem SNPs disclosed herein, and the composition comprises the corresponding exemplary primers of SEQ ID NOS:57-112.

In another embodiment, the composition includes primers for amplifying polymorphic target nucleic acids that each comprise at least one STR. Exemplary STRs include CSF1PO, FGA, TH01, TPOX, vWA, D3S1358, D5S818, D7S820, D8S1179, D135317, D16S539, D18S51, D21S11, D2S1338, Penta D, Penta E, D22S1045, D20S1082, D20S482, D18S853, D17S1301, D17S974, D1451434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627 and D1GATA113, which can be amplified by the corresponding sets of primers provided in Example 5 (Tables 5 and 6) and disclosed as SEQ ID NOs; 113-196.

The compositions of the invention can be included in kits for massively parallel sequencing mixtures of fetal and maternal nucleic acid molecules e.g. cfDNA, present in a maternal sample e.g. a plasma sample. The kits comprise a composition comprising at least one set of primers for amplifying at least one polymorphic target nucleic acid in said fetal and maternal nucleic acid molecules. Polymorphic nucleic acids can comprise a SNP or an STR. Sequencing methods are NGS methods of single nucleic acid molecules or clonally amplified nucleic acid molecules. The NGS methods are massively parallel sequencing methods including pyrosequencing, sequencing by synthesis with reversible dye terminators, real-time sequencing, or sequencing by oligonucleotide probe ligation.

The present invention is described in further detail in the following Examples which are not in any way intended to limit the scope of the invention as claimed. The attached Figures are meant to be considered as integral parts of the specification and description of the invention. The following examples are offered to illustrate, but not to limit the claimed invention.

EXPERIMENTAL

Example 1

Sample Processing and cfDNA Extraction

Peripheral blood samples were collected from pregnant women in their first or second trimester of pregnancy and who were deemed at risk for fetal aneuploidy. Informed consent was obtained from each participant prior to the blood draw. Blood was collected before amniocentesis or chorionic villus sampling. Karyotype analysis was performed using the chorionic villus or amniocentesis samples to confirm fetal karyotype.

Peripheral blood drawn from each subject was collected in ACD tubes. One tube of blood sample (approximately 6-9 mL/tube) was transferred into one 15-mL low speed centrifuge tube. Blood was centrifuged at 2640 rpm, 4° C. for 10 min using Beckman Allegra 6 R centrifuge and rotor model GA 3.8.

For cell-free plasma extraction, the upper plasma layer was transferred to a 15-ml high speed centrifuge tube and centrifuged at 16000×g, 4° C. for 10 min using Beckman Coulter Avanti J-E centrifuge, and JA-14 rotor. The two centrifugation steps were performed within 72 h after blood collection. Cell-free plasma comprising cfDNA was stored at −80° C. and thawed only once before amplification of plasma cfDNA or for purification of cfDNA.

Purified cell-free DNA (cfDNA) was extracted from cell-free plasma using the QIAamp Blood DNA Mini kit (Qiagen) essentially according to the manufacturer's instruction. One milliliter of buffer AL and 100 µl of Protease solution were added to 1 ml of plasma. The mixture was incubated for 15 minutes at 56° C. One milliliter of 100% ethanol was added to the plasma digest. The resulting mixture was transferred to QIAamp mini columns that were assembled with VacValves and VacConnectors provided in the QIAvac 24 Plus column assembly (Qiagen). Vacuum was applied to the samples, and the cfDNA retained on the column filters was washed under vacuum with 750 µl of buffer AW1, followed by a second wash with 750 µl of buffer AW24. The column was centrifuged at 14,000 RPM for 5 minutes to remove any residual buffer from the filter. The cfDNA was eluted with buffer AE by centrifugation at 14,000 RPM, and the concentration determined using Qubit™ Quantitation Platform (Invitrogen).

Example 2

Preparation and Sequencing of Primary and Enriched Sequencing Libraries a. Preparation of Sequencing Libraries All sequencing libraries i.e. primary and enriched libraries, were prepared from approximately 2 ng of purified cfDNA that was extracted from maternal plasma. Library preparation was performed using reagents of the NEBNext™ DNA Sample Prep DNA Reagent Set 1 (Part No. E6000L; New England Biolabs, Ipswich, MA), for Illumina® as follows. Because cell-free plasma DNA is fragmented in nature, no further fragmentation by nebulization or sonication was done on the plasma DNA samples. The overhangs of approximately 2 ng purified cfDNA fragments contained in 40 µl were converted into phosphorylated blunt ends according to the NEBNext® End Repair Module by incubating in a 1.5 ml microfuge tube the cfDNA with 5 µl 10× phosphorylation buffer, 2 µl deoxynucleotide solution mix (10 mM each dNTP), 1 µl of a 1:5 dilution of DNA Polymerase I, 1 µl T4 DNA Polymerase and 1 µl T4 Polynucleotide Kinase provided in the NEBNext™ DNA Sample Prep DNA Reagent Set 1 for 15 minutes at 20° C. The enzymes were then heat inactivated by incubating the reaction mixture at 75° C. for 5 minutes. The mixture was cooled to 4° C., and dA tailing of the blunt-ended DNA was accomplished using 10 µl of the dA-tailing master mix containing the Klenow fragment (3' to 5' exo minus) (NEBNext™ DNA Sample Prep DNA Reagent Set 1), and incubating for 15 minutes at 37° C. Subsequently, the Klenow fragment was heat inactivated by incubating the reaction mixture at 75° C. for 5 minutes. Following the inactivation of the Klenow fragment, 1 µl of a 1:5 dilution of Illumina Genomic Adaptor Oligo Mix (Part No. 1000521; Illumina Inc., Hayward, CA) was used to ligate the Illumina adaptors (Non-Index Y-Adaptors) to the dA-tailed DNA using 4 µl of the T4 DNA ligase provided in the NEBNext™ DNA Sample Prep DNA Reagent Set 1, by incubating the reaction mixture for 15 minutes at 25° C. The mixture was cooled to 4° C., and the adaptor-ligated cfDNA was purified from unligated adaptors, adaptor dimers, and other reagents using magnetic beads provided in the Agencourt AMPure XP PCR purification system (Part No. A63881; Beckman Coulter Genomics, Danvers, MA). Eighteen cycles of PCR were performed to selectively enrich adaptor-ligated cfDNA (25 µl) using Phusion® High-Fidelity Master Mix (25 µl; Finnzymes, Woburn, MA) and Illumina's PCR primers (0.5 µM each) complementary to the adaptors (Part No. 1000537 and 1000537). The adaptor-ligated DNA was subjected to PCR (98° C. for 30 seconds; 18 cycles of 98° C. for 10 seconds, 65° C. for 30 seconds, and 72° C. for 30; final extension at 72° C. for 5 minutes, and hold at 4° C.) using Illumina Genomic PCR Primers (Part Nos. 100537 and 1000538) and the Phusion HF PCR Master Mix provided in the NEBNext™ DNA Sample Prep DNA Reagent Set 1, according to the manufacturer's instructions. The amplified product was purified using the Agencourt AMPure XP PCR purification system (Agencourt Bioscience Corporation, Beverly, MA) according to the manufacturer's instructions available at www.beckmangenomics.com/products/AMPureXPProtocol_000387v001.pdf. The purified amplified product was eluted in 40 µl of Qiagen EB Buffer, and the concentration and size distribution of the amplified libraries was analyzed using the Agilent DNA 1000 Kit for the 2100 Bioanalyzer (Agilent technologies Inc., Santa Clara, CA).

b. Sequencing

Sequencing of library DNA was performed using the Genome Analyzer II (Illumina Inc., San Diego, CA, USA) according to standard manufacturer protocols. Copies of the protocol for whole genome sequencing using Illumina/Solexa technology may be found at BioTechniques® Protocol Guide 2007 Published December 2006: p 29, and on the world wide web at biotechniques.com/default.asp?page=protocol&subsection=article_display&id=112378.

The DNA library was diluted to 1 nM and denatured. Library DNA (5 pM) was subjected to cluster amplification according to the procedure described in Illumina's Cluster Station User Guide and Cluster Station Operations Guide, available on the world wide web at illumina.com/systems/genome_analyzer/cluster_station.ilmn. The amplified DNA was sequenced using Illumina's Genome Analyzer II to obtain single-end reads of 36 bp. Only about 30 bp of random sequence information are needed to identify a sequence as belonging to a specific human chromosome. Longer sequences can uniquely identify more particular targets. In the present case, a large number of 36 bp reads were obtained, covering approximately 10% of the genome.

Example 3

Analysis of Sequencing Data for the Determination of Aneuploidy and Fetal Fraction a. Analysis of Sequencing Data for the Determination of Aneuploidy Upon completion of sequencing of the sample, the Illumina "Sequencer Control Software" transferred image and base call files to a Unix server running the Illumina "Genome Analyzer Pipeline" software version 1.51. The Illumina "Gerald" program was run to align sequences i.e. 36 bp reads, to the hg18 reference human genome provided by National Center for Biotechnology Information (NCBI36/hg18, available on the world wide web at genome.ucsc.edu/cgi-bin/hgGateway?org=Human&db=hg18&hgsid=166260105). The sequence data generated from the above procedure that uniquely aligned to the genome was read from Gerald output (export.txt files) by a program (c2c.pl) running on a computer running the Linux operating system. Sequence alignments with base mis-matches were allowed and included in alignment counts only if they aligned uniquely to the genome. Sequence alignments with identical start and end coordinates (duplicates) were excluded.

Between about 15 and 25 million 36 bp tags with 2 or less mismatches were mapped uniquely to the human genome for each sample. All mapped tags were counted and included in the calculation of chromosome doses in both test and qualifying samples. Regions extending from base 0 to base $2 \times 10^6$, base $10 \times 10^6$ to base $13 \times 10^6$, and base $23 \times 10^6$ to the end of chromosome Y, were specifically excluded from the analysis because tags derived from either male or female fetuses map to these regions of the Y-chromosome.

b. Analysis of Sequencing Data for the Determination of Fetal Fraction

Concomitant to the analysis for determining aneuploidy, the sequencing data was analyzed to determine the fetal fraction. Following the transfer of the image and base call files to the Unix server running the Illumina "Genome Analyzer Pipeline" software version 1.51 as described in a., the 36 bp reads were aligned to a 'SNP genome' using the BOWTIE program. The SNP genome was identified as the grouping of the 30 DNA sequences i.e. SEQ ID NOS: 1-30, that encompass the alleles of the 15 SNP disclosed in Table 5 in Example 5. Only reads that mapped uniquely to the SNP genome were used for the analysis of fetal fraction. Reads that matched perfectly to the SNP genome were counted as tags and filtered. Of the remaining reads, only reads having one or two mismatches were counted as tags and included in the analysis. Tags mapped to each of the SNP alleles were counted, and the fetal fraction was determined as described in Example 6.

Example 4

Identification of Normalizing Chromosomes for Determining Aneuploidy

To identify normalizing chromosomes to be used in determining chromosome doses and subsequent presence or absence of aneuploidy, plasma cfDNA was obtained from peripheral blood of 48 volunteer pregnant as described in Example 1, and sequenced as described in Example 2. The sequencing data provided in this example was obtained from sequencing a library constructed from fetal and maternal cfDNA that had been enriched for target nucleic acids comprised in a second sequencing library that had been constructed from amplified sequences containing SNPs as described below.

The total number of sequence tags that were mapped to each chromosome in the reference genome (sequence tag density) was determined. Alternatively, the number of mapped sequence tags may be normalized to the length of the chromosome to generate a sequence tag density ratio. The normalization to chromosome length is not a required step, and can be performed solely to reduce the number of digits in a number to simplify it for human interpretation. Chromosome lengths that can be used to normalize the sequence tags counts can be the lengths provided on the world wide web at genome.ucsc.edu/goldenPath/stats.html#hg18.

Table 1 provides the computed ratio for chromosomes X, and Y, and autosomes 1-22 in an exemplary cfDNA sample (11351; 46,XY).

TABLE 1

Sequence Tag Density for Chromosomes 1-22, X and Y (n = 1; sample 11351, 46 XY)

| Chromosome Name | Sequence Tag Density |
| --- | --- |
| chr1 | 1,857,858 |
| chr2 | 1,910,676 |
| chr3 | 1,562,572 |
| chr4 | 1,376,498 |
| chr5 | 1,383,453 |
| chr6 | 1,317,821 |
| chr7 | 1,192,136 |
| chr8 | 1,162,856 |
| chr9 | 914,624 |
| chr10 | 1,112,763 |
| chr11 | 1,093,028 |
| chr12 | 1,051,209 |
| chr13 | 717,684 |
| chr14 | 710,878 |
| chr15 | 675,596 |
| chr16 | 683,529 |
| chr17 | 647,571 |
| chr18 | 615,140 |
| chr19 | 432,191 |
| chr20 | 557,068 |
| chr21 | 284,701 |
| chr22 | 305,365 |
| chrX | 1,060,456 |
| chrY | 5380 |

Figure 12:
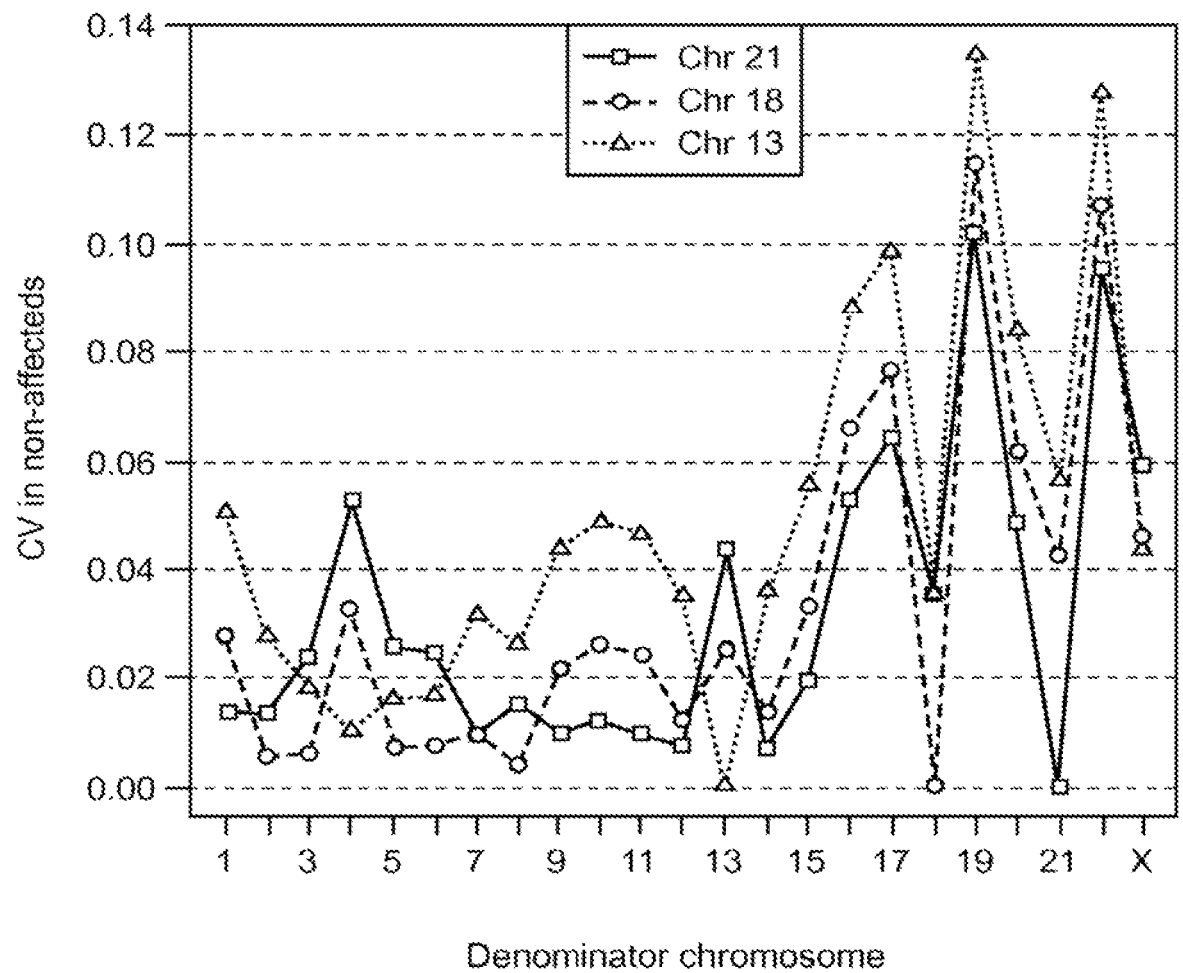
FIG. 12 shows the coefficient of variation (CV) for chromosomes 21 (□), 18 (O) and 13 (Δ) that was determined from the chromosome doses of qualified i.e. non-affected, samples shown in FIGS. 7, 8, and 9, respectively.
Figure 13:
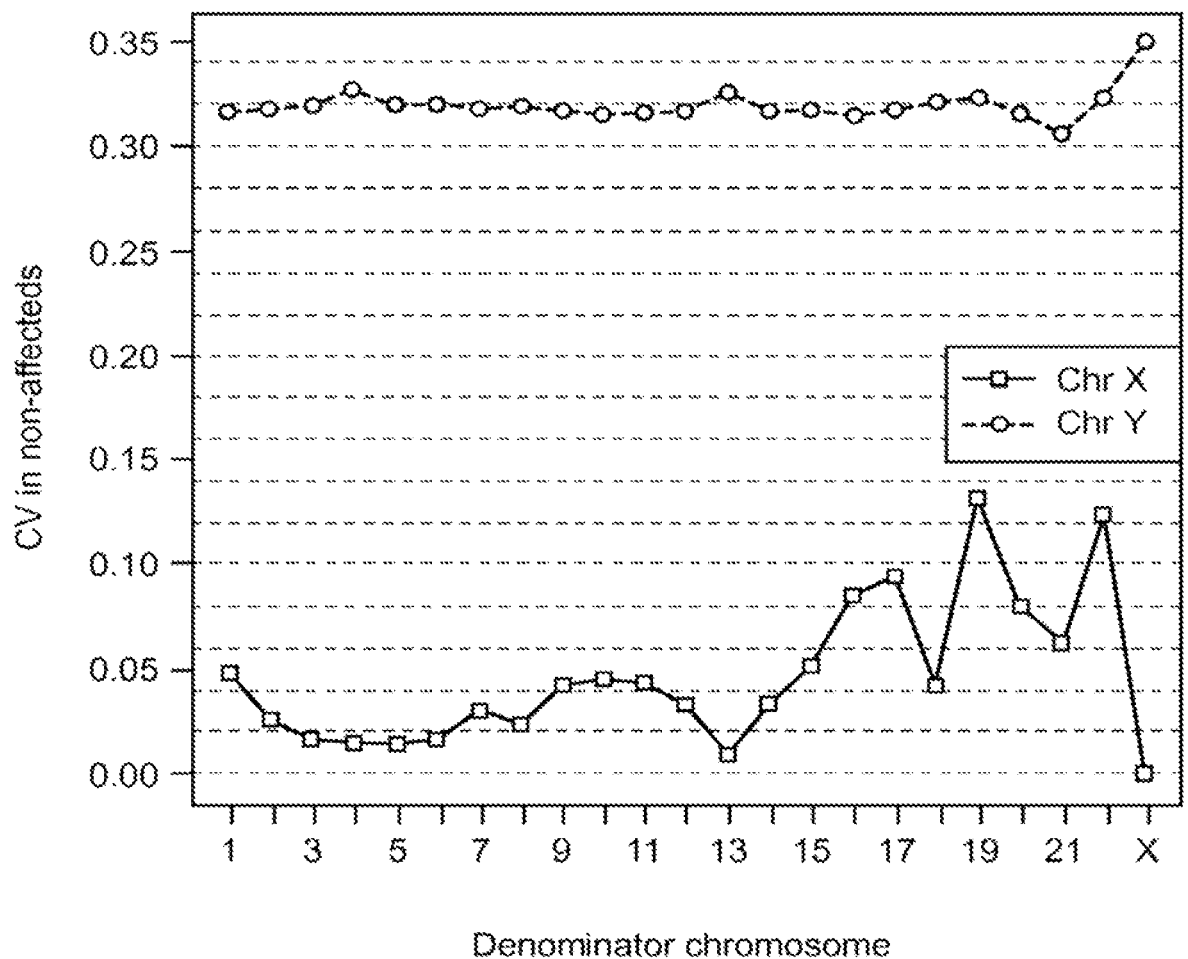
FIG. 13 shows the coefficient of variation (CV) for chromosomes X (□) and Y (O) that was determined from the chromosome doses of qualified i.e. non-affected, samples shown in FIGS. 10 and 11, respectively.

The resulting sequence tag density for each chromosome was related to the sequence tag density of each of the remaining chromosomes to derive a qualified chromosome dose, which was calculated as the ratio of the sequence tag density for the chromosome of interest e.g. chromosome 21, and the sequence tag density of each of the remaining chromosomes i.e. chromosomes 1-20, 22 and X. Chromosomes doses were determined for all chromosomes in all samples, and the average doses for chromosomes of interest 13, 18, 21, X and Y in the qualified samples are provided in Table 2, and depicted in FIGS. 7A-11B. FIGS. 7A-11B also depict the chromosome doses for the test samples. The chromosome doses for each of the chromosomes of interest in the qualified samples provides a measure of the variation in the total number of mapped sequence tags for each chromosome of interest relative to that of each of the remaining chromosomes. Thus, qualified chromosome doses can identify the chromosome or a group of chromosomes i.e. normalizing chromosome, that has a variation among samples that is closest to the variation of the chromosome of interest, and that would serve as ideal sequences for normalizing values for further statistical evaluation. FIGS. 12 and 13 depict the calculated average chromosome doses determined in a population of qualified samples for chromosomes 13, 18, and 21, and chromosomes X and Y.

In some instances, the best normalizing chromosome, may not have the least variation, but may have a distribution of qualified doses that best distinguishes a test sample or samples from the qualified samples i.e. the best normalizing chromosome may not have the lowest variation, but may have the greatest differentiability. Thus, differentiability accounts for the variation in chromosome dose and the distribution of the doses in the qualified samples.

Tables 3 and 4 provide the coefficient of variation as the measure of variability, and student t-test values as a measure of differentiability for chromosomes 18, 21, X and Y, wherein the smallest the T-test value, the greatest the differentiability. The differentiability for chromosome 13 was determined as the ratio of difference between the mean chromosome dose in the qualified samples and the dose for chromosome 13 in the only T13 test sample, and the standard deviation of mean of the qualified dose.

The qualified chromosome doses also serve as the basis for determining threshold values when identifying aneuploidies in test samples as described in the following.

TABLE 2

Qualified Chromosome Dose for Chromosomes 13, 18, 21, X and Y (n = 1; sample 11351, 46 XY)

| Chromosome | chr 21 | chr 18 | chr 13 | chr X | chr Y |
|---|---|---|---|---|---|
| chr1 | 0.153242 | 0.331102 | 0.386296 | 0.570795 | 0.002896 |
| chr2 | 0.149005 | 0.321949 | 0.375618 | 0.555016 | 0.002816 |
| chr3 | 0.1822 | 0.393671 | 0.459297 | 0.678661 | 0.003443 |
| chr4 | 0.20683 | 0.446888 | 0.521384 | 0.770401 | 0.003908 |
| chr5 | 0.20579 | 0.444641 | 0.518763 | 0.766528 | 0.003889 |
| chr6 | 0.216039 | 0.466786 | 0.544599 | 0.804704 | 0.004082 |
| chr7 | 0.238816 | 0.515998 | 0.602015 | 0.889543 | 0.004513 |
| chr8 | 0.244829 | 0.528991 | 0.617174 | 0.911941 | 0.004627 |
| chr9 | 0.311277 | 0.672561 | 0.784677 | 1.159445 | 0.005882 |
| chr10 | 0.255851 | 0.552804 | 0.644957 | 0.952994 | 0.004835 |
| chr11 | 0.26047 | 0.562785 | 0.656602 | 0.9702 | 0.004922 |
| chr12 | 0.270832 | 0.585174 | 0.682722 | 1.008797 | 0.005118 |
| chr13 | 0.396694 | 0.857118 | 1 | 1.477609 | 0.007496 |
| chr14 | 0.400492 | 0.865324 | 1.009574 | 1.491755 | 0.007568 |
| chr15 | 0.421407 | 0.910515 | 1.062298 | 1.56966 | 0.007963 |
| chr16 | 0.416516 | 0.899947 | 1.049969 | 1.551443 | 0.007871 |
| chr17 | 0.439644 | 0.949919 | 1.108271 | 1.63759 | 0.008308 |
| chr18 | 0.462823 | 1 | 1.1667 | 1.723926 | 0.008746 |
| chr19 | 0.658739 | 1.423306 | 1.660571 | 2.453674 | 0.012448 |
| chr20 | 0.51107 | 1.104246 | 1.288324 | 1.903638 | 0.009658 |
| chr21 | 1 | 2.160653 | 2.520834 | 3.724806 | 0.018897 |
| chr22 | 0.93233 | 2.014442 | 2.35025 | 3.472749 | 0.017618 |
| chrX | 0.26847 | 0.580071 | 0.676769 | 1 | 0.005073 |
| chrY | 52.9184 | 114.3383 | 133.3985 | 197.1108 | 1 |

TABLE 3

Qualified Chromosome Dose, Variance and Differentiability for chromosomes 21 and 18

| | 21 (n = 35) | | | | 18 (n = 40) | | | |
|---|---|---|---|---|---|---|---|---|
| | Avg | Stdev | CV | T Test | Avg | Stdev | CV | T Test |
| chr1 | 0.15332 | 0.002129 | 1.39 | 1.06E-10 | 0.32451 | 0.008954 | 2.76 | 2.74E-03 |
| chr2 | 0.15106 | 0.002053 | 1.36 | 8.52E-08 | 0.31984 | 0.001783 | 0.56 | 5.32E-05 |
| chr3 | 0.18654 | 0.004402 | 2.36 | 8.07E-07 | 0.39511 | 0.002364 | 0.60 | 1.93E-05 |
| chr4 | 0.21578 | 0.011174 | 5.18 | 1.47E-04 | 0.45714 | 0.014794 | 3.24 | 1.37E-03 |
| chr5 | 0.21068 | 0.005332 | 2.53 | 1.08E-06 | 0.44626 | 0.003250 | 0.73 | 3.18E-05 |
| chr6 | 0.22112 | 0.005453 | 2.47 | 1.74E-06 | 0.46818 | 0.003434 | 0.73 | 2.24E-05 |
| chr7 | 0.24233 | 0.002314 | 0.96 | 2.39E-08 | 0.51341 | 0.005289 | 1.03 | 1.24E-04 |
| chr8 | 0.24975 | 0.003772 | 1.51 | 1.06E-07 | 0.52898 | 0.002161 | 0.41 | 6.32E-05 |
| chr9 | 0.31217 | 0.003050 | 0.98 | 1.60E-09 | 0.66100 | 0.014413 | 2.18 | 8.17E-04 |
| chr10 | 0.25550 | 0.003164 | 1.24 | 2.42E-11 | 0.54091 | 0.013953 | 2.58 | 2.26E-03 |
| chr11 | 0.26053 | 0.002596 | 1.00 | 1.32E-10 | 0.55158 | 0.013283 | 2.41 | 1.29E-03 |
| chr12 | 0.27401 | 0.002061 | 0.75 | 1.40E-08 | 0.58032 | 0.007198 | 1.24 | 1.57E-04 |
| chr13 | 0.41039 | 0.017637 | 4.30 | 3.09E-05 | 0.86961 | 0.021614 | 2.49 | 2.36E-04 |
| chr14 | 0.40482 | 0.002908 | 0.72 | 1.10E-08 | 0.85732 | 0.011748 | 1.37 | 2.16E-04 |
| chr15 | 0.41821 | 0.008238 | 1.97 | 1.24E-10 | 0.88503 | 0.029199 | 3.30 | 5.72E-03 |
| chr16 | 0.40668 | 0.021232 | 5.22 | 2.91E-05 | 0.86145 | 0.056245 | 6.53 | 1.04E-01 |
| chr17 | 0.42591 | 0.027001 | 6.34 | 5.85E-04 | 0.90135 | 0.068151 | 7.56 | 1.24E-01 |
| chr18 | 0.46529 | 0.016239 | 3.49 | 8.02E-09 | | | | |

TABLE 3-continued

Qualified Chromosome Dose, Variance and Differentiability for chromosomes 21 and 18

| | 21 (n = 35) | | | | 18 (n = 40) | | | |
|---|---|---|---|---|---|---|---|---|
| | Avg | Stdev | CV | T Test | Avg | Stdev | CV | T Test |
| chr19 | 0.63003 | 0.063272 | 10.04 | 3.30E−02 | 1.33522 | 0.150794 | 11.29 | 3.04E−01 |
| chr20 | 0.49925 | 0.023907 | 4.79 | 1.65E−05 | 1.05648 | 0.064440 | 6.10 | 7.98E−02 |
| chr21 | | | | | 2.06768 | 0.087175 | 4.22 | 5.10E−05 |
| chr22 | 0.88726 | 0.083330 | 9.39 | 3.43E−02 | 1.87509 | 0.198316 | 10.58 | 2.43E−01 |
| chrX | 0.27398 | 0.016109 | 5.88 | 1.16E−04 | 0.58665 | 0.027280 | 4.65 | 7.50E−02 |

TABLE 4

Qualified Chromosome Dose, Variance and Differentiability for chromosomes 13, X and Y

| | 13 (n = 47) | | | | X (n = 20) | | | |
|---|---|---|---|---|---|---|---|---|
| | Avg | Stdev | CV | Diff | Avg | Stdev | CV | T Test |
| chr1 | 0.37213 | 0.018589 | 5.00 | 2.41 | 0.58035 | 0.02706 | 4.66 | 5.68E−05 |
| chr2 | 0.36707 | 0.010067 | 2.74 | 3.03 | 0.57260 | 0.01432 | 2.50 | 1.53E−09 |
| chr3 | 0.45354 | 0.008121 | 1.79 | 3.67 | 0.70741 | 0.01126 | 1.59 | 9.04E−13 |
| chr4 | 0.52543 | 0.005306 | 1.01 | 2.39 | 0.82144 | 0.01192 | 1.45 | 5.86E−16 |
| chr5 | 0.51228 | 0.008273 | 1.61 | 3.95 | 0.79921 | 0.01100 | 1.38 | 2.32E−13 |
| chr6 | 0.53756 | 0.008901 | 1.66 | 3.91 | 0.83880 | 0.01261 | 1.50 | 3.64E−13 |
| chr7 | 0.58908 | 0.018508 | 3.14 | 2.83 | 0.91927 | 0.02700 | 2.94 | 1.86E−08 |
| chr8 | 0.60695 | 0.015797 | 2.60 | 3.05 | 0.94675 | 0.02173 | 2.30 | 3.40E−10 |
| chr9 | 0.75816 | 0.033107 | 4.37 | 2.59 | 1.18180 | 0.04827 | 4.08 | 9.63E−06 |
| chr10 | 0.62018 | 0.029891 | 4.82 | 2.56 | 0.96642 | 0.04257 | 4.40 | 4.55E−05 |
| chr11 | 0.63248 | 0.029204 | 4.62 | 2.55 | 0.98643 | 0.04222 | 4.28 | 1.82E−05 |
| chr12 | 0.66574 | 0.023047 | 3.46 | 2.76 | 1.03840 | 0.03301 | 3.18 | 1.26E−07 |
| chr13 | | | | | 1.56355 | 0.01370 | 0.88 | 6.33E−17 |
| chr14 | 0.98358 | 0.035331 | 3.59 | 2.67 | 1.58114 | 0.08076 | 5.11 | 2.29E−04 |
| chr15 | 1.01432 | 0.055806 | 5.50 | 2.39 | 1.53464 | 0.12719 | 8.29 | 2.01E−02 |
| chr16 | 0.98577 | 0.085933 | 8.72 | 2.17 | 1.61094 | 0.14829 | 9.21 | 2.68E−02 |
| chr17 | 1.03217 | 0.100389 | 9.73 | 2.13 | 1.74904 | 0.07290 | 4.17 | 1.62E−04 |
| chr18 | 1.13489 | 0.040058 | 3.53 | 2.62 | 2.38397 | 0.30515 | 12.80 | 1.07E−01 |
| chr19 | 1.52678 | 0.203732 | 13.34 | 1.98 | 1.88186 | 0.14674 | 7.80 | 1.56E−02 |
| chr20 | 1.20919 | 0.100371 | 8.30 | 2.27 | 3.71853 | 0.22406 | 6.03 | 4.21E−04 |
| chr21 | 2.38087 | 0.132418 | 5.56 | 2.29 | 3.35158 | 0.40246 | 12.01 | 8.66E−02 |
| chr22 | 2.14557 | 0.271281 | 12.64 | 2.13 | 0.58035 | 0.02706 | 4.66 | 5.68E−05 |
| chrX | 0.66883 | 0.029157 | 4.36 | 1.04 | | | | |
| chr2-6 | 0.46965 | 0.006987 | 1.49 | 4.17 | | | | |
| chr3-6 | 0.50496 | 0.005373 | 1.06 | 5.16 | | | | |

| | Y (n = 25) | | | |
|---|---|---|---|---|
| | Avg | Stdev | CV | T Test |
| Chr 1-22, X | 0.00728 | 0.00227 | 31.19 | 1.30E−13 |

Examples of diagnoses of T21, T13, T18 and Turner syndrome obtained using the normalizing chromosomes, chromosome doses and differentiability for each of the chromosomes of interest are described in Example 6.

Example 5

Selection of Autosomal SNPs for the Determination of Fetal Fraction

A set of 28 autosomal SNPs were selected from a list of 92 SNPs (Pakstis et al., Hum Genet 127:315-324 [2010]), and SNP sequences available from Applied Biosystems on the world wide web at appliedbiosystems.com, and validated for use in multiplexed PCR amplification and for massively parallel sequencing. Primers were designed to hybridize to a sequence close to the SNPs site on the cfDNA to ensure that it be included in the 36 bp read generated from the massively parallel sequencing on the Illumina Analyzer GII, and to generate amplicons of sufficient length to undergo bridge-amplification during cluster formation. Thus, primers were designed to generate amplicons that were at least 110 bp, which when combined with the universal adaptors (Illumina Inc., San Diego, CA) used for cluster amplification, resulted in DNA molecules of at least 200 bp. Primer sequences were identified, and primer sets i.e. forward and reverse primers, were synthesized by Integrated DNA Technologies (San Diego, CA), and stored as a 1 µM solution to be used for amplifying polymorphic target sequences as described in Examples 5-8. Table 5 provides the RefSNP (rs) accession ID numbers, the primers used for amplifying the target cfDNA sequence, and the sequences of the amplicons comprising the possible SNP alleles that would be generated using the primers. The SNPs given in Table 5 were used for the simultaneous amplification of 13 target sequences in a multiplexed assay. The panel provided in Table 5 is an exemplary SNP panel. Fewer or more SNPs can be employed to enrich the fetal and maternal DNA for polymorphic target nucleic acids. Additional SNPs that can be used include the SNPs given in Table 6. The SNP alleles are shown in bold and are underlined. Other SNPs that can be used to determine fetal fraction according to the present method include rs315791, rs3780962, rs1410059, rs279844, rs38882, rs9951171, rs214955, rs6444724, rs2503107, rs1019029, rs1413212, rs1031825, rs891700, rs1005533, rs2831700, rs354439, rs1979255, rs1454361, rs8037429, and rs1490413, which have been analyzed for determining fetal fraction by TaqMan PCR, and are disclosed in U.S. Provisional applications 61/296,358 and 61/360,837, which are herein incorporated by reference in their entirety.

TABLE 5

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| rs560681 | 1 | CACATGCACAGCCAGCAACCCTGTCAGCAGGAGTTCCCACCAGTTTCTTTCTGAGAACATCTGTTCAGGTTTCTCTCCATCTCTATTTACTCAGGTCACAGGACCTTGGGG (SEQ ID NO: 1) | CACATGCACAGCCAGCAACCCTGTCAGCAGGAGTTCCCACCAGTTTCTTTCTGAGAACATCTGTTCAGGTTTCTCTCCATCTCTGTTTACTCAGGTCACAGGACCTTGGGG (SEQ ID NO: 2) | CACATGCACAGCCAGCAACCC (rs560681_C1_1_F; SEQ ID NO: 57) | CCCCAAGGTCCTGTGACCTGAGT (rs560681_C1_1_R; SEQ ID NO: 58) |
| rs1109037 | 2 | TGAGGAAGTGAGGCTCAGAGGGTAAGAAACTTTGTCACAGAGCTGGTGGTGAGGGTGGAGATTTTACACTCCCTGCCTCCCACACCAGTTTCTCCAGAGTGGAAAGACTTTCATCTCGCACTGGCA (SEQ ID NO: 3) | TGAGGAAGTGAGGCTCAGAGGGTAAGAAACTTTGTCACAGAGCTGGTGGTGAGGGTGGAGATTTTACACTCCCTGCCTCCCACACCAGTTTCTCCGGAGTGGAAAGACTTTCATCTCGCACTGGCA (SEQ ID NO: 4) | TGAGGAAGTGAGGCTCAGAGGGT (rs110937_C2_1_F; SEQ ID NO: 59) | TGCCAGTGCGAGATGAAAGTCTTT (rs110937_C2_1_R; SEQ ID NO: 60) |
| rs9866013 | 3 | GTGCCTTCAGAACCTTTGAGATCTGATTCTATTTTTAAAGCTTCTTAGAAGAGAGATTGCAAAGTGGGTTGTTTCTCTAGCCAGACAGGGCAGGCAAATAGGGGTGGCTGGTGGGATGGGA (SEQ ID NO: 5) | GTGCCTTCAGAACCTTTGAGATCTGATTCTATTTTTAAAGCTTCTTAGAAGAGAGATTGCAAAGTGGGTTGTTTCTCTAGCCAGACAGGGCAGGTAAATAGGGGTGGCTGGTGGGATGGGA (SEQ ID NO: 6) | GTGCCTTCAGAACCTTTGAGATCTGAT (rs9866013_C3_1_F; SEQ ID NO: 61) | TCCCATCCCACCAGCCACCC (rs9866013_C3_1_R; SEQ ID NO: 62) |
| rs13182883 | 5 | AGGTGTGTCTCTCTTTTGTGAGGGGAGGGGTCCCTTCTGGCCTAGTAGAGGGCCTGGCCTGCAGTGAGCATTCAAATCCTCAAGGAACAGGGTGGGGAGGTGGGACAAAGG (SEQ ID NO: 7) | AGGTGTGTCTCTCTTTTGTGAGGGGAGGGGTCCCTTCTGGCCTAGTAGAGGGCCTGGCCTGCAGTGAGCATTCAAATCCTCGAGGAACAGGGTGGGGAGGTGGGACAAAGG (SEQ ID NO: 8) | AGGTGTGTCTCTCTTTTGTGAGGGG (rs13182883_C5_1_F; SEQ ID NO: 63) | CCTTTGTCCCACCTCCCCACC (rs13182883_C5_1_R; SEQ ID NO: 64) |
| rs13218440 | 6 | CCTCGCCTACTGTGCTGTTTCTAACCATCATGCTTTTCCCTGAATCTCTTGAGTCTTTTTCTGCTGTGGACTGAAACTTGATCCTGAGATTCACCTCTAGTCCCTCTGAGCAGCCTCCTGGAATACTCAGCTGGGATGG (SEQ ID NO: 9) | CCTCGCCTACTGTGCTGTTTCTAACCATCATGCTTTTCCCTGAATCTCTTGAGTCTTTTTCTGCTGTGGACTGAAACTTGATCCTGAGATTCACCTCTAGTCCCTCTGGGCAGCCTCCTGGAATACTCAGCTGGGATGG (SEQ ID NO: 10) | CCTCGCCTACTGTGCTGTTTCTAACC (rs13218440_C6_1_F; SEQ ID NO: 65) | CCATCCCAGCTGAGTATTCCAGGAG (rs13218440_C6_1_R; SEQ ID NO: 66) |

TABLE 5-continued

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
| --- | --- | --- | --- | --- | --- |
| rs7041158 | 9 | AATTGCAATGGTGAGAGGTTGATGGTAAAATCAAACGGAACTTGTTATTTTGTCATTCTGATGGACTGGAACTGAGGATTTTCAATTTCCTCTCCAACCCAAGACACTTCTCACTGG (SEQ ID NO: 11) | AATTGCAATGGTGAGAGGTTGATGGTAAAATCAAACGGAACTTGTTATTTTGTCATTCTGATGGACTGGAACTGAGGATTTTCAATTTCCTTTCCAACCCAAGACACTTCTCACTGG (SEQ ID NO: 12) | AATTGCAATGGTGAGAGGTTGATGGT (SEQ ID NO: 67) | CCAGTGAGAAGTGTCTTGGGTTGG (SEQ ID NO: 68) |
| rs740598 | 10 | GAAATGCCTTCTCAGGTAATGGAAGGTTATCCAAATATTTTCGTAAGTATTTCAAATAGCAATGGCTCGTCTATGGTTAGTCTCACAGCCACATTCTCAGAACTGCTCAAACC (SEQ ID NO: 13) | GAAATGCCTTCTCAGGTAATGGAAGGTTATCCAAATATTTTCGTAAGTATTTCAAATAGCAATGGCTCGTCTATGGTTAGTCTCGCAGCCACATTCTCAGAACTGCTCAAACC (SEQ ID NO: 14) | GAAATGCCTTCTCAGGTAATGGAAGGT (SEQ ID NO: 69) | GGTTTGAGCAGTTCTGAGAATGTGGCT (SEQ ID NO: 70) |
| rs10773760 | 12 | ACCCAAAACACTGGAGGGGCCTCTTCTCATTTTCGGTAGACTGCAAGTGTTAGCCGTCGGGACCAGCTTCTGTCTGGAAGTTCGTCAAATTGCAGTTAAGTCCAAGTATGCCACATAGCAGATAAGGG (SEQ ID NO: 15) | ACCCAAAACACTGGAGGGGCCTCTTCTCATTTTCGGTAGACTGCAAGTGTTAGCCGTCGGGACCAGCTTCTGTCTGGAAGTTCGTCAAATTGCAGTTAGGTCCAAGTATGCCACATAGCAGATAAGGG (SEQ ID NO: 16) | ACCCAAAACACTGGAGGGGCCT (SEQ ID NO: 71) | CCCTTATCTGCTATGTGGCATACTTGG (SEQ ID NO: 72) |
| rs4530059 | 14 | GCACCAGAATTTAAACAACGCTGACAATAAATATGCAGTCGATGATGACTTCCCAGAGCTCCAGAAGCAACTCCAGCACACAGAGAGGCGCTGATGTGCCTGTCAGGTGC (SEQ ID NO: 17) | GCACCAGAATTTAAACAACGCTGACAATAAATATGCAGTCGATGATGACTTCCCAGAGCTCCAGAAGCAACTCCAGCACACGGAGAGGCGCTGATGTGCCTGTCAGGTGC (SEQ ID NO: 18) | GCACCAGAATTTAAACAACTGACAA (SEQ ID NO: 73) | GCACCTGACAGGCACATCAGCG (SEQ ID NO: 74) |
| rs7205345 | 16 | TGACTGTATACCCCAGGTGCACCCTTGGGTCATCTCTATCATAGAACTTATCTCACAGAGTATAAGAGCTGATTTCTGTGTCTGCCTCTCACACTAGACTTCCACATCCTTAGTGC (SEQ ID NO: 19) | TGACTGTATACCCCAGGTGCACCCTTGGGTCATCTCTATCATAGAACTTATCTCACAGAGTATAAGAGCTGATTTCTGTGTCTGCCTGTCACACTAGACTTCCACATCCTTAGTGC (SEQ ID NO: 20) | TGACTGTATACCCCAGGTGCACCC (SEQ ID NO: 75) | GCACTAAGGATGTGGAAGTCTAGTGTG (SEQ ID NO: 76) |
| rs8078417 | 17 | TGTACGTGGTCACCAGGGGACGCCTGGCGCTGCGAGGGAGGCCCCGAGCCTCGTGCCCCCGTGAAGCTTCAGCTCCCCTCCCCGGCTGTCCTTGAGGCTCTTCTCACACT (SEQ ID NO: 21) | TGTACGTGGTCACCAGGGGACGCCTGGCGCTGCGAGGGAGGCCCCGAGCCTCGTGCCCCCGTGAAGCTTCAGCTCCCCTCCCTGGCTGTCCTTGAGGCTCTTCTCACACT (SEQ ID NO: 22) | TGTACGTGGTCACCAGGGGACG (SEQ ID NO: 77) | AGTGTGAGAAGAGCCTCAAGGACAGC (SEQ ID NO: 78) |
| rs576261 | 19 | CAGTGGACCCTGCTGCACCTTTCCTCCCCTCCCATCAACCTCTTTTGTGCCTCCCCCTCCGTGTACCACCTTCTCTGTCACCAACCCTGGCCTCACAACTCTCTCCTTTGCCAC (SEQ ID NO: 23) | CAGTGGACCCTGCTGCACCTTTCCTCCCCTCCCATCAACCTCTTTTGTGCCTCCCCCTCCGTGTACCACCTTCTCTGTCACCACCCCTGGCCTCACAACTCTCTCCTTTGCCAC (SEQ ID NO: 24) | CAGTGGACCCTGCTGCACCTT (SEQ ID NO: 79) | GTGGCAAAGGAGAGAGTTGTGAGG (SEQ ID NO: 80) |

TABLE 5-continued

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| rs2567608 | 20 | CAGTGGCATAGTAGTCCAGGGGCTCCTCCTCAGCACCTCCAGCACCTTCCAGGAGGCAGCAGCGCAGGCAGAGAACCCGCTGGAAGAATCGGCGGAAGTTGTCGGAGAGG (SEQ ID NO: 25) | CAGTGGCATAGTAGTCCAGGGGCTCCTCCTCAGCACCTCCAGCACCTTCCAGGAGGCAGCAGCGCAGGCAGAGAACCCGCTGGAAGGATCGGCGGAAGTTGTCGGAGAGG (SEQ ID NO: 26) | CAGTGGCATAGTAGTCCAGGGGCT (SEQ ID NO: 81) | CCTCTCCGACAACTTCCGCCG (SEQ ID NO: 82) |

TABLE 6

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| rs430046 | 16 | AGGTCTGGGGGCCGCTGAATGCCAAGCTGGGAATCTTAAATGTTAAGGAACAAGGTCATACAATGAATGGTGTGATGTAAAAGCTTGGGAGGTGATTTCTGAGGGTAGGTGCTGGGTTTAATGGGAGGA (SEQ ID NO: 27) | AGGTCTGGGGCCGCTGAATGCCAAGCTGGGAATCTTAAATGTTAAGGAACAAGGTCATACAATGAATGGTGTGATGTAAAAGCTTGGGAGGTGATTTTTGAGGGTAGGTGCTGGGTTTAATGGGAGGA (SEQ ID NO: 28) | AGGTCTGGGGCCGCTGAAT (rs430046_C1_1_F; SEQ ID NO: 83) | TCCTCCCATTAAACCCAGCACCT (rs430046_C1_1_R; SEQ ID NO: 84) |
| rs9951171 | 18 | ACGGTTCTGTCCTGTAGGGGAGAAAAGTCCTCGTTGTTCCTCTGGGATGCAACATGAGAGAGCAGCACACTGAGGCTTTATGGATTGCCCTGCCACAAGTGAACAGG (SEQ ID NO: 29) | ACGGTTCTGTCCTGTAGGGGAGAAAAGTCCTCGTTGTTCCTCTGGGATGCAACATGAGAGAGCAGCACACTGAGGCTTTATGGGTTGCCCTGCCACAAGTGAACAGG (SEQ ID NO: 30) | ACGGTTCTGTCCTGTAGGGGAGA (rs9951171_C1_1_F; SEQ ID NO: 85) | CCTGTTCACTTGTGGCAGGGCA (rs9951171_C1_1_R; SEQ ID NO: 86) |
| rs338882 | 5 | GCGCAGTCAGATGGGCGTGCTGGCGTCTGTCTTCTCTCTCTCCTGCTCTCTGGCTTCATTTTTCTCTCCTTCTGTCTCACCTTCTTTCGTGTGCCTGTGCACACACACGTTTGGGACAAGGGCTGGA (SEQ ID NO: 31) | GCGCAGTCAGATGGGCGTGCTGGCGTCTGTCTTCTCTCTCCTGCCTTCTCTGGCTTCATTTTTCTCTCCTTCTGTCTCACCTTCTTTCGTGTGCCTGTGCATACACACGTTTGGGACAAGGGCTGGA (SEQ ID NO: 32) | GCGCAGTCAGATGGGCGTGC (rs338882_C1_1_F; SEQ ID NO: 87) | TCCAGCCCTTGTCCCAAACGT (rs338882_C1_1_R; SEQ ID NO: 88) |
| rs10776839 | 9 | GCCGGACCTGCGAAATCCAAAATGCCAAACATTCCCGCCTCACATGATCCCAGAGAGAGGGGACCCAGTGTTCCCAGCTTGCAGCTGAGGAGCCCGAGGTTGCCGTCAGATCAGAGCCCCAGTTGCCCG (SEQ ID NO: 33) | GCCGGACCTGCGAAATCCAAAATGCCAAACATTCCCGCCTCACATGATCCCAGAGAGAGGGGACCCAGTGTTCCCAGCTTGCAGCTGAGGAGCCCGAGTTTGCCGTCAGATCAGAGCCCCAGTTGCCCG (SEQ ID NO: 34) | GCCGGACCTGCGAAATCCCAA (rs10776839_C1_1_F; SEQ ID NO: 89) | CGGGCAACTGGGGCTCTGATC (rs10776839_C1_1_R; SEQ ID NO: 90) |
| rs9905977 | 17 | AGCAGCCTCCCTCGACTAGCTCACACTACGATAAGGAAAAT | AGCAGCCTCCCTCGACTAGCTCACACTACGATAAGGAAAATTCAT | AGCAGCCTCCCTCGACTAGCT | GGCAGAGGGGAAAGACGAAAGGA |

TABLE 6-continued

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| | | TCATGAGCTGGTGT CCAAGGAGGGCTG GGTGACTCGTGGCT CAGTCAGCATCAAG ATTCCTTTCGTCTTT CCCCTCTGCC (SEQ ID NO: 35) | GAGCTGGTGTCCAAG GAGGGCTGGGTGACT CGTGGCTCAGTCAGC GTCAAGATTCCTTTC GTCTTTCCCCTCTGCC (SEQ ID NO: 36) | (rs9905977_ C1_1_F; SEQ ID NO: 91) | (rs9905977_C1_ 1_R; SEQ ID NO: 92) |
| rs1277284 | 4 | TGGCATTGCCTGTA ATATACATAGCCAT GGTTTTTTATAGGC AATTTAAGATGAAT AGCTTCTAAACTAT AGATAAGTTTCATT ACCCCAGGAAGCT GAACTATAGCTACT TTACCCAAAATCAT TAGAATGGTGCTT (SEQ ID NO: 37) | TGGCATTGCCTGTAA TATACATAGCCATGG TTTTTTATAGGCAATT TAAGATGAATAGCTT CTAAACTATAGATAA GTTTCATTACCCCAG GAAGCTGAACTATAG CTACTTTCCCCAAAA TCATTAGAATGGTGC TT (SEQ ID NO: 38) | TGGCATTG CCTGTAAT ATACATAG (rs1277284_ C4_1_F; SEQ ID NO: 93) | AAGCACCATT CTAATGATTTT GG (rs1277284_C4_ 1_R; SEQ ID NO: 94) |
| rs258684 | 7 | ATGAAGCCTTCCAC CAACTGCCTGTATG ACTCATCTGGGGAC TTCTGCTCTATACT CAAAGTGGCTTAGT CACTGCCAATGTAT TTCCATATGAGGGA CGATGATTACTAAG GAAATATAGAAAC AACAACTGATC (SEQ ID NO: 39) | ATGAAGCCTTCCACC AACTGCCTGTATGAC TCATCTGGGGACTTC TGCTCTATACTCAAA GTGGCTTAGTCACTG CCAATGTATTTCCAT ATGAGGGACGGTGAT TACTAAGGAAATATA GAAACAACAACTGAT C (SEQ ID NO: 40) | ATGAAGCC TTCCACCA ACTG (rs258684_ C7_1_F; SEQ ID NO: 95) | GATCAGTTGTT GTTTCTATATT TCCTT (rs258684_C7_ 1_R; SEQ ID NO: 96) |
| rs1347696 | 8 | ACAACAGAATCAG GTGATTGGAGAAA AGATCACAGGCCTA GGCACCCAAGGCTT GAAGGATGAAAGA ATGAAAGATGGAC GGAACAAAATTAG GACCTTAATTCTTT GTTCAGTTCAG (SEQ ID NO: 41) | ACAACAGAATCAGGT GATTGGAGAAAAGAT CACAGGCCTAGGCAC CCAAGGCTTGAAGGA TGAAAGAATGAAAGA TGGACGGAAGAAAAT TAGGACCTTAATTCTT TGTTCAGTTCAG (SEQ ID NO: 42) | ACAACAGA ATCAGGTG ATTGGA (rs1347696_ C8_4_F; SEQ ID NO: 97) | CTGAACTGAA CAAAGAATTA AGGTC (rs1347696_C8_ 4_F; SEQ ID NO: 98) |
| rs508485 | 11 | TTGGGGTAAATTTT CATTGTCATATGTG GAATTTAAATATAC CATCATCTACAAAG AATTCCACAGAGTT AAATATCTTAAGTT AAACACTTAAAATA AGTGTTTGCGTGAT ATTTTGATGACAGA TAAACAGAGTCTAA TTCCCACCCC (SEQ ID NO: 43) | TTGGGGTAAATTTTC ATTGTCATATGTGGA ATTTAAATATACCAT CATCTACAAAGAATT CCACAGAGTTAAATA TCTTAAGTTAAACAC TTAAAATAAGTGTTT GCGTGATATTTTGAT GATAGATAAACAGAG TCTAATTCCCACCCC (SEQ ID NO: 44) | TTGGGGTA AATTTTCA TTGTCA (rs508485_ C11_1_F; SEQ ID NO: 99) | GGGGTGGGAA TTAGACTCTG (rs508485_C11_ 1_R; SEQ ID NO 100) |
| rs9788670 | 15 | TGCAATTCAAATCA GGAAGTATGACCA AAAGACAGAGATC TTTTTTGGATGATC CCTAGCCTAGCAAT GCCTGGCAGCCATG CAGGTGCAATGTCA ACCTTAAATAATGT ATTGCAAACTCAGA GCTGACAAACCTCG ATGTTGC (SEQ ID NO: 45) | TGCAATTCAAATCAG GAAGTATGACCAAAA GACAGAGATCTTTTT TGGATGATCCCTAGC CTAGCAATGCCTGGC AGCCATGCAGGTGCA ATGTCAACCTTAAAT AATGTATTGCAAATT CAGAGCTGACAAACC TCGATGTTGC (SEQ ID NO: 46) | TGCAATTC AAATCAGG AAGTATG (rs9788670_ c15_2_F; SEQ ID NO: 101) | GCAACATCGA GGTTTGTCAG (rs9788670_c15_ 2_R; SEQ ID NO: 102) |
| rs8137254 | 22 | CTGTGCTCTGCGAA TAGCTGCAGAAGTA ACTTGGGGACCCAA | CTGTGCTCTGCGAAT AGCTGCAGAAGTAAC TTGGGGACCCAAAAT | CTGTGCTC TGCGAATA GCTG | ACCATGCTCAT GGAGAATCC (rs8137254_c22_ |

TABLE 6-continued

SNP Panel for the Determination of Fetal Fraction

| SNP ID | Chr | Amplicon: Allele 1 | Amplicon: Allele 2 | Forward Primer Sequence, name and SEQ ID NO: | Reverse Primer Sequence, name and SEQ ID NO: |
|---|---|---|---|---|---|
| | | AATAAAGCAGAATGCTAATGTCAAGTCCTGAGAACCAAGCCCTGGGACTCTGGTGCCATTTCGGATTCTCCATGAGCATGGT (SEQ ID NO: 47) | AAAGCAGAATGCTAATGTCAAGTCCTGAGAACCAAGCCCTGGGACTCTGGTGCCATTTTGGATTCTCCATGAGCATGGTTGGT (SEQ ID NO: 48) | (rs8137254_c22_2_F: SEQ ID NO: 103) | 2_R; SEQ ID NO: 104) |
| rs3143 | 19 | TTTTTCCAGCCAACTCAAGGCCAAAAAAATTTCTTAATATAGTTATTATGCGAGGGGAGGGGAAGCAAAGGAGCACAGGTAGTCCACAGAATAAGACACAAGAAACCTCAAGCTGTG (SEQ ID NO: 49) | TTTTTCCAGCCAACTCAAGGCCAAAAAAATTTCTTAATATAGTTATTATGCGAGGGGAGGGGAAGCAAAGGAGCACAGGTAGTCCACAGAATAAGGACACAAGAAACCTCAAGCTGTG (SEQ ID NO: 50) | TTTTTCCAGCCAACTCAAGG (rs3143_c19_2_F: SEQ ID NO: 105) | CACAGCTTGAGGTTTCTTGTG (rs3143_c19_2_R; SEQ ID NO: 106) |
| rs2182957 | 13 | TCTTCTCGTCCCCTAAGCAAACAACATCCGCTTGCTTCTGTCTGTGTAACCACAGTGAATGGGTGTGCACGCTTGATGGGCCTCTGAGCCCCTGTTGCACAAACCAGAAA (SEQ ID NO: 51) | TCTTCTCGTCCCCTAAGCAAACAACATCCGCTTGCTTCTGTCTGTGTAACCACAGTGAATGGGTGTGCACGCTTGGTGGGCCTCTGAGCCCCTGTTGCACAAACCAGAAA (SEQ ID NO: 52) | TCTTCTCGTCCCCTAAGCAA (rs2182957_c13_1_F: SEQ ID NO: 107) | TTTCTGGTTTGTGCAACAGG (rs2182957_c13_1_R; SEQ ID NO: 108) |
| rs3739005 | 2 | CACATGGGGCATTAAGAATCGCCCAGGGAGGAGGAGGGAGAACGCGTGCTTTTCACATTTGCATTTGAATTTTGCAGGATGTGTTTTTGTGCTCATCGATGT (SEQ ID NO: 53) | CACATGGGGCATTAAGAATCGCCCAGGGAGGAGGAGGGAGAACGCGTGCTTTTCACATTTGCATTTGAATTTTGAGTTCCCAGGATGTGTTTTTGTGCTCATCGATGT TGT (SEQ ID NO: 54) | CACATGGGGCATTAAGAAT (rs3739005_c2_2_F; SEQ ID NO: 109) | ACATCGATGAGCACAAAAACAC (rs3739005_c2_2_R; SEQ ID NO: 110) |
| rs530022 | 1 | GGGCTCTGAGGTGTGTGAAATAAAAACAAATGTCCATGTCTGTCCTTTTATGCATTTTGGGACTTTACATTTCAAACATTTCAGACATGTATCACAACACGAAGGAATAACAGTTCCAGGGATATCT (SEQ ID NO: 55) | GGGCTCTGAGGTGTGTGAAATAAAAACAAATGTCCATGTCTGTCCTTTATGGCATTTTGGGACTTTACATTTCAAACATTTCAGACATGTATCACAACACGAGGGAATAACAGTTCCAGGGATATCT (SEQ ID NO: 56) | GGGCTCTGAGGTGTGTGAAA (rs530022_c1_2_F; SEQ ID NO: 111) | AGATATCCCTGGAACTGTTATCC (rs530022_c1_2_R; SEQ ID NO: 112) |

Example 6

Simultaneous Determination of Aneuploidy and Fetal Fraction: Enrichment of Fetal and Maternal Nucleic Acids in a cfDNA Sequencing Library Sample To enrich the fetal and maternal cfDNA contained in a primary sequencing library constructed using purified fetal and maternal cfDNA, a portion of a purified cfDNA sample was used for amplifying polymorphic target nucleic acid sequences, and for preparing a sequencing library of amplified polymorphic target nucleic acids, which was used to enrich the fetal and maternal nucleic acid sequences comprised in the primary library.

A primary sequencing library was prepared using purified cfDNA as described in Example 1.

A target sequencing library was prepared as follows. cfDNA contained in 5 µl of purified cfDNA was amplified in a reaction volume of 50 µl containing 7.5 µl of a 1 µM primer mix (Table 5), 10 µl of NEB 5× Mastermix and 27 µl water. Thermal cycling was performed with the Gene Amp9700 (Applied Biosystems). Using the following cycling conditions: incubating at 95° C. for 1 minute, followed by 30 cycles at 95° C. for 20 seconds, 68° C. for 1 minute, and 68° C. for 30 s, which was followed by a final incubation at 68° C. for 5 minutes. A final hold at 4° C. was added until the samples were removed for combining with the unamplified portion of the purified cfDNA sample. The amplified product was purified using the Agencourt AMPure XP PCR purification system (Part No. A63881; Beckman Coulter Genomics, Danvers, MA). A final hold at 4° C. was added until the samples were removed for preparing the target library. The amplified product was analyzed with a 2100 Bioanalyzer (Agilent Technologies, Sunnyvale, CA), and the concentration of amplified product determined. One fifth of the purified amplified product was used to prepare a target sequencing library of amplified polymorphic nucleic acids as described in Example 2. The primary and the target sequencing libraries were each diluted to 10 nM, and the target library was combined at a ratio of 1:9 with the sequencing library to provide an enriched sequencing library. Sequencing of the enriched library and analysis of the sequencing data was performed as described in Example 3.

a. Determination of Fetal Fraction

Determination of fetal fraction was performed as described in Example 5, and fetal fraction was calculated as described above i.e.

% fetal fraction allele$_x$=((Fetal sequence tags for allele$_x$)/(ΣMaternal sequence tags for allele$_x$))× 100 b. Determination of Aneuploidy

Determination of aneuploidy of chromosomes 21, 13, 18 and X was performed using chromosome doses as described in Example 4. Chromosome 21 dose was determined using chromosome 14 as the normalizing chromosome; chromosome 13 dose was determined using the group of chromosomes 3, 4, 5, and 6 as the normalizing chromosome; chromosome 18 dose was determined using chromosome 8 as the normalizing chromosome; and chromosome X dose was determined using chromosome 4 as the normalizing chromosome. Thresholds were calculated to be 2 standard deviations above and below the mean determined in the qualified samples.

Table 7 shows the data for the determination of fetal fraction in exemplary samples. Calculated chromosome dose values for chromosomes 21, 18, 13, X and Y in corresponding exemplary test samples are given in Tables 8, 9, 10, 11, and 12, respectively.

TABLE 7

Simultaneous Determination of Aneuploidy and Fetal Fraction: Determination of Fetal Fraction

| Sample ID (karyotype) | SNP | SNP TAG COUNTS | FETAL FRACTION (%) |
|---|---|---|---|
| 11409 (47, XY + 21) | rs13182883.1\|Chr.5\|length = 111\|allele = A | 261 | 4.41 |
| | rs13182883.2\|Chr.5\|length = 111\|allele = G | 5918 | |
| | rs740598.1\|Chr.10\|length = 114\|allele = A | 5545 | 7.30 |
| | rs740598.2\|Chr.10\|length = 114\|allele = G | 405 | |
| | rs8078417.1\|Chr.17\|length = 110\|allele = C | 8189 | 6.74 |
| | rs8078417.2\|Chr.17\|length = 110\|allele = T | 121470 | |
| | rs576261.1\|Chr.19\|length = 114\|allele = A | 58342 | 7.62 |
| | rs576261.2\|Chr.19\|length = 114\|allele = C | 4443 | |
| | Fetal Fraction (Mean ± S.D.) = 6.5 ± 1.5 | | |
| Sample ID | | | |
| 95133 (47, XX + 18) | rs1109037.1\|Chr.2\|length = 126\|allele = A | 12229 | 2.15 |
| | rs1109037.2\|Chr.2\|length = 126\|allele = G | 263 | |
| | rs13218440.1\|Chr.6\|length = 139\|allele = A | 55949 | 3.09 |
| | rs13218440.2\|Chr.6\|length = 139\|allele = G | 1729 | |
| | rs7041158.1\|Chr.9\|length = 117\|allele = C | 7281 | 4.12 |
| | rs7041158.2\|Chr.9\|length = 117\|allele = T | 300 | |
| | rs7205345.1\|Chr.16\|length = 116\|allele = C | 53999 | 2.14 |
| | rs7205345.2\|Chr.16\|length = 116\|allele = G | 1154 | |
| | Fetal Fraction (Mean ± S.D.) = 2.9 ± 0.9 | | |
| Sample ID | | | |
| 51236 (46, XY + 13) | rs13218440.1\|Chr.6\|length = 139\|allele = A | 1119 | 1.65 |
| | rs13218440.2\|Chr.6\|length = 139\|allele = G | 67756 | |
| | rs560681.1\|Chr.1\|length = 111\|allele = A | 14123 | 5.18 |
| | rs560681.21C1ir.1\|length = 111\|allele = G | 732 | |
| | rs7205345.1\|Chr.16\|length = 116\|allele = C | 18176 | 1.63 |
| | rs7205345.2\|Chr.16\|length = 116\|allele = G | 296 | |
| | rs9866013.1\|Chr.3\|length = 121\|allele = C | 117 | 2.33 |
| | rs9866013.2\|Chr.3\|length = 121\|allele = T | 5024 | |
| | Fetal Fraction (Mean ± S.D.) = 2.7 ± 1.7 | | |
| Sample ID | | | |
| 54430 (45, XO) | rs1109037.1\|Chr.2\|length = 126\|allele = A | 19841 | 1.80 |
| | rs1109037.2\|Chr.2\|length = 126\|allele = G | 357 | |
| | rs9866013.1\|Chr.3\|length = 121\|allele = C | 12931 | 3.81 |
| | rs9866013.2\|Chr.3\|length = 121\|allele = T | 493 | |
| | rs7041158.1\|Chr.9\|length = 117\|allele = C | 2800 | 4.25 |
| | rs7041158.2\|Chr.9\|length = 117\|allele = T | 119 | |
| | rs740598.1\|Chr.10\|length = 114\|allele = A | 12903 | 4.87 |
| | rs740598.2\|Chr.10\|length = 114\|allele = G | 628 | |
| | rs10773760.1\|Chr.12\|length = 128\|allele = A | 46324 | 4.65 |
| | rs10773760.2\|Chr.12\|length = 128\|allele = G | 2154 | |
| | Fetal Fraction (Mean ± S.D.) = 3.9 ± 1.2 | | |

Trisomy 21

Table 8 provides the calculated dose for chromosome 21 in the test sample (11409). Chromosome 14 was used as the normalizing chromosomes. The calculated threshold for the positive diagnosis of T21 aneuploidy was set at 2 standard deviations from the mean of the qualified (normal) samples. A diagnosis for T21 was given based on the chromosome dose in the test sample being greater than the set threshold. All twelve of the T21 samples that were confirmed to be T21 by karyotype were identified in a population of 48 blood samples.

TABLE 8

Chromosome Dose for a T21 aneuploidy

| Chromosome | Sequence Tag Density | Chromosome Dose for Chr 21 | Threshold |
|---|---|---|---|
| Chr21 | 264,404 | 0.439498 | 0.410634 |
| Chr14 | 601,605 | | |

Trisomy 18

Table 9 provides the calculated dose for chromosome 18 in a test sample (95133). Chromosome 8 was used as the normalizing chromosome. In this instance, chromosome 8 had the lowest variability and greatest differentiability. The calculated threshold for the positive diagnosis of T18 aneuploidy was set at greater than 2 standard deviations from the mean of the qualified (non-T18) samples. A diagnosis for T18 was given based on the chromosome dose in the test sample being greater than the set threshold. Eight T18 samples were identified using chromosome doses, and were confirmed to be T18 by karyotyping.

TABLE 9

Chromosome Dose for a T18 aneuploidy

| Chromosome | Sequence Tag Density | Chromosome Dose for Chr 18 | Threshold |
|---|---|---|---|
| Chr18 | 604,291 | 0.550731 | 0.533297 |
| Chr8 | 1,097,253 | | |

Trisomy 13

Tables 10 and 11 provide the calculated dose for chromosome 13 in a test sample (51236). The calculated threshold for the positive diagnosis of T13 aneuploidy was set at 2 standard deviations from the mean of the qualified (non-T13) samples. The chromosome dose for chromosome 13 provided in Table 10 was calculated using sequence tag density for chromosome 4 as the normalizing chromosome, while the dose given on Table 11 was determined using the average of the sequence tag densities ratios for the group of chromosomes 3, 4, 5, and 6 as the normalizing chromosome. A diagnosis for T13 was given based on the chromosome dose in the test sample being greater than the set threshold. One T13 sample was identified using chromosome doses, and were confirmed to be T13 by karyotyping.

The data show that the combination of chromosomes 3, 4, 5, and 6 provide a variability (1.06) that is similar than that of chromosome 4 (1.01), demonstrating that a group of chromosomes can be used as the normalizing chromosome to determine chromosome doses and identify aneuploidies.

TABLE 10

Chromosome Dose for a T13 aneuploidy

| Chromosome | Sequence Tag Density | Chromosome Dose for Chr 13 | Threshold |
|---|---|---|---|
| Chr13 | 669,872 | 0.538140 | 0.536044 |
| Chr4 | 1,244,791 | | |

TABLE 11

Chromosome Dose for a T13 aneuploidy

| Chromosome | Sequence Tag Density | Chromosome Dose for Chr 13 | Threshold |
|---|---|---|---|
| Chr13 | 669,872 | 0.532674 | 0.515706 |
| Chr3 | 1,385,881 | | |
| Chr4 | 1,244,791 | | |
| Chr5 | 1,229,257 | | |
| Chr6 | 1,170,331 | | |

Turner Syndrome (Monosomy X)

Three samples having a chromosome dose less than that of the set threshold were identified as having less than one X chromosome. The same samples were determined to have a Y chromosome dose that was less than the set threshold, indicating that the samples did not have a Y chromosome.

The calculated doses for chromosomes X and Y in the exemplary monosomy X test sample (54430) are given in Table 12. Chromosome 4 was selected as the normalizing chromosome to calculate the dose for chromosome X; and all chromosomes i.e. 1-22, and Y, were used as the normalizing chromosomes. The calculated threshold for the positive diagnosis of Turner Syndrome (monosomy X) was set for the X chromosome at <−2 standard deviations from the mean, and for the absence of the Y chromosome at <−2 standard deviations from the mean for qualified (non-monosomy X) samples.

TABLE 12

Chromosome Dose for a Turner Syndrome (monosomy X)

| Chromosome | Sequence Tag Density | Chromosome Dose for Chr X | Threshold |
|---|---|---|---|
| ChrX | 904,049 | 0.777990 | 0.797603 |
| Chr4 | 1,162,031 | | |
| ChrY | 390 | 0.0004462 | 0.002737754 |
| Chr (1-22, X) [average] | 874,108.1 | | |

Thus, the method enables the simultaneous determination of chromosomal aneuploidies and fetal fraction by massively parallel sequencing of a maternal sample comprising a mixture of fetal and maternal cfDNA that has been enriched for a plurality of polymorphic sequences each comprising a SNP. In this example, the mixture of fetal and maternal nucleic acids was enriched by combining a portion of a sequencing library that was constructed from amplified fetal and maternal polymorphic sequences with a sequencing library that was constructed from the remaining unamplified original fetal and maternal cfDNA mixture.

Example 7

Simultaneous Determination of Aneuploidy and Fetal Fraction: Enrichment of Fetal and Maternal Nucleic Acids in a Purified cfDNA Sample To enrich the fetal and maternal cfDNA contained in a purified sample of cfDNA extracted from a maternal plasma sample, a portion of the purified cfDNA was used for amplifying polymorphic target nucleic acid sequences each comprising one SNP chosen from the panel of SNPs given in Table 6.

Cell-free plasma was obtained from a maternal blood sample, and cfDNA was purified from the plasma sample as described in Example 1. The final concentration was determined to be 92.8 pg/μl.

cfDNA contained in 5 μl of purified cfDNA was amplified in a reaction volume of 50 μl containing 7.5 μl of a 1 uM primer mix (Table 5), 10 μl of NEB 5× Mastermix and 27 μl water. Thermal cycling was performed with the Gene Amp9700 (Applied Biosystems). Using the following cycling conditions: incubating at 95° C. for 1 minute, followed by 30 cycles at 95° C. for 20 seconds, 68° C. for 1 minute, and 68° C. for 30 s, which was followed by a final incubation at 68° C. for 5 minutes. A final hold at 4° C. was added until the samples were removed for combining with the unamplified portion of the purified cfDNA sample. The amplified product was purified using the Agencourt AMPure XP PCR purification system (Part No. A63881; Beckman Coulter Genomics, Danvers, MA), and the concentration quantified using the Nanodrop 2000 (Thermo Scientific, Wilmington, DE). The purified amplification product was diluted 1:10 in water and 0.9 μl (371 pg) added to 40 μl of purified cfDNA sample to obtain a 10% spike. The enriched fetal and maternal cfDNA present in the purified cfDNA sample was used for preparing a sequencing library, and was sequenced as described in Example 2.

Table 13 provides the tag counts obtained for each of chromosomes 21, 18, 13, X and Y i.e. sequence tag density, and the tag counts obtained for the informative polymorphic sequences contained in the SNP reference genome i.e. SNP tag density. The data show that sequencing information can be obtained from sequencing a single library constructed from a purified maternal cfDNA sample that has been enriched for sequences comprising SNPs to simultaneously determine the presence or absence of aneuploidy and the fetal fraction. In the example given, the data show that the fraction of fetal DNA in plasma sample AFR105 was quantifiable from the sequencing results of five informative SNPs and determined to be 3.84%. Sequence tag densities are provided for chromosomes 21, 13, 18, X and Y. Sample AFR105 was the only sample that was subjected to the protocol of enriching purified cfDNA for amplified polymorphic sequences. Thus, coefficients of variation and tests for differentiability were not provided. However, the example shows that the enrichment protocol provides the requisite tag counts for determining aneuploidy and fetal fraction from a single sequencing process.

TABLE 13

Simultaneous Determination of Aneuploidy and Fetal Fraction:
Enrichment of fetal and maternal nucleic acids in a purified cfDNA sample

| Aneuploidy | | | | | |
|---|---|---|---|---|---|
| | Chromosome 21 | Chromosome 18 | Chromosome 13 | Chromosome X | Chromosome Y |
| Sequence Tag Density | 178763 | 359529 | 388204 | 572330 | 2219 |
| Karyotype | Unaffected | Unaffected | Unaffected | Unaffected | Unaffected |

| Fetal Fraction | | |
|---|---|---|
| SNP | SNP TAG DENSITY | FETAL FRACTION (%) |
| rs10773760.1\|Chr.12\|length = 128\|allele = A | 18903 | 2.81 |
| rs10773760.2\|Chr.12\|length = 128\|allele = G | 532 | |
| rs1109037.1\|Chr.2\|length = 126\|allele = A | 347 | 5.43 |
| rs1109037.2\|Chr.2\|length = 126\|allele = G | 6394 | |
| rs2567608.1\|Chr.20\|length = 110\|allele = A | 94503 | 1.74 |
| rs2567608.2\|Chr.20\|length = 110\|allele = G | 1649 | |
| rs7041158.1\|Chr.9\|length = 117\|allele = C | 107 | 5.61 |
| rs7041158.2\|Chr.9\|length = 117\|allele = T | 6 | |
| rs8078417.1\|Chr.17\|length = 110\|allele = C | 162668 | 3.61 |
| rs8078417.2\|Chr.17\|length = 110\|allele = T | 5877 | |

Fetal Fraction (Mean ± S.D.) = 3.8 ± 1.7

Example 8

Simultaneous Determination of Aneuploidy and Fetal Fraction: Enrichment of Fetal and Maternal Nucleic Acids in a Plasma Sample To enrich the fetal and maternal cfDNA contained in an original plasma sample derived from a pregnant woman, a portion the original plasma sample was used for amplifying polymorphic target nucleic acid sequences each comprising one SNP chosen from the panel of SNPs given in Table 14, and a portion of the amplified product was combined with the remaining original plasma sample.

cfDNA contained in 15 µl of cell-free plasma was amplified in a reaction volume of 50 µl containing 9 ul of a 1 µM mixture of primers (15 plexTable 5), 1 µl of Phusion blood DNA polymerase, 25 ul of the 2× Phusion blood PCR buffer containing deoxynucleotide triphosphates (dNTPs: dATP, dCTP, dGTP and dTTP). Thermal cycling was performed with the Gene Amp9700 (Applied Biosystems) using the following cycling conditions: incubating at 95° C. for 3 minutes, followed by 35 cycles at 95° C. for 20 seconds, 55° C. for 30 s, and 70° C. for 1 minute, which was followed by a final incubation at 68° C. for 5 minutes. A final hold at 4° C. was added until the samples were removed for combining with the unamplified portion of the cell-free plasma. The amplified product was diluted 1:2 with water and analyzed using the Bioanalyzer. An additional 3 µl of amplified product was diluted with 11.85 µl of water to obtain a final concentration of 2 ng/µl. 2.2 µl of the diluted amplified product was combined with the remaining plasma sample. The enriched fetal and maternal cfDNA present in the plasma sample was purified as described in Example 1, and used for preparing a sequencing library. Sequencing and analysis of the sequencing data was performed as described in Examples 2 and 3.

The results are given in Table 14. In the example given, the data show that the fraction of fetal DNA in plasma sample SAC2517 was quantifiable from the sequencing results of one informative SNP and determined to be 9.5%. In the example given, sample SAC2517 was shown by karyotyping to be unaffected for aneuploidies of chromosomes 21, 13, 18, X and Y. Sequence tag densities are provided for chromosomes 21, 13, 18, X and Y. Sample SAC2517 was the only sample that was subjected to the protocol of enriching plasma cfDNA for amplified polymorphic sequences. Thus, coefficients of variation and tests for differentiability could not determined. The example demonstrates that enriching the mixture of fetal and maternal cfDNA present in a plasma sample for nucleic acid sequences that comprise at least one informative SNP can be used to provide the requisite sequence and SNP tag counts for determining aneuploidy and fetal fraction from a single sequencing process.

TABLE 14

Simultaneous Determination of Aneuploidy and fetal fraction:
Enrichment of fetal and maternal nucleic acids in a plasma sample

| | Aneuploidy | | | | |
|---|---|---|---|---|---|
| | Chromosome 21 | Chromosome 18 | Chromosome 13 | Chromosome X | Chromosome Y |
| Sequence Tag Density | 183851 | 400582 | 470526 | 714055 | 2449 |
| Karyotype | Unaffected | Unaffected | Unaffected | Unaffected | Unaffected |

| | Fetal Fraction | |
|---|---|---|
| SNP | TAG COUNTS | FETAL FRACTION (%) |
| rs10773760.1|Chr.12|length = 128|allele = A | 8536 | 9.49 |
| rs10773760.2|Chr.12|length = 128|allele = G | 89924 | |

Example 9

Simultaneous Determination of Aneuploidy and Fetal Fraction in Maternal Samples Enriched for Polymorphic Sequences Comprising STRs To simultaneously determine the presence or absence of an aneuploidy and the fetal fraction in a mixture of fetal and maternal cfDNA obtained from a maternal sample, the mixture is enriched for polymorphic sequences comprising STRs, sequenced and analyzed. Enrichment can be of a sequencing library as described in Example 6, of a purified cfDNA sample as described in Example 7, or of a plasma sample as described in Example 8. In each case, sequencing information is obtained from sequencing a single library, which enables for simultaneously determining the presence or absence of an aneuploidy and the fetal fraction. STRs that are amplified are chosen from the codis and non-codis STRs disclosed in Table 9, and amplification of the polymorphic STR sequences is obtained using the corresponding sets of primers provided. The STRs of Table 9 have been disclosed previously, and STRs CSF1PO, FGA, D7S820, D13S317, D16S539, D18S51, D21S11, D2S1338 (see Table 5), have been used to determine fetal fraction in plasma cfDNA samples obtained from women pregnant with either male or female fetuses (see U.S. Provisional applications 61/296,358 and 61/360,837). Quantification of the STRs was performed using capillary electrophoresis (see Example 11). Example 11 shows that STRs can be used to determine fetal fraction.

TABLE 15

CODIS and NON-CODIS miniSTRs

| STR Locus (Marker Name) | Chromosome Location | Size Range (bp) | GenBank Accession | Primer Sequences (Forward/Reverse) |
|---|---|---|---|---|
| Codis miniSTR loci* | | | | |
| CSF1PO | 5q33.1 | 89-129 | X14720 | ACAGTAACTGCCTTCATAGATAG (CSF1PO_F; SEQ ID NO: 113) GTGTCAGACCCTGTTCTAAGTA (CSF1PO_R; SEQ ID NO: 114) |
| FGA | 4q31.3 | 125-281 | M64982 | AAATAAAATTAGGCATATTTACAAGC (FGA_F; SEQ ID NO: 115) GCTGAGTGATTTGTCTGTAATTG (FGA_R; SEQ ID NO: 116) |
| TH01 | 11p15.5 | 51-98 | D00269 | CCTGTTCCTCCCTTATTTCCC (TH01_F; SEQ ID NO: 117) GGGAACACAGACTCCATGGTG (TH01_R; SEQ ID NO: 118) |
| TPOX | 2p25.3 | 65-101 | M68651 | CTTAGGGAACCCTCACTGAATG (TPOX_F; SEQ ID NO: 119) GTCCTTGTCAGCGTTTATTTGC (TPOX_R; SEQ ID NO: 120) |
| vWA | 12p13.31 | 88-148 | M25858 | AATAATCAGTATGTGACTTGGATTGA (vWA_F; SEQ ID NO: 121) ATAGGATGGATGGATAGATGGA (vWA_R; SEQ ID NO: 122) |
| D3S1358 | 3p21.31 | 72-120 | NT_005997 | CAGAGCAAGACCCTGTCTCAT (D3S1358_F; SEQ ID NO: 123) TCAACAGAGGCTTGCATGTAT (D3S1358_R; SEQ ID NO: 124) |
| D5S818 | 5q23.2 | 81-117 | AC008512 | GGGTGATTTTCCTCTTTGGT (D5S818_F; SEQ ID NO: 125) AACATTTGTATCTTTATCTGTATCCTTATTTAT (D5S818_R; SEQ ID NO: 126) |
| D7S820 | 7q21.11 | 136-176 | AC004848 | GAACACTTGTCATAGTTTAGAACGAAC (D7S820_F; SEQ ID NO: 127) TCATTGACAGAATTGCACCA (D7S820_R; SEQ ID NO: 128) |
| D8S1179 | 8q24.13 | 86-134 | AF216671 | TTTGTATTTCATGTGTACATTCGTATC (D7S820_F; SEQ ID NO: 129) ACCTATCCTGTAGATTATTTTCACTGTG (D7S820_R; SEQ ID NO: 130) |
| D13S317 | 13q31.1 | 88-132 | AL353628 | TCTGACCCATCTAACGCCTA (D13S317_F; SEQ ID NO: 131) CAGACAGAAAGATAGATAGATGATTGA (D13S317_R; SEQ ID NO: 132) |
| D16S539 | 16q24.1 | 81-121 | AC024591 | ATACAGACAGACAGACAGGTG (D16S539_F; SEQ ID NO: 133) GCATGTATCTATCATCCATCTCT (D16S539_R; SEQ ID NO: 134) |
| D18S51 | 18q21.33 | 113-193 | AP001534 | TGAGTGACAAATTGAGACCTT (D18S51_F; SEQ ID NO: 135) GTCTTACAATAACAGTTGCTACTATT (D18S51_R; SEQ ID NO: 136) |
| D21S11 | 21q21.1 | 153-221 | AP000433 | ATTCCCCAAGTGAATTGC (D21S11_F; SEQ ID NO: 137) GGTAGATAGACTGGATAGATAGACGA (D21S11_R; SEQ ID NO: 138) |
| D2S1338 | 2q35 | 90-142 | AC01036 | TGGAAACAGAAATGGCTTGG (D2S1338_F; SEQ ID NO: 139) GATTGCAGGAGGGAAGGAAG (D2S1338_R; SEQ ID NO: 140) |

TABLE 15-continued

CODIS and NON-CODIS miniSTRs

| STR Locus (Marker Name) | Chromosome Location | Size Range (bp) | GenBank Accession | Primer Sequences (Forward/Reverse) |
|---|---|---|---|---|
| Penta D | 21q22.3 | 94-167 | AP001752 | GAGCAAGACACCATCTCAAGAA (Penta D_F; SEQ ID NO: 141)<br>GAAATTTTACATTTATGTTTATGATTCTCT (Penta D_R; SEQ ID NO: 142) |
| Penta E | 15q26.2 | 80-175 | AC027004 | GGCGACTGAGCAAGACTC (Penta E_F; SEQ ID NO: 143)<br>GGTTATTAATTGAGAAAACTCCTTACA (Penta E_R; SEQ ID NO: 144) |

Non-Codis miniSTR loci*

| STR Locus | Chromosome | Size Range | GenBank | Primer Sequences |
|---|---|---|---|---|
| D22S1045 | 22q12.3 | 82-115 | AL022314 (17) | ATTTTCCCCGATGATAGTAGTCT (D22S1045_F; SEQ ID NO: 145)<br>GCGAATGTATGATTGGCAATATTTTT (D22S1045_R; SEQ ID NO: 146) |
| D20S1082 | 20q13.2 | 73-101 | AL158015 | ACATGTATCCCAGAACTTAAAGTAAAC (D20S1082_F; SEQ ID NO: 147)<br>GCAGAAGGGAAAATTGAAGCTG (D20S1082_R; SEQ ID NO: 148) |
| D20S482 | 20p13 | 85-126 | AL121781 (14) | CAGAGACACCGAACCAATAAGA (D20S482_F; SEQ ID NO: 149)<br>GCCACATGAATCAATTCCTATAATAAA (D20S482_R; SEQ ID NO: 150) |
| D18S853 | 18p11.31 | 82-104 | AP005130 (11) | GCACATGTACCCTAAAACTTAAAAT (D18S853_F; SEQ ID NO: 151)<br>GTCAACCAAAACTCAACAAGTAGTAA (D18S853_R; SEQ ID NO: 152) |
| D17S1301 | 17q25.1 | 114-139 | AC016888 (12) | AAGATGAAATTGCCATGTAAAAATA (D17S1301_F; SEQ ID NO: 153)<br>GTGTGTATAACAAAATTCCTATGATGG (D17S1301_R; SEQ ID NO: 154) |
| D17S974 | 17p13.1 | 114-139 | AC034303 (10) | GCACCCAAAACTGAATGTCATA (D17S974_F; SEQ ID NO: 155)<br>GGTGAGAGTGAGACCCTGTC (D17S974_R; SEQ ID NO: 156) |
| D14S1434 | 14q32.13 | 70-98 | AL121612 (13) | TGTAATAACTCTACGACTGTCTGTCTG (D14S1434_F; SEQ ID NO: 157)<br>GAATAGGAGGTGGATGGATGG (D14S1434_R; SEQ ID NO: 158) |
| D12ATA63 | 12q23.3 | 76-106 | AC009771 (13) | GAGCGAGACCCTGTCTCAAG (D12ATA63_F; SEQ ID NO: 159)<br>GGAAAAGACATAGGATAGCAATTT (D12ATA63_R; SEQ ID NO: 160) |
| D11S4463 | 11q25 | 88-116 | AP002806 (14) | TCTGGATTGATCTGTCTGTCC (D11S4463_F; SEQ ID NO: 161)<br>GAATTAAATACCATCTGAGCACTGAA (D11S4463_R; SEQ ID NO: 162) |
| D10S1435 | 10p15.3 | 82-139 | AL354747 (11) | TGTTATAATGCATTGAGTTTTATTCTG (D10S1435_F; SEQ ID NO: 163)<br>GCCTGTCTCAAAAATAAAGAGATAGACA (D10S1435_R; SEQ ID NO: 164) |
| D10S1248 | 10q26.3 | 79-123 | AL391869 (13) | TTAATGAATTGAACAAATGAGTGAG (D10S1248_F; SEQ ID NO: 165)<br>GCAACTCTGGTTGTATTGTCTTCAT (D10S1248_R; SEQ ID NO: 166) |
| D9S2157 | 9q34.2 | 71-107 | AL162417 (10) | CAAAGCGAGACTCTGTCTCAA (D9S2157_F; SEQ ID NO: 167)<br>GAAAATGCTATCCTCTTTGGTATAAAT (D9S2157_R; SEQ ID NO: 168) |

TABLE 15-continued

CODIS and NON-CODIS miniSTRs

| STR Locus (Marker Name) | Chromosome Location | Size Range (bp) | GenBank Accession | Primer Sequences (Forward/Reverse) |
|---|---|---|---|---|
| D9S1122 | 9q21.2 | 93-125 | AL161789 (12) | GGGTATTTCAAGATAACTGTAGATAGG (D9S1122_F; SEQ ID NO: 168) GCTTCTGAAAGCTTCTAGTTTACC (D9S1122_R; SEQ ID NO: 170) |
| D8S1115 | 8p11.21 | 63-96 | AC090739 (9) | TCCACATCCTCACCAACAC (D8S1115_F; SEQ ID NO: 171) GCCTAGGAAGGCTACTGTCAA (D8S1115_R; SEQ ID NO: 172) |
| D6S1017 | 6p21.1 | 81-110 | AL035588 (10) | CCACCCGTCCATTTAGGC (D6S1017_F; SEQ ID NO: 173) GTGAAAAAGTAGATATAATGGTTGGTG (D6S1017_R; SEQ ID NO: 174) |
| D6S474 | 6q21 | 107-136 | AL357514 (17) | GGTTTTCCAAGAGATAGACCAATTA (D6S474_F; SEQ ID NO: 175) GTCCTCTCATAAATCCCTACTCATATC (D6S474_R; SEQ ID NO: 176) |
| D5S2500 | 5q11.2 | 85-126 | AC008791 (17) | CTGTTGGTACATAATAGGTAGGTAGGT (D5S2500_F; SEQ ID NO: 177) GTCGTGGGCCCCATAAATC (D5S2500_R; SEQ ID NO: 178) |
| D4S2408 | 4p15.1 | 85-109 | AC110763 (9) | AAGGTACATAACAGTTCAATAGAAAGC (D4S2408_F; SEQ ID NO: 179) GTGAAATGACTGAAAAATAGTAACCA (D4S2408_R; SEQ ID NO: 180) |
| D4S2364 | 4q22.3 | 67-83 | AC022317 (9) | CTAGGAGATCATGTGGGTATGATT (D4S2364U_F; SEQ ID NO: 181) GCAGTGAATAAATGAACGAATGGA (D4S2364_R; SEQ ID NO: 182) |
| D3S4529 | 3p12.1 | 111-139 | AC117452 (13) | CCCAAAATTACTTGAGCCAAT (D3S452_F; SEQ ID NO: 183) GAGACAAAATGAAGAAACAGACAG (D3S452_R; SEQ ID NO: 184) |
| D3S3053 | 3q26.31 | 84-108 | AC069259 (9) | TCTTTGCTCTCATGAATAGATCAGT (D3S3053_F; SEQ ID NO: 185) GTTTGTGATAATGAACCCACTCAG (D3S3053_R; SEQ ID NO: 186) |
| D2S1776 | 2q24.3 | 127-161 | AC009475 (11) | TGAACACAGATGTTAAGTGTGTATATG (D2S1776_F; SEQ ID NO: 187) GTCTGAGGTGGACAGTTATGAAA (D2S1776_R; SEQ ID NO: 188) |
| D2S441 | 2p14 | 78-110 | AC079112 (12) | CTGTGGCTCATCTATGAAAACTT (D2S441_F; SEQ ID NO: 189) GAAGTGGCTGTGGTGTTATGAT (D2S441_R; SEQ ID NO: 190) |
| D1S1677 | 1q23.3 | 81-117 | AL513307 (15) | TTCTGTTGGTATAGAGCAGTGTTT (D1S1677_F; SEQ ID NO: 191) GTGACAGGAAGGACGGAATG (D1S1677_R; SEQ ID NO: 192) |
| D1S1627 | 1p21.1 | 81-100 | AC093119 (13) | CATGAGGTTTGCAAATACTATCTTAAC (D1S1627_F; SEQ ID NO: 193) GTTTTAATTTTCTCCAAATCTCCA (D1S1627_R; SEQ ID NO: 194) |
| D1GATA113 | 1p36.23 | 81-105 | Z97987 (11) | TCTTAGCCTAGATAGATACTTGCTTCC (D1GATA113_F; SEQ ID NO: 195) GTCAACCTTTGAGGCTATAGGAA (D1GATA113_R; SEQ ID NO: 196) |

*(Butler et al., J Forensic Sci 5:1054-1064; Hill et al., Poster #44-17th International Symposium on Human Identification-2006)

Sequencing of the library enriched for polymorphic STR sequences is performed using a NGS technology e.g. sequencing by synthesis. Sequence reads of lengths of at least 100 bp are aligned to a reference genome e.g. the human reference genome NCBI36/hg18 sequence, and to an STR genome, and the number of sequence tags and STR tags obtained is used to determine the presence or absence of aneuploidy and the fetal fraction, respectively. The STR reference genome includes the sequences of amplicons amplified from the given primers.

Example 10

Simultaneous Determination of Aneuploidy and Fetal Fraction in Maternal Samples Enriched for Polymorphic Sequences Comprising Tandem SNPs To determine simultaneously aneuploidy and fetal fraction in maternal samples comprising fetal and maternal nucleic acids, plasma samples, purified cfDNA samples, and sequencing library samples are enriched for polymorphic target nucleic acid sequences each comprising a pair of tandem SNPs selected from rs7277033-rs2110153; rs2822654-rs1882882; rs368657-rs376635; rs2822731-rs2822732; rs1475881-rs7275487; rs1735976-rs2827016; rs447340-rs2824097; rs418989-rs13047336; rs987980-rs987981; rs4143392-rs4143391; rs1691324-rs13050434; rs11909758-rs9980111; rs2826842-rs232414; rs1980969-rs1980970; rs9978999-rs9979175; rs1034346-rs12481852; rs7509629-rs2828358; rs4817013-rs7277036; rs9981121-rs2829696; rs455921-rs2898102; rs2898102-rs458848; rs961301-rs2830208; rs2174536-rs458076; rs11088023-rs11088024; rs1011734-rs1011733; rs2831244-rs9789838; rs8132769-rs2831440; rs8134080-rs2831524; rs4817219-rs4817220; rs2250911-rs2250997; rs2831899-rs2831900; rs2831902-rs2831903; rs11088086-rs2251447; rs2832040-rs11088088; rs2832141-rs2246777; rs2832959-rs9980934; rs2833734-rs2833735; rs933121-rs933122; rs2834140-rs12626953; rs2834485-rs3453; rs9974986-rs2834703; rs2776266-rs2835001; rs1984014-rs1984015; rs7281674-rs2835316; rs13047304-rs13047322; rs2835545-rs4816551; rs2835735-rs2835736; rs13047608-rs2835826; rs2836550-rs2212596; rs2836660-rs2836661; rs465612-rs8131220; rs9980072-rs8130031; rs418359-rs2836926; rs7278447-rs7278858; rs385787-rs367001; rs367001-rs386095; rs2837296-rs2837297; and rs2837381-rs4816672. The primers used for amplifying the target sequences comprising the tandem SNPs are designed to encompass both SNP sites. For example, the forward primer is designed to encompass the first SNP, and the reverse primer is designed to encompass the second of the tandem SNP pair i.e. each of the SNP sites in the tandem pair is encompassed within the 36 bp generated by the sequencing method. Paired-end sequencing can be used to identify all sequences encompassing the tandem SNP sites. Exemplary sets of primers that are used to amplify the tandem SNPs disclosed herein are set rs7277033-rs2110153_F: TCCTGGAAACAAAGTATT (SEQ ID NO:197) and rs7277033-rs2110153_R: AACCTTACAACAAAGCTAGAA (SEQ ID NO:198), set rs2822654-rs1882882_F: ACTAAGCCTTGGGGATCCAG (SEQ ID NO:199) and rs2822654-rs1882882_R: TGCTGTGGAAATACTAAAAGG (SEQ ID NO:200), set rs368657-rs376635_F:CTCCAGAGGTAATCCTGTGA (SEQ ID NO:201) and rs368657-rs376635_R:TGGTGTGAGATGGTATCTAGG (SEQ ID NO:202), rs2822731-rs2822732_F:GTATAATCCATGAATCTTGTTT (SEQ ID NO:203) and rs2822731-rs2822732_R:TTCAAATTGTATATAAGAGAGT (SEQ ID NO:204), rs1475881-rs7275487_F:GCAGGAAAGTTATTTTAAT (SEQ ID NO:205) and rs1475881-rs7275487_R:TGCTTGAGAAAGCTAACACTT (SEQ ID NO:206), rs1735976-rs2827016F:CAGTGTTTGGAAATTGTCTG (SEQ ID NO:207) and rs1735976-rs2827016_R:GGCACTGGGAGATTATTGTA (SEQ ID NO:208), rs447349-rs2824097_F:TCCTGTTGTTAAGTACACAT (SEQ ID NO:209) and rs447349-rs2824097_R:GGGCCGTAATTACTTTTG (SEQ ID NO:210), rs418989-rs13047336_F: ACTCAGTAGGCACTTTGTGTC (SEQ ID NO:211) and rs418989-rs13047336_R:TCTTCCACCACACCAATC (SEQ ID NO:212), rs987980-rs987981_F:TGGCTTTTCAAAGGTAAAA (SEQ ID NO:213) and rs987980-rs987981_R: GCAACGTTAACATCTGAATTT (SEQ ID NO:214), rs4143392-rs4143391_F: rs4143392-rs4143391 (SEQ ID NO:215) and rs4143392-rs4143391R:ATTTTATATGTCATGATCTAAG (SEQ ID NO:216), rs1691324-rs13050434_F: AGAGATTACAGGTGTGAGC (SEQ ID NO:217) and rs1691324-rs13050434_R: ATGATCCTCAACTGCCTCT (SEQ ID NO:218), rs11909758-rs9980111_F: TGAAACTCAAAAGAGAAAAG (SEQ ID NO:219) and rs11909758-rs9980111_R: ACAGATTTCTACTTAAAATT (SEQ ID NO:220), rs2826842-rs232414_F: TGAAACTCAAAAGAGAAAAG (SEQ ID NO:221) and rs2826842-rs232414_R: ACAGATTTCTACTTAAAATT (SEQ ID NO:22), rs2826842-rs232414_F: GCAAAGGGGTACTCTATGTA (SEQ ID NO:223) and rs2826842-rs232414_R: TATCGGGTCATCTTGTTAAA (SEQ ID NO:224), rs1980969-rs1980970_F: TCTAACAAAGCTCTGTCCAAAA (SEQ ID NO:225) and rs1980969-rs1980970_R: CCACACTGAATAACTGGAACA (SEQ ID NO:226), rs9978999-rs9979175_F: GCAAGCAAGCTCTCTACCTTC (SEQ ID NO:227) and rs9978999-rs9979175_R: TGTTCTTCCAAAATTCACATGC (SEQ ID NO:228), rs1034346-rs12481852_F: ATTTCACTATTCCTTCATTTT (SEQ ID NO:229) and rs1034346-rs12481852_R: TAATTGTTGCACACTAAATTAC (SEQ ID NO:230), rs4817013-rs7277036_F: AAAAAGCCACAGAAATCAGTC (SEQ ID NO:231) and rs4817013-rs7277036_R: TTCTTATATCTCACTGGGCATT (SEQ ID NO:232), rs9981121-rs2829696_F: GGATGGTAGAAGAGAAGAAAGG (SEQ ID NO:233) and rs9981121-rs2829696_R: GGATGGTAGAAGAGAAGAAAGG (SEQ ID NO:234), rs455921-rs2898102_F: TGCAAAGATGCAGAACCAAC (SEQ ID NO:235) and rs455921-rs2898102_R: TTTTGTTCCTTGTCCTGGCTGA (SEQ ID NO:236), rs2898102-rs458848_F: TGCAAAGATGCAGAACCAAC (SEQ ID NO:237) and rs2898102-rs458848_R: GCCTCCAGCTCTATCCAAGTT (SEQ ID NO:238), rs961301-rs2830208_F: CCTTAATATCTTCCCATGTCCA (SEQ ID NO:239) and rs961301-rs2830208_R: ATTGTTAGTGCCTCTTCTGCTT (SEQ ID NO:240), rs2174536-rs458076_F: GAGAAGTGAGGTCAGCAGCT (SEQ ID NO:241) and rs2174536-rs458076_R: TTTCTAAATTTCCATTGAACAG (SEQ ID NO:242), rs11088023-rs11088024_F: GAAATTGGCAATCTGATTCT (SEQ ID NO:243) and rs11088023-rs11088024_R: CAACTTGTCCTTTATTGATGT (SEQ ID NO:244), rs1011734-rs1011733_F: CTATGTTGATAAAACATTGAAA (SEQ ID NO:245) and rs1011734-rs1011733_R: GCCTGTCTGGAATATAGTTT (SEQ ID NO:246), rs2831244-rs9789838_F: CAGGGCATATAATCTAAGCTGT (SEQ ID NO:247) and rs2831244-rs9789838_R: CAATGACTCTGAGTT- GAGCAC (SEQ ID NO:248), rs8132769-rs2831440_F: ACTCTCTCCCTCCCCTCT (SEQ ID NO:249) and rs8132769-rs2831440_R: TATGGCCCCAAAACTATTCT (SEQ ID NO:250), rs8134080-rs2831524_F: ACAAGTACTGGGCAGATTGA (SEQ ID NO:251) and rs8134080-rs2831524_R: GCCAGGTTTAGCTTTCAAGT (SEQ ID NO:252), rs4817219-rs4817220_F: TTTTATATCAGGAGAAACACTG (SEQ ID NO:253) and rs4817219-rs4817220_R: CCAGAATTTTGGAGGTTTAAT (SEQ ID NO:254), rs2250911-rs2250997_F: TGTCATTCCTCCTTTATCTCCA (SEQ ID NO:255) and rs2250911-rs2250997_R: TTCTTTTGCCTCTCCCAAAG (SEQ ID NO:256), rs2831899-rs2831900_F: ACCCTGGCACAGTGTTGACT (SEQ ID NO:257) and rs2831899-rs2831900_R: TGGGCCTGAGTTGAGAAGAT (SEQ ID NO:258), rs2831902-rs2831903_F: AATTTGTAAGTATGTGCAACG (SEQ ID NO:259) and rs2831902-rs2831903_R: TTTTTCCCATTTCCAACTCT (SEQ ID NO:260), rs11088086-rs2251447_F: AAAAGATGAGACAGGCAGGT (SEQ ID NO:261) and rs11088086-rs2251447_R: ACCCCTGTGAATCTCAAAAT (SEQ ID NO:262), rs2832040-rs11088088_F: GCACTTGCTTCTATTGTTTGT (SEQ ID NO:263) and rs2832040-rs11088088_R: CCCTTCCTCTCTTCCATTCT (SEQ ID NO:264), rs2832141-rs2246777_F: AGCACTGCAGGTA (SEQ ID NO:265) and rs2832141-rs2246777_R: ACAGATACCAAAGAACTGCAA (SEQ ID NO:266), rs2832959-rs9980934_F: TGGACACCTTTCAACTTAGA (SEQ ID NO:267) and rs2832959-rs9980934_R: GAACAGTAATGTTGAACTTTTT (SEQ ID NO:268), rs2833734-rs2833735_F: TCTTGCAAAAGCTTAGCACA (SEQ ID NO:269) and rs2833734-rs2833735_R: AAAAAGATCTCAAAGGGTCCA (SEQ ID NO:270), rs933121-rs933122_F: GCTTTTGCTGAACATCAAGT (SEQ ID NO:271) and rs933121-rs933122_R: CCTTCCAGCAGCATAGTCT (SEQ ID NO:272), rs2834140-rs12626953_F: AAATCCAGGATGTGCAGT (SEQ ID NO:273) and rs2834140-rs12626953_R: ATGATGAGGTCAGTGGTGT (SEQ ID NO:274), rs2834485-rs3453_F: CATCACAGATCATAGTAAATGG (SEQ ID NO:275) and rs2834485-rs3453_R: AATTATTATTTTGCAGGCAAT (SEQ ID NO:276), rs9974986-rs2834703_F: CATGAGGCAAACACCTTTCC (SEQ ID NO:277) and rs9974986-rs2834703_R: GCTGGACTCAGGATAAAGAACA (SEQ ID NO:278), rs2776266-rs2835001_F: TGGAAGCCTGAGCTGACTAA (SEQ ID NO:279) and rs2776266-rs2835001_R: CCTTCTTTTCCCCCAGAATC (SEQ ID NO:280), rs1984014-rs1984015_F:TAGGAGAACAGAAGATCAGAG (SEQ ID NO:281) and rs1984014-rs1984015_R:AAAGACTATTGCTAAATGCTTG (SEQ ID NO:282), rs7281674-rs2835316_F: TAAGCGTAGGGCTGTGTGTG (SEQ ID NO:283) and rs7281674-rs2835316_R: GGACGGATAGACTCCAGAAGG (SEQ ID NO:284), rs13047304-rs13047322_F: GAATGACCTTGGCACTTTTATCA (SEQ ID NO:285) and rs13047304-rs13047322_R: AAGGATAGAGATATACAGATGAATGGA (SEQ ID NO:286), rs2835735-rs2835736_F: CATGCACCGCGCAAATAC (SEQ ID NO:287) and rs2835735-rs2835736_R: ATGCCTCACCCACAAACAC (SEQ ID NO:288), rs13047608-rs2835826_F: TCCAAGCCCTTCTCACTCAC (SEQ ID NO:289) and rs13047608-rs2835826_R: CTGGGACGGTGACATTTTCT (SEQ ID NO:290), rs2836550-rs2212596_F: CCCAGGAAGAGTGGAAAGATT (SEQ ID NO:291) and rs2836550-rs2212596_R: TTAGCTTGCATGTACCTGTGT (SEQ ID NO:292), rs2836660-rs2836661_F: AGCTAGATGGGGTGAATTTT (SEQ ID NO:293) and _R: TGGGCTGAGGGGAGATTC (SEQ ID NO:294), rs465612-rs8131220_F: ATCAAGCTAATTAATGTTATCT (SEQ ID NO:295) and rs465612-rs8131220_R: AATGAATAAGGTCCTCAGAG (SEQ ID NO:296), rs9980072-rs8130031_F:TTTAATCTGATCATTGCCCTA (SEQ ID NO:297) and rs9980072-rs8130031_R: AGCTGTGGGTGACCTTGA (SEQ ID NO:298), rs418359-rs2836926_F: TGTCCCACCATTGTGTATTA (SEQ ID NO:299) and rs418359-rs2836926_R: TCAGACTTGAAGTCCAGGAT (SEQ ID NO:300), rs7278447-rs7278858_F: GCTTCAGGGGTGTTAGTTTT (SEQ ID NO:301) and rs7278447-rs7278858_R: CTTTGTGAAAAGTCGTCCAG (SEQ ID NO:302), rs385787-rs367001_F:CCATCATGGAAAGCATGG (SEQ ID NO:303) and rs385787-rs367001_R: TCATCTCCATGACTGCACTA (SEQ ID NO:304), rs367001-rs386095_F: GAGATGACGGAGTAGCTCAT (SEQ ID NO:305) and rs367001-rs386095_R: CCCAGCTGCACTGTCTAC (SEQ ID NO:306), rs2837296-rs2837297_F: TCTTGTTCCAATCACAGGAC (SEQ ID NO:307) and rs2837296-rs2837297_R: ATGCTGTTAGCTGAAGCTCT (SEQ ID NO:308), and rs2837381-rs4816672_F: TGAAAGCTCCTAAAGCAGAG (SEQ ID NO:309) and rs2837381-rs4816672_R:TTGAAGAGATGTGCTATCAT (SEQ ID NO:310). Polynucleotide sequences e.g. GC clamp sequences, can be included to ensure specific hybridization of AT-rich primers (Ghanta et al., PLOS ONE 5(10): doi10.1371/journal.pone.0013184 [2010], available on the world wide web at plosone.org). An example of a GC clamp sequence that can be included either 5' of the forward primer or 3' of the reverse primer is GCCGCCTGCAGCCCGCGCCCCCGTGCCCCGCCCCGCCGCCGGCCCGGGCGCC (SEQ ID NO:311). Sample preparation and enrichment of cfDNA sequencing library, a purified cfDNA sample, and a plasma sample is performed according to the method described in Examples 6, 7, and 8, respectively. All sequencing libraries are prepared as described in Example 2a., and sequencing is performed as described in Example 2b and including paired-end sequencing. Analysis of the sequencing data for the determination of fetal aneuploidy is performed as described in Examples 3 and 4. Concomitant to the analysis for determining aneuploidy, the sequencing data is analyzed to determine the fetal fraction as follows. Following the transfer of the image and base call files to the Unix server running the Illumina "Genome Analyzer Pipeline" software version 1.51 as described in Example 3a., the 36 bp reads are aligned to a 'tandem SNP genome' using the BOWTIE program. The tandem SNP genome is identified as the grouping of the DNA sequences that encompass the alleles of the 58 tandem SNP pairs disclosed above. Only reads that mapped uniquely to the tandem SNP genome are used for the analysis of fetal fraction. Reads that match perfectly to the tandem SNP genome are counted as tags and filtered. Of the remaining reads, only reads having one or two mismatches are counted as tags and included in the analysis. Tags mapped to each of the tandem SNP alleles are counted, and the fetal fraction is determined essentially as described in Example 6 above but accounting for tags mapped to the two tandem SNP alles x and y present on each of the amplified polymorphic target nucleic acid sequences that are amplified to enrich the samples i.e.

% fetal fraction allele$_{x+y}$=(($\Sigma$Fetal sequence tags for allele$_{x+y}$)/($\Sigma$Maternal sequence tags for allele$_{x+y}$))×100

Only informative tandem SNPs are used to determine the fetal fraction.

Optionally, the fraction of fetal nucleic acids in the mixture of fetal and maternal nucleic acids is calculated for each of the informative allele (allele$_{x+y}$) as follows:

% fetal fraction allele$_{x+y}$=((2×ΣFetal sequence tags for allele$_{x+y}$)/(ΣMaternal sequence tags for allele$_{x+y}$))×100, to compensate for the presence of 2 sets of tandem fetal alleles, one being masked by the maternal background.

The percent fetal fraction is calculated for at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40 or more informative sets of tandem alleles. In one embodiment, the fetal fraction is the average fetal fraction determined for at least 3 informative sets of tandem alleles.

Example 11

Determination of Fetal Fraction by Capillary Electrophoresis of Polymorphic Sequences Comprising STRs To determine fetal fraction in maternal samples comprising fetal and maternal cfDNA, peripheral blood samples were collected from volunteer pregnant women carrying either male or female fetuses. Peripheral blood samples were obtained and processed to provide purified cfDNA as described in Example 1.

Ten microliters of cfDNA samples were analyzed using the AmpFlSTR® MiniFiler™ PCR amplification kit (Applied Biosystems, Foster City, CA) according to the manufacturer's instructions. Briefly, cfDNA contained in 10 μl was amplified in a reaction volume of 25 μl containing 5 μL fluorescently labeled primers (AmpF/STR® MiniFiler™ Primer Set), and the AmpF/STR® MiniFiler™ Master Mix, which includes AmpliTaq Gold® DNA polymerase and associated buffer, salt (1.5 mM MgCl2), and 200 μM deoxynucleotide triphosphates (dNTPs: dATP, dCTP, dGTP and dTTP). The fluorescently labeled primers are forward primers that are labeled with 6FAM™, VIC™, NED™, and PET™ dyes. Thermal cycling was performed with the Gene Amp9700 (Applied Biosystems) using the following cycling conditions: incubating at 95° C. for 10 minutes, followed by 30 cycles at 94° C. for 20 seconds, 59° C. for 2 minute, and 72° C. for 1 minute, which was followed by a final incubation at 60° C. for 45 minutes. A final hold at 4° C. was added until the samples were removed for analysis. The amplified product was prepared by diluting 1 ul of amplified product in 8.7 ul Hi-Di™ formamide (Applied Biosystems) and 0.3 μl GeneScan™-500 LIZ_internal size standard (Applied Biosystems), and analyzed with an ABI PRISM3130xl Genetic Analyzer (Applied Biosystems) using Data Collection HID_G5_POP4 (Applied Biosystems), and a 36-cm capillary array. All genotyping was performed with GeneMapper_ID v3.2 software (Applied Biosystems) using manufacturer provided allelic ladders and bins and panels.

All genotyping measurement were performed on the Applied Biosystems 3130xl Genetic Analyzer, using a ±0.5-nt "window" around the size obtained for each allele to allow for detection and correct assignment of alleles. Any sample allele whose size was outside the ±0.5-nt window was determined to be OL i.e. "Off Ladder". OL alleles are alleles of a size that is not represented in the AmpF/STR® MiniFiler™ Allelic Ladder or an allele that does not correspond to an allelic ladder, but whose size is just outside a window because of measurement error. The minimum peak height threshold of >50 RFU was set based on validation experiments performed to avoid typing when stochastic effects are likely to interfere with accurate interpretation of mixtures. The calculation of fetal fraction is based on averaging all informative markers. Informative markers are identified by the presence of peaks on the electropherogram that fall within the parameters of preset bins for the STRs that are analyzed.

Calculations of fetal fraction were performed using the average peak height for major and minor alleles at every STR locus determined from triplicate injections. The rules applied to the calculation are:

1. off-ladder allele (OL) data for alleles are not included in the calculation; and 2. only peak heights derived from >50 RFU (relative fluorescence units) are included in the calculation 3. if only one bin is present the marker is deemed non-informative; and 4. if a second bin is called but the peaks of the first and second bins are within 50-70% of their relative fluorescence units (RFU) in peak height, the minority fraction is not measured and the marker is deemed not informative.

The fraction of the minor allele for any given informative marker is calculated by dividing the peak height of the minor component by the sum of the peak height for the major component, and expressed as a percent was first calculated for each informative locus as fetal fraction=(peak height of minor allele/Σpeak height of major allele(s))×100, The fetal fraction for a sample comprising two or more informative STRs, would be calculated as the average of the fetal fractions calculated for the two or more informative markers.

Table 16 provides the data obtained from analyzing cfDNA of a subject pregnant with a male fetus.

TABLE 16

Fetal Fraction Determined in cfDNA of a Pregnant Subject by Analysis of STRs

| STR | Allele 1 | Allele 2 | Allele 3 | Allele1 Height | Allele 2 Height | Allele 3 Height | Fetal Fraction | Fetal Fraction (Mean/STR) |
|---|---|---|---|---|---|---|---|---|
| AMEL | X | Y | | | 3599 | 106 | 2.9 | |
| AMEL | X | Y | | | 3602 | 110 | 3.1 | |
| AMEL | X | Y | | | 3652 | 109 | 3.0 | 3.0 |
| CSF1PO | 11 | 12 | | | 2870 | 2730 | | |
| CSF1PO | 11 | 12 | | | 2924 | 2762 | | |
| CSF1PO | 11 | 12 | | | 2953 | 2786 | | |
| D13S317 | 11 | 12 | | | 2621 | 2588 | | |
| D13S317 | 11 | 12 | | | 2680 | 2619 | | |
| D13S317 | 11 | 12 | | | 2717 | 2659 | | |
| D16S539 | 9 | 11 | | | 1056 | 1416 | | |
| D16S539 | 9 | 11 | | | 1038 | 1394 | | |

TABLE 16-continued

Fetal Fraction Determined in cfDNA of a Pregnant Subject by Analysis of STRs

| STR | Allele 1 | Allele 2 | Allele 3 | Allele1 Height | Allele 2 Height | Allele 3 Height | Fetal Fraction | Fetal Fraction (Mean/STR) |
|---|---|---|---|---|---|---|---|---|
| D16S539 | 9 | 11 | | | 1072 | 1437 | | |
| D18S51 | 13 | 15 | | | 2026 | 1555 | | |
| D18S51 | 13 | 15 | | | 2006 | 1557 | | |
| D18S51 | 13 | 15 | | | 2050 | 1578 | | |
| D21S11 | 28 | 31.2 | | | 2450 | 61 | 2.5 | |
| D21S11 | 28 | 31.2 | | | 2472 | 62 | 2.5 | |
| D21S11 | 28 | 31.2 | | | 2508 | 67 | 2.7 | 2.6 |
| D2S1338 | 20 | 23 | | | 3417 | 3017 | | |
| D2S1338 | 20 | 23 | | | 3407 | 3020 | | |
| D2S1338 | 20 | 23 | | | 3493 | 3055 | | |
| D7S820 | 9 | 12 | 13 | 2373 | 178 | 1123 | 5.1 | |
| D7S820 | 9 | 12 | 13 | 2411 | 181 | 1140 | 5.1 | |
| D7S820 | 9 | 12 | 13 | 2441 | 182 | 1156 | 5.1 | 5.1 |
| FGA | 17.2 | 22 | 25 | 68 | 1140 | 896 | 3.3 | |
| FGA | 17.2 | 22 | 25 | 68 | 1144 | 909 | 3.1 | |
| FGA | 17.2 | 22 | 25 | 68 | 1151 | 925 | 3.3 | 3.2 |

Fetal Fraction = 3.5

The results show that miniSTRs can be used to discern fetal and maternal alleles in cfDNA from a maternal plasma sample. It is expected that the miniSTRs can be used in massively parallel sequencing for the simultaneous determination of aneuploidy and fetal fraction.

What is claimed is:

1. A method for simultaneously determining fetal aneuploidy and fetal fraction in a maternal plasma, serum, or urine sample comprising an unamplified mixture of fetal and maternal cell-free DNA (cfDNA) nucleic acid molecules, said method comprising:
  (a) enriching a portion of said unamplified mixture for a plurality of polymorphic target nucleic acids, wherein said enriching comprises:
    (i) dividing said unamplified mixture into a first portion and a second portion, and specifically amplifying said plurality of target nucleic acids in the first portion using primer pairs each capable of amplifying a target nucleic acid sequence comprising a polymorphic site in a multiplex PCR reaction to generate an amplified product comprising a panel of amplified polymorphic sites that contains a sufficient number of polymorphic sites such that at least two are informative polymorphic sites; and
    (ii) combining at least a portion or all of the amplified product with at least a portion of the second portion of said unamplified mixture to obtain an enriched mixture;
  (b) performing massively parallel sequencing of at least a portion of the enriched mixture obtained in step (a), wherein said sequencing comprises providing a plurality of sequence reads and aligning each sequence read to a chromosome in a reference genome to identify a plurality of sequence tags; and
  (c) based on said sequencing, simultaneously determining said fetal fraction and said aneuploidy, wherein:
    (i) determining said fetal fraction is performed by a processor using computer readable software code and comprises:
      (1) using the mapped sequence tags to identify at least two informative polymorphic sites in said panel of amplified polymorphic sites; and
      (2) calculating the fetal fraction based on the total number of mapped sequence tags that map to a first allele and the total number of mapped sequence tags that map to a second allele at each of said informative polymorphic sites; and
    (ii) determining said fetal aneuploidy is performed by a processor using computer readable software code and comprises quantification of the number of mapped sequence tags aligning to a chromosome of interest, and comparing the results obtained for the chromosome of interest to a threshold value, wherein the threshold value is a number that serves as a limit of diagnosis of an aneuploidy and wherein the presence of an aneuploidy for the chromosome of interest is identified if the threshold value is exceeded by the results obtained for the chromosome of interest.

2. The method of claim 1, wherein said maternal plasma, serum, or urine sample is a plasma sample.

3. The method of claim 1, wherein said enriching comprises amplifying a plurality of polymorphic target nucleic acids in a portion of a purified mixture of fetal and maternal nucleic acids.

4. The method of claim 1, wherein said polymorphic target nucleic acids are located on the same or on different chromosomes.

5. The method of claim 1, wherein each of said plurality of polymorphic target nucleic acids comprises at least one single nucleotide polymorphism (SNP).

6. The method of claim 5, wherein said at least one single SNP is rs560681.

7. The method of claim 5, wherein said at least one SNP is a tandem SNP.

8. The method of claim 7, wherein said tandem SNP is selected from sets of tandem SNPs rs7277033-rs2110153; rs2822654-rs1882882; rs368657-rs376635; rs2822731-rs2822732; rs1475881-rs7275487; rs1735976-rs2827016; rs447340-rs2824097; rs418989-rs13047336; rs987980-rs987981; rs4143392-rs4143391; rs1691324-rs13050434; rs11909758-rs9980111; rs2826842-rs232414; rs1980969-rs1980970; rs9978999-rs9979175; rs1034346-rs12481852; rs7509629-rs2828358; rs4817013-rs7277036; rs9981121-rs2829696; rs455921-rs2898102; rs2898102-rs458848; rs961301-rs2830208; rs2174536-rs458076; rs11088023-rs11088024; rs1011734-rs1011733; rs2831244-rs9789838;

rs8132769-rs2831440; rs8134080-rs2831524; rs4817219-rs4817220; rs2250911-rs2250997; rs2831899-rs2831900; rs2831902-rs2831903; rs11088086-rs2251447; rs2832040-rs11088088; rs2832141-rs2246777; rs2832959-rs9980934; rs2833734-rs2833735; rs933121-rs933122; rs2834140-rs12626953; rs2834485-rs3453; rs9974986-rs2834703; rs2776266-rs2835001; rs1984014-rs1984015; rs7281674-rs2835316; rs13047304-rs13047322; rs2835545-rs4816551; rs2835735-rs2835736; rs13047608-rs2835826; rs2836550-rs2212596; rs2836660-rs2836661; rs465612-rs8131220; rs9980072-rs8130031; rs418359-rs2836926; rs7278447-rs7278858; rs385787-rs367001; rs367001-rs386095; rs2837296-rs2837297; and rs2837381-rs4816672.

9. The method of claim 1, wherein each of said plurality of polymorphic target nucleic acids comprises at least one short tandem repeat (STR).

10. The method of claim 1, wherein each of said plurality of polymorphic target nucleic acids is an STR selected from CSF1PO, FGA, TH01, TPOX, vWA, D3S1358, D5S818, D7S820, D8S1179, D13S317, D16S539, D18S51, D21S11, D2S1338, Penta D, Penta E, D22S1045, D20S1082, D20S482, D18S853, D17S1301, D17S974, D14S1434, D12ATA63, D11S4463, D10S1435, D10S1248, D9S2157, D9S1122, D8S1115, D6S1017, D6S474, D5S2500, D4S2408, D4S2364, D3S4529, D3S3053, D2S1776, D2S441, D1S1677, D1S1627 and D1GATA113.

11. The method of claim 9, wherein said at least one STR is less than about 300 base pairs.

12. The method of claim 1, wherein said sequencing is next generation sequencing (NGS).

13. The method of claim 1, wherein said sequencing is massively parallel sequencing using sequencing-by-synthesis with reversible dye terminators.

14. The method of claim 1, wherein said sequencing is sequencing-by-ligation.

15. The method of claim 1, wherein said sequencing comprises an amplification.

16. The method of claim 1, wherein said sequencing is single molecule sequencing.

17. The method of claim 1, wherein said aneuploidy is a chromosomal aneuploidy.

18. The method of claim 1, wherein the plurality of mapped sequence tags comprises at least $3 \times 10^6$ sequence tags.

19. The method of claim 5, wherein said at least one single SNP is selected from rs1109037, rs9866013, rs13182883, rs13218440, rs7041158, rs740598, rs10773760, rs4530059, rs7205345, rs8078417, rs576261, rs2567608, rs430046, rs9951171, rs338882, rs10776839, rs9905977, rs1277284, rs258684, rs1347696, rs508485, rs9788670, rs8137254, rs3143, rs2182957, rs3739005, and rs530022.

* * * * *